US010501499B2

(12) United States Patent
Sorensen et al.

(10) Patent No.: US 10,501,499 B2
(45) Date of Patent: Dec. 10, 2019

(54) PEPTIDES DERIVED FROM VIRAL PROTEINS FOR USE AS IMMUNOGENS AND DOSAGE REACTANTS

(71) Applicant: Bionor Immuno AS, Skien (NO)

(72) Inventors: Birger Sorensen, Oslo (NO); Mats Okvist, Oslo (NO); Arnt Ove Hovden, Oslo (NO); Maja Sommerfelt Gronvold, Oslo (NO)

(73) Assignee: BIONOR IMMUNO AS, Skien (NO)

( * ) Notice: Subject to any disclaimer, the term of this patent is extended or adjusted under 35 U.S.C. 154(b) by 413 days.

(21) Appl. No.: 14/406,016

(22) PCT Filed: Jun. 6, 2013

(86) PCT No.: PCT/EP2013/061751
§ 371 (c)(1),
(2) Date: Dec. 5, 2014

(87) PCT Pub. No.: WO2013/182661
PCT Pub. Date: Dec. 12, 2013

(65) Prior Publication Data
US 2015/0152140 A1    Jun. 4, 2015

Related U.S. Application Data

(60) Provisional application No. 61/656,256, filed on Jun. 6, 2012.

(51) Int. Cl.
| C07K 14/05 | (2006.01) |
| C07K 14/005 | (2006.01) |
| C07K 7/08 | (2006.01) |
| C07K 14/00 | (2006.01) |
| C07K 7/06 | (2006.01) |
| G01N 33/569 | (2006.01) |

(52) U.S. Cl.
CPC .............. *C07K 14/005* (2013.01); *C07K 7/06* (2013.01); *C07K 7/08* (2013.01); *C07K 14/001* (2013.01); *G01N 33/56977* (2013.01); *G01N 2333/045* (2013.01); *G01N 2333/11* (2013.01); *G01N 2333/186* (2013.01); *G01N 2469/20* (2013.01)

(58) Field of Classification Search
None
See application file for complete search history.

(56) References Cited

U.S. PATENT DOCUMENTS

| 2006/0182763 A1 | 8/2006 | Kim et al. |
| 2008/0171040 A1 | 7/2008 | Ebens et al. |
| 2008/0305044 A1 | 12/2008 | McDonagh et al. |

FOREIGN PATENT DOCUMENTS

| EP | 0935662 B1 | 8/1999 |
| EP | 1652858 A1 | 5/2006 |
| WO | WO 1995/007707 A1 | 3/1995 |
| WO | WO 1995/012677 A2 | 5/1995 |
| WO | WO 1995/025122 A1 | 9/1995 |
| WO | WO 1995/027733 A1 | 10/1995 |
| WO | WO 1997/034621 A1 | 9/1997 |
| WO | WO 2000/052040 A1 | 9/2000 |
| WO | WO 2001/021189 A1 | 3/2001 |
| WO | WO 2002/020035 A1 | 3/2002 |
| WO | WO 2002/020554 A2 | 3/2002 |
| WO | WO 2002/020555 A2 | 3/2002 |
| WO | WO 2002/026785 A2 | 4/2002 |
| WO | WO 2002/034770 A1 | 5/2002 |
| WO | WO 2003/105058 A2 | 12/2003 |
| WO | WO 2004/024182 A2 | 3/2004 |
| WO | WO 2008/107400 A1 | 9/2008 |
| WO | WO 2011/000962 A2 | 1/2011 |
| WO | WO 2012/072088 A1 | 6/2012 |
| WO | WO 2012/092934 A1 | 7/2012 |

OTHER PUBLICATIONS

Barouch, D. H., 2008, Challenges in the development of an HIV-1 vaccine, Nature 455:613-619.*
Girard, M. P., et al., 2011, Human immunodeficiency virus (HIV) immunopathogenesis and vaccine development: A review, Vaccine 29:6191-6218.*
Walker, B. D., and D. R. Burton, May 2008, Toward an AIDS vaccine, Science 320:760-764.*
International Search Report and Written Opinion for International Patent Application No. PCT/EP2013/061751, dated Aug. 22, 2013.
Assarsson, E., et al., "Immunomic Analysis of the Repertoire of T-Cell Specificities for Influenza A Virus in Humans," *Journal of Virology*, 2008, vol. 82(24), pp. 12241-12251.
Khan, N., et al., "T Cell Recognition Patterns of Immunodominant Cytomegalovirus Antigens in Primary and Persistent Infection," *The Journal of Immunology*, 2007, vol. 178, pp. 4455-4465.
Sundaram, R., et al., "A novel multivalent human CTL peptide construct elicits robust cellular immune response in HLA-A*0201 transgenic mice: implications for HTLV-1 vaccine design," *Vaccine*, 2003, vol. 21, pp. 2767-2781.

* cited by examiner

*Primary Examiner* — Jeffrey S Parkin
(74) *Attorney, Agent, or Firm* — Womble Bond Dickinson (US) LLP

(57) ABSTRACT

The present invention relates to novel peptides and methods for treatment, diagnosis and prognosis of virus infections including infections with HCV, HIV, HPV, CMV and Influenza. The invention further relates to methods for identifying and providing peptides useful for the treatment and diagnosis.

9 Claims, 5 Drawing Sheets

Figure 1:
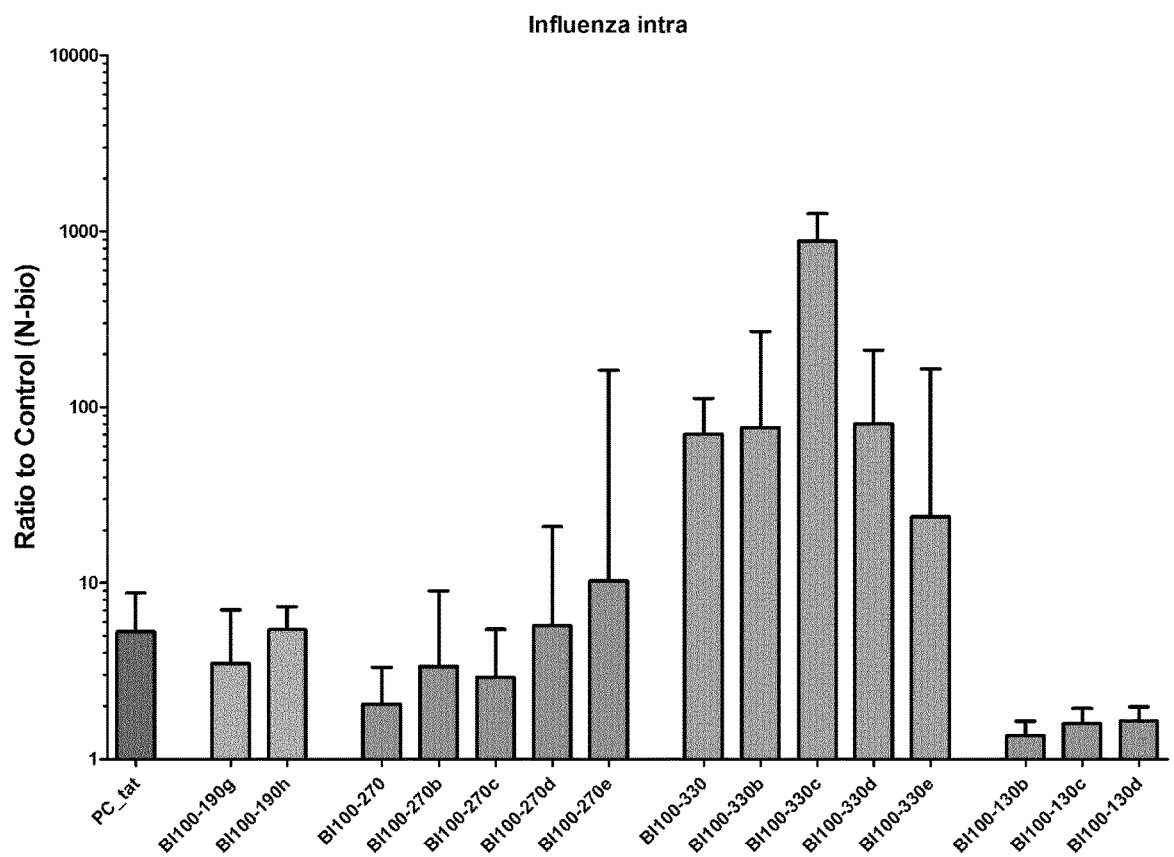

Specification includes a Sequence Listing.

PEPTIDES DERIVED FROM VIRAL PROTEINS FOR USE AS IMMUNOGENS AND DOSAGE REACTANTS

CROSS-REFERENCE TO RELATED APPLICATIONS

This application is a national stage filing under 35 U.S.C. 371 of PCT/EP2013/061751, filed Jun. 6, 2013, which claims priority of U.S. Provisional Application No. 61/656,256, filed Jun. 6, 2012, which is hereby incorporated herein in its entirety by reference.

FIELD OF THE INVENTION

The present invention relates to novel peptides and methods for treatment, diagnosis and prognosis of virus infections and various cancer and inflamatory diseases including infections with HCV, HIV, HPV, CMV and Influenza. The invention further relates to methods for identifying and providing peptides useful for the treatment and diagnosis.

BACKGROUND OF THE INVENTION

Conventional approaches to vaccine development have implemented either whole replication competent virus which has been attenuated (e.g. Sabin polio vaccine, measles, mumps, rubella (MMR)) or inactivated virions that are not replication competent. On occasions, the inactivated virus vaccines may include split vaccines where the virus particles have been disrupted. Molecular techniques have also been used to develop the subunit vaccine (e.g. hepatitis B vaccine) that consists only of the surface glycoproteins of hepatitis B virus. The inactivated virus vaccines tend to induce primarily antibody responses to the viruses in question, whereas the live attenuated vaccines induce both cell-mediated immunity as well as an antibody response since the vaccine induces a transient infection.

The only disease which has been eliminated by virtue of a successful vaccination campaign is smallpox. A campaign is currently in progress to eradicate polio. Features of virus infections that can be eliminated by vaccination are infections caused by viruses with stable virus antigens (i.e. very low mutation frequency, few subtypes), that lack a reservoir in other animal species, viruses that do not persist in the body once the infection is over and where vaccination leads to long lasting immunity. Viruses such as polio and measles fulfill these criteria whereas viruses such as influenza virus (Flu), HCV, and HIV that vary their protein sequences do not. It is for this reason that new and alternate approaches are required to develop vaccines for these diseases.

Vaccination aims to stimulate the immune response to a specific pathogen in advance of infection. When an individual is exposed to that pathogen, a memory response is triggered which prevents the establishment of infection. Vaccines therefore stimulate the adaptive immune response which unlike innate immunity, is long lived and has memory. There are two major arms to the adaptive immune system. Humoral immunity which involves the development of antibodies that can bind virus particles and certain antibodies that can neutralize infection. Cell mediated immunity that leads to the development of cytotoxic T-cells that kill infected cells exposing viral epitopes in the context of human leukocyte antigen (HLA) class I, in this way eliminating infected cells.

The challenge of providing vaccines suitable for stimulation of the adaptive immune system is that peptide epitopes need to be taken up by the antigen presenting cells.

Several peptides have been demonstrated to translocate across the plasma membrane of eukaryotic cells by a seemingly energy-independent pathway. These peptides are defined as cell-penetrating peptides (CPPs). Cellular delivery using these cell-penetrating peptides offers several advantages over conventional techniques. It is non-invasive, energy-independent, is efficient for a broad range of cell types and can be applied to cells en masse.

For humoral responses and development of antibodies it may not be needed to obtain cell-penetrating properties since stimulation of B-cells are also done by extracellular peptide antigens. Hepatitis means inflammation of the liver which can be caused by a variety of factors including toxins, certain drugs, some diseases, heavy alcohol use, and bacterial and viral infections. Hepatitis is also the name of a family of viral infections that affect the liver; the most common types in the developed world are hepatitis A, hepatitis B, and hepatitis C.

Hepatitis C is a liver disease that results from infection with the hepatitis C virus (HCV). It can range in severity from a mild illness lasting a few weeks to a serious, lifelong illness. Hepatitis C is spread via blood; the most common form of transmission is through sharing needles or other equipment used to inject drugs. The infection can be either "acute" or "chronic". Acute HCV infection is an asymptomatic, short-term illness that occurs within the first 6 months after someone is exposed to the hepatitis C virus. For most people, acute infection leads to chronic infection, which can result in long-term complications and even death.

HCV is an enveloped positive stranded ribonucleic acid (RNA) virus with a diameter of about 50 nm, belonging to the genus Hepacivirus in the family Flaviviridae that replicate in the cytoplasm of infected cells. The only known reservoir for HCV is humans, although the virus has experimentally been transmitted to chimpanzees. The natural targets of HCV are hepatocytes and possibly B-lymphocytes. As of 2008, six different genotypes and more than 100 subtypes of the virus are known. Replication occurs through an RNA-dependent RNA polymerase that lacks a proofreading function, which results in a very high rate of mutations. Rapid mutations in a hypervariable region of the HCV genome coding for the envelope proteins enable the virus to escape immune surveillance by the host. As a consequence, most HCV-infected people proceed to chronic infection.

It is estimated that 170 million people are infected with HCV worldwide, equating to approximately 3% of the global population. There are also approximately 3-4 million people who are infected every year; with an estimated 80% of these newly infected patients progressing to chronic infection.

The 6 genotypes of HCV have different geographical spread. The disease in the early stages is generally asymptomatic; the majority of patients with chronic infection eventually progress to complications such as liver fibrosis and cirrhosis, and, in 1-5% of cases, hepatocellular carcinoma.

HCV is the major cause of non-A, non-B hepatitis worldwide. Acute infection with HCV frequently leads to chronic hepatitis and end-stage cirrhosis. It is estimated that up to 20% of HCV chronic carriers may develop cirrhosis over a time period of about 20 years and that of those with cirrhosis between 1 to 4% is at risk to develop liver carcinoma.

The about 9.6 kb single-stranded RNA genome of the HCV virus comprises a 5'- and 3'-noncoding region (NCRs)

and, in between these NCRs a single long open reading frame of about 9 kb encoding an HCV polyprotein of about 3000 amino acids.

HCV polypeptides are produced by translation from the open reading frame and cotranslational proteolytic processing. Structural proteins are derived from the amino-terminal one-fourth of the coding region and include the capsid or Core protein (about 21 kDa), the E1 envelope glycoprotein (about 35 kDa) and the E2 envelope glycoprotein (about 70 kDa, previously called NS1), and p7 (about 7 kDa). The E2 protein can occur with or without a C-terminal fusion of the p7 protein (Shimotohno et al. 1995). An alternative open reading frame in the Core-region has been found which is encoding and expressing a protein of about 17 kDa called F (Frameshift) protein (Xu et al. 2001; Ou & Xu in US Patent Application Publication No. US2002/0076415). In the same region, ORFs for other 14-17 kDa ARFPs (Alternative Reading Frame Proteins), A1 to A4, were discovered and antibodies to at least A1, A2 and A3 were detected in sera of chronically infected patients (Walewski et al. 2001). From the remainder of the HCV coding region, the non-structural HCV proteins are derived which include NS2 (about 23 kDa), NS3 (about 70 kDa), NS4A (about 8 kDa), NS4B (about 27 kDa), NS5A (about 58 kDa) and NS5B (about 68 kDa) (Grakoui et al. 1993).

Influenza remains a significant cause of mortality and morbidity worldwide. The World Health Organisation (WHO) estimates that seasonal epidemics affect 3-5 million people with severe illness annually and result in 250,000-500,000 mortalities. Influenza is caused by viruses in the family Orthomyxoviridae which are negative stranded RNA viruses. The influenza virus exists as three types, A, B and C of which only A is associated with pandemics. Types A viruses are found in both humans and animals, particularly birds but also other mammals such as pigs. Type A viruses are further typed into subtypes according to different kinds and combinations of virus surface proteins. Among many subtypes in 2009 influenza A (H1N1) and A (H3N2) subtypes were circulating among humans. Influenza A and B are included in the seasonal vaccine, whereas influenza C occurs only rarely, and so it is not included in the seasonal vaccine. Type B viruses are human specific and Type C viruses cause a very mild disease. The genomes of Orthomyxoviruses are segmented. Influenza viruses Types A and B have 8 segments whereas type C has seven. Pandemics may arise as a result of re-assortment of gene segments when two different type A viruses infect the same cell. There is no immunity in the population to this novel re-assorted virus. Three pandemics occurred in the twentieth century: "Spanish influenza" in 1918, "Asian influenza" in 1957, and "Hong Kong influenza" in 1968. The 1918 pandemic killed an estimated 40-50 million people worldwide. Subsequent pandemics were much milder, with an estimated 2 million deaths in 1957 and 1 million deaths in 1968. In June 2009 the WHO declared a pandemic from influenza virus H1N1 (swine Influenza) which was declared over in August 2010.

Human papillomaviruses are made up of a group of DNA viruses in the family Papillomaviridae which infect the skin and mucous membranes. Two groups which are derived from more than 100 different identified subtypes are the main cause for clinical concern: those causing warts (both benign and genital warts), and a group of 12 "high risk" subtypes that can result in cervical cancer. This latter group has been attributed as a contributory factor in the development of nearly all types of cervical cancer. Worldwide, cervical cancer remains the second most common malignancy in women, and is a leading cause of cancer-related death for females in developing countries. HPV 16 and 18 have been mainly associated with cervical cancer, however, the virus is also a cause of throat cancer in both men and women. HPV is transmitted through contact and enters the skin through abrasions. An abortive infection, where only the early proteins are expressed is associated with cancer development.

OBJECT OF THE INVENTION

It is an object of embodiments of the invention to provide peptides that may be used as immunogens to stimulate an adaptive immune response in a subject.

It is a further object of embodiments of the invention to provide peptides, including multimeric, such as dimeric peptides, that may be used as immunogens to stimulate the humoral immunity in a subject.

In particular, it is an object of embodiments of the invention to provide peptides that may be taken up by antigen presenting cells (macrophages and dendritic cells) such that epitopes within the peptides are correctly processed and presented to T-lymphocytes in order to stimulate an effective immune response.

It is a further object of object of embodiments of the invention to provide peptides including multimeric, such as dimeric peptides comprising epitopes of an antigen that stimulates cells of the B lymphocyte lineage (B-cells) to secrete antibodies against this antigen.

The B-cell activation provided by the peptides according to the present invention may be both T cell-independent and T cell-dependent. Accordingly, the peptides according to the present invention or parts thereof may interact with B-cell receptors to activate the B-cells either through a T helper cell dependent or independent manner leading to the production of specific antibodies. Furthermore, the peptides may be taken up by antigen presenting cells (macrophages and/or dendritic cells) such that epitopes within the peptides are correctly processed and presented to T-lymphocytes, such as a helper T cell, which in turn helps to activate the B cells in order to stimulate an effective immune response. The peptides may also be taken up by activated B-cells which can also act as antigen presenting cells. Peptides interact with the B-cells through the B-cell receptor and are then internalised into the cell. The epitopes within the peptides will be processed and presented to T-lymphocytes such as helper cells.

However, in some important aspects of the present invention, the peptides according to the present invention are designed to not effectively penetrate and be taken up by antigen presenting cells. Accordingly, in these aspects of the invention, the peptides according to the present invention may provide B-cell activation through interaction at the cell surface via the B-cell receptor. It is to be understood that in order to provide sustained B-cell stimulation, it is preferred that the peptides according to the present invention are designed to comprise a helper epitope that may be taken up by antigen presenting cells in order to stimulate CD4+ T-helper cells that can sustain effective humoral immunity in a subject.

Further, it is an object of embodiments of the invention to provide peptides that may be used as antigens, to provide immunogenic compositions and methods for inducing an immune response in a subject against an antigen.

Further, it is an object of embodiments of the invention to provide peptides that may be used as antigens that can serve as targets in diagnostic assays.

SUMMARY OF THE INVENTION

The present invention pertains to a peptide design promoting efficient activation of a humoral immune response against antigens contained within this peptide design as well as to a peptide design promoting uptake of peptide epitopes by antigen presenting cells (macrophages and dendritic cells) such that the epitopes can be correctly processed and presented in the context of HLA class I and II to stimulate both CD4+ and CD8+ T-lymphocytes. CD8+ T-lymphocytes with cytotoxic capacity will kill infected cells bearing the epitope of interest. CD4+ T-lymphocyte provide 'help' to sustain effective CD8+ T-lymphocyte responses.

It has been found by the present inventor(s) that peptide constructs—amino acid sequences with a particular pattern or scaffold design, and in particular multimeric, such as dimeric peptides of this design—have the ability to effectively elicit a humoral immune response in a subject in response to the administration of these peptides.

The peptide constructs according to the present invention may be designed to be able to attach or bind to the cell surface. The peptide constructs or parts thereof may then be taken up by the antigen presenting cells (such as macrophages and dendritic cells) and stimulate helper T-cells in order to elicit efficient and long lasting T-cell dependent B-cell activation. Alternatively the B-cells themselves may provide for the induction of help to activate the B-cells.

Accordingly the peptides according to the present invention may penetrate the cells and may be used to load cells with an immunogenically effective amount of a peptide or fragments of this peptide that can be presented by macrophages and dendritic cells. Accordingly these peptide constructs may elicit both a Cytotoxic T-lymphocyte immune (CTL) response and/or a humoral immune response.

It has been found by the present inventor(s) that peptide constructs—amino acid sequences with a particular pattern or scaffold design—have the ability to effectively penetrate the cell membrane. Accordingly, the peptide constructs according to the present invention may be used to load cells with an immunogenically effective amount of a peptide or fragments of this peptide that can be presented by macrophages and dendritic cells. Accordingly these peptide constructs may elicit a Cytotoxic T-lymphocyte immune (CTL) response and/or a Humoral Immune Response.

So, in a first aspect the present invention relates to an isolated monomeric peptide comprising the following structure

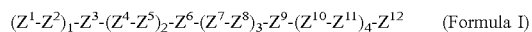   (Formula I)

wherein $Z^1$, $Z^4$, and optional $Z^2$ and $Z^{10}$ defines a linear sequence of one, two, or three arginine residues or derivatives thereof optionally followed by a glycine (G) or an alanine (A); $Z^2$, $Z^5$, $Z^8$ and $Z^{11}$ defines an optional amino acid selected from cysteine (C), lysine (K), aspartic acid (D), asparagine (N), glutamic acid (E), glutamine (Q), 2,3-Diaminopropionic acid (Dpr), tryptophan (W), or tyrosine (Y) or a derivative thereof; $Z^3$, and optional $Z^6$, $Z^9$ and $Z^{12}$ defines any chemical moiety, such as a linear amino acid sequence.

It is to be understood that the amino acid sequence of formula I unless otherwise indicated refers to a peptide sequence in a standard N- to C-terminal direction, wherein the first amino acid mentioned is the N-terminal amino acid that may have an amino (—NH$_2$) group or alternatively an —NH$_3^+$ group. The last amino acid mentioned is the C-terminal that may have a free carboxyl group (—COOH) or a carboxylate group. In some embodiments the N- and/or C-terminal amino acid is modified, such as by N-terminal acetylation or C-terminal amidation. The symbol "-" used in formula I refers to a standard peptide bond, such as a standard peptide bond between $Z^1$ and $Z^2$ in "$Z^1$-$Z^2$".

It is further to be understood that the peptides according to the invention primarily are intended for synthetic peptide synthesis, which is preferred for peptides shorter than 60 amino acids. However, the peptides may be longer than 60 amino acids, if the peptides are produced by recombinant means.

In a further aspect the peptides of the present invention is not an isolated peptide consisting of $X^1$-$X^5$ of formula II as defined in any one of table 1 or table 2.

In a further aspect the peptides of the present invention is not an isolated peptide consisting of $X^1$-$X^6$ of formula III as defined in table 8.

In a further aspect the peptides of the present invention is not an isolated multimeric, such as dimeric peptide as defined in table 8.

In a further aspect the present invention relates to a dimer peptide comprising two peptide monomers, wherein each peptide monomer is according to the invention.

In a further aspect the present invention relates to a composition comprising two or more compounds selected from a monomeric peptide according to the present invention, and an isolated multimeric peptide according to the present invention.

In a further aspect the present invention relates to an isolated nucleic acid or polynucleotide encoding a peptide according to the invention.

In a further aspect the present invention relates to a vector comprising the nucleic acid or polynucleotide encoding a peptide according to the invention.

In a further aspect the present invention relates to a host cell comprising the vector comprising the nucleic acid or polynucleotide encoding a peptide according to the invention.

In a further aspect the present invention relates to an immunogenic composition comprising at least one monomeric peptide, an isolated multimeric peptide according to the invention, a peptide composition, the nucleic acid or polynucleotide, or the vector according the invention; in combination with a pharmaceutically acceptable diluent or vehicle and optionally an immunological adjuvant. In some embodiments this immunogenic composition is in the form of a vaccine composition.

In a further aspect the present invention relates to a method for inducing an immune response in a subject against an antigen which comprises administration of at least one monomeric peptide, an isolated multimeric peptide, a peptide composition, the nucleic acid or polynucleotide, or the vector, or the composition of the invention.

In a further aspect the present invention relates to a method for reducing and/or delaying the pathological effects of a disease antigen, such as an infectious agent in a subject infected with said agent or having said disease caused by said antigen, the method comprising administering an effective amount of at least one monomeric peptide, an isolated multimeric peptide, a peptide composition, the nucleic acid or polynucleotide, or the vector, or the composition according to the invention.

In a further aspect the present invention relates to a peptide according to the invention for use as a medicament.

In a further aspect the present invention relates to a peptide according to the invention for treating the pathological effects of a virus in a subject infected with said virus.

In a further aspect the present invention relates to the use of a peptide selected from a monomeric peptide according to the present invention, and an isolated multimeric peptide according to the present invention for inducing a humoral immune response in a subject.

In a further aspect the present invention relates to a peptide according to the invention for use as a medicament, or for treating the pathological effects of a disease antigen, such as an infectious agent in a subject infected with said agent or having said disease caused by said antigen.

In a further aspect the present invention relates to a peptide according to the invention for use in a diagnostic assay. In a further aspect the present invention relates to a peptide according to the invention for use in an in vitro assay.

LEGENDS TO THE FIGURES

FIG. 1. Intracellular uptake of influenza scaffold peptides. Median and intequartile range of readouts from buffy coats from ten donors and three concentrations of peptide each, normalized by value for N-biotin for each donor.

Figure 2:
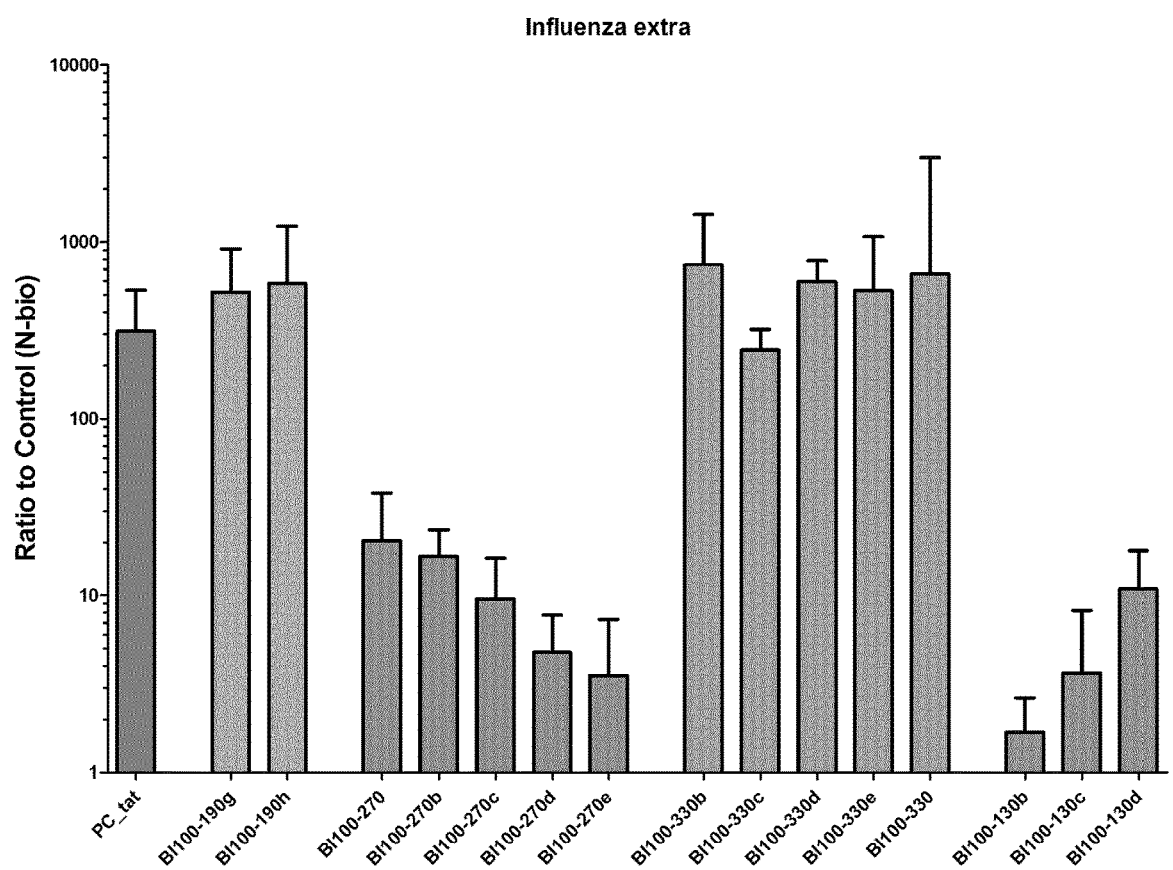

FIG. 2. Extracellular uptake of influenza scaffold peptides. Median and intequartile range of readouts from buffy coats from ten donors and three concentrations of peptide each, normalized by value for N-biotin for each donor.

Figure 3:
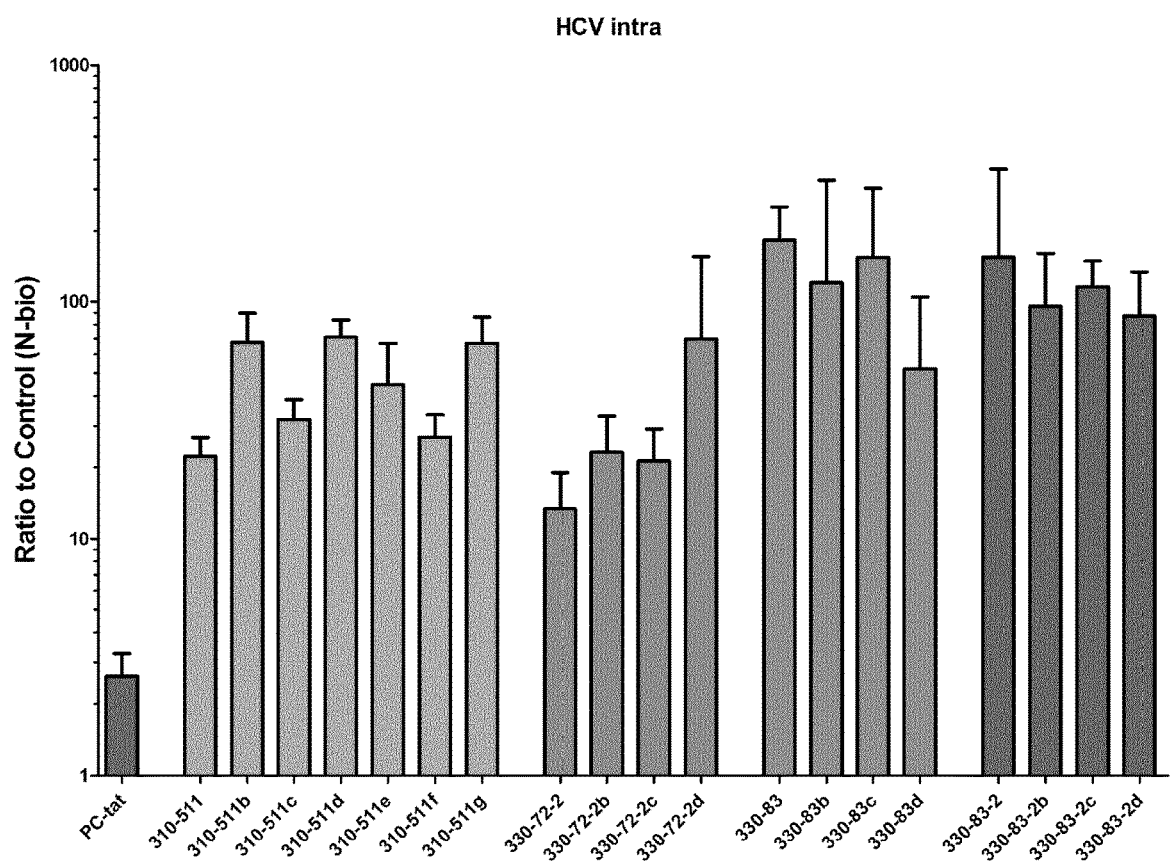

FIG. 3. Intracellular uptake of HCV scaffold peptides. Median and intequartile range of readouts from buffy coats from five donors at four different concentrations of peptide each, normalized by value for N-biotin for each donor.

Figure 4:
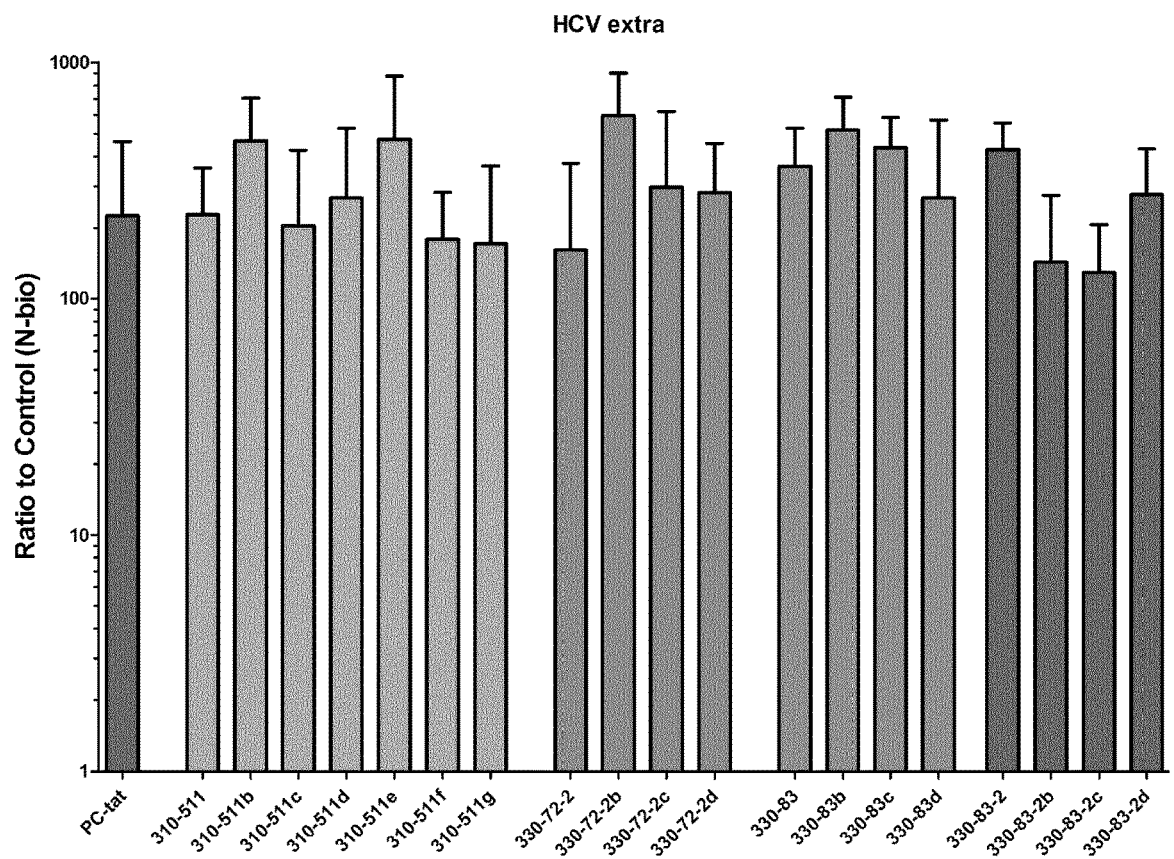

FIG. 4. Extracellular uptake of HCV scaffold peptides. Median and intequartile range of readouts from buffy coats from five donors at four different concentrations of peptide each, normalized by value for N-biotin for each donor.

Figure 5:
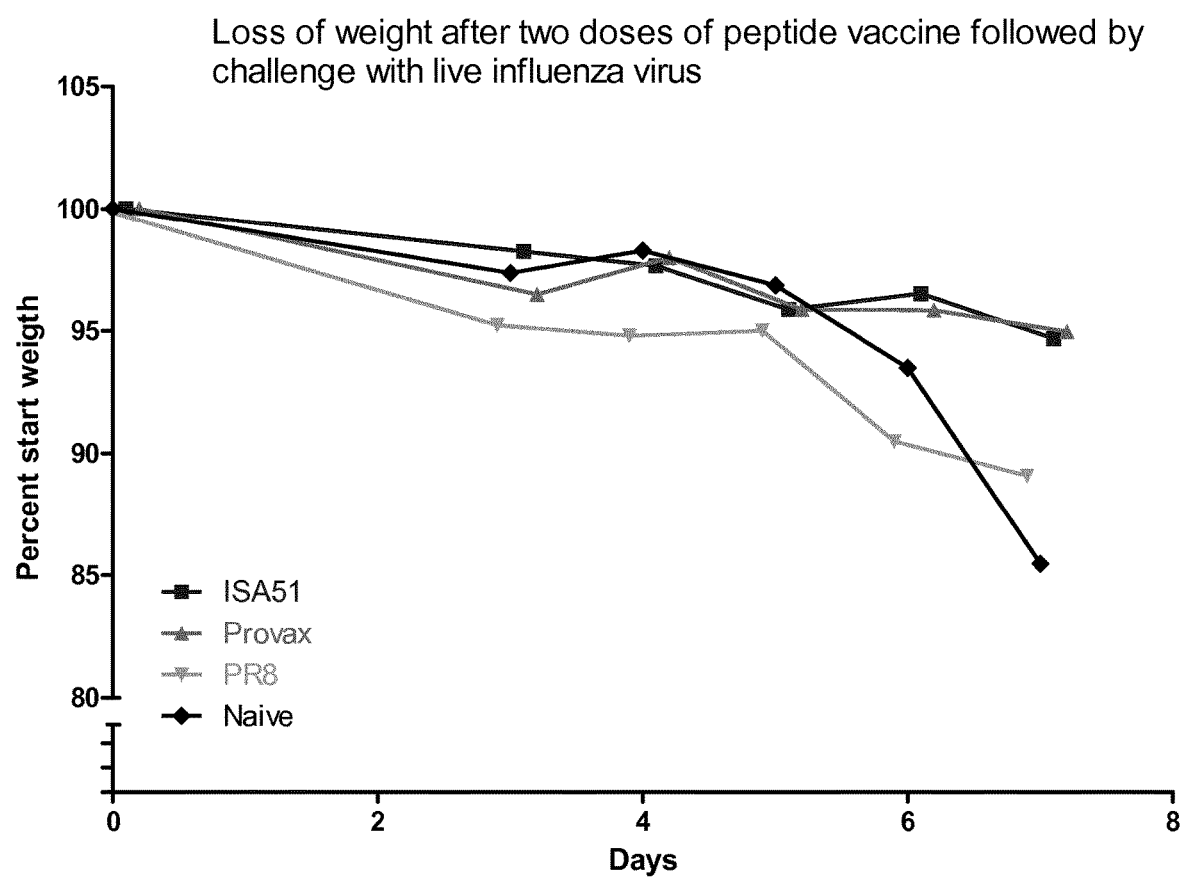

FIG. 5. Median loss of weight by treatment group after challenge. The median weight by treatment groups; ISA5: peptides and ISA51, Provax: peptides and Provax, PR8: inactivated influenza A/PR8 (H1N1) virus, Naïve: no treatment before challenge. For animals lost to humane endpoints a last observation carried forward method was employed for the weights

DETAILED DISCLOSURE OF THE INVENTION

Definitions

When terms such as "one", "a" or "an" are used in this disclosure they mean "at least one", or "one or more" unless otherwise indicated. Further, the term "comprising" is intended to mean "including" and thus allows for the presence of other constituents, features, conditions, or steps than those explicitly recited.

As used herein a "multimeric peptide" or "oligomeric peptide" refers to an assembly of two or more different or identical linear peptide sequences or subunits, preferably interconnected or assembled by one or more chemical bond of a linker. Preferably the peptide sequences are interconnected by one or more, such as one covalent bond, such as an intermolecular disulfide (S—S) bond between two Cys residues, a methylated peptide bond between a N-ε-methylated Lys side-chain and the side-chain of an Asp or Glu residue, an oxime bond, a thioether bond, or a non-covalent bond, such as in a π-stacking of rings wherein a W residue in $Z^2$ of the first $Z^1$-$Z^2$ peptide repeat is linked to an Y residue in $Z^2$ of the second $Z^1$-$Z^2$ peptide repeat. The term includes a dimeric (or dimer) peptide suitably formed by a chemical linking of two linear peptide sequences. The term "multimeric peptide" further includes an assembly of 2, 3, 4, 5, 6, 7, 8, 9 or 10 different or identical peptide sequences. In some embodiments, the multimeric peptide is a dimeric peptide.

As used herein a "linker" refers to any compound suitable for assembly of the two or more different or identical linear peptide sequences or subunits into a multimeric peptide, or to any other therapeutically active compound, such as an immunomodulating compound. The term includes any linker found useful in peptide chemistry. Since the multimeric peptide may be assembled or connected by standard peptide bonds in a linear way, the term linker also includes a "peptide spacer", also referred to as a "spacer".

In some embodiments, the linker is not a peptide sequence. In some embodiments, the linker is not a branched peptide sequence.

In some embodiments, the linker does not itself contain a peptide sequence derived from or identical to a natural antigen.

In some embodiments, the linker has a molecular weight of less than 10 kDa, such as less than 9 kDa, such as less than 8 kDa, such as less than 7 kDa, such as less than 6 kDa, such as less than 5 kDa, such as less than 4 kDa, such as less than 3 kDa, such as less than 2 kDa, such as less than 1.5 kDa, such as less than 1 kDa, such as less than 0.5 kDa, such as less than 0.2 kDa. In some embodiments, wherein the multimeric peptide is a dimeric peptide, the linker is not linking the two peptide sequences from one terminal cysteine in the first peptide to a second terminal cysteine in the second peptide.

In some embodiments, the linker is not linking the two or more peptide sequences through a terminal cysteine in any one of the peptides.

In some embodiments, the linker is not linking from a cysteine residue.

"HIV" generally denotes human immunodeficiency virus I.

"HIV disease" is composed of several stages including the acute HIV infection which often manifests itself as an influenza-like infection and the early and medium stage symptomatic disease, which has several non-characteristic symptoms such as skin rashes, fatigue, night sweats, slight weight loss, mouth ulcers, and fungal skin and nail infections. Most HIV infected will experience mild symptoms such as these before developing more serious illnesses. It is generally believed that it takes five to seven years for the first mild symptoms to appear. As HIV disease progresses, some individuals may become quite ill even if they have not yet been diagnosed with AIDS (see below), the late stage of HIV disease. Typical problems include chronic oral or vaginal thrush (a fungal rash or spots), recurrent herpes blisters on the mouth (cold sores) or genitals, ongoing fevers, persistent diarrhea, and significant weight loss. "AIDS" is the late stage HIV disease and is a condition which progressively reduces the effectiveness of the immune system and leaves individuals susceptible to opportunistic infections and tumors.

The term "cell-penetrating peptide" as used herein refers to any peptide with the capability to translocate across the plasma membrane into either cytoplasmic and/or nuclear compartments of eukaryotic and/or prokaryotic cells, such as into cytoplasm, nucleus, lysosome, endoplasmatic reticulum, golgi apparatus, mitocondria and/or chloroplast, seemingly energy-independently. This capability to translocate across the plasma membrane of a "cell-penetrating peptide" according to the invention may be non-invasive, energy-independent, non-saturable, and/or receptor independent. In one embodiment the term "cell-penetrating peptide" refers to a peptide, which is demonstrated to translocate across a plasma membrane as determined by the assay in example 5. It is to be understood that a cell-penetrating peptide according to the present invention may be translocated across the membrane with the sequence complete and intact, or alternatively partly degraded, but in a form where the antigens contained within this peptide is able to be presented within the cell to stimulate an immune response. Accordingly, a cell-penetrating peptide according to the present invention is a peptide that may be demonstrated to translocate across a plasma membrane as determined by the assay in example 5 and be demonstrated to stimulate an effective immune response.

The monomeric peptide according to the present invention may be provided in any pharmaceutically acceptable salt, such as in a salt of acetat or HCl.

The term "derived from an antigen" when in reference to a peptide derived from a source (such as a virus etc.) as used herein is intended to refer to a peptide which has been obtained (e.g., isolated, purified, etc.) from the source. Preferably, the peptide may be genetically engineered and/or chemically synthesized to be essentially identical to the native peptide of the source. The term includes the use of variants of known native peptide sequences, such as peptide sequences, where 1, 2, 3, 4, 5, 6, 7, 8, 9, or 10 amino acids of the native peptide sequence have been substituted with any other amino acid, such as conservative substitutions. Alternatively, 1, 2, 3, 4, 5, 6, 7, 8, 9, or 10 amino acids have been removed or added to the native peptide sequence. Accordingly, in some embodiments, the peptides according to the present invention comprises an amino acid sequence $Z^3$, and optional $Z^6$, $Z^9$ and $Z^{12}$, that is defined as a sequence of 8-30 amino acids, such as 8-20 amino acids derived from an antigen, wherein the peptide sequence of the antigen comprises 1, 2, 3, 4, 5, 6, 7, 8, 9, or 10 substitutions, additions or deletions relative to the antigen, such as the addition of an arginine in the N- or C-terminal of the amino acid sequence of $Z^3$, and optional $Z^6$, $Z^9$ and $Z^{12}$. In some embodiments, the peptides according to the present invention comprises an amino acid sequence $Z^3$, and optional $Z^6$, $Z^9$ and $Z^{12}$, that is defined as a sequence of 8-30 amino acids, such as 8-20 amino acids identical in sequence to a native antigen. In some embodiments, the peptides according to the present invention comprises an amino acid sequence $Z^3$, and optional $Z^6$, $Z^9$ and $Z^{12}$, that is defined as a sequence of 8-30 amino acids, such as 8-20 amino acids that is not identical in sequence to a native antigen.

It is to be understood that "derived from an antigen" does not exclude that an amino acid sequence defined by $Z^3$, and optional $Z^6$, $Z^9$ and $Z^{12}$ may be derived from more than one antigenic peptide sequence, such as from two or three different proteins or peptide sources or different sequences within the same proteins or peptide of the same virus, any different virus, or any disease antigen. However, in one embodiment $Z^3$, and optional $Z^6$, $Z^9$ and $Z^{12}$ are derived from one specific continuous peptide sequence. In one embodiment $Z^3$, and optional $Z^6$, $Z^9$ and $Z^{12}$ are derived from two different specific continuous peptide sequences of the same or different protein derived from the same virus, any different virus, or any disease antigen.

The amino acids used in the amino acid sequences according to the invention may be in both L- and/or D-form. It is to be understood that both L- and D-forms may be used for different amino acids within the same peptide sequence. In some embodiments the amino acids within the peptide sequence are in L-form, such as natural amino acids. It is to be understood that any known antigen may be used in the constructs according to the present invention.

In some specific embodiments, the first 1, 2, or 3 amino acids in the N-terminal of the amino acid sequences according to the invention are in the D-form. It is assumed that the N-terminal trimming and thereby degradation of the peptides are somewhat delayed by having amino acids of the D-form in the N-terminal of these peptides according to the present invention. Alternatively and in some embodiments, the first 1, 2, or 3 amino acids in the N-terminal of the amino acid sequences according to the invention are amino acids in beta or gamma forms. Beta amino acids have their amino group bonded to the beta carbon rather than the alpha carbon as in the 20 standard natural amino acids.

Alternatively the first 1, 2, or 3 amino acids in the N-terminal of the amino acid sequences according to the invention may be modified by incorporation of fluorine, or alternatively cyclic amino acids or other suitable non-natural amino acids are used.

A "variant" or "analogue" of a peptide refers to a peptide having an amino acid sequence that is substantially identical to a reference peptide, typically a native or "parent" polypeptide. The peptide variant may possess one or more amino acid substitutions, deletions, and/or insertions at certain positions within the native amino acid sequence.

"Conservative" amino acid substitutions are those in which an amino acid residue is replaced with an amino acid residue having a side chain with similar physicochemical properties. Families of amino acid residues having similar side chains are known in the art, and include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). A particular form of conservative amino acid substitutions include those with amino acids, which are not among the normal 20 amino acids encoded by the genetic code. Since preferred embodiments of the present invention entail use of synthetic peptides, it is unproblematic to provide such "non-naturally occurring" amino acid residues in the peptides disclosed herein, and thereby it is possible to exchange the natural saturated carbon chains in the side chains of amino acid residues with shorter or longer saturated carbon chains—for instance, lysine may be substituted with an amino acid having an the side chain —$(CH_2)_nNH_3$, where n is different from 4, and arginine may be substituted with an amino acid having the side chain —$(CH_2)_nNHC(=NH_2)NH_2$, where n is different from 3, etc. Similarly, the acidic amino acids aspartic acid and glutamic acid may be substituted with amino acid residues having the side chains —$(CH_2)_nCOOH$, where n>2.

The term "substantially identical" in the context of two amino acid sequences means that the sequences, when optimally aligned, such as by the programs GAP or BEST-FIT using default gap weights, share at least about 50, at least about 60, at least about 70, at least about 80, at least about 90, at least about 95, at least about 98, or at least about 99 percent sequence identity. In one embodiment, residue positions that are not identical differ by conservative amino acid substitutions. Sequence identity is typically measured using sequence analysis software. Protein analysis software matches similar sequences using measures of similarity assigned to various substitutions, deletions and other modifications, including conservative amino acid substitutions. For instance, the publicly available GCG software contains programs such as "Gap" and "BestFit" which can be used with default parameters to determine sequence homology or sequence identity between closely related polypeptides, such as homologous polypeptides from different species of organisms or between a wild-type protein and a mutein thereof. See, e.g., GCG Version 6.1. Polypeptide sequences can also be compared using FASTA or ClustalW, applying default or recommended parameters. A program in GCG Version 6.1., FASTA (e.g., FASTA2 and FASTA3) provides alignments and percent sequence identity of the regions of the best overlap between the query and search sequences (Pearson, Methods Enzymol. 1990; 183:63-98; Pearson, Methods Mol. Biol. 2000; 132:185-219). Another preferred algorithm when comparing a sequence to a database containing a large number of sequences from various organisms, or when deducing the is the computer program BLAST, especially blastp, using default parameters. See, e.g., Altschul et al., J. Mol. Biol. 1990; 215:403-410; Altschul et al., Nucleic Acids Res. 1997; 25:3389-402 (1997); each herein incorporated by reference. "Corresponding" amino acid positions in two substantially identical amino acid sequences are those aligned by any of the protein analysis software mentioned herein, typically using default parameters.

An "isolated" molecule is a molecule that is the predominant species in the composition wherein it is found with respect to the class of molecules to which it belongs (i.e., it makes up at least about 50% of the type of molecule in the composition and typically will make up at least about 70%, at least about 80%, at least about 85%, at least about 90%, at least about 95%, or more of the species of molecule, e.g., peptide, in the composition). Commonly, a composition of a peptide molecule will exhibit 98%-99% homogeneity for peptide molecules in the context of all present peptide species in the composition or at least with respect to substantially active peptide species in the context of proposed use.

The term "linear sequence" as used herein refers to the specific sequence of amino acids connected by standard peptide bonds in standard N- to C-terminal direction. The peptide may contain only peptide bonds. However the term does not exclude that an amino acid within a sequence, such as within $Z^3$, may be connected, such as through the side chains, with another amino acid at a distant location within the peptide sequence, such as a distant location within $Z^3$.

In the context of the present invention, "treatment" or "treating" refers to preventing, alleviating, managing, curing or reducing one or more symptoms or clinically relevant manifestations of a disease or disorder, unless contradicted by context. For example, "treatment" of a patient in whom no symptoms or clinically relevant manifestations of a disease or disorder have been identified is preventive or prophylactic therapy, whereas "treatment" of a patient in whom symptoms or clinically relevant manifestations of a disease or disorder have been identified generally does not constitute preventive or prophylactic therapy.

The term "antigen" denotes a substance of matter which is recognized by the immune system's specifically recognizing components (antibodies, T-cells).

The term "immunogen" is in the present context intended to denote a substance of matter, which is capable of inducing an adaptive immune response in an individual, where said adaptive immune response targets the immunogen. In relation to the present invention, an immunogen will induce a humoral and/or cell-mediated immune response. In other words, an immunogen is an antigen, which is capable of inducing immunity.

The terms "epitope", "antigenic determinant" and "antigenic site" are used interchangeably herein and denotes the region in an antigen or immunogen which is recognized by antibodies (in the case of antibody binding epitopes, also known as "B-cell epitopes") or by T-cell receptors when the epitope is complexed to a Major histocompatibility complex (MHC) molecule (in the case of T-cell receptor binding epitopes, i.e. "T-cell epitopes").

"B cell antigen" means any antigen that naturally is or could be engineered to be recognized by a B cell, and that triggers an immune response in a B cell (e.g., an antigen that is specifically recognized by a B cell receptor on a B cell).

The term "immunogenically effective amount" has its usual meaning in the art, i.e. an amount of an immunogen, which is capable of inducing an immune response, which significantly engages pathogenic agents, which share immunological features with the immunogen.

The term "vaccine" is used for a composition comprising an immunogen and which is capable of inducing an immune response which is either capable of reducing the risk of developing a pathological condition or capable of inducing a therapeutically effective immune response which may aid in the cure of (or at least alleviate the symptoms of) a pathological condition.

The term "pharmaceutically acceptable" has its usual meaning in the art, i.e. it is used for a substance that can be accepted as part of a medicament for human use when treating the disease in question and thus the term effectively excludes the use of highly toxic substances that would worsen rather than improve the treated subject's condition.

A "T helper lymphocyte epitope" (a $T_H$ epitope) is peptide, which binds an MHC Class II molecule and can be presented on the surface of an antigen presenting cell (APC) bound to the MHC Class II molecule. An "immunological carrier" is generally a substance of matter which includes one or many $T_H$ epitopes, and which increase the immune response against an antigen to which it is coupled by ensuring that T-helper lymphocytes are activated and proliferate. Examples of known immunological carriers are the tetanus and diphtheria toxoids and keyhole limpet hemocyanin (KLH).

In the scaffold design according to the present invention, $Z^3$, and optional $Z^6$, $Z^9$ and $Z^{12}$ may define a sequence of amino acids, such as 8-30 amino acids, such as 8-20 amino acids derived from the antigen. This sequence of amino acids derived from an antigen may herein be referred to as an epitope.

The peptides according to the present invention may be a helper T lymphocyte (HTL) inducing peptide comprising HTL epitopes. A "HTL inducing peptide" is a HLA Class II binding peptide that is capable of inducing a HTL response. Also the peptides according to the present invention may in other embodiments be CTL inducing peptides comprising CTL epitopes in addition to or as an alternative to being a HTL inducing peptide. A "CTL inducing peptide" is a HLA Class I binding peptide that is capable of inducing a CTL response.

In some embodiments the epitopes used in the scaffold according to the present invention are CTL epitopes. A "CTL inducing peptide" is a HLA Class I binding peptide that is capable of inducing a CTL response. In other embodiments the epitopes used in the scaffold design according to the present invention are HTL inducing peptides. A "HTL inducing peptide" is a HLA Class II binding peptide that is capable of inducing a HTL response.

In other alternative embodiments, tryptophan or tryptophan derivatives are used in the sequence defined by $Z^2$, $Z^5$, $Z^8$ and $Z^{11}$. Any suitable tryptophan derivatives may be used. As used herein "tryptophan derivatives" means an unnatural modified tryptophan amino acid residue including those disclosed in U.S. Pat. No. 7,232,803, such as tri tert.-butyltryptophan, di-tert-butyl tryptophan, 7-benzyloxytryptophan, homotryptophan, 5'-aminoethyltryptophan (available as side chain Boc and N-alpha FMOC derivative from RSP Amino Acids Analogues Inc, Boston, Mass., USA), N-Acetylhomotryptophan (Toronto Research), 7-Benzyloxytryptophan (Toronto Research), Homotryptophan (Toronto Research), and tryptophan residues which have been substituted at the 1-, 2-, 5- and/or 7-position of the indole ring, positions 1- or 2- being preferred e.g. 5' hydroxy tryptophan.

The term "amino acid derivative", sometimes used in the context of a "derivative thereof" referring to a specific amino acid, means an amino acid compound, wherein one or more chemical groups has been modified, added or removed as compared to the amino acid to which the amino acid compound is a derivative of, while still having an amine group and a carboxylic acid group, as well as a side chain of an amino acid and still being able to form peptide bonds. In some embodiments an amino acid derivative is a standard amino acid that has only been modified in the side chain of the amino acid. In some embodiments an amino acid derivative is a non-natural amino acid such as Dpr. In some embodiments an amino acid is a modified moiety which is incorporated into the chemically synthesized peptide or polypeptide and that comprises an activatable group that is linkable, after activation, to another peptide, such as Dpr (Ser), Lys(Ser), or Ornithine(Ser).

The term "basic amino acid" as used herein refers to any amino acid including both natural and non-natural amino acids that has an isoelectric point above 6.3 (such as above 7.4) as measured according to Kice & Marvell "Modern Principles of organic Chemistry" (Macmillan, 1974) or Matthews and van Holde "Biochemistry" Cummings Publishing Company, 1996. Included within this definition are Arginine, Lysine, Homoarginine (Har), and Histidine as well as derivatives thereof. Suitable non-natural basic amino acids are e.g. as described in U.S. Pat. No. 6,858,396. Suitable positively charged amino acids includes non-natural alpha amino acids available from Bachem AG and includes alpha-amino-glycine, alpha,gamma-diaminobutyric acid, ornithine, alpha, beta-diaminoproprionic acid, alpha-difluoromethyl-ornithine, 4-amino-piperidine-4-carboxylic acid, 2,6-diamino-4-hexynoic acid, beta-(1-piperazinyl)-alanine, 4,5-dehydro-lysine, delta-hydroxy-lysine, omega-hydroxy-norarginine, homoarginine, omega-amino-arginine, omega-methyl-arginine, alpha-methyl-histidine, 2,5-diiodo-histidine, 1-methyl-histidine, 3-methyl-histidine, beta-(2-pyridyl)-alanine, beta-(3-pyridyl)-alanine, beta-(2-quinolyl)-alanine, 3-amino-tyrosine, 4-amino-phenylalanine, and spinacine. Furthermore, any mono or dicarboxylic amino acid is a suitable positively charged amino acid.

The term "neutral amino acid" as used herein refers to an amino acid that has an isoelectric point above between 4.8 and 6.3 as measured according to Kice & Marvell "Modern Principles of organic Chemistry" (Macmillan, 1974). The term "acidic amino acid" as used herein refers to an amino acid that has an isoelectric point below 4.8 as measured according to Kice & Marvell "Modern Principles of organic Chemistry" (Macmillan, 1974).

Unless otherwise indicated amino acids are abbreviated and mentioned by their standard nomenclature known to the person skilled in the art, such as with reference to "nomenclature and symbolism for amino acids and peptides" by the international union of pure and applied chemistry (IUPAC) (www.iupac.org).

The term "antibody response" refers to the production of antibodies (e.g., IgM, IgA, IgG) which bind to an antigen of interest, this response is measured for instance by assaying sera by antigen ELISA.

The term "adjuvant" as used herein refers to any compound which, when delivered together or simultaneously with an antigen, non-specifically enhances the immune response to that antigen. Exemplary adjuvants include but are not limited to oil in water and water in oil adjuvants, aluminum-based adjuvants (e.g., AlOH, AlPO4, etc), and Montanide ISA 720.

The terms "patient" and "subject" refer to a mammal that may be treated using the methods of the present invention.

As used herein, the term "immune response" refers to the reactivity of an organism's immune system in response to an antigen. In vertebrates, this may involve antibody production, induction of cell-mediated immunity, and/or complement activation (e.g., phenomena associated with the vertebrate immune system's prevention and resolution of infection by microorganisms). In preferred embodiments, the term immune response encompasses but is not limited to one or more of a "lymphocyte proliferative response," a "cytokine response," and an "antibody response."

The term "net charge" as used herein with reference to a peptide sequence refers to the total electric charge of the peptide sequence represented by the sum of charges of each individual amino acid in the peptide sequence, wherein each basic amino acid are given a charge of +1, each acidic amino acid a charge of −1, and each neutral amino acid a charge of 0. Accordingly, the net charge will depend on the number and identities of charged amino acids.

Table 1—Specific peptides not part of the present invention

Table 1 and 2 represent peptides not part of the present invention comprising the structure $X^1$-$X^2$-$X^3$-$X^4$-$X^5$ (formula II), wherein $X^1$ and $X^3$ independently defines a linear sequence of any 1, 2, 3 or 4 amino acid independently selected from any basic amino acid, citrulline, tryptophan, or a derivative thereof; $X^2$ defines a linear sequence of 8-30 amino acids derived from an antigen; $X^4$ defines a linear sequence of 8-30 amino acids derived from said antigen, said sequence $X^4$ being different from $X^2$; and wherein $X^5$ is any one optional amino acid selected from a basic amino acid, citrulline, tryptophan, or a derivative thereof. Citrulline is in this document referred to with the one-letter symbol "B".

TABLE 1

| | | | | | | | Placement with reference to positions in SEQ ID NO: 3; SEQ ID NO: 6; SEQ ID NO: 7, SEQ ID NO: 11, SEQ ID NO: 12, SEQ ID NO: 46, and SEQ ID NO: 126. | |
|---|---|---|---|---|---|---|---|---|
| Antigen | Reference ID | x1 | x2 | x3 | x4 | x5 | Modified (m) | X2-seq | x4-seq |
| | P-biotin | R | QIKIWFQN SEQ ID NO: 483 | RR | MKWKK SEQ ID NO: 484 | | | |
| | N-Biotin | | PVVHLTL SEQ ID NO: 485 | R | QAGDDFSR SEQ ID NO: 486 | | | |
| HCV | SP_2 | RR | GYIPLVGAPLG | BGR | VARALAHGVRV | | | 135-145 | 147-157 |
| HCV | SP_3 | R | GYIPLVGAPLG | RR | VARALAHGVRV | | | 135-145 | 147-157 |
| HCV | SP_4 | R | GYIPLVGAPLG | RRR | VARALAHGVRV | R | | 135-145 | 147-157 |
| HCV | SP_5 | RR | GYIPLVGAPLG | RR | VARALAHGVRV | | | 135-145 | 147-157 |
| HCV | SP_6 | RR | GYIPLVGAPLG | RRR | VARALAHGVRV | | | 135-145 | 147-157 |
| HCV | SP_7 | BR | GYIPLVGAPLG | RR | VARALAHGVRV | | | 135-145 | 147-157 |
| HCV | SP_8 | RRR | GYIPLVGAPLG | BR | VARALAHGVRV | | | 135-145 | 147-157 |
| HCV | SP_9 | R | GYIPLVGAPLG | KKK | VARALAHGVRV | | | 135-145 | 147-157 |
| HCV | SP_10 | R | GYIPLVGAPLG | RRR | VARALAHGVRV | | | 135-145 | 147-157 |
| HCV | SP_11 | KK | GYIPLVGAPLG | KK | VARALAHGVRV | | | 135-145 | 147-157 |
| HCV | SP_12 | W | GYIPLVGAPLG | RR | VARALAHGVRV | | | 135-145 | 147-157 |
| HCV | SP_13 | WW | GYIPLVGAPLG | RR | VARALAHGVRV | | | 135-145 | 147-157 |
| HCV | SP_14 | EE | GYIPLVGAPLG | EE | VARALAHGVRV | | | 135-145 | 147-157 |
| HCV | SP_15 | GG | GYIPLVGAPLG | GG | VARALAHGVRV | | | 135-145 | 147-157 |
| HCV | SP_16 | EE | GYIPLVGAPLG | RR | VARALAHGVRV | | | 135-145 | 147-157 |
| HCV | SP_17 | RR | GYIPLVGAPLG | LRR | VARALAHGVRV | | | 135-145 | 147-157 |
| HCV | SP21: | WW | GYIPLVGAPLG | RR | VARALAHGVRV | | | 135-145 | 147-157 |
| HCV | SP22: | WW | GYIPLVGAPLG | RRR | VARALAHGVRV | | | 135-145 | 147-157 |
| HCV | SP23: | WW | GYIPLVGAPLG | R | VARALAHGVRV | | | 135-145 | 147-157 |

TABLE 1-continued

Placement with reference to positions in SEQ ID NO: 3; SEQ ID NO: 6; SEQ ID NO: 7, SEQ ID NO: 11, SEQ ID NO: 12, SEQ ID NO: 46, and SEQ ID NO: 126.

| Antigen | Reference ID | x1 | x2 | x3 | x4 | x5 | Modified (m) | X2-seq | x4-seq |
|---|---|---|---|---|---|---|---|---|---|
| HCV | SP24: | R | GYIPLVGAPLG | RR | VARALAHGVRV | | | 135-145 | 147-157 |
| HCV | 51_Biotin | RR | GYLPAVGAPIG | BR | VIRVIAHGLRL | | m | 135-144 | 147-157 |
| HCV | 51b_Biotin | RR | GYIPLVGAPLG | BR | VARALAHGVRV | | | 135-145 | 147-157 |
| HCV | 51_n | | GYIPLVGAPLG | G | VARALAHGVRV | | | 135-145 | 147-157 |
| HCV | SP51_1: | WW | GYLPAVGAPI | RR | VIRVIAHGLRL | | m | 135-144 | 147-157 |
| HCV | SP1_C* | | GYIPLVGAPLG | G | VARALAHGVRV | | | 135-145 | 147-157 |
| HCV | SP2_c | RR | GYIPLVGAPLG | BGR | VARALAHGVRV | | | 135-145 | 147-157 |
| HCV | SP3_c | R | GYIPLVGAPLG | RR | VARALAHGVRV | | | 135-145 | 147-157 |
| HCV | SP4_c | R | GYIPLVGAPLG | RRR | VARALAHGVRV | | | 135-145 | 147-157 |
| HCV | SP5_c | RR | GYIPLVGAPLG | RR | VARALAHGVRV | | | 135-145 | 147-157 |
| HCV | SP6_c | RR | GYIPLVGAPLG | RRR | VARALAHGVRV | | | 135-145 | 147-157 |
| HCV | SP7_c | BR | GYIPLVGAPLG | RR | VARALAHGVRV | | | 135-145 | 147-157 |
| HCV | SP8_c | RRR | GYIPLVGAPLG | BR | VARALAHGVRV | | | 135-145 | 147-157 |
| HCV | SP9_c | R | GYIPLVGAPLG | KKK | VARALAHGVRV | | | 135-145 | 147-157 |
| HCV | SP10_c | R | GYIPLVGAPLG | RRR | VARALAHGVRV | | | 135-145 | 147-157 |
| HCV | SP11_c | KK | GYIPLVGAPLG | KK | VARALAHGVRV | | | 135-145 | 147-157 |
| HCV | SP12_c | W | GYIPLVGAPLG | RR | VARALAHGVRV | | | 135-145 | 147-157 |
| HCV | SP13_c | WW | GYIPLVGAPLG | RR | VARALAHGVRV | | | 135-145 | 147-157 |
| HCV | SP17_c | RR | GYIPLVGAPLG | LRR | VARALAHGVRV | | | 135-145 | 147-157 |
| HCV | SP61_2_ | RR | NYVTGNIPG | BR | GITFSIFLIVS | | | 163-171 | 171-181 |

TABLE 1-continued

Placement with reference to positions in SEQ ID NO: 3; SEQ ID NO: 6; SEQ ID NO: 7, SEQ ID NO: 11, SEQ ID NO: 12, SEQ ID NO: 46, and SEQ ID NO: 126.

| Antigen | Reference ID | x1 | x2 | x3 | x4 | x5 | Modified (m) | X2-seq | x4-seq |
|---|---|---|---|---|---|---|---|---|---|
| HCV | SP61b_2_ | WW | NYATGNLPG | RR | CSFSIFLLAL | | m | 163-171 | 171-181 |
| HCV | SP61_3_ | WW | NYVTGNIPG | BR | GITFSIFLIVS | | | 163-171 | 171-181 |
| HCV | SP61_4_ | WW | NYVTGNIPG | RR | GITFSIFLIVS | | | 163-171 | 171-181 |
| HCV | 61b_BIotin | RR | NYATGNLPG | RR | GCSFSIFLLAL | | | 163-171 | 171-181 |
| HCV | SP25 | RR | VTGNIPGSTYS | GBR | GITFSIYLIVS | | m | 165-175 | 171-181 |
| HCV | 42_BIotin | RR | IRNLGRVIETLTG | BR | LNleGYIPLIGA | | m | 116-128 | 133-142 |
| HCV | 42b_BIotin | RR | SRNLGKVIDTLTC | BR | LMGYIPLVGA | | | 116-128 | 133-142 |
| HCV | 42n-BIOTIN | | SRNLGKVIDTLTC | GFAD | LMGYIPLVGA | | | 116-129 | 133-142 |
| HCV | SP42_1_ | WW | IRNLGRVIETLT | RR | LNleGYIPLIGA | | m | 116-128 | 133-142 |
| HCV | SP42b_1_ | WW | SRNLGKVIDTLTC | RR | LMGYIPLVGA | | | 116-129 | 133-142 |
| HCV | BI310-11_Biotin | RR | GGGQIIGGNYLIP | RB | PBIGVRATB | | | 26-38 | 42-50 |
| HCV | BI310-11n_Biotin | | GGGQIVGGVYLLP | RR | GPRLGVRATR | | | 26-38 | 42-50 |
| HCV | BI310-11n_sc_Biotin | RR | GGGQIVGGVYLLP | RR | GPRLGVRATR | | | 26-38 | 42-50 |
| HCV | SP11b-1- | WW | GGGQIVGGVYLLP | RR | GPRLGVRAT | | | 26-38 | 42-50 |
| FLU | BI100-12 | BR | LIFLARSALIV | | RGSVAHKS | | | 256-266 | 267-274 |
| FLU | BI100-22b | ED | LIFLARSALIL | | RGSVAHKS | | | 255-266 | 267-274 |
| FLU | 120b_BIotin | BR | LIFLARSALIL | BGR | SALILRGSVAHK | | | 255-266 | 267-274 |
| FLU | BI100-18b | | SAYERMCNIL | KGK | FQTAAQRAMM | | | 217-226 | 230-239 |
| FLU | BI100-19 | | SAYERNleVNIL | KGK | FQTAAQRAVNle | | | 217-226 | 230-239 |

TABLE 1-continued

| Antigen | Reference ID | x1 | x2 | x3 | x4 | x5 | Modified (m) | X2-seq | x4-seq |
|---|---|---|---|---|---|---|---|---|---|
| | | | | | | | | Placement with reference to positions in SEQ ID NO: 3; SEQ ID NO: 6; SEQ ID NO: 7, SEQ ID NO: 11, SEQ ID NO: 12, SEQ ID NO: 46, and SEQ ID NO: 126. | |
| FLU | 190_BIotin | BR | TAYERNleCNIL | BRGR | FQTVVQBA | | | 217-226 | 230-237 |
| FLU | 190b_BIotin | BR | IAYERMCNIL | LBRGK | FQTAAQRA | | | 217-226 | 230-237 |
| FLU | 190n-BIOTIN | | IAYERMCNIL | KGK | FQTAAQRA | | | 217-226 | 230-237 |
| FLU | BI100-24b | | LFFKCIYRLFKHGL | KR | GPSTEGVPESM | | | 46-59 | 62-72 |
| FLU | BI100-26 | BRR | LFFKTITRLFBHGL | RR | LLSTEGVPNSNle | | | 46-59 | 62-72 |
| FLU | 260_Biotin | BR | GLEPLVIAGILA | RR | GSLVGLLHIVL | | | 23-33 | 30-40 |
| FLU | 260b_Biotin | BR | GSDPLVVAASIV | RR | ASIVGILHLIL | | | 23-33 | 30-40 |
| CMV | BI 050-sc1 | R | NLVPMVATV | RR | NLVPMVATV | B | | 485-493 | 485-493 |
| CMV | BI 050-sc2 | R | NLVPMVATV | BRR | NLVPMVATV | B | | 485-493 | 485-493 |
| CMV | BI 050-sc5 | R | NIVPNleVVTA | RR | NIVPNleVVTA | B | m | 485-493 | 485-493 |
| HIV | N10 | | PEVIPMFSALS | EGA | TPQDLNTMLN | | | | |
| HIV | V10 | R | FIIPXFTALSG | GRR | ALLYGATPYAIG | | | | |
| HIV | N13 | K | ALGPAATL | EE | MMTACQGVG | | | | |
| Neg c mod | SP_18 | RR | GPVVHLTL | RRR | GQAGDDFS | | | | |
| Neg c mod | SP_19 | RR | GPVVHLTL | RRR | GQAGDDFS | | | | |
| Neg c mod | SP_20 | RR | GPVVHLTL | RGRR | GQAGDDFS | | | | |
| HPV | | RR | LECVYCKQQLL | RR | EVYDFAFRDLC | | | 35-45 | 48-58 |
| HPV | | RR | GVYDFAFRDLC | RR | GFAFRDLCIVY | R | | 49-58 | 52-61 |
| HPV | | RR | GVFDYAFRDIN | RR | GFAYRDINLAY | R | | 49-58 | 52-61 |

TABLE 1-continued

| Antigen | Reference ID | x1 | x2 | x3 | x4 | x5 | Modified (m) | X2-seq Placement with reference to positions in SEQ ID NO: 3; SEQ ID NO: 6; SEQ ID NO: 7, SEQ ID NO: 11, SEQ ID NO: 12, SEQ ID NO: 46, and SEQ ID NO: 126. | x4-seq |
|---|---|---|---|---|---|---|---|---|---|
| CMV | | RR | GATPVDLLGA | RR | GALNLCLPM | R | | 498-506 | 505-514 |
| CMV | | RR | GVTPAGLIGV | RR | GALQIBLPL | R | | 498-506 | 505-514 |
| HPV | | RR | VDIRTLEDLL | RR | GTLGIVCPIG | R | | 74-83 | 84-93 |

As used herein the one-letter-code 'Nle' refers to the non-natural amino acid norleucine.

TABLE 2

Specific peptides not part of the present invention

| Antigen | $X^1$ | $X^2$ | $X^3$ | $X^4$ | $X^5$ |
|---|---|---|---|---|---|
| HCV | R | GYIPLVGAPLG | RRR | VARALAHGVRV | R |
| HCV | R | GYLPAVGAPIG | RRR | VIRVIAHGLRL | R |
| HCV | RR | GYIPLVGAPLG | RR | VARALAHGVRV | |
| HCV | RR | GYIPLVGAPLG | RRR | VARALAHGVRV | |
| HCV | RR | SRNLGKVIDTLTC | RR | LMGYIPLVGA | |
| HCV | RR | GGGQIVGGVYLLP | RR | GPRLGVRATR | |
| HCV | W | GYIPLVGAPLG | RR | VARALAHGVRV | |
| HCV | RR | IRNLGRVIETLTLNleGYIPLIGA | RR | IRNLGRVIETLTLNleGYIPLIGA | R |
| Flu | BR | TAYERNleCNIL | BRGR | FQTVVQBA | |
| cmv | R | NLVPMVATV | BRR | NLVPMVATV | B |

As used herein the one-letter-code Z or 'Nle' refers to the non-natural amino acid norleucine.

Antigens

The specific natural antigen used in the peptide constructs according to the present invention may be a protein or peptide sequence derived from any B cell antigen, such as from any disease antigen, such as an infectious agent. Suitable antigens to be used according to the present invention include antigens derived from a bacteria, a mycobacterium, a virus, a parasite such as protozoa, a fungus, a cancer antigen, such as an oncogene, such as a thelomerase, a prion, an atopic disease antigen, an addictive or abused substance or a toxin or an antigen of an autoimmune disease, such as rheumatoid arthritis, insulin dependent diabetes, multiple sclerosis and the like.

As used herein a "disease antigen" refers to any antigen confirmed or suspected to be involved in a specific disease.

In some embodiments, the antigen is an abused or addictive substance or a portion thereof, including, but are not limited to, nicotine, a narcotic, a cough suppressant, a tranquilizer, and a sedative. In some embodiments, the antigen is a toxin, such as a toxin from a chemical weapon or natural sources, or a pollutant.

Examples of bacteria for which antigens may be provided include, but are not limited to, *M. tuberculosis, Mycobacterium, mycoplasma, neisseria* and *legionella*. Examples of parasites include, but are not limited to, *rickettsia* and *chlamydia*.

Examples of an infectious disease antigen is TbH9 (also known as Mtb 39A), a tuberculosis antigen. Other tuberculosis antigens include, but are not limited to DPV (also known as Mtb8.4), 381, Mtb41, Mtb40, Mtb32A, MA9.9A, Mtb9.8, Mtb16, Mtb72f, Mtb59f, Mtb88f, Mtb71f, Mtb46f and Mtb31f ("f" indicates that it is a fusion or two or more proteins).

Examples of cancer antigens may be a tumor associated antigen such as HER2, HER3 or HER4 receptor or one or more tumor-associated antigens or cell-surface receptors disclosed in US Publication No. 20080171040 or US Publication No. 20080305044 and are incorporated in their entirety by reference.

Other suitable cancer antigens that may be used by the present invention include CD proteins such as CD2, CD3, CD4, CD5, CD6, CD8, CD11, CD14, CD18, CD19, CD22, CD21, CD22, CD25, CD26, CD27, CD28, CD30, CD33, CD36, CD37, CD38, CD40, CD44, CD52, CD55, CD56, CD70, CD79, CD80, CD81, CD103, CD105, CD134, CD137, CD138, and CD152; members of the ErbB receptor family such as the EGF receptor, HER2, HER3 or HER4 receptor; cell adhesion molecules such as LFA-I, Mac1, pi 50.95, VLA-4, ICAM-1, VCAM, EpCAM, alpha4/beta7 integrin, and alpha v/beta3 integrin including either alpha or beta subunits thereof (e.g. anti-CD11a, anti-CD18 or anti-CD11b antibodies); growth factors such as VEGF; tissue factor (TF); TGF-$\beta$.; alpha interferon (alpha-IFN); an interleukin, such as IL-8; IgE; blood group antigens Apo2, death receptor; flk2/flt3 receptor; obesity (OB) receptor; mpl receptor; CTLA-4; protein C etc. In some embodiment the antigen is selected from IGF-IR, CanAg, EphA2, MUC1, MUC16, VEGF, TF, CD19, CD20, CD22, CD27, CD33, CD37, CD38, CD40, CD44, CD56, CD138, CA6, Her2/neu, EpCAM, CRIPTO (a protein produced at elevated levels in a majority of human breast cancer cells), darpins, alpha$_v$/beta$_3$ integrin, alpha$_v$/beta$_5$ integrin, alpha y/beta integrin, TGF-$\beta$, CD11a, CD18, Apo2 and C242. In some embodiment the antigen is selected from a CD proteins such as CD3, CD4, CD8, CD19, CD20, CD27, CD34, CD37, CD38, CD46, CD56, CD70 and CD138; members of the ErbB receptor family such as the EGF receptor, HER2, HER3 or HER4 receptor; cell adhesion molecules such as LFA-I, Mac1, p150.95, VLA-4, ICAM-1, VCAM, EpCAM, alpha4/beta7 integrin, and alpha v/beta3 integrin including either alpha or beta subunits thereof (e.g. anti-CD11a, anti-CD18 or anti-CD11b antibodies); growth factors such as VEGF; tissue factor (TF); TGF-$\beta$.; alpha interferon (alpha-IFN); an interleukin, such as IL-8; IgE; blood group antigens Apo2, death receptor; flk2/flt3 receptor; obesity (OB) receptor; mpl receptor; CTLA-4; protein C, etc. The most preferred targets herein are IGF-IR, CanAg, EGF-R, EGF-RvIII, EphA2, MUC1, MUC16, VEGF, TF, CD19, CD20, CD22, CD27, CD33, CD37, CD38, CD40, CD44, CD56, CD70, CD138, CA6, Her2/neu, CRIPTO (a protein produced at elevated levels in a majority of human breast cancer cells), alpha$_v$/beta$_3$ integrin, alpha$_v$/beta$_5$ integrin, TGF-$\beta$, CD11a, CD18, Apo2, EpCAM and C242. In some embodiment the antigen is selected from a cellular oncogene, such as ras or myc.

Examples of viral antigens for use with the present invention include, but are not limited to, e.g., HIV, HCV, CMV, HPV, Influenza, adenoviruses, retroviruses, picornaviruses, etc. Non-limiting example of retroviral antigens such as retroviral antigens from the human immunodeficiency virus (HIV) antigens such as gene products of the gag, pol, and env genes, the Nef protein, reverse transcriptase, and other HIV components; hepatitis viral antigens such as the S, M, and L proteins of hepatitis B virus, the pre-S antigen of hepatitis B virus, and other hepatitis, e.g., hepatitis A, B, and C, viral components such as hepatitis C viral RNA; influenza viral antigens such as hemagglutinin and neuraminidase and other influenza viral components; measles viral antigens such as the measles virus fusion protein and other measles virus components; rubella viral antigens such as proteins E1 and E2 and other rubella virus components; rotaviral antigens such as VP7sc and other rotaviral components; cytomegaloviral antigens such as envelope glycoprotein B and other cytomegaloviral antigen components; respiratory syncytial viral antigens such as the RSV fusion protein, the M2 protein and other respiratory syncytial viral antigen components; herpes simplex viral antigens such as immediate early proteins, glycoprotein D, and other herpes simplex viral antigen components; varicella zoster viral antigens such as gpl, gpll, and other varicella zoster viral antigen components; Japanese encephalitis viral antigens such as proteins E, M-E, M-E-NSI, NSI, NS1-NS2A, 80% E, and other Japanese encephalitis viral antigen components; rabies viral antigens such as rabies glycoprotein, rabies nucleoprotein and other rabies viral antigen components. See Fundamental Virology, Second Edition, eds. Fields, B. N. and Knipe, D. M. (Raven Press, New York, 1991) for additional examples of viral antigens.

The epitopes to be incorporated into the scaffold design according to the present invention may be derived from an adenovirus, retrovirus, picornavirus, herpesvirus, rotavirus, hantavirus, coronavirus, togavirus, flavirvirus, rhabdovirus, paramyxovirus, orthomyxovirus, bunyavirus, arenavirus, reovirus, papilomavirus, parvovirus, poxvirus, hepadnavirus, degngue virus, or spongiform virus. In certain specific, non-limiting examples, the viral antigen are peptides obtained from at least one of HIV, CMV, hepatitis A, B, and C, influenza, measles, polio, smallpox, rubella; respiratory syncytial, herpes simplex, varicella zoster, Epstein-Barr, Japanese encephalitis, rabies, Influenza, and/or cold viruses.

HCV:

Peptides according to the present invention may comprise a known antigen. For antigens derived from HCV these antigens may be derived from the Core, E1, E2, P7, NS2, NS3, NS4 (NS4A and NS4B) and NS5 (NS5A and NS5B) protein of the Hepatitis C Virus (HCV). The epitopes are those which elicit a HLA class I and/or class II restricted T lymphocyte response in an immunized host. More specific, the HLA class I restricted peptides of the present invention may bind to at least one HLA molecule of the following HLA class I groups: HLA-A*01, HLA-A*02, HLA-A*03, HLA-A*11, HLA-A*24, HLA-B*07, HLA-B*08, HLA-B*35, HLA-B*40, HLA-B*44, HLA-Cw3, HLA-Cw4, HLA-Cw6 or HLA-Cw7. The HLA class II restricted peptides of the present invention may bind to at least one HLA molecule of the following HLA class II groups: HLA-DRB1, -DRB2, -DRB3, -DRB4, -DRB5, -DRB6, -DRB7, -DRB8 or -DRB9.

MHC binding HCV peptides that may be used according to the present invention as epitopes are disclosed in e.g. WO02/34770 (Imperial College Innovations Ltd), WO01/21189 and WO02/20035 (Epimmune), WO04/024182 (Intercell), WO95/25122 (The Scripps Research Institute), WO95/27733 (Government of the USA, Department of Health and Human Services), EP 0935662 (Chiron), WO02/26785 (Immusystems GmbH), WO95/12677 (Innogenetics N.V), WO97/34621 (Cytel Corp), and EP 1652858 (Innogenetics N.V.).

In other embodiments, the scaffold design according to the present invention comprises a PADRE peptide, such as the universal T cell epitope called PADRE as disclosed in WO95/07707 (Epimmune) the content of which are enclosed herein by reference. A 'PanDR binding peptide or PADRE peptide" is a member of a family of molecules that binds more that one HLA class II DR molecule. PADRE binds to most HLA-DR molecules and stimulates in vitro and in vivo human helper T lymphocyte (HTL) responses. Alternatively T-help epitopes can be used from universally used vaccines such as tetanos toxoid.

In a further embodiment, the peptides in the composition or polyepitopic peptide are characterized in that they are derived from a HCV protein, or more specifically from at least one of the following HCV regions selected from the group consisting of Core, E1, E2/NS1, NS2, NS3, NS4A, NS4B, NS5A and NS5B. Even more preferred is that peptides are characterized in that they are present in the HCV consensus sequence of genotype 1a, 1b and/or 3 a.

Other HLA class I and II binding peptides that may be used according to the invention may be identified by the method as described in WO03/105058-Algonomics, by the method as described by Epimmune in WO01/21189 and/or by three public database prediction servers, respectively Syfpeithi, BIMAS and nHLAPred. It is also an aspect of this present invention that each peptide may be used within the scaffold design of the invention in combination with the same peptide as multiple repeats, or with any other peptide(s) or epitope(s).

TABLE 3

Specific HCV peptides in their complete length according to the invention:

| Series | Ep.nr | Ver. | Scaf. | Z1 | Z2 | Z3 | Z4 | Z5 | Z6 | Z7 | Z8 | Z9 |
|---|---|---|---|---|---|---|---|---|---|---|---|---|
| BI330 | 72 | | | RR | — | GGQLIGGIYLIPG | RR | — | VITFSIYLIVS | — | — | — |
| BI330 | 72 | | b | RRR | — | GGQLIGGIYLIPG | RR | — | VITFSIYLIVS | — | — | — |
| BI330 | 72 | | c | RR | — | GGQLIGGIYLIPG | RRR | — | VITFSIYLIVS | — | — | — |
| BI330 | 72 | | d | RR | — | GGQLIGGIYLIPG | RR | — | VITFSIYLIVS | R | — | — |
| BI330 | 72 | | e | RR | — | GGQLIGGIYLIPG | RR | — | VITFSIYLIVS | RR | — | — |
| BI330 | 72 | 2 | | *RR* | — | VITYSIFLIVS | *RR* | — | GGNVIGGIYZIPR | — | — | — |
| BI330 | 72 | 2 | b | *RRR* | — | VITYSIFLIVS | *RR* | — | GGNVIGGIYZIPR | — | — | — |
| BI330 | 72 | 2 | c | *RR* | — | VITYSIFLIVS | *RRR* | — | GGNVIGGIYZIPR | — | — | — |
| BI330 | 72 | 2 | d | RRR | — | VITYSIFLIVS | RRR | — | GGNVIGGIYZIPR Z = Nle | — | — | — |
| BI330 | 83 | | | RRG | — | TANWARVIS | R | — | ANWAKVIL | R | — | NWAKVI |
| BI330 | 83 | | b | RG | — | TANWARVIS | RR | — | ANWAKVIL | R | — | NWAKVI |
| BI330 | 83 | | c | RG | — | TANWARVIS | R | — | ANWAKVIL | R | — | NWAKVI |
| BI330 | 83 | | d | RG | — | TANWARVIS | RG | — | ANWAKVIL | R | — | NWAKVI |
| BI330 | 83 | 2 | | *RRG* | — | TANWARVIS | *R* | — | ANWARVIL | R | — | NWAKVI |
| BI330 | 83 | 2 | b | *RG* | — | TANWARVIS | *RR* | — | ANWARVIL | R | — | NWAKVI |
| BI330 | 83 | 2 | c | *RG* | — | TANWARVIS | *R* | — | ANWARVIL | R | — | NWAKVI |
| BI330 | 83 | 2 | d | *RG* | — | TANWARVIS | *RG* | — | ANWARVIL | R | — | NWAKVI |
| BI310 | 511 | | | *R* | — | *GYLPAVGAPI* | *RRR* | — | *VIRVIAHGLRL* | *R* | — | — |
| BI310 | 511 | | b | RR | — | *GYLPAVGAPI* | RR | — | *VIRVIAHGLRL* | R | — | — |
| BI310 | 511 | | c | RR | — | *GYLPAVGAPI* | RRR | — | *VIRVIAHGLRL* | — | — | — |
| BI310 | 511 | | d | RR | — | *GYLPAVGAPI* | RR | — | *VIRVIAHGLRL* | — | — | — |
| BI310 | 511 | | e | R | — | *GYLPAVGAPI* | RR | — | *VIRVIAHGLRL* | R | — | — |
| BI310 | 511 | | f | R | — | *GYLPAVGAPI* | R | — | *VIRVIAHGLRL* | R | — | — |
| BI310 | 511 | | g | R | — | *GYLPAVGAPI* | RR | — | *VIRVIAHGLRL* | — | — | — |

"—" = no amino acid; B = Cit; Z = Nle; X = Har

CMV:

The epitopes to be incorporated into the scaffold design according to the present invention may be derived from cytomegalovirus (CMV) including CMV glycoproteins gB and gH.

TABLE 4

Specific CMV peptides in their complete length according to the invention:

| Series | Nr | Ver. | Scaf. | Z1 | Z2 | Z3 | Z4 | Z5 | Z6 | Z7 | Z8 |
|---|---|---|---|---|---|---|---|---|---|---|---|
| BI050 | 4 | | | RG | — | NIVPZVVTA | RR | — | IGDLIVAQV | — | — |
| BI050 | 4 | | b | RR | — | NIVPZVVTA | RR | — | IGDLIVAQV | — | — |
| BI050 | 4 | | c | RRR | — | NIVPZVVTA | RR | — | IGDLIVAQV | — | — |
| BI050 | 4 | | d | RR | — | NIVPZVVTA | RRR | — | IGDLIVAQV | — | — |
| BI050 | 4 | 2 | | RG | — | NIVPZVVTA | RR | — | IGDLIVQAV | — | — |
| BI050 | 4 | 2 | b | RR | — | NIVPZVVTA | RR | — | IGDLIVQAV | — | — |
| BI050 | 4 | 2 | c | RRR | — | NIVPZVVTA | RR | — | IGDLIVQAV | — | — |
| BI050 | 4 | 2 | d | RR | — | NIVPZVVTA | RRR | — | IGDLIVQAV | — | — |
| BI050 | 5 | | | RG | — | VTPADLIGA | RR | — | QYNPVAVZF | — | — |
| BI050 | 5 | | b | RR | — | VTPADLIGA | RR | — | QYNPVAVZF | — | — |
| BI050 | 5 | | c | RRR | — | VTPADLIGA | RR | — | QYNPVAVZF | — | — |
| BI050 | 5 | | d | RR | — | VTPADLIGA | RRR | — | QYNPVAVZF | — | — |
| BI050 | 6 | | | RRG | — | PRPEGYTLFF | R | — | GYTLFFTS | R | — |
| BI050 | 6 | | b | RG | — | PRPEGYTLFF | RR | — | GYTLFFTS | R | — |
| BI050 | 6 | | c | RRG | — | PRPEGYTLFF | RR | — | GYTLFFTS | R | — |
| BI050 | 6 | | d | RRG | — | PRPEGYTLFF | RRR | — | GYTLFFTS | R | — |
| BI050 | 6 | | e | RRRG | — | PRPEGYTLFF | RR | — | GYTLFFTS | R | — |
| BI050 | 7 | | | RG | — | LPYPRGYTLFV | RR | — | GYTLFVSD | R | — |
| BI050 | 7 | | b | RRG | — | LPYPRGYTLFV | RR | — | GYTLFVSD | R | — |
| BI050 | 7 | | c | RRG | — | LPYPRGYTLFV | RRR | — | GYTLFVSD | R | — |
| BI050 | 7 | | d | RRRG | — | LPYPRGYTLFV | RR | — | GYTLFVSD | R | — |
| BI050 | 7 | | e | RRG | — | LPYPRGYTLFV | RR | — | GYTLFVSD | R | — |
| BI050 | 8 | | | RRG | — | ETILTPRDV | R | — | NTLZTPRDV | R | — |
| BI050 | 8 | | b | RG | — | ETILTPRDV | RR | — | NTLZTPRDV | R | — |
| BI050 | 8 | | c | RG | — | ETILTPRDV | R | — | NTLZTPRDV | R | — |
| BI050 | 8 | | d | RG | — | ETILTPRDV | RG | — | NTLZTPRDV | R | — |
| BI050 | 9 | | | RR | — | SSTSPVYDL | RR | — | SSTSPVYNL | R | — |
| BI050 | 9 | | b | RR | — | SSTSPVYDL | RRR | — | SSTSPVYNL | R | — |
| BI050 | 9 | | c | RRR | — | SSTSPVYDL | RR | — | SSTSPVYNL | R | — |
| BI050 | 9 | | d | RRR | — | SSTSPVYDL | RRR | — | SSTSPVYNL | R | — |

"—" = no amino acid; B = Cit; Z = Nle; X = Har

Influenza:

The epitopes to be incorporated into the scaffold design according to the present invention may be derived from fragments or portions of Influenza hemagglutinin (HA) or Influenza neuraminidase (NA), nucleoprotein (NP), M1, M2, NS1, NEP, PA, PB1, PB1-F2, PB2 for each of the subgroups, such as H1N1, H2N2 og H3N2.

Suitable epitopes may be derived from an HA protein of one, or more than one subtype, including H1, H2, H3, H4, H5, H6, H7, H8, H9, H10, H11, H12, H13, H14, H15 or H16 or fragment or portion thereof. Examples of subtypes comprising such HA proteins include A/New Caledonia/20/99 (H1N1) A/Indonesia/5/2006 (H5N1), A/chicken/New York/1995, A/herring gull/DE/677/88 (H2N8), A/Texas/32/2003, A/mallard/MN/33/00, A/duck/Shanghai/1/2000, A/northern pintail/TX/828189/02, A/Turkey/Ontario/6118/68 (H8N4), A/shoveler/Iran/G54/03, A/chicken/Germany/N/1949 (H10N7), A/duck/England/56 (H11N6), A/duck/Alberta/60/76 (H12N5), A/Gull/Maryland/704/77 (H13N6), A/Mallard/Gurjev/263/82, A/duck/Australia/341/83 (H15N8), A/black-headed gull/Sweden/5/99 (H16N3), B/Lee/40, C/Johannesburg/66, A/PuertoRico/8/34 (H1N1), A/Brisbane/59/2007 (H1N1), A/Solomon Islands 3/2006 (H1N1), A/Brisbane 10/2007 (H3N2), A/Wisconsin/67/2005 (H3N2), B/Malaysia/2506/2004, B/Florida/4/2006, A/Singapore/1/57 (H2N2), A/Anhui/1/2005 (H5N1), A/Vietnam/1194/2004 (H5N1), A/Teal/HongKong/W312/97 (H6N1), A/Equine/Prague/56 (H7N7), A/HongKong/1073/99 (H9N2)).

In some embodiments of the invention, the HA protein may be an H1, H2, H3, H5, H6, H7 or H9 subtype. In other embodiments, the H1 protein may be from the A/New Caledonia/20/99 (H1N1), A/PuertoRico/8/34 (H1N1), A/Brisbane/59/2007 (H1N1), or A/Solomon Islands 3/2006 (H1N1) strain. The H3 protein may also be from the A/Brisbane 10/2007 (H3N2) or A/Wisconsin/67/2005 (H3N2) strain. In other embodiments, the H2 protein may be from the A/Singapore/1/57 (H2N2) strain. The H5 protein may be from the A/Anhui/1/2005 (H5N1), A/Vietnam/1194/2004 (H5N1), or A/Indonesia/5/2005 strain. In other embodiments, the H6 protein may be from the A/Teal/HongKong/W312/97 (H6N1) strain. The H7 protein may be from the A/Equine/Prague/56 (H7N7) strain. In other embodiments, the H9 protein is from the A/HongKong/1073/99 (H9N2) strain. In other embodiments, the HA protein may be from an influenza virus may be a type B virus, including B/Malaysia/2506/2004 or B/Florida/4/2006. The influenza virus HA protein may be H5 Indonesia.

TABLE 5

Specific Influenza peptides according to the invention in their complete length (Z or Nle denotes Norleucine, X or Har denotes homoarginine):

| Series | Ep.nr | version | scaffold | Z1 | Z2 | Z3 | Z4 | Z5 | Z6 | Z7 |
|---|---|---|---|---|---|---|---|---|---|---|
| BI100 | 330 | | | RR | — | TAYERZCNIL | RR | — | GLEPLVIAGILA | — |
| BI100 | 330 | | b | RRR | — | TAYERZCNIL | RR | — | GLEPLVIAGILA | — |
| BI100 | 330 | | c | RR | — | TAYERZCNIL | RRR | — | GLEPLVIAGILA | — |
| BI100 | 330 | | d | RR | — | TAYERZCNIL | RR | — | GLEPLVIAGILA | R |
| BI100 | 330 | | e | RR | — | TAYERZCNIL Z = Nle | RR | — | GLEPLVIAGILA | RR |
| BI100 | 270 | | | RR | — | TVIGASZIPLL | RG | — | TPIXQDWENRAN | — |
| BI100 | 270 | | b | RRR | — | TVIGASZIPLL | RG | — | TPIXQDWENRAN | — |
| BI100 | 270 | | c | RR | — | TVIGASZIPLL | RRG | — | TPIXQDWENRAN | — |
| BI100 | 270 | | d | RRR | — | TVIGASZIPLL | RRG | — | TPIXQDWENRAN | — |
| BI100 | 270 | | e | RRR | — | TVIGASZIPLL Z = Nle | RRG | — | TPIXQDWENRAN X = Har | R |
| BI100 | 130 | | | RR | — | AAFEEZXITS | RR | — | VAFEDLXZZSFI | — |
| BI100 | 130 | | b | RRR | — | AAFEEZXITS | RR | — | VAFEDLXZZSFI | — |
| BI100 | 130 | | c | RRR | — | AAFEEZXITS | RRG | — | VAFEDLXZZSFI | — |
| BI100 | 130 | | d | RRR | — | AAFEEZXITS | RRR | — | VAFEDLXZZSFI | — |
| BI100 | 130 | | e | RRR | — | AAFEEZXITS | RRR | — | VAFEDLXZZSFI | GR |
| BI100 | 190 | | e | RR | — | TAYERZCNIL | RRG | — | RFQTVVQBA | — |
| BI100 | 190 | | f | RR | — | TAYERZCNIL | RRG | — | RFQTVVQBA | R |
| BI100 | 190 | | g | R | — | TAYERZCNIL | RG | — | RFQTVVQBA | R |
| BI100 | 190 | | h | RR | — | TAYERZCNIL | RG | — | RFQTVVQBA | |
| BI100 | 260 | | b | BR | — | GLEPLVIAGILA | RR | — | GSLVGLLHIVL | — |
| BI100 | 260 | | c | RR | — | GLEPLVIAGILA | RR | — | GSLVGLLHIVL | — |
| BI100 | 260 | | d | RR | — | GLEPLVIAGILA | RR | — | GSLVGLLHIVL | R |
| BI100 | 260 | | e | RR | — | GLEPLVIAGILA | RRR | — | GSLVGLLHIVL | — |
| BI100 | 260 | | f | RR | — | GLEPLVIAGILA | RRR | — | GSLVGLLHIVL | R |

TABLE 5-continued

Specific Influenza peptides according to the invention in their complete length (Z or Nle denotes Norleucine, X or Har denotes homoarginine):

| Series | Ep.nr | version | scaffold | Z1 | Z2 | Z3 | Z4 | Z5 | Z6 | Z7 |
|---|---|---|---|---|---|---|---|---|---|---|
| BI100 | 120 | -3 | a | R | — | TAFLVRNVA | R | — | SIARSVTIZXASVVH | — |
| BI100 | 120 | -3 | b | R | — | TAFLVRNVA | RR | — | SIARSVTIZXASVVH | — |
| BI100 | 120 | -3 | c | RR | — | TAFLVRNVA | R | — | SIARSVTIZXASVVH | — |
| BI100 | 120 | -3 | d | RR | — | TAFLVRNVA | RR | — | SIARSVTIZXASVVH | — |
| BI100 | 120 | -3 | e | RR | — | TAFLVRNVA | RR | — | SIARSVTIZXASVVH | R |
| BI100 | 120 | -3 | f | RR | — | TAFLVRNVA | RR | — | SIARSVTIZXASVVH | RR |
|  |  |  |  |  |  |  |  | — | — | — |
|  |  |  |  |  |  |  |  | — | — | — |
| BI100 | 220 |  |  | RG | Dpr(Aoa) | TPI(Har)QDWGNRAN | RG | — | TPTRQEWDCRIS | — |
| BI100 | 220 | -2 |  | RG | Dpr(Aoa) | TPI(Har)QDWGNRAN | RG | — | TPTRQEWDARIS | — |
| BI100 | 220 | -3 |  | RG | — | TPI(Har)QDWGNRAN | RG | — | TPTRQEWDCRIS | — |
| BI100 | 220 | -4 |  | RG | — | TPI(Har)QDWGNRAN | RG | — | TPTRQEWDARIS | — |
| BI100 | 220 | -5 |  | RG | C | TPI(Har)QDWGNRAN | RG | — | TPTRQEWDCRIS | — |
| BI100 | 220 | -6 |  | RG | C | TPI(Har)QDWGNRAN | RG | — | TPTRQEWDARIS | — |
| BI100 | 220 | -7 |  | RG | K | TPI(Har)QDWGNRAN | RG | — | TPTRQEWDCRIS | — |
| BI100 | 220 | -8 |  | RG | K | TPI(Har)QDWGNRAN | RG | — | TPTRQEWDARIS | — |
| BI100 | 220 | -9 |  | RG | Lys(Me) | TPI(Har)QDWGNRAN | RG | — | TPTRQEWDCRIS | — |
| BI100 | 220 | -10 |  | RG | Lys(Me) | TPI(Har)QDWGNRAN | RG | — | TPTRQEWDARIS | — |
| BI100 | 220 | -11 |  | RG | D | TPI(Har)QDWGNRAN | RG | — | TPTRQEWDCRIS | — |
| BI100 | 220 | -12 |  | RG | D | TPI(Har)QDWGNRAN | RG | — | TPTRQEWDARIS | — |
| BI100 | 220 | -13 |  | RG | E | TPI(Har)QDWGNRAN | RG | — | TPTRQEWDCRIS | — |
| BI100 | 220 | -14 |  | RG | E | TPI(Har)QDWGNRAN | RG | — | TPTRQEWDARIS | — |
| BI100 | 240 |  |  | RG | Dpr(Ser) | TPT(Har)NGWDVKLS | RG | — | TPI(Har)QEW(Har)SL(Nle)NQEW | — |
| BI100 | 240 | -3 |  | RG | — | TPT(Har)NGWDVKLS | RG | — | TPI(Har)QEW(Har)SL(Nle)NQEW | — |
| BI100 | 240 | -4 |  | RG | K | TPT(Har)NGWDVKLS | RG | — | TPI(Har)QEW(Har)SL(Nle)NQEW | — |
| BI100 | 240 | -5 |  | RG | C | TPT(Har)NGWDVKLS | RG | — | TPI(Har)QEW(Har)SL(Nle)NQEW | — |
| BI100 | 240 | -6 |  | RG | Lys(Me) | TPT(Har)NGWDVKLS | RG | — | TPI(Har)QEW(Har)SL(Nle)NQEW | — |

TABLE 5-continued

Specific Influenza peptides according to the invention in their complete length (Z or Nle denotes Norleucine, X or Har denotes homoarginine):

| Series | Ep.nr | version | scaffold | Z1 | Z2 | Z3 | Z4 | Z5 | Z6 | Z7 |
|---|---|---|---|---|---|---|---|---|---|---|
| BI100 | 240 | -7 | RG | D | TPT(Har)NGWDV KLS | RG | — | TPI(Har)QEW(Har)SL (Nle)NQEW | — |
| BI100 | 240 | -8 | RG | E | TPT(Har)NGWDV KLS | RG | — | TPI(Har)QEW(Har)SL (Nle)NQEW | — |

"—" = no amino acid; B = Cit; Z = Nle; X = Har

TABLE 6

Specific dimeric Influenza peptides according to the invention in their complete length (Z or Nle denotes Norleucine, X or Har denotes homoarginine, residues linking A and B monomer peptides to dimers are underlined):

| Dimeric Peptide | Dimeric peptides, composed of peptides A and B. Linked residues underlined | Constituent monomers |
|---|---|---|
| BI-155 | | |
| A | RG(Dpr(Aoa))-TPI(Har)QDWGNRAN-RG-TPTRQEWDCRIS-NH2 | BI-100-220 |
| B | RG(Dpr(Ser))-TPT(Har)NGWDVKLS-RG-TPI(Har)QEW(Har)SL(Nle)NQEW-NH2 | BI-100-240 |
| BI-155-2 | | |
| A | RG(Dpr(Aoa))-TPI(Har)QDWGNRAN-RG-TPTRQEWDARIS-NH2 | BI-100-220-2 |
| B | RG(Dpr(Ser))-TPT(Har)NGWDVKLS-RG-TPI(Har)QEW(Har)SL(Nle)NQEW-NH2 | BI-100-240 |
| BI-155-3 | | |
| A | RGC-TPI(Har)QDWGNRAN-RG-TPTRQEWDCRIS-NH2 | BI-100-220-5 |
| B | RGK-TPT(Har)NGWDVKLS-RG-TPI(Har)QEW(Har)SL(Nle)NQEW-NH2 | BI-100-240-4 |
| BI-155-4 | | |
| A | RGC-TPI(Har)QDWGNRAN-RG-TPTRQEWDARIS-NH2 | BI-100-220-6 |
| B | RGK-TPT(Har)NGWDVKLS-RG-TPI(Har)QEW(Har)SL(Nle)NQEW-NH2 | BI-100-240-4 |
| BI-155-5 | | |
| A | RGK-TPI(Har)QDWGNRAN-RG-TPTRQEWDCRIS-NH2 | BI-100-220-7 |
| B | RGC-TPT(Har)NGWDVKLS-RG-TPI(Har)QEW(Har)SL(Nle)NQEW-NH2 | BI-100-240-5 |
| BI-155-6 | | |
| A | RGK-TPI(Har)QDWGNRAN-RG-TPTRQEWDARIS-NH2 | BI-100-220-8 |
| B | RGC-TPT(Har)NGWDVKLS-RG-TPI(Har)QEW(Har)SL(Nle)NQEW-NH2 | BI-100-240-5 |
| BI-155-7 | | |
| A | RG(Lys(Me))-TPI(Har)QDWGNRAN-RG-TPTRQEWDCRIS-NH2 | BI-100-220-9 |

TABLE 6-continued

Specific dimeric Influenza peptides according to the invention in their complete length (Z or Nle denotes Norleucine, X or Har denotes homoarginine, residues linking A and B monomer peptides to dimers are underlined):

| Dimeric Peptide | Dimeric peptides, composed of peptides A and B. Linked residues underlined | Constituent monomers |
|---|---|---|
| B | RG<u>D</u>-TPT(Har)NGWDVKLS-RG-TPI(Har)QEW(Har)SL(Nle)NQEW-NH2 | BI-100-240-7 |
| BI-155-8 | | |
| A | RG<u>(Lys(Me))</u>-TPI(Har)QDWGNRAN-RG-TPTRQEWDCRIS-NH2 | BI-100-220-9 |
| B | RG<u>E</u>-TPT(Har)NGWDVKLS-RG-TPI(Har)QEW(Har)SL(Nle)NQEW-NH2 | BI-100-240-8 |
| BI-155-9 | | |
| A | RG<u>(Lys(Me))</u>-TPI(Har)QDWGNRAN-RG-TPTRQEWDARIS-NH2 | BI-100-220-10 |
| B | RG<u>D</u>-TPT(Har)NGWDVKLS-RG-TPI(Har)QEW(Har)SL(Nle)NQEW-NH2 | BI-100-240-7 |
| BI-155-10 | | |
| A | RG<u>(Lys(Me))</u>-TPI(Har)QDWGNRAN-RG-TPTRQEWDARIS-NH2 | BI-100-220-10 |
| B | RG<u>E</u>-TPT(Har)NGWDVKLS-RG-TPI(Har)QEW(Har)SL(Nle)NQEW-NH2 | BI-100-240-8 |
| BI-155-11 | | |
| A | RG<u>D</u>-TPI(Har)QDWGNRAN-RG-TPTRQEWDCRIS-NH2 | BI-100-220-11 |
| B | RG<u>(Lys(Me))</u>-TPT(Har)NGWDVKLS-RG-TPI(Har)QEW(Har)SL(Nle)NQEW-NH2 | BI-100-240-6 |
| BI-155-12 | | |
| A | RG<u>D</u>-TPI(Har)QDWGNRAN-RG-TPTRQEWDARIS-NH2 | BI-100-220-12 |
| B | RG<u>(Lys(Me))</u>-TPT(Har)NGWDVKLS-RG-TPI(Har)QEW(Har)SL(Nle)NQEW-NH2 | BI-100-240-6 |
| BI-155-13 | | |
| A | RG<u>E</u>-TPI(Har)QDWGNRAN-RG-TPTRQEWDCRIS-NH2 | BI-100-220-13 |
| B | RG<u>(Lys(Me))</u>-TPT(Har)NGWDVKLS-RG-TPI(Har)QEW(Har)SL(Nle)NQEW-NH2 | BI-100-240-6 |
| BI-155-14 | | |
| A | RG<u>E</u>-TPI(Har)QDWGNRAN-RG-TPTRQEWDARIS-NH2 | BI-100-220-14 |
| B | RG<u>(Lys(Me))</u>-TPT(Har)NGWDVKLS-RG-TPI(Har)QEW(Har)SL(Nle)NQEW-NH2 | BI-100-240-6 |
| BI-155-15 | | |
| A | RG<u>C</u>-TPI(Har)QDWGNRAN-RG-TPTRQEWDCRIS-NH2 | BI-100-220-5 |
| B | RG<u>C</u>-TPT(Har)NGWDVKLS-RG-TPI(Har)QEW(Har)SL(Nle)NQEW-NH2 | BI-100-240-5 |
| BI-155-16 | | |
| A | RG<u>C</u>-TPI(Har)QDWGNRAN-RG-TPTRQEWDARIS-NH2 | BI-100-220-6 |

TABLE 6-continued

Specific dimeric Influenza peptides according to the invention in their complete length (Z or Nle denotes Norleucine, X or Har denotes homoarginine, residues linking A and B monomer peptides to dimers are underlined):

| Dimeric Peptide | Dimeric peptides, composed of peptides A and B. Linked residues underlined | Constituent monomers |
|---|---|---|
| B | RG<u>C</u>-TPT(Har)NGWDVKLS-RG-TPI(Har)QEW(Har)SL(Nle)NQEW-NH2 | BI-100-240-5 |
| *A-monomer peptide variants:* | | |
| | RG(Dpr(Aoa))-TPI(Har)QDWGNRAN-RG-TPTRQEWDCRIS-NH2 | BI-100-220 |
| | RG(Dpr(Aoa))-TPI(Har)QDWGNRAN-RG-TPTRQEWDARIS-NH2 | BI-100-220-2 |
| | RG-TPI(Har)QDWGNRAN-RG-TPTRQEWDCRIS-NH2 | BI-100-220-3 |
| | RG-TPI(Har)QDWGNRAN-RG-TPTRQEWDARIS-NH2 | BI-100-220-4 |
| | RGC-TPI(Har)QDWGNRAN-RG-TPTRQEWDCRIS-NH2 | BI-100-220-5 |
| | RGC-TPI(Har)QDWGNRAN-RG-TPTRQEWDARIS-NH2 | BI-100-220-6 |
| | RGK-TPI(Har)QDWGNRAN-RG-TPTRQEWDCRIS-NH2 | BI-100-220-7 |
| | RGK-TPI(Har)QDWGNRAN-RG-TPTRQEWDARIS-NH2 | BI-100-220-8 |
| | RG(Lys(Me))-TPI(Har)QDWGNRAN-RG-TPTRQEWDCRIS-NH2 | BI-100-220-9 |
| | RG(Lys(Me))-TPI(Har)QDWGNRAN-RG-TPTRQEWDARIS-NH2 | BI-100-220-10 |
| | RGD-TPI(Har)QDWGNRAN-RG-TPTRQEWDCRIS-NH2 | BI-100-220-11 |
| | RGD-TPI(Har)QDWGNRAN-RG-TPTRQEWDARIS-NH2 | BI-100-220-12 |
| | RGE-TPI(Har)QDWGNRAN-RG-TPTRQEWDCRIS-NH2 | BI-100-220-13 |
| | RGE-TPI(Har)QDWGNRAN-RG-TPTRQEWDARIS-NH2 | BI-100-220-14 |
| *B-monomer peptide variants:* | | |
| | RG(Dpr(Ser))-TPT(Har)NGWDVKLS-RG-TPI(Har)QEW(Har)SL(Nle)NQEW-NH2 | BI-100-240 |
| | RG-TPT(Har)NGWDVKLS-RG-TPI(Har)QEW(Har)SL(Nle)NQEW-NH2 | BI-100-240-3 |
| | RGK-TPT(Har)NGWDVKLS-RG-TPI(Har)QEW(Har)SL(Nle)NQEW-NH2 | BI-100-240-4 |
| | RGC-TPT(Har)NGWDVKLS-RG-TPI(Har)QEW(Har)SL(Nle)NQEW-NH2 | BI-100-240-5 |
| | RG(Lys(Me))-TPT(Har)NGWDVKLS-RG-TPI(Har)QEW(Har)SL(Nle)NQEW-NH2 | BI-100-240-6 |
| | RGD-TPT(Har)NGWDVKLS-RG-TPI(Har)QEW(Har)SL(Nle)NQEW-NH2 | BI-100-240-7 |
| | RGE-TPT(Har)NGWDVKLS-RG-TPI(Har)QEW(Har)SL(Nle)NQEW-NH2 | BI-100-240-8 |

Human Immunodeficiency Virus (HIV):

For HIV, the epitopes to be incorporated into the scaffold design according to the present invention may be derived from the group consisting of gp120, gp160, gp41, p24gag or p55gag derived from HIV, including members of the various genetic subtypes.

Human Papillomavirus (HPV):

For HPV, the epitopes to be incorporated into the scaffold design according to the present invention may be derived from the group consisting E1, E2, E3, E4, E6 and E7, L1 and L2 proteins. The epitopes may be derived from any type including types 8, 11, 16, 18, 31, 33, 35, 39, 45, 51, 52, 56, 58, and 59.

TABLE 7

Specific HPV peptides in their complete length according to the invention:

| Series | Nr | Version | Scaffold | Z1 | Z2 | Z3 | Z4 | Z5 | Z6 | Z7 | Z8 |
|---|---|---|---|---|---|---|---|---|---|---|---|
| | | | Native: | | | 35-45 | | | 48-58 | | |
| BI500 | 1 | | | RR | — | LECVYCKQQLL | RR | — | EVYDFAFRDLC | — | |
| BI500 | 1 | | b | RR | — | LECVYCKQQLL | RRRG | — | EVYDFAFRDLC | — | |
| BI500 | 1 | | c | RRR | — | LECVYCKQQLL | RRG | — | EVYDFAFRDLC | — | |
| BI500 | 1 | | d | RRR | — | LECVYCKQQLL | RRRG | — | EVYDFAFRDLC | — | |
| BI500 | 1 | | e | RRRG | — | LECVYCKQQLL | RRRG | — | EVYDFAFRDLC | — | |
| | | | Native: | | | 49-58 | | | 52-61 | | |
| BI500 | 2 | | | RR | — | GVYDFAFRDLC | RR | — | GFAFRDLCIVRY | | — |
| BI500 | 2 | | b | RR | — | GVYDFAFRDLC | RRRG | — | GFAFRDLCIVY | — | |
| BI500 | 2 | | c | RRR | — | GVYDFAFRDLC | RRG | — | GFAFRDLCIVRY | | |
| BI500 | 2 | | d | RRR | — | GVYDFAFRDLC | RRRG | — | GFAFRDLCIVY | — | |
| BI500 | 2 | | e | RRRG | — | GVYDFAFRDLC | RRRG | — | GFAFRDLCIVRY | | — |
| | | | Native: | | | 49-58 | | | 52-61 | | |
| BI500 | 3 | | | RR | — | GVFDYAFRDIN | RR | — | GFAYRDINLARY | | — |
| BI500 | 3 | | b | RR | — | GVYDFAFRDLC | RRRG | — | GFAFRDLCIVY | — | — |
| BI500 | 3 | | c | RRR | — | GVYDFAFRDLC | RRG | — | GFAFRDLCIVRY | | — |
| BI500 | 3 | | d | RRR | — | GVYDFAFRDLC | RRRG | — | GFAFRDLCIVY | — | — |
| BI500 | 3 | | e | RRRG | — | GVYDFAFRDLC | RRRG | — | GFAFRDLCIVRY | | — |
| | | | Native: | | | 74-83 | | | 84-93 | | |
| BI500 | 4 | | | RR | — | VDIRTLEDLL | RR | — | GTLGIVCPIGR | | — |
| BI500 | 4 | | b | RR | — | VDIRTLEDLL | RRRG | — | GTLGIVCPIG | — | — |
| BI500 | 4 | | c | RRR | — | VDIRTLEDLL | RRG | — | GTLGIVCPIGR | | — |
| BI500 | 4 | | d | RRR | — | VDIRTLEDLL | RRRG | — | GTLGIVCPIG | — | — |
| BI500 | 4 | | e | RRRG | — | VDIRTLEDLL | RRRG | — | GTLGIVCPIGR | | — |

The present invention further relates to compositions comprising two or three peptides of the invention.

TABLE 8

The table represent 10 different suitable combinations of three monomeric peptides each peptide comprising a specific natural antigen of a protein or peptide sequence derived from HCV.

| # | Peptide IDs | Peptide 1 sequence | Peptide 2 sequence | Peptide 3 sequence | SEQ ID | SEQ ID | SEQ ID |
|---|---|---|---|---|---|---|---|
| 1 | BI3-30-72, BI3-30-83, BI3-10-511d | RRGGQLIGGIYLIPGRRVITFSIYLIVS | RRGTANWARVISRANWAKVILRNWAKVI | RRGYLPAVGAPIRRVIRVIAHGLRL | (SEQ ID NO: 357) | (SEQ ID NO: 366) | (SEQ ID NO: 377) |
| 2 | BI3-30-72b, BI3-30-83b, BI3-10-511f | RRRGGQLIGGIYLIPGRRVITFSIYLIVS | RGTANWARVISRRANWAKVILRNWAKVI | RGYLPAVGAPIRVIRVIAHGLRLR | (SEQ ID NO: 358) | (SEQ ID NO: 367) | (SEQ ID NO: 379) |
| 3 | BI3-30-72c, BI3-30-83c, BI3-10-511g | RRGGQLIGGIYLIPGRRVITFSIYLIVS | RGTANWARVISRANWAKVILRNWAKVI | RGYLPAVGAPIRRVIRVIAHGLRL | (SEQ ID NO: 359) | (SEQ ID NO: 368) | (SEQ ID NO: 380) |
| 4 | BI3-30-72d, BI3-30-83d, BI3-10-511 | RRGGQLIGGIYLIPGRRVITFSIYLIVSR | RGTANWARVISRGANWAKVILRNWAKVI | RGYLPAVGAPIRRRVIRVIAHGLRLR | (SEQ ID NO: 360) | (SEQ ID NO: 369) | (SEQ ID NO: 374) |
| 5 | BI3-30-72e, BI3-30-832, BI3-10-511b | RRGGQLIGGIYLIPGRRVITFSIYLIVSRR | RRGTANWARVISRANWARVILRNWAKVI | RRGYLPAVGAPIRRVIRVIAHGLRLR | (SEQ ID NO: 361) | (SEQ ID NO: 370) | (SEQ ID NO: 375) |
| 6 | BI3-30-722, BI3-30-832b, BI3-10-511c | RRVITYSIFLIVSRRGGNVIGGIYZIPR | RGTANWARVISRRANWARVILRNWAKVI | RRGYLPAVGAPIRRRVIRVIAHGLRL | (SEQ ID NO: 362) | (SEQ ID NO: 371) | (SEQ ID NO: 376) |
| 7 | BI3-30-722, BI3-30-83, BI3-10-511d | RRVITYSIFLIVSRRGGNVIGGIYZIPR | RRGTANWARVISRANWAKVILRNWAKVI | RRGYLPAVGAPIRRVIRVIAHGLRL | (SEQ ID NO: 362) | (SEQ ID NO: 366) | (SEQ ID NO: 377) |
| 8 | BI3-30-722b, BI3-30-83b, BI3-10-511e | RRRVITYSIFLIVSRRGGNVIGGIYZIPR | RGTANWARVISRRANWAKVILRNWAKVI | RGYLPAVGAPIRRVIRVIAHGLRLR | (SEQ ID NO: 363) | (SEQ ID NO: 367) | (SEQ ID NO: 378) |
| 9 | BI3-30-722c, BI3-30-832c, BI3-10-511f | RRVITYSIFLIVSRRGGNVIGGIYZIPR | RGTANWARVISRANWARVILRNWAKVI | RGYLPAVGAPIRVIRVIAHGLRLR | (SEQ ID NO: 364) | (SEQ ID NO: 372) | (SEQ ID NO: 379) |
| 10 | BI3-30-722d, BI3-30-832d, BI3-10-511g | RRRVITYSIFLIVSRRRGGNVIGGIYZIPR | RGTANWARVISRGANWARVILRNWAKVI | RGYLPAVGAPIRRVIRVIAHGLRL | (SEQ ID NO: 365) | (SEQ ID NO: 373) | (SEQ ID NO: 380) |

TABLE 9

The table represent 10 different suitable combinations of three monomeric peptides and one dimeric peptide each peptide comprising specific natural antigen of a protein or peptide sequence derived from influenza.

| # | Dimer ID | Peptide 1 (BI100-330) | Peptide 2 (BI100-270) | Peptide 3 (BI100-130) |
|---|---|---|---|---|
| 1 | BI-155-5 | RRTAYERZCNILRRGLEPLVIAGILA (SEQ ID NO: 407) | RRTVIGASZIPLLRGTPIXQDWENRAN (SEQ ID NO: 412) | RRAAFEEZXITSRRVAFEDLXZZSFI (SEQ ID NO: 417) |
| 2 | BI-155-4 | RRRTAYERZCNILRRGLEPLVIAGILA (SEQ ID NO: 408) | RRRTVIGASZIPLLRGTPIXQDWENRAN (SEQ ID NO: 413) | RRAAFEEZXITSRRVAFEDLXZZSFI (SEQ ID NO: 418) |
| 3 | BI-155- | RRTAYERZCNILRRGLE | RRTVIGASZIPLLRGTPIXQ | RRAAFEEZXITSRRGVAFE |

TABLE 9-continued

The table represent 10 different suitable combinations of three monomeric peptides and one dimeric peptide each peptide comprising specific natural antigen of a protein or peptide sequence derived from influenza.

| | | | | |
|---|---|---|---|---|
| 3 | | PLVIAGILA (SEQ ID NO: 409) | DWENRAN (SEQ ID NO: 414) | DLXZZSFI (SEQ ID NO: 419) |
| 4 | BI-155-2 | BI100-330d RRTAYERZCNILRRGLEP LVIAGILAR (SEQ ID NO: 410) | BI100-270d RRRTVIGASZIPLLRRGTPIX QDWENRAN (SEQ ID NO: 415) | BI100-130d RRRAAFEEZXITSRRRVAFE DLXZZSFI (SEQ ID NO: 420) |
| 5 | BI-155 | BI100-330e RRTAYERZCNILRRGLEP LVIAGILARR (SEQ ID NO: 411) | BI100-270e RRRTVIGASZIPLLRRGTPIX QDWENRANR (SEQ ID NO: 416) | BI100-130e RRRAAFEEZXITSRRRVAFE DLXZZSFIGR (SEQ ID NO: 421) |
| 6 | BI-155-2 | BI100-330e RRTAYERZCNILRRGLEP LVIAGILARR (SEQ ID NO: 411) | BI100-270e RRRTVIGASZIPLLRRGTPIX QDWENRANR (SEQ ID NO: 416) | BI100-130e RRRAAFEEZXITSRRRVAFE DLXZZSFIGR (SEQ ID NO: 421) |
| 7 | BI-155-3 | BI100-330d RRTAYERZCNILRRGLEP LVIAGILAR (SEQ ID NO: 410) | BI100-270c RRTVIGASZIPLLRRGTPIXQ DWENRAN (SEQ ID NO: 414) | BI100-130c RRRAAFEEZXITSRRGVAFE DLXZZSFI (SEQ ID NO: 419) |
| 10 | BI-155 | BI100-330 RRTAYERZCNILRRGLEP LVIAGILA (SEQ ID NO: 407) | BI100-270d RRRTVIGASZIPLLRRGTPIX QDWENRAN (SEQ ID NO: 415) | BI100-130b RRRAAFEEZXITSRRVAFED LXZZSFI (SEQ ID NO: 418) |

Carriers, Adjuvants and Vehicles—Delivery

The isolated peptides according to the invention may be delivered by various means and within various compositions, herein referred to as "compositions", "vaccine compositions" or "pharmaceutical compositions". The peptides of the present invention and pharmaceutical and vaccine compositions of the invention are useful for administration to mammals, particularly humans, to treat and/or prevent virus infection. Vaccine compositions containing the peptides of the invention are administered to a patient infected with the virus in question or to an individual susceptible to, or otherwise at risk for, virus infection to elicit an immune response against the specific antigens and thus enhance the patient's own immune response capabilities.

Various art-recognized delivery systems may be used to deliver the peptides, into appropriate cells. The peptides can be delivered in a pharmaceutically acceptable carrier or as colloidal suspensions, or as powders, with or without diluents. They can be "naked" or associated with delivery vehicles and delivered using delivery systems known in the art.

A "pharmaceutically acceptable carrier" or "pharmaceutically acceptable adjuvant" is any suitable excipient, diluent, carrier and/or adjuvant which, by themselves, do not induce the production of antibodies harmful to the individual receiving the composition nor do they elicit protection. Preferably, a pharmaceutically acceptable carrier or adjuvant enhances the immune response elicited by an antigen. Suitable carriers or adjuvant typically comprise one or more of the compounds included in the following non-exhaustive list: large slowly metabolized macromolecules such as proteins, polysaccharides, polylactic acids, polyglycolic acids, polymeric amino acids, amino acid copolymers and inactive virus particles; aluminium hydroxide, aluminium phosphate (see International Patent Application Publication No. WO93/24148), alum (KAl(SO4)2.12H2O), or one of these in combination with 3-0-deacylated monophosphoryl lipid A (see International Patent Application Publication No. WO93/19780); N-acetyl-muramyl-L-threonyl-D-isoglutamine (see U.S. Pat. No. 4,606,918), N-acetyl-normuramyl-L-alanyl-D-isoglutamine, N-acetylmuramyl-L-alanyl-D-isoglutamyl-L-alanine-2-(1',2'-dipalmitoyl-sn-glycero-3-hydroxyphosphoryloxy)ethylamine; RIBI (ImmunoChem Research Inc., Hamilton, Mont., USA) which contains monophosphoryl lipid A (i.e., a detoxified endotoxin), trehalose-6,6-dimycolate, and cell wall skeleton (MPL+TDM+CWS) in a 2% squalene/Tween 80 emulsion. Any of the three components MPL, TDM or CWS may also be used alone or combined 2 by 2; adjuvants such as Stimulon (Cambridge Bioscience, Worcester, Mass., USA), SAF-1 (Syntex); adjuvants such as combinations between QS21 and 3-de-O-acetylated monophosphoryl lipid A (see International Application No. WO94/00153) which may be further supplemented with an oil-in-water emulsion (see, e.g., International Application Nos. WO95/17210, WO97/01640 and WO9856414) in which the oil-in-water emulsion comprises a metabolisable oil and a saponin, or a metabolisable oil, a saponin, and a sterol, or which may be further supplemented with a cytokine (see International Application No. WO98/57659); adjuvants such as MF-59 (Chiron), or poly[di(carboxylatophenoxy) phosphazene] based adjuvants (Virus Research Institute); blockcopolymer based adjuvants such as Optivax (Vaxcel, Cytrx) or inulin-based adjuvants, such as Algammulin and Gammalnulin (Anutech); Complete or Incomplete Freund's Adjuvant (CFA or IFA, respectively) or Gerbu preparations (Gerbu Biotechnik); a saponin such as QuilA, a purified saponin such as QS21, QS7 or QS17, -escin or digitonin; immunostimulatory oligonucleotides comprising unmethylated CpG dinucleotides such as [purine-purine-CG-pyrimidine-pyrimidine] oligonucleotides. These immunostimulatory oligonucleotides include CpG class A, B, and C molecules (Coley Pharmaceuticals), ISS (Dynavax), Immunomers (Hybridon). Immunostimulatory oligonucleotides may also be combined with cationic peptides as described, e.g., by Riedl et al. (2002); Immune Stimulating Complexes comprising saponins, for example Quil A (ISCOMS); excipients and diluents, which are inherently non-toxic and non-therapeutic, such as water, saline, glycerol, ethanol, isopropyl alcohol, DMSO, wetting or emulsifying agents, pH buffering substances, preservatives, and the like; a biodegradable and/or biocompatible oil such as squalane, squalene, eicosane, tetratetracontane, glycerol, peanut oil, vegetable oil, in a concentration of, e.g., 1 to 10% or 2.5 to 5%; vitamins such as vitamin C (ascorbic acid or its salts or esters), vitamin E (tocopherol), or vitamin A; carotenoids, or natural or synthetic flavanoids; trace elements, such as selenium; any Toll-like receptor ligand as reviewed in Barton and Medzhitov (2002).

For a further enhancement of the vaccine antigenic properties, could be to combine a well known adjuvant with an oral immune modulant, such as IMID or adjuvant such as a Cox-2 inhibitor or a immunomodulating compound.

A further aspect of the invention is the use of the vaccine combined with adjuvant, with an (oral) immunemodulating agent and a reservoir purging agent.

Other suitable adjuvants includes response-selective C5a agonists, such as EP54 and EP67 described in Hung C Y et al. An agonist of human complement fragment C5a enhances vaccine immunity against *Coccidioides* infection. Vaccine (2012) and Kollessery G et al. Tumor-specific peptide based vaccines containing the conformationally biased, response-selective C5a agonists EP54 and EP67 protect against aggressive large B cell lymphoma in a syngeneic murine model. Vaccine (2011) 29: 5904-10.

Other suitable adjuvants include an oil-in-water emulsion containing a stabilizing detergent, a micelle-forming agent and a biodegradable oil, such as Provax described in e.g. U.S. Pat. No. 5,585,103.

Any of the afore-mentioned adjuvants comprising 3-de-O-acetylated monophosphoryl lipid A, said 3-de-O-acetylated monophosphoryl lipid A may be forming a small particle (see International Application No. WO94/21292).

In any of the aforementioned adjuvants MPL or 3-de-O-acetylated monophosphoryl lipid A can be replaced by a synthetic analogue referred to as RC-529 or by any other amino-alkyl glucosaminide 4-phosphate (Johnson et al. 1999, Persing et al. 2002). Alternatively it can be replaced by other lipid A analogues such as OM-197 (Byl et al. 2003).

A "pharmaceutically acceptable vehicle" includes vehicles such as water, saline, physiological salt solutions, glycerol, ethanol, etc. Auxiliary substances such as wetting or emulsifying agents, pH buffering substances, preservatives may be included in such vehicles. Delivery systems known in the art are e.g. lipopeptides, peptide compositions encapsulated in poly-DL-lactide-co-glycolide ("PLG"), microspheres, peptide compositions contained in immune stimulating complexes (ISCOMS), multiple antigen peptide systems (MAPs), viral delivery vectors, particles of viral or synthetic origin, adjuvants, liposomes, lipids, microparticles or microcapsules, gold particles, nanoparticles, polymers, condensing agents, polysaccharides, polyamino acids, dendrimers, saponins, QS21, adsorption enhancing materials, fatty acids or, naked or particle absorbed cDNA.

The peptides may be delivered in oils such as Endocine™ and Montanide™ (Eurocine)-Montanide™ ISA 51 VG or Montanide™ ISA 720 VG (Seppic).

The adjuvant may be stimulators of the innate immune system that can be given separately from the peptide such as Leukotriene B4 (LTB4) and granulocyte macrophage colony stimulating factor (GM-CSF), such as Sargramostim/Leukine (glycosylated GM-CSF) and Molgramostim (nonglycosylated GM-CSF).

Typically, a vaccine or vaccine composition is prepared as an injectable, either as a liquid solution or suspension. Injection may be subcutaneous, intramuscular, intravenous, intraperitoneal, intrathecal, intradermal, or intraepidermal. Other types of administration comprise electroporation, implantation, suppositories, oral ingestion, enteric application, inhalation, aerosolization or nasal spray or drops. Solid forms, suitable for dissolving in, or suspension in, liquid vehicles prior to injection may also be prepared. The preparation may also be emulsified or encapsulated in liposomes for enhancing adjuvant effect.

A liquid formulation may include oils, polymers, vitamins, carbohydrates, amino acids, salts, buffers, albumin, surfactants, or bulking agents. Preferably carbohydrates include sugar or sugar alcohols such as mono-, di-, tri-, oligo- or polysaccharides, or water-soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or mixtures thereof. Sucrose is most preferred. "Sugar alcohol" is defined as a C4 to C8 hydrocarbon having an —OH group and includes galactitol, inositol, mannitol, xylitol, sorbitol, glycerol, and arabitol. Mannitol is most preferred. These sugars or sugar alcohols mentioned above may be used individually or in combination. There is no fixed limit to the amount used as long as the sugar or sugar alcohol is soluble in the aqueous preparation. Preferably, the sugar or sugar alcohol concentration is between 1.0% (w/v) and 7.0% (w/v), more preferable between 2.0 and 6.0% (w/v). Preferably amino acids include levorotary (L) forms of carnitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. It is also preferred to use a buffer in the composition to minimize pH changes in the solution before lyophilization or after reconstitution. Any physiological buffer may be used, but citrate, phosphate, succinate, and glutamate buffers or mixtures thereof are preferred. Most preferred is a citrate buffer. Preferably, the concentration is from 0.01 to 0.3 molar. Surfactants that can be added to the formulation are shown in EP patent applications No. EP 0 270 799 and EP 0 268 110.

Additionally, the peptides according to the present invention may be chemically modified by covalent conjugation to a polymer to increase their circulating half-life, for example. Preferred polymers, and methods to attach them to peptides, are shown in U.S. Pat. Nos. 4,766,106; 4,179,337; 4,495,285; and 4,609,546. Preferred polymers are polyoxyethylated polyols and polyethylene glycol (PEG). PEG is soluble in water at room temperature and has the general formula:

R(O—CH2-CH2)nO—R where R can be hydrogen, or a protective group such as an alkyl or alkanol group. Preferably, the protective group has between 1 and 8 carbons, more preferably it is methyl. The symbol n is a positive integer, preferably between 1 and 1.000, more preferably between 2 and 500. The PEG has a preferred average molecular weight between 1000 and 40.000, more preferably between 2000 and 20.000, most preferably between 3.000 and 12.000. Preferably, PEG has at least one hydroxy group, more preferably it is a terminal hydroxy group. It is this hydroxy group which is preferably activated. However, it will be understood that the type and amount of the reactive groups may be varied to achieve a covalently conjugated PEG/polypeptide of the present invention.

Water soluble polyoxyethylated polyols are also useful in the present invention. They include polyoxyethylated sorbitol, polyoxyethylated glucose, polyoxyethylated glycerol (POG), etc. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in Knauf et al., 1988, and a discussion of POG/IL-2 conjugates is found in U.S. Pat. No. 4,766,106.

Another drug delivery system for increasing circulatory half-life is the liposome. The peptides and nucleic acids of the invention may also be administered via liposomes, which serve to target a particular tissue, such as lymphoid tissue, or to target selectively infected cells, as well as to increase the half-life of the peptide and nucleic acids composition. Liposomes include emulsions, foams, micelles, insoluble monolayers, liquid crystals, phospholipid dispersions, lamellar layers and the like. In these preparations, the peptide or nucleic acids to be delivered is incorporated as part of a liposome or embedded, alone or in conjunction with a molecule which binds to a receptor prevalent among lymphoid cells, such as monoclonal antibodies which bind to the CD45 antigen, or with other therapeutic or immunogenic compositions. Thus, liposomes either filled or decorated with a desired peptide or nucleic acids of the invention can be directed to the site of lymphoid cells, where the liposomes then deliver the peptide and nucleic acids compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al, 1980, and U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated. For example, liposomes carrying either immunogenic polypeptides are known to elicit CTL responses in vivo (Reddy et al., 1992; Collins et al., 1992; Fries et al., 1992; Nebel et al., 1992).

After the liquid pharmaceutical composition is prepared, it is preferably lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is preferably administered to subjects using those methods that are known to those skilled in the art.

Another aspect of the present invention relates to conjugates of the isolated peptides or isolated multimeric peptides according to the present invention. Accordingly, the isolated peptides or isolated multimeric peptides according to the present invention may be an amino acid sequence conjugated at any amino acid sidechain or within the amino acid sequence with any chemical moiety, such as any therapeutic agent, such as any immunomodulating compound.

The terms "therapeutic agent", such as "immunomodulating agent" or virus reservoir purging agent as used herein, includes but is not limited to cytokines, such as interferons, monoclonal antibodies, such as ant-PD1 antibodies, cyclophosphamide, Thalidomide, Levamisole, and Lenalidomide.

"A virus reservoir purging agent", includes but is not limited to auranofin, IL-7, prostratin, bryostatin, HDAC inhibitors, such as vorinostat, and Disulfuram.

Use of the peptides for evaluating immune responses:

The peptides according to the present invention may be used as diagnostic reagents. For example, a peptide of the invention may be used to determine the susceptibility of a particular individual to a treatment regimen which employs the peptide or related peptides, and thus may be helpful in modifying an existing treatment protocol or in determining a prognosis for an affected individual. In addition, the peptides may also be used to predict which individuals will be at substantial risk for developing a chronic virus infection.

Accordingly, the present invention relates to a method of determining the outcome for a subject exposed to a virus, comprising the steps of determining whether the subject has an immune response to one or more peptides according to the present invention.

In a preferred embodiment of the invention, the peptides as described herein can be used as reagents to evaluate an immune response. The immune response to be evaluated can be induced by using as an immunogen any agent that may result in the production of antigen-specific CTLs or HTLs that recognize and bind to the peptide(s) to be employed as the reagent. The peptide reagent need not be used as the immunogen. Assay systems that can be used for such an analysis include relatively recent technical developments such as tetramers, staining for intracellular lymphokines and interferon release assays, or ELISPOT assays.

For example, a peptide of the invention may be used in a tetramer staining assay to assess peripheral blood mononuclear cells for the presence of antigen-specific CTLs following exposure to an antigen or an immunogen. The HLA-tetrameric complex is used to directly visualize antigen-specific CTLS (see, e.g., Ogg et al., 1998; and Altman et al., 1996) and determine the frequency of the antigen-specific CTL population in a sample of peripheral blood mononuclear cells. A tetramer reagent using a peptide of the invention may be generated as follows: a peptide that binds to an HLA molecule is refolded in the presence of the corresponding HLA heavy chain and beta2-microglobulin to generate a trimolecular complex. The complex is biotinylated at the carboxyl terminal end of the heavy chain at a site that was previously engineered into the protein. Tetramer formation is then induced by the addition of streptavidin. By means of fluorescently labeled streptavidin, the tetramer can be used to stain antigen-specific cells. The cells may then be identified, for example, by flow cytometry. Such an analysis may be used for diagnostic or prognostic purposes. Cells identified by the procedure can also be used for therapeutic purposes. As an alternative to tetramers also pentamers or dimers can be used (Current Protocols in Immunology (2000) unit 17.2 supplement 35)

Peptides of the invention may also be used as reagents to evaluate immune recall responses. (see, e.g., Bertoni et al., 1997 and Perma et al., 1991.). For example, patient PBMC samples from individuals with HCV infection may be analyzed for the presence of antigen-specific CTLs or HTLs using specific peptides. A blood sample containing mononuclear cells may be evaluated by cultivating the PBMCs and stimulating the cells with a peptide of the invention. After an appropriate cultivation period, the expanded cell population may be analyzed, for example, for cytotoxic activity (CTL) or for HTL activity.

The peptides may also be used as reagents to evaluate the efficacy of a vaccine.

PBMCs obtained from a patient vaccinated with an immunogen may be analyzed using, for example, either of the methods described above. The patient is HLA typed, and peptide epitope reagents that recognize the allele-specific molecules present in that patient are selected for the analysis. The immunogenicity of the vaccine is indicated by the presence of epitope-specific CTLs and/or HTLs in the PBMC sample.

The peptides of the invention may also be used to make antibodies, using techniques well known in the art (see, e.g. CURRENT PROTOCOLS IN IMMUNOLOGY, Wiley/Greene, N.Y.; and Antibodies A Laboratory Manual, Harlow and Lane, Cold Spring Harbor Laboratory Press, 1989). Such antibodies include those that recognize a peptide in the context of an HLA molecule, i.e., antibodies that bind to a peptide-MHC complex.

In certain embodiments a first monomeric peptide and the at least one second monomeric peptide are associated via a linker; the linker may comprise any peptide linker, or peptide spacer, such as a glycine, a lysine or an arginine linker/spacer, a polyhistidinyl tag, Protein G, and Protein A but it is also possible to use a bis-maleimide linker/spacer, a disulfide linker, or a polyethylene glycol (PEG) linker. In practice, any linker found useful in peptide chemistry is also useful as a linker according to the present invention. Thus, the invention contemplates the use of "simple" linear peptides which are conjugated or fused to each other, but also peptide combinations where the individual peptides derived from a natural antigen are linked via non-peptide linkers. Use of multiple linker types are also within the scope of the present invention, and it is e.g. also a part of the invention to utilise linear peptides which include intrachain disulphide linkers.

Particularly interesting peptide combinations of the invention are set forth in the preamble to the examples.

In certain embodiments, at least one of the first and at least one second peptides in the peptide combination comprises an N- or C-terminal modification, such as an amidation, acylation, or acetylation.

Since the peptide combinations are contemplated as vaccine agents or diagnostic agents, they are in certain embodiments coupled to a carrier molecule, such as an immunogenic carrier. The peptides of the peptide combinations may thus be linked to other molecules either as recombinant fusions (e.g. via CLIP technology) or through chemical linkages in an oriented (e.g. using heterobifunctional cross-linkers) or nonoriented fashion. Linking to carrier molecules such as for example diphtheria toxin, latex beads (convenient in diagnostic and prognostic embodiments), and magnetic beads (also convenient in diagnostic and prognostic embodiments), polylysine constructs etc, are all possible according to the invention.

The immunogenic carrier is conveniently selected from carrier proteins such as those conventionally used in the art (e.g. diphtheria or tetanus toxoid, KLH etc.), but it is also possible to use shorter peptides (T-helper epitopes) which can induce T-cell immunity in larger proportions of a population. Details about such T-helper epitopes can e.g. be found in WO 00/20027, which is hereby incorporated by reference herein—all immunologic carriers and "promiscuous" (i.e. universal) T-helper epitopes discussed therein are useful as immunogenic carriers in the present invention.

In certain embodiments, the carrier is a virus like particle, i.e. a particle sharing properties with virions without being infectious. Such virus-like particles may be provided chemically (e.g. Jennings and Bachmann Ann Rev Pharmacol. Toxicol. 2009. 49:303-26 Immunodrugs: Therapeutic VLP-based vaccines for chronic diseases) or using cloning techniques to generate fusion proteins (e.g. Peabody et al. J. Mol. Biol. 2008; 380: 252-63. Immunogenic display of diverse peptides on virus-like particles of RNA phage MS2). Another example is "Remune", an HIV vaccine originally made by Immune Response Corporation, which consists of formalin inactivated HIV that has been irradiated to destroy the viral genome.

In an embodiment, a nucleic acid is encoding one or more monomeric peptide of the multimeric, such as dimeric peptide according to the invention, where the encoded first peptide and the encoded at least one second peptide of a multimeric peptide are associated via a peptide linker, including a peptide spacer, and/or a disulphide bridge. The peptide linker/spacer is typically selected from the group consisting of a glycine, an arginine, a lysine linker/spacer, or a glycine-lysine linker/spacer, but any peptide linker known in the art may be useful. The term peptide linker thus also is intended to denote coupling between the first and second peptide via a peptide bond. A peptide linker that links a first and second peptide by standard peptide bonds may also be referred to as a peptide spacer. Also, the first and second peptides may be linked via a peptide linker and a disulphide bond, as is the case when an intrachain disulphide bond is established.

In one embodiment, the nucleic acid according to the invention encodes the peptide combination, which is coupled (by fusion) to a carrier molecule, such as an immunogenic carrier; useful carriers are discussed above.

In some embodiments the linker is selected from the group consisting of a bis-maleimide linker, a disulfide linker, a polyethylene glycol (PEG) linker, a glycine linker/spacer, a lysine linker/spacer, and an arginine linker/spacer.

In some embodiments the multimeric peptide, such as a dimeric peptide contain a linker in the free amino group of the N-terminal of a monomeric peptide linking said monomeric peptide to another monomeric peptide.

In some embodiments the multimeric peptide, such as a dimeric peptide contain a linker in the free carboxyl group of the C-terminal of a monomeric peptide linking said monomeric peptide to another monomeric peptide.

At least two options for such linkers are described in A. R Jacobson et al, J. Med. Chem. 1989, 32, 1708-1717 and in D Giannotti et al, Journal of Medicinal Chemistry, 2000, Vol. 43, No. 22, the disclosures of which is hereby incorporated by reference.

Alternatively a link between the N-termini of peptides may be established by reacting with Br—$(CH_2)_n$—Br.

The length of the linker may be varied by the addition of glycine residues, for example Fmoc-NH—$CH_2CH_2$—NH-Gly-$NH_2$ may be used.

An example of such a synthesis, wherein a dimeric peptide is prepared by conjugation through succinic acid, may be as follows:

(H-Arg-Gly-Thr-Pro-Ile-Har-Gln-Asp-Trp-Gly-Asn-

Arg-Ala-Asn-Arg-Gly-Thr-Pro-Thr-Arg-Gln-Glu-

Trp-Asp-Cys-Arg-Ile-Ser-NH2Arg-Gly-Thr-Pro-Ile-

Har-Gln-Asp-Trp-Gly-Asn-Arg-Ala-Asn-Arg-Gly-Thr-

Pro-Thr-Arg-Gln-Glu-Trp-Asp-Cys-Arg-Ile-Ser-NH₂)

E(H-Arg-Gly-Thr-Pro-Thr-Har-Asn-Gly-Trp-Asp-Val-

Lys-Leu-Ser-Arg-Gly-Thr-Pro-Ile-Har-Gln-Glu-Trp-

Har-Ser-Leu-Nle-Asn-Gln-Glu-Trp-NH₂) F
(Succinic acid linker between Arg¹E and Arg¹F)

This dimer was produced from the reaction of the following 2 monomers:

Monomer E
H-Arg-Gly-Thr-Pro-Ile-Har-Gln-Asp-Trp-Gly-Asn-Arg-

Ala-Asn-Arg-Gly-Thr-Pro-Thr-Arg-Gln-Glu-Trp-Asp-

Cys-Arg-Ile-Ser-NH2Arg-Gly-Thr-Pro-Ile-Har-Gln-

Asp-Trp-Gly-Asn-Arg-Ala-Asn-Arg-Gly-Thr-Pro-Thr-

Arg-Gln-Glu-Trp-Asp-Cys-Arg-Ile-Ser-NH₂

Monomer F
H-Arg-Gly-Thr-Pro-Thr-Har-Asn-Gly-Trp-Asp-Val-Lys-

Leu-Ser-Arg-Gly-Thr-Pro-Ile-Har-Gln-Glu-Trp-Har-

Ser-Leu-Nle-Asn-Gln-Glu-Trp-NH₂

The two monomers are reacted to give a heterodimer according to the reaction scheme outlined below; where the link is between N-terminal on Arg¹ of on chain E and the N-terminal on Arg¹ in chain F.

Monomers E and F are synthesized separately on a Sieber Amid resin. The Fmoc-groups on N-terminal Gly are removed while the peptides are still on resin. The peptides are cleaved from resin. The resulting protected peptide E is reacted with succinic acid anhydride and thereafter reacted with the protected peptide F. Protective groups are subsequently removed with 95% TFA. The formed heterodimer may be purified from un-reacted monomers by conventional purification methods known to the person skilled in the art.

An example of a synthesis, wherein a dimeric peptide is prepared by conjugation through di-amino propane, may be as follows:

(H-Gly-Gly-Ala-Lys-Arg-Arg-Val-Val-Gln-Arg-Glu-

Lys-Arg-Ala-Gly-Glu-Arg-Glu-Lys-Arg-Ala-Gly-Gly)

G(H-Gly-Gly-Ile-Glu-Glu-Glu-Gly-Gly-Arg-Asp-Arg-

Asp-Arg-Gly-Gly-Glu-Gln-Asp-Arg-Asp-Arg-Gly-Gly)H
trifluoroacetate salt (Diamino propane linker
between Gly²³ and Gly²³)

This dimer was produced from the reaction of the following 2 protected monomers

Monomer G
H-Arg-Gly-Thr-Pro-Ile-Har-Gln-Asp-Trp-Gly-Asn-Arg-

Ala-Asn-Arg-Gly-Thr-Pro-Thr-Arg-Gln-Glu-Trp-Asp-

Cys-Arg-Ile-Ser-COOH

Monomer H
H-Arg-Gly-Thr-Pro-Thr-Har-Asn-Gly-Trp-Asp-Val-Lys-

Leu-Ser-Arg-Gly-Thr-Pro-Ile-Har-Gln-Glu-Trp-Har-

Ser-Leu-Nle-Asn-Gln-Glu-Trp-COOH

The two monomers G and H are reacted to give a heterodimer according to the reaction scheme outlined below; where the link is between C-terminal on Ser²⁸ of on chain G and the C-terminal on Trp³¹ in chain H.

Monomers G and H are synthesized separately on a 2-chlorotrityl resin. Boc-Gly-OH is coupled to the peptides on the resin before cleaving them of the resin. The resulting peptides are then Boc-protected, alternatively they may me acetylated before being cleaved of the resin. The resulting protected peptide G is reacted with Fmoc-diaminopropane, Fmoc is deprotected and G is coupled to the C-terminal of the protected peptide H via a peptide bond. Protective groups are subsequently removed with 95% TFA. The formed heterodimer may be purified from un-reacted monomers by conventional purification methods known to the person skilled in the art.

Method for Synthesis of Cys-Lys Bridge:

Exemplified with the preparation of BI-155-3 trifluoroacetate salt (H-Arg-Gly-Cys(2-oxo-ethyl)-Thr-Pro-Ile-Har-Gln- Asp-Trp-Gly-Asn-Arg-Ala-Asn-Arg-Gly-Thr-Pro-Thr- Arg-Gln-Glu-Trp-Asp-Cys-Arg-Ile-Ser-NH₂)A(H-Arg- Gly-Lys-Thr-Pro-Thr-Har-Asn-Gly-Trp-Asp-Val-Lys- Leu-Ser-Arg-Gly-Thr-Pro-Ile-Har-Gln-Glu-Trp-Har- Ser-Leu-Nle-Asn-Gln-Glu-Trp-NH₂)B
trifluoroacetate salt (Thioether bond
between Cys(2-oxo-ethyl) ³A and Lys³B)

This dimer was produced from the reaction of the following 2 protected monomers

Monomer A
H-Arg-Gly-Cys-Thr-Pro-Ile-Har-Gln-Asp-Trp-Gly-

Asn-Arg-Ala-Asn-Arg-Gly-Thr-Pro-Thr-Arg-Gln-

Glu-Trp-Asp-Cys-Arg-Ile-Ser-NH₂

Monomer B
H-Arg-Gly-Lys(bromoacetyl)-Thr-Pro-Thr-Har-Asn-

Gly-Trp-Asp-Val-Lys-Leu-Ser-Arg-Gly-Thr-Pro-Ile-

Har-Gln-Glu-Trp-Har-Ser-Leu-Nle-Asn-Gln-Glu-Trp-

NH₂

Or with the preparation of BI-155-4 trifluoroacetate salt (H-Gly-Ala-Lys-Arg-Arg-Val-Val-Gly-Gly-Cys(2-oxoethyl)-Gly-Gly-Ala-Lys-Arg-Arg-Val-Val-Gln-Arg- Glu-Lys-Arg-Ala-Gly-Glu-Arg-Glu-Lys-Arg-Ala-NH₂)

A(H-Gly-Lys-Gly-Gly-Ile-Glu-Glu-Glu-Gly-Gly-Arg-

-continued

Asp-Arg-Asp-Arg-Gly-Gly-Gln-Asp-Arg-Asp-Arg-NH$_2$)B
trifluoroacetate salt (Thioether bond
between Cys(2-oxo-ethyl)$^9$A and Lys$^3$B)

This dimer was produced from the reaction of the following 2 protected monomers:

Monomer A
H-Arg-Gly-Cys-Thr-Pro-Ile-Har-Gln-Asp-Trp-Gly-

Asn-Arg-Ala-Asn-Arg-Gly-Thr-Pro-Thr-Arg-Gln-

Glu-Trp-Asp-Ala-Arg-Ile-Ser-NH$_2$

Monomer B
H-Arg-Gly-Lys(bromoacetyl)-Thr-Pro-Thr-Har-Asn-

Gly-Trp-Asp-Val-Lys-Leu-Ser-Arg-Gly-Thr-Pro-Ile-

Har-Gln-Glu-Trp-Har-Ser-Leu-Nle-Asn-Gln-Glu-Trp-

NH$_2$

The 2 monomers are reacted to give a heterodimer according to the reaction scheme outlined below; where the link is created between Lys$^3$ (bromoacetyl) side chain on chain B and Cys in chain A.

At neutral pH and room temperature, bromoacetyl moieties in buffered aqueous solutions are very reactive towards SH-containing moieties, such as the thiol group in cysteine. Thus, if a cysteine is present on the other peptide sequence, the SH will attack the bromoacetyl to form a intermolecular thioether bridge. When the reaction is buffered with a sodium-containing buffer, such as NaHCO$_3$, the only byproduct of the reaction is NaBr, an innocuous salt.

The formed heterodimer may be purified from un-reacted monomers by conventional purification methods known to the person skilled in the art.

Method for synthesis of oxime bond between two peptide sequences, an intermolecular bond:

Exemplified with the preparation of BI-155 trifluoroacetate salt (H-Arg-Gly-Dpr(Ser)-Thr-Pro-Thr-Har-Asn-Gly-Trp- Asp-Val-Lys-Leu-Ser-Arg-Gly-Thr-Pro-Ile-Har-Gln- Glu-Trp-Har-Ser-Leu-Nle-Asn-Gln-Glu-Trp-NH$_2$)D(H-

Arg-Gly-Dpr(Aoa)-Thr-Pro-Ile-Har-Gln-Asp-Trp-Gly-

Asn-Arg-Ala-Asn-Arg-Gly-Thr-Pro-Thr-Arg-Gln-Glu-

Trp-Asp-Cys-Arg-Ile-Ser-NH$_2$)C
trifluoroacetate salt (oxime is created
between Dpr(Ser)$^3$D and Dpr(Aoa)$^3$C)

This dimer is produced from the reaction of the following two monomers:

Monomer C
H-Arg-Gly-Dpr(Aoa)-Thr-Pro-Ile-Har-Gln-Asp-Trp-

Gly-Asn-Arg-Ala-Asn-Arg-Gly-Thr-Pro-Thr-Arg-

Gln-Glu-Trp-Asp-Cys-Arg-Ile-Ser-NH$_2$

Monomer D
H-Arg-Gly-Dpr(Ser)-Thr-Pro-Thr-Har-Asn-Gly-Trp-

Asp-Val-Lys-Leu-Ser-Arg-Gly-Thr-Pro-Ile-Har-Gln-

Glu-Trp-Har-Ser-Leu-Nle-Asn-Gln-Glu-Trp-NH$_2$

The two monomers are reacted to give a heterodimer according to the reaction scheme outlined below; where the link is created between Dpr(Aoa)$^3$ side chain on chain C and oxidized Dpr(Ser) in chain D.

After removal of the Mtt group from Lys and while the peptide was still attached to the resin aminooxyacetylated (AoA) monomer C was synthesized by coupling aminooxyacetic acid to Lys. The peptide was then cleaved from the solid phase support and purified by conventional purification methods. The monomer D was, after cleavage from resin and purification, created by oxidation of the serinyl diaminopropionic acid residue (Dpr(Ser)) with periodate to the aldehyde function. Equimolar amounts of monomer A and B were dissolved in acetonitrile and acetate buffer (pH 4). After reaction for 16 h at room temperature, the product C-oxime-D was isolated by conventional purification methods known to the person skilled in the art.

Dpr=diaminopropionic acid
Fmoc-Dpr (Boc-Ser(tBu))-OH Merck 04-12-1186
Method for Synthesis of Dimers with PEG-Linker:

A multimeric, such as dimeric peptide, such as a heterodimeric peptide may be synthesized by, but are not restricted to the following protocol:

To the peptidyl resin containing deblocked Asp or Glu residue (monomer 1) is added HBTU, DIPEA and Trt-amino PEG amine in DMF. The mixture is allowed to couple over night. The resin is filtered from the solution and washed by standard protocol. The Trt group is removed from the Trt-PEGylated peptide. The monomer 2 containing deblocked Asp or Glu residue is then coupled to the exposed amino group using HBTU and DIPEA. After cleavage the desired product is purified using any suitable technique to give the desired multimeric peptide.

In some embodiments the isolated monomeric peptide contain intramolecular bonds, such as in the form of intramolecular Cys-Cys bonds. It is to be understood that the "intramolecular bond", used interchangeably with "intrachain bond", is a bond between two different amino acids within the same peptide chain, which however is not necessarily adjacent to each other in the peptide sequence. Accordingly, in some embodiments, the isolated multimeric peptide according to the invention may contain both intramolecular bonds within one or more of the monomers, as well as an intermolecular bond between two chains of the multimeric peptide, such as a dimer. This intramolecular bond may be in the form of Cys-Cys bonds formed with cysteine residues within the same peptide sequence. In some embodiments the monomer contains an intramolecular bond derived from a Lys residue or other amino acid residue, such as a Ser, Cys, Asp or Glu that make the bond, such as a thioether bond or an oxime bond or through a PEG linker, to an amino acid residue on the other monomer peptide sequence.

Method for Synthesis of Multimeric Peptides with PolyLys or MAPS:

PolyLys or MAPS (multiple antigen peptides)—has been extensively used over the last 20 years as a carrier protein to produce strong immunogenic response. The MAP system utilizes a peptidyl core of three or more radially branched lysine core to form a backbone for which the epitope sequences of interest can be built parallel using standard solid-phase chemistry.

The MAP system is a commercial product available from several companies such as AnaSpec, Bio-synthesis Inc. and others. The product, as offered in the catalogue only allows attachment of two (identical) peptide sequence to the polyLys core. It is however possible also to link two different peptide sequences by using different protecting groups for alfa- and epsylon-amino functional groups of lysine on the two different peptide sequences.

Use of the MAP system has been described in references including: Wang, C. Y et al. "Long-term high-titer neutralizing activity induced by octameric synthetic HIV antigen" Science 254, 285-288 (1991). Posnett, D. et al. "A novel method for producing anti-peptide antibodies" J. Biol. Chem. 263, 1719-1725 (1988), and in Tam, J. P. "Synthetic peptide vaccine design: synthesis and properties of a high-density multiple antigenic peptide system" PNAS USA 85, 5409-5413 (1988).

The MAP system could also be prepared by chemical (thioether, oxime, hydrazone) ligation of appropriately functionalized tetra- or octavalent polylysine constructs with the peptide antigen. By the use of this chemical ligation, the two peptide sequences being linked together would not have to be identical as they are synthesized separately.

Additionally a novel application of the MAP-based system is to synthesize on solid support a "probe" containing a poly(ethylene glycol) (PEG) chain in the dendritic arms of MAP.

Use of the MAP system will increase the size of a multimeric complex and may increase the immunogenic response.

Methods for the Synthesis of Multimeric Peptides Using PEG:

Suitable Multi-Arm Activated PEG to be used for a PEG linker are commercially available, e.g. a compound with the following structure:

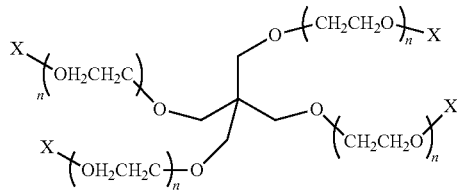

Wherein X may be ethanethiol —CH2CH2SH (could be used to form S—S bridge with the epitope or a thioether link) or propylamine —CH2CH2CH2NH2, among others. These handles preferably allows for the linking of two identical peptide sequences and may be seen as a polymonomeric epitope presenting construct. One could, however, anchor a dimer (two epitopes linked together) to the PEG above.

Method for Synthesis of Peptide-Poly-L-Lys (PLL)-Polyethylene Glycol (PEG) Construct:

Peptide—PLL-PEG constructs, may be synthesized by, but are not restricted to the following protocol:

Fmoc-Poly-L-Lys-resin (a commercial product) is de-protected with 20% piperifine-DMF. Fmoc-NH-PEG$_4$-COOH, in a mixed solvent of $CH_2Cl_2$-NMP is added followed by HBTU and DIPEA and the reaction is allowed to proceed for 24 h. The resultant pegylated poly-L-Lys-resin is washed and the pegylation step is repeated. The reaction is monitored by Kaiser's ninhydrin test until a negative reading is obtained. After de-protection of Fmoc group, four identical peptide chains are synthesized directly on the branched poly-L-Lys-polyethylene glycol core by a stepwise solid-phase procedure. All residues activated with HBTU and DIPEA are allowed to couple for 2 h. The coupling is monitored by Kaiser's ninhydrin test and is repeated if needed. After cleavage the desired product is purified using any suitable technique to give the desired peptide-construct.

Table 8 Specific peptides not part of the present invention. (Amino acids underlined refers to place of linker in dimeric molecules; Letter C in a large font refers to a cysteine residue optionally involved in an intramolecular bond with another cysteine residue in the same peptide sequence. Homoarginine is abbreviated Har, Norleucine is abbreviated as Nle or alternatively with the single letter "Z", N-ε-methylated Lys is abbreviated Lys(Me), Citrulline is abbreviated with the single letter "B", diaminopropionic acid is abbreviated with Dpr and serinyl diaminopropionic acid is abbreviated Dpr(Ser). Flu; abbreviation for Influenza).

Table 8 represent peptides not part of the present invention. These peptides relates to monomeric peptides as well as multimeric peptides comprising two or more of these monomeric peptides, each monomeric peptide independently consisting of not more than 60 amino acids with the following structure $$X^1-X^2-X^3-X^4-X^5-X^6 \quad \text{(formula III)},$$

wherein $X^1$, $X^3$ and optional moiety $X^5$ independently defines a linear sequence of any 1, 2, 3, 4, or 5 amino acid independently selected from glycine, arginine, norleucine, glutamine, serine, lysine, tryptophan, cysteine, or a derivative thereof; $X^2$, $X^4$, and optional moiety $X^6$ each independently defines a linear sequence of 5-17 amino acids, each having more than 50% sequence identity to a specific natural antigen, said monomeric peptides being covalently joined by one or more intermolecular bond.

| Chain | Antigen | Reference ID | X1 | X2 | X3 | X4 | X5 | X6 | X2-SEQ | X4-SEQ | X6-SEQ | Protein |
|---|---|---|---|---|---|---|---|---|---|---|---|---|
| | Flu | BI100_CGnat | RR | SLLTEVETP | GCG | VETPIR | G | TPIRNEWG | 2-10 | 7-12 | 9-16 | M2 |

Position with reference to positions in SEQ ID NO: 200, SEQ ID NO: 202, and SEQ ID NO: 203.

-continued

| Chain | Antigen | Reference ID | X1 | X2 | X3 | X4 | X5 | X6 | X2-SEQ | X4-SEQ | X6-SEQ | Protein |
|---|---|---|---|---|---|---|---|---|---|---|---|---|
| | Flu | BI100_CG | RR | SLZTDIETP | GCG | IDTPIR | G | TPIBQDWG | 2-10 | 7-12 | 9-16 | M2 |
| | Flu | BI100-CGcyc | WWGC | TDIET | CG | IDTPIR | G | TPIBQDWG | 5-9 | 7-12 | 9-16 | M2 |
| | Flu | BI100-Cyc_2 | RRG | CSLLT | C | SLLTEVQTPIRN | GRR | SEWGSRSN | 2-5 | 2-13 | 13-20 | M2 |
| A | Flu | BI150-Dimer | RRZC | SLLTEVQTPIRN | GRR | VETPIRN | | | 2-13 | 7-13 | — | M2 |
| B | Flu | BI150-Dimer | WWQC | TPIRSEWGCRSN | GRR | SNDSS | G | | 9-20 | 19-23 | — | M2 |
| A | Flu | BI150-new | WW | SLZTDIETP | GCG | IDTPIR | G | TPIBQDWG | 2-10 | 7-12 | 9-16 | M2 |
| B | Flu | BI150-new | RR (Har) | IDTPIR | G | TPIBQDWG | KG | SLZTDIETPG | 7-12 | 9-16 | 2-11 | M2 |
| A | Flu | BI150-2mod | R | SLZTDIETP | Dpr | IDTPIR | G | TPIBQDWG | 2-10 | 7-12 | 9-16 | M2 |
| B | Flu | BI150-2mod | RR | IDTPIR | GG | TPI(Har)QEW | Dpr (Ser) | SLZTDIETPG | 7-12 | 9-15 | 2-11 | M2 |
| A | Flu | BI150-dim_2 | RR | SLZTDIETP | GCG | IDTPIR | G | TPIBQDWG | 2-10 | 7-12 | 9-16 | M2 |
| B | Flu | BI150-dim_2 | Har | IDTPIR | G | TPIBQDWG | KG | SLZTDIETPG | 7-12 | 9-16 | 2-11 | M2 |
| | HIV | BI450-AdjBT1 | W_DWGC | AKRRV | CGG | AKRRVVQREKRA | | | 501-505 | 501-512 | — | gp120 |
| | HIV | BI450-AdjBT2 | W_DWGC | IEEEG | CGG | IEEEGGERDR | | | 222-226 | 222- | — | gp41 |
| | HIV | | CGG | AKRRVV | GG | AKRRVV | G | QREKRAV | 501-506 | 501-506 | 507-513 | |
| | HIV | | CGGG | DQQLL | GG | AEEEIV | GG | IEEEGGERDRDR | 257-261 | 266-271 | 221-232 | |
| | HIV | | CGG | AKRRVV | GG | AKRRVV | GG | QREKR | 501-506 | 501-506 | 507-511 | |
| | HIV | | CGGG | DQQLL | GG | AEEEIV | GG | IEEEGG | 257-261 | 266-271 | 222-227 | |
| | HIV | | CGG | AEEEVV | GG | DQQLL | | | 266-271 | 257-261 | — | |
| | HIV | | GCGG | AKRRVV | GG | AKRRVV | | | 501-506 | 501-506 | — | |
| A | HIV | BI400-B (a-chain) | G | AKRRVV | GGCGG | AKRRVVQREKRA | G | EREKRA | 501-506 | 501-512 | 507-512 | gp120 |
| B | HIV | BI400-B (b-chain) | GKG | GIEEE | GG | RDRDR | GG | EQDRDR | 221-225 | 229-233 | 228-233 | gp41 |

-continued

| Chain | Antigen | Reference ID | X1 | X2 | X3 | X4 | X5 | X6 | X2-SEQ | X4-SEQ | X6-SEQ | Protein |
|---|---|---|---|---|---|---|---|---|---|---|---|---|
| E | HIV | | GG | AKRRVVQREKRA | G | EREKRA | | | 501-512 | 507-512 | | gp120 |
| F | HIV | | G | GIEEE | GG | RDRDR | GG | EQDRDR | 221-225 | 229-233 | 228-233 | gp41 |
| G | HIV | | GG | AKRRVVQREKRA | G | EREKRA | GG | | 501-512 | 507-512 | | gp120 |
| H | HIV | | G | GIEEE | GG | RDRDR | GG | EQDRDRGG | 221-225 | 229-233 | 228-235 | gp41 |
| A | HIV | 400-Seq B (a-chain) | G | AKRRVV | GGCGG | AKRRVVQREKRA | G | EREKRA | 501-506 | 501-512 | 507-512 | gp120 |
| B | HIV | 400-Seq B (b-chain) | GKG | GIEEE | GG | RDRDR | GG | QDRDR | 221-225 | 229-233 | 229-233 | gp41 |
| D | HIV | 400-Seq B* (a-chain) | G | AKRRVV | GG(Dpr(Ser))GG | AKRRVVQREKRA | G | EREKRA | 501-506 | 501-512 | 507-512 | gp120 |
| C | HIV | 400-Seq B* (b-chain) | GKG | GIEEE | GG | RDRDR | GG | QDRDR | 221-225 | 229-233 | 229-233 | gp41 |
| A | HIV | BI400-Bu1 (a-chain) | G | AKRRVV | GGCGG | AKRRVVQREKRA | G | EREKRA | 501-506 | 501-512 | 507-512 | gp120 |
| B | HIV | BI400-Bu1 (b-chain) | GKG | GIEEE | GG | ERDRDR | GG | QDRDR | 221-225 | 228-233 | 229-233 | gp41 |
| A | HIV | BI400-Bu2 (a-chain) | G | AKRRVV | GGCGG | AKRRVVEREKRA | G | QREKRA | 501-506 | 501-512 | 507-512 | gp120 |
| B | HIV | BI400-Bu2 (b-chain) | GKG | GIEEE | GG | QDRDR | GG | RDRDR | 221-225 | 229-233 | 229-233 | gp41 |
| A | HIV | BI400-Bu3 (a-chain) | G | AKRRVV | GGCGG | AKRRVVEREKRA | G | QREKRA | 501-506 | 501-512 | 507-512 | gp120 |
| B | HIV | BI400-Bu3 (b-chain) | GKG | GIEEE | GG | EQDRDR | GG | ERDRD | 221-225 | 228-233 | 228-232 | gp41 |
| A | HIV | SEQ400_B (Cyc) | GC | AKRRVV | CGGKG | AKRRVVQREKRA | G | EREKRA | 501-506 | 501-512 | 507-512 | gp120 |

-continued

| Chain | Antigen | Reference ID | X1 | X2 | X3 | X4 | X5 | X6 | X2-SEQ | X4-SEQ | X6-SEQ | Protein |
|---|---|---|---|---|---|---|---|---|---|---|---|---|
| B | HIV | SEQ400_B (Cyc) | GKG | GIEEE | GG | RDRDR | GG | EQDRDR | 221-225 | 229-233 | 228-233 | gp41 |
| A | HIV | SEQ400_B (Cyc) | GC | AKRRVV | CGG<u>K</u>G | GAKRRVVQREKRA | G | EREKRA | 501-506 | 501-512 | 506-512 | gp120 |
| B | HIV | SEQ400_B (Cyc) | G<u>C</u>GG | IEEEGGRDRDR | GG | QDRDR | | | 222-233 | 229-233 | | gp41 |
| A | HIV | BI400-bu1 (Cyc) | G | CAKRRVVC | GG<u>K</u>GG | AKRRVVQREKRA | G | EREKRA | 501-506 | 501-512 | 507-512 | gp120 |
| B | HIV | BI400-bu1 (Cyc) | <u>C</u>GG | IEEEGGERDRDR | GG | QDRDR | | | 222-233 | 229-233 | | gp41 |
| A | HIV | BI400-bu2 (Cyc) | G | CAKRRVVC | GG<u>K</u>GG | AKRRVVEREKRA | G | QREKRA | 501-506 | 501-512 | 507-512 | gp120 |
| B | HIV | BI400-bu2 (Cyc) | <u>C</u>GG | IEEEGGQDRDR | GG | RDRDR | | | 222-233 | 229-233 | | gp41 |
| A | HIV | BI400-bu3 (Cyc) | G | CAKRRVVC | GG<u>K</u>GG | AKRRVVEREKRA | G | QREKRA | 501-506 | 501-512 | 507-512 | gp120 |
| B | HIV | BI400-bu3 (Cyc) | <u>C</u>GG | IEEEGGEQDRDR | GG | RDRDR | | | 222-233 | 229 233 | | gp41 |
| A | HIV | BI400-rev (Cyc) | G | CAKRRVVC | GG<u>K</u>GG | AKRRVVQREKRA | G | EREKRA | 501-506 | 501-512 | 507-512 | gp120 |
| B | HIV | BI400-rev (Cyc) | <u>C</u>GG | EEEIGGRDRD | GG | RDRDQ | | | 222-233 | 229-233 | | gp41 |
| A | HIV | BI450-1 (a-chain) | GG | RLEPWKH | G<u>C</u> | GSQPKTA | G | HPGSQ | 7-13 | 15-21 | 13-17 | Tat |
| B | HIV | BI450-1 (b-chain) | GG | FHSQV | <u>C</u> | FITKGLGISYGRK | | | 32-36 | 38-50 | — | Tat |
| A | HIV | BI450-1_2 (a-chain) | | RLEPWKH | G<u>C</u> | GSQPKTA | GWK | HPGSQ | 7-13 | 15-21 | 13-17 | Tat |
| B | HIV | BI450-1_2 (b-chain) | <u>C</u> | FITKGLGISY | G | FITKGLGISYGRK | | | 38-47 | 38-50 | | Tat |
| A | HCV | BI350-1 (a-chain) | RR | LLADARV<u>C</u>S | GG | LLADARVSA | | | 342-350 | 342-350 | | E2 |

-continued

| Chain | Antigen | Reference ID | X1 | X2 | X3 | X4 | X5 | X6 | X2-SEQ | X4-SEQ | X6-SEQ | Protein |
|---|---|---|---|---|---|---|---|---|---|---|---|---|
| B | HCV | BI350-1 (b-chain) | R | GV(Nle)AGIAYFS | C | GVLAGIAYYS | | | 163-172 | 163-172 | | E1 |
| A | HCV | BI350-1mod1 | RR | GNWAKVL | K | NWAKVI | | | 366-372 | 367-372 | — | E1 |
| B | HCV | BI350-1mod1 | RRG | LLADARV | GCG | SGADRV | CS | | 342-348 | 342-348 | — | E2 |
| A | HCV | BI350-1mod2 | RR | GNWAKVL | Dpr | NWAKVI | | | 366-372 | 367-372 | — | E1 |
| B | HCV | BI350-1mod2 | RRG | LLADARV | G(Dpr(Ser))G | SGADRV | CS | | 342-348 | 342-348 | — | E2 |
| A | HCV | | RR | GNWAKVL | Lys(Me) | NWAKVI | | | 366-372 | 367-372 | — | E1 |
| B | HCV | | RRG | LLADARV | GEG | SGADRV | CS | | 342-348 | 342-348 | — | E2 |
| A | HCV | | RR | GNWAKVL | Lys(Me) | NWAKVI | | | 366-372 | 367-372 | — | E1 |
| B | HCV | | RRG | LLADARV | GDG | SGADRV | CS | | 342-348 | 342-348 | — | E2 |
| A | HCV | | RR | GNWAKVL | E | NWAKVI | | | 366-372 | 367-372 | — | E1 |
| B | HCV | | RRG | LLADARV | G(Lys(Me))G | SGADRV | CS | | 342-348 | 342-348 | — | E2 |
| A | HCV | | RR | GNWAKVL | D | NWAKVI | | | 366-372 | 367-372 | — | E1 |
| B | HCV | | RRG | LLADARV | G(Lys(Me))G | SGADRV | CS | | 342-348 | 342-348 | — | E2 |

Position with reference to positions in SEQ ID NO: 200, SEQ ID NO: 202, and SEQ ID NO: 203.

SPECIFIC EMBODIMENTS OF THE INVENTION

In some embodiments the isolated peptide according to the present invention has a total of not more than 60 amino acids.

In some embodiments the sequence of amino acids defined by $(Z^1-Z^2)_1-Z^3-(Z^4-Z^5)_2-Z^6-(Z^7-Z^8)_3-Z^9-(Z^{10}-Z^{11})_4-Z^{12}$ is not found in any native sequence of a protein.

In some embodiments the peptide according to the present invention is demonstrated to translocate across a plasma membrane in the assay based on biotinylation of peptides as described in example 5.

In some embodiments $Z^3$, and optional $Z^6$, $Z^9$ and $Z^{12}$ defines an amino acid sequence identical to the native sequence of a known antigen.

In some embodiments $Z^3$, and optional $Z^6$, $Z^9$ and $Z^{12}$ defines an amino acid sequence not identical to the native sequence of any known antigen.

In some embodiments $Z^3$, and optional $Z^6$, $Z^9$ and $Z^{12}$ defines any chemical moiety, which is any therapeutical compound, such as an immunomodulating compound, such as a Cox-2 inhibitor.

In some embodiments the peptide according to the present invention is capable of inducing a T-lymphocyte response.

In some embodiments the peptide according to the present invention is capable of inducing a CD4+ and/or a CD8+ T-lymphocyte response.

In some embodiments the antigen is a viral protein, such as a capsid protein.

In some embodiments the viral protein is selected from a protein of the Hepatitis C virus, such as a core protein; protein of influenza virus, such as an M2 protein.

In some embodiments the viral protein of Hepatitis C virus is selected from HCV consensus sequence of genotype 1, such as subtypes 1a and 1b, genotype 2 such as 2a and 2b and genotype 3, such as 3a.

In some embodiments, in the peptide according to the present invention, the specific natural antigen is a protein or peptide sequence derived from a disease antigen, such as an infectious agent, such as bacteria, virus, parasite, fungus, or cancer antigens such as oncogene (lung, stomach, breast cancer) or an antigen causing an autoimmune disease such as diabetes, multiple sclerosis (MS), celiac disease, Myalgic Encephalomyelitis (ME), psoriasis, and/or Crohn's Disease.

Accordingly confirmed and suspected autoimmune diseases, where relevant antigens may be derived include Achlorhydra Autoimmune Active Chronic Hepatitis, Acute Disseminated Encephalomyelitis, Acute hemorrhagic leukoencephalitis, Addison's Disease, Agammaglobulinemia, Alopecia greata, Amyotrophic Lateral Sclerosis, Ankylosing Spondylitis, Anti-GBM/TBM Nephritis, Antiphospholipid syndrome, Antisynthetase syndrome, Arthritis, Atopic allergy, Atopic Dermatitis, Autoimmune Aplastic Anemia, Autoimmune cardiomyopathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome Types I, II, & III, Autoimmune progesterone dermatitis, Autoimmune thrombocytopenic purpura, Autoimmune uveitis, Balo disease/Balo concentric sclerosis, Bechets Syndrome, Berger's disease, Bickerstaff's encephalitis, Blau syndrome, Bullous Pemphigoid, Castleman's disease, Chagas disease, Chronic Fatigue Immune Dysfunction Syndrome, Chronic inflammatory demyelinating polyneuropathy, Chronic recurrent multifocal ostomyelitis, Chronic lyme disease, Chronic obstructive pulmonary disease, Churg-Strauss syndrome, Cicatricial Pemphigoid, Coeliac Disease, Cogan syndrome, Cold agglutinin disease, Complement component 2 deficiency, Cranial arteritis, CREST syndrome, Crohns Disease (one of two types of idiopathic inflammatory bowel disease "IBD"), Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Dressler's syndrome, Discoid lupus erythematosus, Eczema, Endometriosis, Enthesitis-related arthritis, Eosinophilic fasciitis, Epidermolysis bullosa acquisita, Erythema nodosum, Essential mixed cryoglobulinemia, Evan's syndrome, Fibrodysplasia ossificans progressiva, Fibromyalgia, Fibromyositis, Fibrosing aveolitis, Gastritis, Gastrointestinal pemphigoid, Giant cell arteritis, Glomerulonephritis, Goodpasture's syndrome, Graves' disease, Guillain-Barré syndrome (GBS), Hashimoto's encephalitis, Hashimoto's thyroiditis, Haemolytic anaemia, Henoch-Schonlein purpura, Herpes gestationis, Hidradenitis suppurativa, Hughes syndrome (See Antiphospholipid syndrome), Hypogammaglobulinemia, Idiopathic Inflammatory Demyelinating Diseases, Idiopathic pulmonary fibrosis, Idiopathic thrombocytopenic purpura (See Autoimmune thrombocytopenic purpura), IgA nephropathy (Also Berger's disease), Inclusion body myositis, Inflammatory demyelinating polyneuopathy, Interstitial cystitis, Irritable Bowel Syndrome (IBS), Juvenile idiopathic arthritis, Juvenile rheumatoid arthritis, Kawasaki's Disease, Lambert-Eaton myasthenic syndrome, Leukocytoclastic vasculitis, Lichen planus, Lichen sclerosus, Linear IgA disease (LAD), Lou Gehrig's Disease (Also Amyotrophic lateral sclerosis), Lupoid hepatitis, Lupus erythematosus, Majeed syndrome, Ménière's disease, Microscopic polyangiitis, Miller-Fisher syndrome, Mixed Connective Tissue Disease, Morphea, Mucha-Habermann disease, Muckle-Wells syndrome, Multiple Myeloma, Multiple Sclerosis, Myasthenia gravis, Myositis, Narcolepsy, Neuromyelitis optica (Also Devic's Disease), Neuromyotonia, Occular cicatricial pemphigoid, Opsoclonus myoclonus syndrome, Ord thyroiditis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis, Pemphigus, Pemphigus vulgaris, Pernicious anaemia, Perivenous encephalomyelitis, POEMS syndrome, Polyarteritis nodosa, Polymyalgia rheumatica, Polymyositis, Primary biliary cirrhosis, Primary sclerosing cholangitis, Progressive inflammatory neuropathy, Psoriasis, Psoriatic Arthritis, Pyoderma gangrenosum, Pure red cell aplasia, Rasmussen's encephalitis, Raynaud phenomenon, Relapsing polychondritis, Reiter's syndrome, Restless leg syndrome, Retroperitoneal fibrosis, Rheumatoid arthritis, Rheumatoid fever, Sarcoidosis, Schizophrenia, Schmidt syndrome, Schnitzler syndrome, Scleritis, Scleroderma, Sjögren's syndrome, Spondyloarthropathy, Sticky blood syndrome, Still's Disease, Stiff person syndrome, Subacute bacterial endocarditis (SBE), Susac's syndrome, Sweet syndrome, Sydenham Chorea, Sympathetic ophthalmia, Takayasu's arteritis, Temporal arteritis (also known as "giant cell arteritis"), Tolosa-Hunt syndrome, Transverse Myelitis, Ulcerative Colitis (one of two types of idiopathic inflammatory bowel disease "IBD"), Undifferentiated connective tissue disease, Undifferentiated spondyloarthropathy, Vasculitis, Vitiligo, Wegener's granulomatosis, Wilson's syndrome, and Wiskott-Aldrich syndrome.

In some embodiments, in the peptide according to the present invention, the specific natural antigen is a viral protein, such as a structural protein, such as a capsid protein, a regulatory protein, an enzymatic protein, and a proteolytic protein.

In some embodiments, in the peptide according to the present invention, the viral protein is a protein, such as a structural protein, such as a core or envelope protein, of a virus selected from the Hepatitis C virus; influenza virus such as an M2 protein, human immunodeficiency virus (HIV), cytomegalovirus (CMV), and Human papillomavirus (HPV).

In some embodiments, in the peptide according to the present invention, the viral protein is a viral protein of Hepatitis C virus selected from any one HCV consensus sequence of a specific genotype, such as 1, such as subtypes is and 1b, genotype 2, such as 2a and 2b, genotype 3, such as 3a, genotype 4, genotype 5, and genotype 6.

In some embodiments the peptide according to the present invention is of 19-60 amino acids, such as of 20-60 amino acids, such as of 21-60 amino acids, such as of 22-60 amino acids, such as of 23-60 amino acids, such as of 24-60 amino acids, such as of 25-60 amino acids, such as of 26-60 amino acids, such as of 27-60 amino acids, such as of 28-60 amino acids, such as of 29-60 amino acids, such as of 30-60 amino acids, such as of 31-60 amino acids, such as of 32-60 amino acids, such as of 33-60 amino acids, such as of 34-60 amino acids, such as of 35-60 amino acids.

In some embodiments the peptide according to the present invention is of 18-60 amino acids, such as 18-59 amino acids, such as 18-58 amino acids, such as 18-57 amino acids, such as 18-56 amino acids, such as 18-55 amino acids, such as 18-54 amino acids, such as 18-53 amino acids, such as 18-52 amino acids, such as 18-51 amino acids, such as 18-50 amino acids, such as 18-49 amino acids, such as 18-48 amino acids, such as 18-47 amino acids, such as 18-46 amino acids, such as 18-45 amino acids, such as 18-44 amino acids, such as 18-43 amino acids, such as 18-42 amino acids, such as 18-41 amino acids, such as 18-40 amino acids, such as 18-39 amino acids, such as 18-38 amino acids, such as 18-37 amino acids, such as 18-35 amino acids, such as of 18-34 amino acids, such as of 18-33 amino acids, such as of 18-32 amino acids, such as of 18-31 amino acids, such as of 18-30 amino acids, such as of 18-29 amino acids, such as of 18-28 amino acids, such as of 18-27 amino acids, such as of 18-26 amino acids, such as of 18-25 amino acids, such as of 18-24 amino acids, such as of 18-23 amino acids, such as of 18-22 amino acids, such as of 18-21 amino acids, such as of 18-20 amino acids, such as of 18-19 amino acids.

In some embodiments in the peptide according to the present invention, the monomeric peptide contain one or more intramolecular bond, such as one or more Cys-Cys bond.

In some embodiments in the peptide according to the present invention, the monomeric peptide has delayed proteolytic degradation in the N-terminal, such as by incorporation of the first 1, 2, or 3 amino acids in the N-terminal in the D-form, or by incorporation of the first 1, 2, or 3 amino acids in the N-terminal in beta or gamma form.

In some embodiments, in the multimeric, such as a dimeric peptide according to the present invention, the two or more monomeric peptides are identical in sequence.

In some embodiments, in the multimeric, such as dimeric peptide according to the present invention, the two or more monomeric peptides are different in sequence.

In some embodiments, in the multimeric, such as dimeric peptide according to the present invention, one, two or more of the peptide strands of the multimeric, such as dimeric peptide has delayed proteolytic degradation in the N-terminal, such as by incorporation of the first 1, 2, or 3 amino acids in the N-terminal in the D-form, or by incorporation of the first 1, 2, or 3 amino acids in the N-terminal in beta or gamma form.

In some embodiments, in the multimeric, such as dimeric peptide according to the present invention, the linker is placed within any sequence selected from $Z^1, Z^2, Z^3, Z^4, Z^5, Z^6, Z^7, Z^8, Z^9, Z^{10}, Z^{11}$, and $Z^{12}$, such as in $Z^1, Z^2, Z^3, Z^4, Z^5, Z^6, Z^7, Z^8, Z^9, Z^{10}, Z^{11}$, and $Z^{12}$ of the first monomeric peptide to anywhere on the at least one second monomeric peptide, such as within the sequence of $Z^1, Z^2, Z^3, Z^4, Z^5, Z^6, Z^7, Z^8, Z^9, Z^{10}, Z^{11}$, and $Z^{12}$.

In some embodiments, in the multimeric, such as dimeric peptide according to the present invention, the linker is placed at an amino acid position selected from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 of the first monomeric peptide to a position selected from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 of the at least one second monomeric peptide.

In some embodiments, in the multimeric, such as dimeric peptide according to the present invention, the multimeric, such as dimeric peptide contain a helper epitope of at least 12 amino acids, such as at least 13, 14, 15 or 17 amino acids, which helper epitope consist of a combined sequence of amino acids, which is a sequence of amino acids from a first specific continuous antigenic peptide sequences, and a sequence of amino acids from at least one second specific continuous antigenic peptide sequence of the same or different protein derived from the same virus, any different virus, or any disease antigen, such as between 2-12 amino acids from the first specific continuous antigenic peptide sequences and 2-12 amino acids from the at least one second specific continuous antigenic antigenic peptide sequence.

In some embodiments, in the isolated peptide according to the present invention, the peptide contain a helper epitope of at least 12 amino acids, such as at least 13, 14, 15 or 17 amino acids, which helper epitope consist of a combined sequence of amino acids, which is a sequence of amino acids from a first specific continuous antigenic peptide sequences, and a sequence of amino acids from at least one second specific continuous antigenic peptide sequence of the same or different protein derived from the same virus, any different virus, or any disease antigen, such as between 2-12 amino acids from the first specific continuous antigenic peptide sequences and 2-12 amino acids from the at least one second specific continuous antigenic antigenic peptide sequence.

It is to be understood that an epitope may not only be present within the sequence of the monomeric peptide. An epitope may also be present with a combination of amino acids of the first and the at least one second monomeric peptide in a multimeric, such as dimeric peptide sequence, wherein this combination of amino acids forms a sequence that span from the first to the at least one second monomeric peptide sequence. This epitope may be a continuous sequence of amino acids or it may be a three-dimensional epitope with amino acids found in both monomeric peptides.

In some embodiments, in the multimeric, such as dimeric peptide according to the present invention, the intermolecular bond is a disulfide (S—S) bond between two Cys residues.

In some embodiments, in the multimeric, such as dimeric peptide according to the present invention, the intermolecular bond is a methylated peptide bond between a N-ε-methylated Lys side-chain and the side-chain of an Asp or Glu residue.

In some embodiments, in the multimeric, such as dimeric peptide according to the present invention, the intermolecular bond is a thioether bond between a Cys residue in the first monomeric peptide and a modified Lys residue in the at least one second monomeric peptide.

In some embodiments, in the multimeric, such as dimeric peptide according to the present invention, the intermolecular bond is an oxime bond.

In some embodiments, in the multimeric, such as dimeric peptide according to the present invention, the intermolecular bond is an oxime bond between a derivatized Lys residue in the first monomeric peptide and a derivatized Ser residue in the at least one second monomeric peptide.

In some embodiments, in the multimeric, such as dimeric peptide according to the present invention, the intermolecular bond is an oxime bond between a derivatized lysine, ornitine or diaminopropionic acid residue in the first monomeric peptide and a derivatized serine moiety, such as a serine residue, such as in a serinyl diaminopropionic acid residue, such as in a serinyl lysin residue or such as in a serinyl ornitine residue, in the at least one second monomeric peptide.

In some embodiments, in the multimeric, such as dimeric peptide according to the present invention, the monomeric peptides are linked by a polyethylene glycol (PEG) linker, such as through an Asp or a Glu residue in the first monomeric peptide and an Asp or a Glu residue in the at least one second monomeric peptide.

In some embodiments, in the multimeric, such as dimeric peptide according to the present invention, any one of the monomeric peptides is independently as defined herein.

In some embodiments, the peptide according to the present invention is essentially a non-cell-penetrating peptide. In other embodiments, the peptide according to the present invention is a cell-penetrating peptide. In some embodiments, the peptide according to the present invention is able to attach to the cell membrane of an antigen presenting cell.

It is to be understood that when referring to the peptides ability to attach to and enter a cell, such as an antigen presenting cell, it may be with reference to the complete sequence of the peptide as well as a fragment thereof, such as a fragment representing an epitope. Accordingly, it may be the case that the entire sequence is essentially a non-cell-penetrating peptide, whereas a fragment of the peptide is able to efficiently enter a cell, such as an antigen presenting cell.

In some embodiments, the peptide according to the present invention is not a peptide or a dimeric peptide as specifically disclosed in International Patent Application No: PCT/DK2011/050460.

In some embodiments, the peptide according to the present invention is not a peptide or a dimeric peptide as specifically disclosed in International Patent Application No: PCT/EP2010/059513, such as one selected from:

```
                                         (SEQ ID NO: 267)
CGGAKRRVVGGAKRRVVGQREKRAV (SEQ ID NO: 268)
CGGGDQQLLGGAEEEIVGGIEEEGGERDRDR (SEQ ID NO: 269)
CGGAKRRVVGGAKRRVVGGQREKR (SEQ ID NO: 270)
CGGGDQQLLGGAEEEIVGGIEEEGG (SEQ ID NO: 271)
CGGAEEEVVGGDQQLL (SEQ ID NO: 272)
GCGGAKRRVVGGAKRRVV (SEQ ID NO: 273)
GAKRRVVGGCGGAKRRVVQREKRAGEREKRA (SEQ ID NO: 274)
GKGGIEEEGGRDRDRGGEQDRDR (SEQ ID NO: 275)
GAKRRVVGGCGGAKRRVVQREKRAGEREKRA (SEQ ID NO: 276)
GKGGIEEEGGERDRDRGGQDRDR (SEQ ID NO: 277)
GAKRRVVGGCGGAKRRVVEREKRAGQREKRA (SEQ ID NO: 278)
GKGGIEEEGGQDRDRGGRDRDR (SEQ ID NO: 279)
GAKRRVVGGCGGAKRRVVEREKRAGQREKRA (SEQ ID NO: 280)
GKGGIEEEGGEQDRDRGGERDRD
```

In some embodiments, the peptide according to the present invention is not a dimeric peptide selected from (The peptides are linked via the underlined amino acid):

```
CGGAKRRVVGGAKRRVVGQREKRAV
|
CGGGDQQLLGGAEEEIVGGIEEEGGERDRDR;
CGGAKRRVVGGAKRRVVGGQREKR
|
CGGGDQQLLGGAEEEIVGGIEEEGG;
 CGGAEEEVVGGDQQLL
 |
GCGGAKRRVVGGAKRRVV;
GAKRRVVGGCGGAKRRVVQREKRAGEREKRA
      |
      GKGGIEEEGGRDRDRGGEQDRDR;
GAKRRVVGGCGGAKRRVVQREKRAGEREKRA
      |
      GKGGIEEEGGERDRDRGGQDRDR;
GAKRRVVGGCGGAKRRVVEREKRAGQREKRA;
      |
      GKGGIEEEGGQDRDRGGRDRDR
GAKRRVVGGCGGAKRRVVEREKRAGQREKRA
      |
      GKGGIEEEGGEQDRDRGGERDRD;
CGGAKRRVVGGAKRRVVGQREKRAV
|
CGGGDQQLLGGAEEEIVGGIEEEGG;
 CGGAKRRVVGGAKRRVVGQREKRAV;
 |
GCGGAKRRVVGGAKRRVV
CGGAKRRVVGGAKRRVVGGQREKR
|
CGGGDQQLLGGAEEEIVGGIEEEGGERDRDR;
 CGGAKRRVVGGAKRRVVGGQREKR;
 |
GCGGAKRRVVGGAKRRVV
CGGAEEEVVGGDQQLL
|
CGGGDQQLLGGAEEEIVGGIEEEGGERDRDR;
CGGAEEEVVGGDQQLL
|
CGGGDQQLLGGAEEEIVGGIEEEGG;
GAKRRVVGGCGGAKRRVVQREKRAGEREKRA;
      |
      GKGGIEEEGGQDRDRGGRDRDR
GAKRRVVGGCGGAKRRVVQREKRAGEREKRA
      |
      GKGGIEEEGGEQDRDRGGERDRD;
GAKRRVVGGCGGAKRRVVEREKRAGQREKRA         ; or
      |
      GKGGIEEEGGRDRDRGGEQDRDR
GAKRRVVGGCGGAKRRVVEREKRAGQREKRA
      |
      GKGGIEEEGGERDRDRGGQDRDR.
```

In some embodiments $Z^3$, and optional $Z^6$, $Z^9$ and $Z^{12}$ consist of a sequence selected from GYIPLVGAPLG, GYLPAVGAPIG, GYLPAVGAPI, NYVTGNIPG, NYATGNLPG, NYATGNLPG, VTGNIPGSTYS, IRNLGRVIETLTG, SRNLGKVIDTLTC, IRNLGRVIETLT, GGGQIIGGNYLIP, GGGQIVGGVYLLP, LIFLARSALIV, LIFLARSALIL, LIFLARSALIL, SAYERMCNIL, SAYERNleVNIL, TAYERNleCNIL, IAYERMCNIL, IAYERMCNIL, LFFKClYRLFKHGL, LFFKTITRLFBHGL, GLEPLVIAGILA, GSDPLVVAASIV, NLVPMVATV, NLVPMVATV, NIVPNleVVTA, PEVIPMFSALS, FIIPXFTALSG, ALGPAATL, GPVVHLTL, LECVYCKQQLL, GVYDFAFRDLC, GVFDYAFRDIN, GATPVDLLGA, GVTPAGLIGV, VARALAHGVRV, VIRVIAHGLRL, GITFSIFLIVS, CSFSIFLLAL, GCSFSIFLLAL, GITFSIYLIVS, LNleGYIPLIGA, LMGYIPLVGA, LNleGYIPLIGA, PBIGVRATB, GPRLGVRATR, GPRLGVRAT, RGSVAHKS, SALILRGSVAHK, FQTAAQRAMM, FQTAAQRAVNle, FQTVVQBA, FQTAAQRA, GPSTEGVPESM, LLSTEGVPNSNle, GSLVGLLHIVL, ASIVGILHLIL, NLVPMVATV, NIVPNleVVTA, TPQDLNTMLN, ALLYGATPYAIG, MMTACQGVG, GQAGDDFS, EVYDFAFRDLC, GFAFRDLCIVY, GFAYRDINLAY, GALNLCLPM, and GALQIBLPL, IRNLGRVIETLTLNleGYIPLIGA, or a fragment or variant thereof.

In some embodiments $Z^3$, and optional $Z^6$, $Z^9$ and $Z^{12}$ consist of a sequence derived from an amino acid sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:126, SEQ ID NO:198, SEQ ID NO:198, SEQ ID NO:200, SEQ ID NO:201, SEQ ID NO:202, SEQ ID NO:203, SEQ ID NO:204, and SEQ ID NO:205, or a fragment or variant thereof.

In some embodiments the peptide according to the invention is not a peptide selected from RRGYIPLVGAPLGBGRVARALAHGVRV, RGYIPLVGAPLGRRVARALAHGVRV, RGYIPLVGAPLGRRRVARALAHGVRVR, RRGYIPLVGAPLGRRVARALAHGVRV, RRGYIPLVGAPLGRRRVARALAHGVRV, BRGYIPLVGAPLGRRVARALAHGVRV, RRRGYIPLVGAPLGBRVARALAHGVRV, RGYIPLVGAPLGKKKVARALAHGVRV, RGYIPLVGAPLGRRRVARALAHGVRV, KKGYIPLVGAPLGKKVARALAHGVRV, WGYIPLVGAPLGRRVARALAHGVRV, WWGYIPLVGAPLGRRVARALAHGVRV, EEGYIPLVGAPLGEEVARALAHGVRV, GGGYIPLVGAPLGGGVARALAHGVRV, EEGYIPLVGAPLGRRVARALAHGVRV, RRGYIPLVGAPLGLRRVARALAHGVRV, WWGYIPLVGAPLGRRVARALAHGVRV, WWGYIPLVGAPLGRRRVARALAHGVRV, WWGYIPLVGAPLGRVARALAHGVRV, RGYIPLVGAPLGRRVARALAHGVRV, RRGYLPAVGAPIGBRVIRVIAHGLRL, RRGYIPLVGAPLGBRVARALAHGVRV, GYIPLVGAPLGGVARALAHGVRV, WWGYLPAVGAPIRRVIRVIAHGLRL, GYIPLVGAPLGGVARALAHGVRV, RRGYIPLVGAPLGBGRVARALAHGVRV, RGYIPLVGAPLGRRVARALAHGVRV, RGYIPLVGAPLGRRRVARALAHGVRV, RRGYIPLVGAPLGRRVARALAHGVRV, RRGYIPLVGAPLGRRRVARALAHGVRV, BRGYIPLVGAPLGRRVARALAHGVRV, RRRGYIPLVGAPLGBRVARALAHGVRV, RGYIPLVGAPLGKKKVARALAHGVRV, RGYIPLVGAPLGRRRVARALAHGVRV, KKGYIPLVGAPLGKKVARALAHGVRV, WGYIPLVGAPLGRRVARALAHGVRV, WWGYIPLVGAPLGRRVARALAHGVRV, RRGYIPLVGAPLGLRRVARALAHGVRV, RRNYVTGNIPGBRGITFSIFLIVS, WWNYATGNLPGRRCSFSIFLLAL, WWNYVTGNIPGBRGITFSIFLIVS, WWNYVTGNIPGRRGITFSIFLIVS, RRNYATGNLPGRRGCSFSIFLLAL, RRVTGNIPGSTYSGBRGITFSIYLIVS, RRIRNLGRVIETLTGBRLNleGYIPLIGA, RRSRNLGKVIDTLTCBRLMGYIPLVGA, SRNLGKVIDTLTCGFADLMGYIPLVGA, WWIRNLGRVIETLTRRLNleGYIPLIGA, WWSRNLGKVIDTLTCRRLMGYIPLVGA, RRGGGQIIGGNYLIPRBPBIGVRATB, GGGQIVGGVYLLPRRGPRLGVRATR, RRGGGQIVGGVYLLPRRGPRLGVRATR, WWGGGQIVGGVYLLPRRGPRLGVRAT, BRLIFLARSALIVRGSVAHKS, EDLIFLARSALILRGSVAHKS, BRLIFLARSALILBGRSALILRGSVAHK, SAYERMCNILKGKFQTAAQRAMM, SAYERNleVNILKGKFQTAAQRAVNle, BRTAYERNleCNILBRGRFQTVVQBA, BRIAYERMCNILLBRGKFQTAAQRA, IAYERMCNILKGKFQTAAQRA, LFFKClYRLFKHGLKRGPSTEGVPESM, BRRLFFKTITRLFBHGLRRLLSTEGVPNSNle, BRGLEPLVIAGILARRGSLVGLLHIVL, BRGSDPLVVAASIVRRASIVGILHLIL, RNLVPMVATVRRNLVPMVATVB, RNLVPMVATVBRRNLVPMVATVB, RNIVPNleVVTARRNIVPNleVVTAB, PEVIPMFSALSEGATPQDLNTMLN, RFIIPXFTALSGGRRALLYGATPYAIG, KALGPAATLEEMMTACQGVG, RRGPVVHLTLRRRGQAGDDFS, RRGPVVHLTLRRRGQAGDDFS, RRGPVVHLTLRGRRGQAGDDFS, RRLECVYCKQQLLRREVYDFAFRDLC, RRGVYDFAFRDLCRRGFAFRDLCIVYR, RRGVFDYAFRDINRRGFAYRDINLAYR, RRGATPVDLLGARRGALNLCLPMR, RRGVTPAGLIGVRRGALQIBLPLR, RGYLPAVGAPIGRRRVIRVIAHGLRLR, RRSRNLGKVIDTLTCRRLMGYIPLVGA, RRIRNLGRVIETLTLNleGYIPLIGARRIRNLGRVIETLTLNleGYIPLIGAR, or a fragment or variant thereof.

In some embodiments the peptide according to the invention is not a peptide consisting of a sequence selected from $X^1$-NYVTGNIPG-$X^3$-GITFSIYLIVS; $X^1$-IRNLGRVIETLT-$X^3$-LNleGYIPLIGA; $X^1$-GYLPAVGAP$^1$-$X^3$-VIRVIAHGLRL; $X^1$-GGGQIIGGNYLIP-$X^3$-PBIGVRATB; $X^1$-NYATGNLPG-$X^3$-GCSFSIFLLAL; $X^1$-SRNLGKVIDTLTC-$X^3$-LMGYIPLVGA; $X^1$-GYIPLVGAPL-$X^3$-VARALAHGVRV; $X^1$-GGGQIVGGVYLLP-$X^3$-PRLGVRATR; $X^1$-LTFLVRSVLL$^1$-$X^3$-GSVLIVRGSLVH; $X^1$-TAYERNleCNIL-$X^3$-GRFQTVVQBA; $X^1$-SDPLVVAASIV-$X^3$-ASIVGILHLIL; $X^1$-LIFLARSALIL-$X^3$-SALILRGSVAH; $X^1$-IAYERMCNIL-$X^3$-GKFQTAAQRA; and $X^1$-LEPLVIAGILA-$X^3$-GSLVGLLHIVL; $X^1$-NLVPMVATV-$X^3$-NLVPMATV; $X^1$-GYLPAVGAPIG-$X^3$-VIRVIAHGLRL; $X^1$-IRNLGRVIETLTG-$X^3$-LNleGYIPLIGA; $X^1$-GVYDFAFRDLC-$X^3$-GFAFRDLCIVYR, $X^1$-GVFDYAFRDIN-$X^3$-GFAYRDINLAYR, $X^1$-GATPVDLLGA-$X^3$-GALNLCLPMR, $X^1$-GVTPAGLIGV-$X^3$-GALQIBLPLR, and $X^1$-IRNLGRVIETLTLNleGYIPLIGA-$X^3$-IRNLGRVIETLTLNleGYIPLIGA; optionally with an $X^5$ in the C-terminal of the peptide wherein $X^1$, $X^3$ and $X^5$ refers to $X^1$, $X^3$, and $X^5$ of formula II.

In some embodiments the peptide according to the invention is not a peptide consisting of a sequence selected from RRGYIPLVGAPLGBGRVARALAHGVRV (SEQ ID NO:47), RGYIPLVGAPLGRRVARALAHGVRV (SEQ ID NO:48), RGYIPLVGAPLGRRRVARALAHGVRVR (SEQ ID NO:49), RRGYIPLVGAPLGRRVARALAHGVRV (SEQ ID NO:50), RRGYIPLVGAPLGRRRVARALAHGVRV (SEQ ID NO:51), BRGYIPLVGAPLGRRVARALAHGVRV (SEQ ID NO:52), RRRGYIPLVGAPLGBRVARALAHGVRV (SEQ ID NO:53), RGYIPLVGAPLGKKKVARALAHGVRV (SEQ ID NO:54), RGYIPLVGAPLGRRRVARALAHGVRV (SEQ ID NO:55), KKGYIPLVGAPLGKKVARALAHGVRV (SEQ ID NO:56), WGYIPLVGAPLGRRVARALAHGVRV (SEQ ID NO:57), WWGYIPLVGAPLGRRVARALAHGVRV (SEQ ID NO:58), EEGYIPLVGAPLGEEVARALAHGVRV (SEQ ID NO:59), GGGYIPLVGAPLGGGVARALAHGVRV (SEQ ID NO:60), EEGYIPLVGAPLGRRVARALAHGVRV (SEQ ID NO:61), RRGYIPLVGAPLGLRRVARALAHGVRV (SEQ ID NO:62), WWGYIPLVGAPLGRRVARALAHGVRV (SEQ ID NO:63), WWGYIPLVGAPLGRRRVARALAHGVRV (SEQ ID NO:64), WWGYIPLVGAPLGRVARALAHGVRV (SEQ ID NO:65), RGYIPLVGAPLGRRVARALAHGVRV (SEQ ID NO:66), RRGYLPAVGAPIGBRVIRVIAHGLRL (SEQ ID NO:67), RRGYIPLVGAPLGBRVARALAHGVRV (SEQ ID NO:68), GYIPLVGAPLGGVARALAHGVRV (SEQ ID NO:69), WWGYLPAVGAPIRRVIRVIAHGLRL (SEQ ID NO:70), GYIPLVGAPLGGVARALAHGVRV (SEQ ID NO:71), RRGYIPLVGAPLGBGRVARALAHGVRV (SEQ ID NO:72), RGYIPLVGAPLGRRVARALAHGVRV (SEQ ID NO:73), RGYIPLVGAPLGRRRVARALAHGVRV (SEQ ID NO:74), RRGYIPLVGAPLGRRVARALAHGVRV (SEQ ID NO:75), RRGYIPLVGAPLGRRRVARALAHGVRV (SEQ ID NO:76), BRGYIPLVGAPLGRRVARALAHGVRV (SEQ ID NO:77), RRRGYIPLVGAPLGBRVARALAHGVRV (SEQ ID NO:78), RGYIPLVGAPLGKKKVARALAHGVRV (SEQ ID NO:79), RGYIPLVGAPLGRRRVARALAHGVRV (SEQ ID NO:80), KKGYIPLVGAPLGKKVARALAHGVRV (SEQ ID NO:81), WGYIPLVGAPLGRRVARALAHGVRV (SEQ ID NO:82), WWGYIPLVGAPLGRRVARALAHGVRV (SEQ ID NO:83), RRGYIPLVGAPLGLRRVARALAHGVRV (SEQ ID NO:84), RRNYVTGNIPGBRGITFSIFLIVS (SEQ ID NO:85), WWNYATGNLPGRRCSFSIFLLAL (SEQ ID NO:86), WWNYVTGNIPGBRGITFSIFLIVS (SEQ ID NO:87), WWNYVTGNIPGRRGITFSIFLIVS (SEQ ID NO:88), RRNYATGNLPGRRGCSFSIFLLAL (SEQ ID NO:89), RRVTGNIPGSTYSGBRGITFSIYLIVS (SEQ ID NO:90), RRIRNLGRVIETLTGBRLNleGYIPLIGA (SEQ ID NO:91), RRSRNLGKVIDTLTCBRLMGYIPLVGA (SEQ ID NO:92), SRNLGKVIDTLTCGFADLMGYIPLVGA (SEQ ID NO:93), WWIRNLGRVIETLTRRLNleGYIPLIGA (SEQ ID NO:94), WWSRNLGKVIDTLTCRRLMGYIPLVGA (SEQ ID NO:95), RRGGGQIIGGNYLIPRBPBIGVRATB (SEQ ID NO:96), GGGQIVGGVYLLPRRGPRLGVRATR (SEQ ID NO:97), RRGGGQIVGGVYLLPRRGPRLGVRATR (SEQ ID NO:98), WWGGGQIVGGVYLLPRRGPRLGVRAT (SEQ ID NO:99), BRLIFLARSALIVRGSVAHKS (SEQ ID NO:100), EDLIFLARSALILRGSVAHKS (SEQ ID NO:101), BRLIFLARSALILBGRSALILRGSVAHK (SEQ ID NO:102), SAYERMCNILKGKFQTAAQRAMM (SEQ ID NO:103), SAYERNleVNILKGKFQTAAQRAVNle (SEQ ID NO:104), BRTAYERNleCNILBRGRFQTVVQBA (SEQ ID NO:105), BRIAYERMCNILLBRGKFQTAAQRA (SEQ ID NO:106), IAYERMCNILKGKFQTAAQRA (SEQ ID NO:107), LFFKCIYRLFKHGLKRGPSTEGVPESM (SEQ ID NO:108), BRRLFFKTITRLFBHGLRRLLSTEGVPNSNle (SEQ ID NO:109), BRGLEPLVIAGILARRGSLVGLLHIVL (SEQ ID NO:110), BRGSDPLVVAASIVRRASIVGILHLIL (SEQ ID NO:111), RNLVPMVATVRRNLVPMVATVB (SEQ ID NO:112), RNLVPMVATVBRRNLVPMVATVB (SEQ ID NO:113), RNIVPNleVVTARRNIVPNleVVTAB (SEQ ID NO:114), PEVIPMFSALSEGATPQDLNTMLN (SEQ ID NO:115), RFIIPXFTALSGGRRALLYGATPYAIG (SEQ ID NO:116), KALGPAATLEEMMTACQGVG (SEQ ID NO:117), RRGPVVHLTLRRRGQAGDDFS (SEQ ID NO:118), RRGPVVHLTLRRRGQAGDDFS (SEQ ID NO:119), RRGPVVHLTLRGRRGQAGDDFS (SEQ ID NO:120), RRLECVYCKQQLLRREVYDFAFRDLC (SEQ ID NO:121), RRGVYDFAFRDLCRRGFAFRDLCIVYR (SEQ ID NO:122), RRGVFDYAFRDINRRGFAYRDINLAYR (SEQ ID NO:123), RRGATPVDLLGARRGALNLCLPMR (SEQ ID NO:124), RRGVTPAGLIGVRRGALQIBLPLR (SEQ ID NO:125), RGYLPAVGAPIGRRRVIRVIAHGLRLR (SEQ ID NO:196), RRSRNLGKVIDTLTCRRLMGYIPLVGA (SEQ ID NO:197), and RRIRNLGRVIETLTLNleGYIPLIGARRIRNLGRVIETLTLNleGYIPLIGAR (SEQ ID NO:199), or a fragment or variant thereof.

In some embodiments the peptide according to the invention is not a peptide consisting of a sequence selected from $X^1$-NYVTGNIPG-$X^3$-GITFSIYLIVS; $X^1$-IRNLGRVIETLT-$X^3$-LNleGYIPLIGA; $X^1$-GYLPAVGAP$^1$-$X^3$-VIRVIAHGLRL; $X^1$-GGGQIIGGNYLIP-$X^3$-PBIGVRATB; $X^1$-NYATGNLPG-$X^3$-GCSFSIFLLAL; $X^1$-SRNLGKVIDTLTC-$X^3$-LMGYIPLVGA; $X^1$-GYIPLVGAPL-$X^3$-VARALAHGVRV; $X^1$-GGGQIVGGVYLLP-$X^3$-PRLGVRATR; $X^1$-LTFLVRSVLL$^1$-$X^3$-GSVLIVRGSLVH; $X^1$-TAYERNleCNIL-$X^3$-GRFQTVVQBA; $X^1$-SDPLVVAASIV-$X^3$-ASIVGILHLIL; $X^1$-LIFLARSALIL-$X^3$-SALILRGSVAH; $X^1$-IAYERMCNIL-$X^3$-GKFQTAAQRA; and $X^1$-LEPLVIAGILA-$X^3$-GSLVGLLHIVL; $X^1$-NLVPMVATV-$X^3$-NLVPMATV; $X^1$-GYLPAVGAPIG-$X^3$-VIRVIAHGLRL; $X^1$-IRNLGRVIETLTG-$X^3$-LNleGYIPLIGA; $X^1$-GVYDFAFRDLC-$X^3$-GFAFRDLCIVYR, $X^1$-GVFDYAFRDIN-$X^3$-GFAYRDINLAYR, $X^1$-GATPVDLLGA-$X^3$-GALNLCLPMR, $X^1$-GVTPAGLIGV-$X^3$-GALQIBLPLR, and $X^1$-IRNLGRVIETLTLNleGYIPLIGA-$X^3$-IRNLGRVIETLTLNleGYIPLIGA; optionally with an $X^5$ in the C-terminal of the peptide, wherein $X^1$ and $X^3$ and $X^5$ refers to $X^1$, $X^3$, and $X^5$ of formula II.

In some embodiments the peptide comprises one or more cysteine.

In some embodiments the peptide contain intramolecular bonds, such as intramolecular disulfide (S—S) bonds between two cys residues.

In other embodiments the peptide contains intramolecular bonds, such as in the form of a acylal moiety (COO—CH2-OOC. COO—CHR—OOC or COO—CR2-OOC).

In some embodiments the peptide according to the present invention is not more than 58 amino acids, such as not more than 56, 54, 52, 50, 48, 46, 44, 42, 40, 38, 36, 34, 32, 30, 28, 26, 24, 22, 20, 18 amino acid residues.

In some embodiments an isolated peptide according to the present invention is not a peptide consisting of a sequence of $X^2$ or $X^4$ as defined in table 1, table 2, or table 8.

In some embodiments an isolated peptide according to the present invention comprises a sequence of $X^2$ and/or $X^4$ as defined in table 1, table 2, table 5, or a fragment thereof.

In some embodiments the dimer peptide according to the invention consist of two identical peptide monomers.

In some embodiments the immunogenic composition according to the invention is in the form of a vaccine composition.

In some embodiments, the peptide of the invention comprises at most 60, at most 59, at most 58, at most 57, at most 56, at most 55, at most 54, at most 53, at most 52, at most 51, at most 50, at most 49, at most 48, at most 47, at most 46, at most 45, at most 44, at most 43, at most 42, at most 41, at most 40, at most 39, at most 38, at most 37, at most 36, at most 35, at most 34, at most 33, at most 32, at most 31, at most 30, at most 29, at most 28, at most 27, at most 26, at most 25, at most 24, at most 23, at most 22, at most 21, at most 20, at most 19, at most 18 amino acids.

In some embodiments, the peptide of the invention comprises at least 18, at least 19, at least 20, at least 21, at least 22, at least 23, at least 24, at least 25, at least 26, at least 27, at least 28, at least 29, at least 30, at least 31, at least 32, at least 33, at least 34, at least 35 at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60 amino acid residues.

In some embodiments, the peptide of the invention consists of 18 amino acid residues or 19 amino acid residues or 20 amino acid residues or 21 amino acid residues or 22 amino acid residues or 23 amino acid residues or 24 amino acid residues or 25 amino acid residues or 26 amino acid residues or 27 amino acid residues or 28 amino acid residues or 29 amino acid residues or 30 amino acid residues or 31 amino acid residues or 32 amino acid residues or 33 amino acid residues or 34 amino acid residues or 35 amino acid residues or 36 amino acid residuesor 37 amino acid residues or 38 amino acid residues or 39 amino acid residues or 40 amino acid residues or 41 amino acid residues or 42 amino acid residues or 43 amino acid residues or 44 amino acid residues or 45 amino acid residues or 46 amino acid residues or 47 amino acid residues or 48 amino acid residues or 49 amino acid residues or 50 amino acid residues or 51 amino acid residues or 52 amino acid residues or 53 amino acid residues or 54 amino acid residues or 55 amino acid residues or 56 amino acid residues or 57 amino acid residues or 58 amino acid residues or 59 amino acid residues or 60 amino acid residues.

In some embodiments the peptide of the invention does not consist of the following sequence RFIIP[Nle]FTAL-SGGRRALLYGATPYAIG, where Nle denotes a nor-leucine.

In some embodiments $Z^3$, and optional $Z^6$, $Z^9$ and $Z^{12}$ is not derived from HIV.

Numbered embodiments according to the invention:

1. An isolated monomeric peptide comprising the following structure

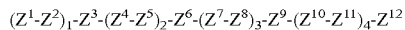

wherein $Z^1$, $Z^4$, and optional $Z^7$ and $Z^{10}$ defines a linear sequence of one, two, or three arginine residues or derivatives thereof optionally followed by a glycine (G) or an alanine (A); $Z^2$, $Z^5$, $Z^8$ and $Z^{11}$ defines an optional amino acid selected from cysteine (C), lysine (K), aspartic acid (D), asparagine (N), glutamic acid (E), glutamine (Q), 2,3-Diaminopropionic acid (Dpr), tryptophan (W), or tyrosine (Y) or a derivative thereof; $Z^3$, and optional $Z^6$, $Z^9$ and $Z^{12}$ defines any chemical moiety, such as a linear amino acid sequence.

2. The isolated monomeric peptide according to embodiment 1, wherein said chemical moiety of $Z^3$, and optional $Z^6$, $Z^9$ and $Z^{12}$ is a linear amino acid sequence of 8-30 amino acids or a compound with our without immune modulating properties.

3. The isolated monomeric peptide according to embodiments 1 or 2, wherein $Z^2$ defines an amino acid selected from cysteine (C), lysine (K), aspartic acid (D), asparagine (N), glutamic acid (E), glutamine (Q), 2,3-Diaminopropionic acid (Dpr), tryptophan (W), or tyrosine (Y) or a derivative thereof.

4. The isolated monomeric peptide according to any one of embodiments 1-3, wherein $Z^5$ defines an amino acid selected from cysteine (C), lysine (K), aspartic acid (D), asparagine (N), glutamic acid (E), glutamine (Q), 2,3-Diaminopropionic acid (Dpr), tryptophan (W), or tyrosine (Y) or a derivative thereof.

5. The isolated monomeric peptide according to embodiments 1-4, wherein $Z^8$ defines an amino acid selected from cysteine (C), lysine (K), aspartic acid (D), asparagine (N), glutamic acid (E), glutamine (Q), 2,3-Diaminopropionic acid (Dpr), tryptophan (W), or tyrosine (Y) or a derivative thereof.

6. The isolated monomeric peptide according to embodiments 1-5, wherein $Z^{11}$ defines an amino acid selected from cysteine (C), lysine (K), aspartic acid (D), asparagine (N), glutamic acid (E), glutamine (Q), 2,3-Diaminopropionic acid (Dpr), tryptophan (W), or tyrosine (Y) or a derivative thereof.

7. The isolated monomeric peptide according to any one of embodiments 1-6, wherein $Z^7$ defines a linear sequence of one, two, or three arginine residues or derivatives thereof optionally followed by a glycine (G) or an alanine (A).

8. The isolated monomeric peptide according to any one of embodiments 1-7, wherein $Z^{10}$ defines a linear sequence of one, two, or three arginine residues or derivatives thereof optionally followed by a glycine (G) or an alanine (A).

9. The isolated monomeric peptide according to any one of embodiments 1-8, wherein $Z^6$ defines any chemical moiety, such as a linear amino acid sequence.

10. The isolated monomeric peptide according to any one of embodiments 1-9, wherein $Z^9$ defines any chemical moiety, such as a linear amino acid sequence.

11. The isolated monomeric peptide according to any one of embodiments 1-10, wherein $Z^{12}$ defines any chemical moiety, such as a linear amino acid sequence.

12. The isolated monomeric peptide according to any one of embodiments 1-11, wherein $Z^1$, $Z^4$, and optional $Z^7$ and $Z^{10}$ is followed by a glycine (G) or an alanine (A).

13. The isolated monomeric peptide according to any one of embodiments 1-12, wherein $Z^3$, and optional $Z^6$, $Z^9$ and $Z^{12}$ is a linear amino acid sequence of 8-30 amino acids derived from an antigen with more than 40%, such as more than 45%, such as more than 50%, such as more than 55%, such as more than 60%, such as more than 65%, such as more than 70%, such as more than 75%, such as more than 80%, such as more than 85%, such as more than 90%, such as more than 95%, such as more than 96%, such as more than 97%, such as more than 98%, such as more than 99%, such as 100% sequence identity to a specific natural antigen.

14. The isolated monomeric peptide according to any one of embodiments 1-13, wherein $Z^3$, and optional $Z^6$, $Z^9$ and $Z^{12}$ defines a specific natural antigen of a protein or peptide sequence derived from a disease antigen, such as an infectious agent, such as bacteria, virus, parasite, fungus, or cancer antigens such as oncogene (lung, stomach, breast cancer) or an antigen causing an autoimmune disease such as diabetes, multiple sclerosis (MS), celiac disease, Myalgic Encephalomyelitis (ME), psoriasis, and/or Crohn's Disease.

15. The isolated monomeric peptide according to embodiment 14, wherein said specific natural antigen is a viral protein, such as a structural protein, such as a capsid protein, a regulatory protein, an enzymatic protein, and a proteolytic protein.

16. The isolated monomeric peptide according to any one of embodiments 14-15, wherein said viral protein is selected from a core protein or an envelope protein, of a virus selected from the Hepatitis C virus, influenza virus, such as an M2 protein, human immunodeficiency virus (HIV), cytomegalovirus (CMV), and Human papillomavirus (HPV).

17. The isolated monomeric peptide according to embodiment 16, wherein said viral protein is a viral protein of Hepatitis C virus selected from any one HCV consensus sequence of a specific genotype, such as 1, such as subtypes 1a and 1b, genotype 2, such as 2a and 2b, genotype 3, such as 3a, genotype 4, genotype 5, and genotype 6.

18. The isolated monomeric peptide according to any one of embodiments 1-17, wherein a sequence of amino acids defined by $(Z^1-Z^2)_1-Z^3-(Z^4-Z^5)_2-Z^6-(Z^7-Z^8)_3-Z^9-(Z^{10}-Z^{11})_4-Z^{12}$ is not found in the native sequence of a natural antigen.

19. The isolated monomeric peptide according to any one of embodiments 1-18, which monomeric peptide is of 10-60 amino acids, such as of 11-60 amino acids, such as of 12-60 amino acids, such as of 13-60 amino acids, such as of 14-60 amino acids, such as of 15-60 amino acids, such as of 16-60 amino acids, such as of 17-60 amino acids, such as of 18-60 amino acids, such as of 19-60 amino acids, such as of 20-60 amino acids, such as of 21-60 amino acids, such as of 22-60 amino acids, such as of 23-60 amino acids, such as of 24-60 amino acids, such as of 25-60 amino acids, such as of 26-60 amino acids, such as of 27-60 amino acids, such as of 28-60 amino acids, such as of 29-60 amino acids, such as of 30-60 amino acids, such as of 31-60 amino acids, such as of 32-60 amino acids, such as of 33-60 amino acids, such as of 34-60 amino acids, such as of 35-60 amino acids, such as of 36-60 amino acids, such as of 37-60 amino acids, such as of 38-60 amino acids, such as of 39-60 amino acids, such as of 40-60 amino acids, such as of 42-60 amino acids, such as of 44-60 amino acids, such as of 46-60 amino acids, such as of 48-60 amino acids, such as of 50-60 amino acids, such as of 52-60 amino acids, such as of 54-60 amino acids, such as of 56-60 amino acids, such as of 58-60 amino acids.

20. The isolated monomeric peptide according to any one of embodiments 1-19, which monomeric peptide is of 10-60 amino acids, such as 10-58 amino acids, such as 10-56 amino acids, such as 10-54 amino acids, such as 10-52 amino acids, such as 10-50 amino acids, such as 10-48 amino acids, such as 10-46 amino acids, such as 10-44 amino acids, such as 10-42 amino acids, such as 10-40 amino acids, such as 10-39 amino acids, such as 10-38 amino acids, such as 10-37 amino acids, such as 10-36 amino acids, such as 10-35 amino acids, such as 10-34 amino acids, such as 10-33 amino acids, such as 10-32 amino acids, such as 10-31 amino acids, such as 10-30 amino acids, such as 10-29 amino acids, such as 10-28 amino acids, such as 10-27 amino acids, such as 10-26 amino acids, such as 10-25 amino acids, such as 10-24 amino acids, such as 10-23 amino acids, such as 10-22 amino acids, such as 10-21 amino acids, such as 10-20 amino acids, such as 10-19 amino acids, such as 10-18 amino acids, such as 10-17 amino acids, such as 10-16 amino acids, such as 10-15 amino acids, such as 10-14 amino acids, such as 10-13 amino acids, such as 10-12 amino acids, such as 10-11 amino acids.

21. The isolated monomeric peptide according to any one of embodiments 1-20, which monomeric peptide consist of not more than about 55 amino acids, such as not more than about 50 amino acids, such as not more than about 45 amino acids, such as not more than about 40 amino acids, such as not more than about 38 amino acids, such as not more than about 36 amino acids, such as not more than about 34 amino acids, such as not more than about 32 amino acids, such as not more than about 30 amino acids, such as not more than about 28 amino acids, such as not more than about 26 amino acids, such as not more than about 24 amino acids, such as not more than about 22 amino acids, such as not more than about 20 amino acids, such as not more than about 18 amino acids, such as not more than about 16 amino acids, such as not more than about 14 amino acids, such as not more than about 12 amino acids, such as not more than about 10 amino acids.

22. The isolated monomeric peptide according to any one of embodiments 1-21, which monomeric peptide consist of at least about 10 amino acids, such as at least about 12 amino acids, such as at least about 14 amino acids, such as at least about 16 amino acids, such as at least about 18 amino acids, such as at least about 20 amino acids, such as at least about 22 amino acids, such as at least about 24 amino acids, such as at least about 26 amino acids, such as at least about 28 amino acids, such as at least about 30 amino acids, such as at least about 32 amino acids, such as at least about 34 amino acids, such as at least about 36 amino acids, such as at least about 38 amino acids, such as at least about 40 amino acids, such as at least about 45 amino acids, such as at least about 50 amino acids, such as at least about 55 amino acids, such as at least about 60.

23. The isolated monomeric peptide according to any one of embodiments 1-22, wherein the overall net charge of $(Z^1-Z^2)_1-Z^3-(Z^4-Z^5)_2-Z^6-(Z^7-Z^8)_3-Z^9-(Z^{10}-Z^{11})_4-Z^{12}$ is equal to or above 0, such as above 1, 2, 3, 4, or 5.

24. The isolated monomeric peptide according to any one of embodiments 1-23, wherein said monomeric peptide is capable of inducing a humoral immune response.

25. The isolated monomeric peptide according to any one of embodiments 1-24, wherein said monomeric peptide comprises at least one amino acid selected from a Cys, a Lys, an Asp, and a Glu residue, or derivatives thereof.

26. The isolated monomeric peptide according to any one of embodiments 1-25, which monomeric peptide contain one or more intramolecular bond, such as one or more Cys-Cys bond.

27. The isolated monomeric peptide according to any one of embodiments 1-26, which monomeric peptide has delayed proteolytic degradation in the N-terminal, such as by incorporation of the first 1, 2, or 3 amino acids in the N-terminal in the D-form, or by incorporation of the first 1, 2, or 3 amino acids in the N-terminal in beta or gamma form.

28. The isolated peptide according to any one of embodiment 1-27, wherein said peptide is demonstrated to translocate across a plasma membrane in the assay based on biotinylation of peptides as described in example 5.

29. The isolated peptide according to any one of embodiments 1-28, wherein said peptide is capable of inducing a T lymphocyte response.

30. The isolated peptide according to any one of embodiments 1-29, wherein the net charge of $Z^3$, and/or optional $Z^6$, $Z^9$ and $Z^{12}$ is below or equal to 0.

31. The isolated peptide according to any one of embodiments 1-30, wherein the net charge of $Z^3$ is below or equal to 0; and wherein the net charge of $Z^6$ and/or optional $Z^9$ and $Z^{12}$ is above or equal to 1.

32. The isolated peptide according to any one of embodiments 1-31, wherein the net charge of $Z^3$, and/or optional $Z^6$, $Z^9$ and $Z^{12}$ are above or equal to 1.

33. The isolated peptide according to any one of embodiments 1-32, wherein the net charge of $Z^3$ is above or equal to 1; and wherein the net charge of $Z^6$ and/or optional $Z^9$ and $Z^{12}$ is below or equal to 0.

34. The isolated peptide according to any one of embodiments 1-33, wherein the peptide comprises one or more cysteine.

35. The isolated peptide according to any one of embodiments 1-34, wherein the N- and/or C-terminal amino acid in $Z^3$, and/or optional $Z^6$, $Z^9$ and $Z^{12}$ is a hydrophilic or polar amino acid.

36. The isolated peptide according to any one of embodiments 1-35, wherein $Z^3$, and/or optional $Z^6$, $Z^9$ and $Z^{12}$ defines a sequence of 8-25 amino acids, such as 8-20 amino acids, such as 8-15 amino acids.

37. The isolated peptide according to any one of embodiments 1-36, wherein $Z^3$, and/or optional $Z^6$, $Z^9$ and $Z^{12}$ defines a sequence of less than 25, such as less than 24, 23, 22, 21, 20, 19, 18, 17, 16, 15, 14, 13, 12, 11, 10, 9, 8, 7 or 6 amino acids.

38. The isolated peptide according to any one of embodiments 1-37, wherein $Z^3$, and/or optional $Z^6$, $Z^9$ and $Z^{12}$ defines a sequence of more than 8, such as more than 9, 10, 11, 12, 13, 14, 15, 16, 17, 18, 19, 20, 21, 22, 23, 24, 25, 26, 27, 28, 29 amino acids.

39. The isolated peptide according to any one of embodiments 1-38, which does not consist of the following sequence RFIIP[Nle]FTALSGGRRALLYGATPYAIG, where Nle denotes a nor-leucine.

40. The isolated peptide according to any one of embodiments 1-39, wherein $Z^3$, and/or optional $Z^6$, $Z^9$ and $Z^{12}$ is not derived from HIV.

41. The isolated peptide according to any one of embodiments 1-40, wherein $Z^3$, and/or optional $Z^6$, $Z^9$ and $Z^{12}$ is a linear sequence of less than 12 amino acids.

42. The isolated peptide according to any one of embodiments 1-41, wherein $Z^3$, and/or optional $Z^6$, $Z^9$ and $Z^{12}$ is a linear sequence of less than 12 amino acids.

43. The isolated peptide according to any one of embodiments 1-42, wherein $Z^3$, and/or optional $Z^6$, $Z^9$ and $Z^{12}$ do not contain nor-leucine.

44. The isolated peptide according to any one of embodiments 1-43, wherein $Z^3$, and/or optional $Z^6$, $Z^9$ and $Z^{12}$ do not contain nor-leucine.

45. The isolated peptide according to any one of embodiments 1-44, wherein $Z^3$, and/or optional $Z^6$, $Z^9$ and $Z^{12}$ only contains natural amino acids.

46. The isolated peptide according to any one of embodiments 1-45, wherein $Z^3$, and/or optional $Z^6$, $Z^9$ and $Z^{12}$ only contains natural amino acids.

47. The isolated peptide according to any one of embodiments 1-46, wherein $Z^3$, and/or optional $Z^6$, $Z^9$ and $Z^{12}$ only contains natural amino acids if derived from HIV.

48. The isolated peptide according to any one of embodiments 1-47, wherein $Z^3$, and/or optional $Z^6$, $Z^9$ and $Z^{12}$ is derived from HCV, CMV, HPV, Influenza, adenoviruses, herpesviruses, or picornaviruses.

49. The isolated peptide according to any one of embodiments 1-48, wherein $Z^1$ is as defined in any one of table 3, table 4, table 5, or table 7, such as any one selected from R, RR, RRR, RG, RRG and RRRG.

50. The isolated peptide according to any one of embodiments 1-49, wherein $Z^2$ is as defined in any one of table 3, table 4, table 5, or table 7, such as any one selected from Dpr(Aoa), C, K, Lys(Me), D, E, Dpr(Ser).

51. The isolated peptide according to any one of embodiments 1-50, wherein $Z^3$ is as defined in any one of table 3, table 4, table 5, or table 7, such as any one selected from GGQLIGGIYLIPG (SEQ ID NO:313), VITYSIFLIVS (SEQ ID NO:314), TANWARVIS (SEQ ID NO:315), GYLPAVGAPI (SEQ ID NO:316), NIVPZVVTA (SEQ ID NO:317), VTPADLIGA (SEQ ID NO:318), PRPEGYTLFF (SEQ ID NO:319), LPYPRGYTLFV (SEQ ID NO:320), ETILTPRDV (SEQ ID NO:321), SSTSPVYDL (SEQ ID NO:322), TAYERZCNIL (SEQ ID NO:323), TVIGASZIPLL (SEQ ID NO:324), AAFEEZXITS (SEQ ID NO:325), GLEPLVIAGILA (SEQ ID NO:326), TAFLVRNVA (SEQ ID NO:327), TPI(Har)QDWGNRAN (SEQ ID NO:328), TPT(Har)NGWDVKLS (SEQ ID NO:329), LECVYCK-QQLL (SEQ ID NO:330), GVYDFAFRDLC (SEQ ID NO:331), GVFDYAFRDIN (SEQ ID NO:332), and VDIRTLEDLL (SEQ ID NO:333).

52. The isolated peptide according to any one of embodiments 1-51, wherein $Z^4$ is as defined in any one of table 3, table 4, table 5, or table 7, such as any one selected from R, RR, RRR, RG, RRG and RRRG.

53. The isolated peptide according to any one of embodiments 1-52, wherein $Z^5$ is as defined in any one of table 3, table 4, table 5, or table 7, such as any one selected from Dpr(Aoa), C, K, Lys(Me), D, E, Dpr(Ser).

54. The isolated peptide according to any one of embodiments 1-53, wherein $Z^6$ is as defined in any one of table 3, table 4, table 5, or table 7, such as any one selected from EVYDFAFRDLC (SEQ ID NO:334), GFAFRDLCIVY (SEQ ID NO:335), GFAYRDINLAY (SEQ ID NO:336), GTLGIVCPIG (SEQ ID NO:337), GLEPLVIAGILA (SEQ ID NO:338), TPIXQDWENRAN (SEQ ID NO:339), VAFEDLXZZSFI (SEQ ID NO:340), RFQTVVQBA (SEQ ID NO:341), GSLVGLLHIVL (SEQ ID NO:342), SIARSVTIZXASVVH (SEQ ID NO:343), TPTRQEWDCRIS (SEQ ID NO:344), TPTRQEWDARIS (SEQ ID NO:345), TPI(Har)QEW(Har)SL(Nle)NQEW (SEQ ID NO:346), IGDLIVAQV (SEQ ID NO:347), QYNPVAVZF (SEQ ID NO:348), GYTLFFTS (SEQ ID NO:349), GYTLFVSD (SEQ ID NO:350), NTLZTPRDV (SEQ ID NO:351), SSTSPVYNL (SEQ ID NO:352), VITFSIYLIVS (SEQ ID NO:353), GGNVIGGIYZIPR (SEQ ID NO:354), ANWAKVIL (SEQ ID NO:355), VIRVIAHGLRL (SEQ ID NO:356), and IGDLIVQAV (SEQ ID NO:478).

55. The isolated peptide according to any one of embodiments 1-54, wherein $Z^7$ is as defined in any one of table 3, table 4, table 5, or table 7, such as any one selected from R, RR, RRR, RG, RRG and RRRG.

56. The isolated peptide according to any one of embodiments 1-55, wherein $Z^8$ is as defined in any one of table 3, table 4, table 5, or table 7, such as any one selected from Dpr(Aoa), C, K, Lys(Me), D, E, Dpr(Ser).

57. The isolated peptide according to any one of embodiments 1-56, wherein $Z^9$ is as defined in any one of table 3, table 4, table 5, or table 7, such as NWAKVI.

58. The isolated peptide according to any one of embodiments 1-57, which peptide consist of $(Z^1\text{-}Z^2)_1\text{-}Z^3\text{-}(Z^4\text{-}Z^5)_2\text{-}Z^6\text{-}(Z^7\text{-}Z^8)_3\text{-}Z^9$ as defined in any one of table 3, table 4, table 5, or table 7, such as any one selected from RRGGQLIGGIYLIPGRRVITFSIYLIVS (SEQ ID NO:357), RRRG-GQLIGGIYLIPGRRVITFSIYLIVS (SEQ ID NO:358), RRGGQLIGGIYLIPGRRRVITFSIYLIVS (SEQ ID NO:359), RRGGQLIGGIYLIPGRRVITFSIYLIVSR (SEQ ID NO:360), RRGGQLIGGIYLIPGRRVITFSIYLIVSRR (SEQ ID NO:361), RRVITYSIFLIVSRGGNVIGGIYZIPR (SEQ ID NO:362), RRRVITYSIFLIVSRGGNVIGGIYZIPR (SEQ ID NO:363), RRVITYSIFLIVSRRRGGNVIGGIYZIPR (SEQ ID NO:364), RRRVITYSIFLIVSRRRGGNVIGGIYZIPR (SEQ ID NO:365), RRGTANWARVISRANWAKVILRNWAKVI (SEQ ID NO:366), RGTANWARVISRRANWAKVILRNWAKVI (SEQ ID NO:367), RGTANWARVISRANWAKVILRNWAKVI (SEQ ID NO:368), RGTANWARVISRGANWAKVILRNWAKVI (SEQ ID NO:369), RRGTANWARVISRANWARVILRNWAKVI (SEQ ID NO:370), RGTANWARVISRRANWARVILRNWAKVI (SEQ ID NO:371), RGTANWARVISRANWARVILRNWAKVI (SEQ ID NO:372), RGTANWARVISRGANWARVILRNWAKVI (SEQ ID NO:373), RGYLPAVGAPIRRRVIRVIAHGLRLR (SEQ ID NO:374), RRGYLPAVGAPIRRVIRVIAHGLRLR (SEQ ID NO:375), RRGYLPAVGAPIRRRVIRVIAHGLRL (SEQ ID NO:376), RRGYLPAVGAPIRRVIRVIAHGLRL (SEQ ID NO:377), RGYLPAVGAPIRRVIRVIAHGLRLR (SEQ ID NO:378), RGYLPAVGAPIRVIRVIAHGLRLR (SEQ ID NO:379), RGYLPAVGAPIRRVIRVIAHGLRL (SEQ ID NO:380), RGNIVPZVVTARRIGDLIVAQV (SEQ ID NO:381), RRNIVPZVVTARRIGDLIVAQV (SEQ ID NO:382), RRRNIVPZVVTARRIGDLIVAQV (SEQ ID NO:383), RRNIVPZVVTARRRIGDLIVAQV (SEQ ID NO:384), RGVTPADLIGARRQYNPVAVZF (SEQ ID NO:385), RRVTPADLIGARRQYNPVAVZF (SEQ ID NO:386), RRRVTPADLIGARRQYNPVAVZF (SEQ ID NO:387), RRVTPADLIGARRRQYNPVAVZF (SEQ ID NO:388), RRGPRPEGYTLFFRGYTLFFTSR (SEQ ID NO:389), RGPRPEGYTLFFRRGYTLFFTSR (SEQ ID NO:390), RRGPRPEGYTLFFRRGYTLFFTSR (SEQ ID NO:391), RRGPRPEGYTLFFRRRGYTLFFTSR (SEQ ID NO:392), RRRGPRPEGYTLFFRRRGYTLFFTSR (SEQ ID NO:393), RGLPYPRGYTLFVRRGYTLFVSDR (SEQ ID NO:394), RRGLPYPRGYTLFVRRGYTLFVSDR (SEQ ID NO:395), RRGLPYPRGYTLFVRRRGYTLFVSDR (SEQ ID NO:396), RRRGLPYPRGYTLFVRRGYTLFVSDR (SEQ ID NO:397), RRGLPYPRGYTLFVRRGYTLFVSDR (SEQ ID NO:398), RRGETILTPRDVRNTLZTPRDVR (SEQ ID NO:399), RGETILTPRDVRRNTLZTPRDVR (SEQ ID NO:400), RGETILTPRDVRNTLZTPRDVR (SEQ ID NO:401), RGETILTPRDVRGNTLZTPRDVR (SEQ ID NO:402), RRSSTSPVYDLRRSSTSPVYNLR (SEQ ID NO:403), RRSSTSPVYDLRRRSSTSPVYNLR (SEQ ID NO:404), RRRSSTSPVYDLRRSSTSPVYNLR (SEQ ID NO:405), RRRSSTSPVYDLRRRSSTSPVYNLR (SEQ ID NO:406), RRTAYERZCNILRRGLEPLVIAGILA (SEQ ID NO:407), RRRTAYERZCNILRRGLEPLVIAGILA (SEQ ID NO:408), RRTAYERZCNILRRRGLEPLVIAGILA (SEQ ID NO:409), RRTAYERZCNILRRGLEPLVIAGILAR (SEQ ID NO:410), RRTAYERZCNILRRGLEPLVIAGILARR (SEQ ID NO:411), RRTVIGASZIPLLRGTPIXQDWENRAN (SEQ ID NO:412), RRRTVIGASZIPLLRGTPIXQDWENRAN (SEQ ID NO:413), RRTVIGASZIPLLRRGTPIXQDWENRAN (SEQ ID NO:414), RRRTVIGASZIPLLRGTPIXQDWENRAN (SEQ ID NO:415), RRRTVIGASZIPLLRRGTPIXQDWENRANR (SEQ ID NO:416), RRAAFEEZXITSRRVAFEDLXZZSFI (SEQ ID NO:417), RRRAAFEEZXITSRRVAFEDLXZZSFI (SEQ ID NO:418), RRRAAFEEZXITSRRGVAFEDLXZZSFI (SEQ ID NO:419), RRRAAFEEZXITSRRRVAFEDLXZZSFI (SEQ ID NO:420), RRRAAFEEZXITSRRRVAFEDLXZZSFIGR (SEQ ID NO:421), RRTAYERZCNILRRGRFQTVVQBA (SEQ ID NO:422), RRTAYERZCNILRRGRFQTVVQBAR (SEQ ID NO:423), RTAYERZCNILRGRFQTVVQBAR (SEQ ID NO:424), RRTAYERZCNILRGRFQTVVQBA (SEQ ID NO:425), BRGLEPLVIAGILARRGSLVGLLHIVL (SEQ ID NO:426), RRGLEPLVIAGILARRGSLVGLLHIVL (SEQ ID NO:427), RRGLEPLVIAGILARRGSLVGLLHIVLR (SEQ ID NO:428), RRGLEPLVIAGILARRRGSLVGLLHIVL (SEQ ID NO:429), RRGLEPLVIAGILARRRGSLVGLLHIVLR (SEQ ID NO:430), RTAFLVRNVARSIARSVTIZXASVVH (SEQ ID NO:431), RTAFLVRNVARRSIARSVTIZXASVVH (SEQ ID NO:432), RRTAFLVRNVARSIARSVTIZXASVVH (SEQ ID NO:433), RRTAFLVRNVARRSIARSVTIZXASVVH (SEQ ID NO:434), RRTAFLVRNVARRSIARSVTIZXASVVHR (SEQ ID NO:435), RRTAFLVRNVARRSIARSVTIZXASVVHRR (SEQ ID NO:436), RGDpr(Aoa)TPI(Har)QDWGNRANRGTPTRQEWDCRIS (SEQ ID NO:437), RGDpr(Aoa)TPI(Har)QDWGNRANRGTPTRQEWDARIS (SEQ ID NO:438), RGTPI(Har)QDWGNRANRGTPTRQEWDCRIS (SEQ ID NO:439), RGTPI(Har)QDWGNRANRGTPTRQEWDARIS (SEQ ID NO:440), RGCTPI(Har)QDWGNRANRGTPTRQEWDCRIS (SEQ ID NO:441), RGCTPI(Har)QDWGNRANRGTPTRQEWDARIS (SEQ ID NO:442), RGKTPI(Har)QDWGNRANRGTPTRQEWDCRIS (SEQ ID NO:443), RGKTPI(Har)QDWGNRANRGTPTRQEWDARIS (SEQ ID NO:444), RGLys(Me)TPI(Har)QDWGNRANRGTPTRQEWDCRIS (SEQ ID NO:445), RGLys(Me)TPI(Har)QDWGNRANRGTPTRQEWDARIS (SEQ ID NO:446), RGDTPI(Har)QDWGNRANRGTPTRQEWDCRIS (SEQ ID NO:447), RGDTPI(Har)QDWGNRANRGTPTRQEWDARIS (SEQ ID NO:448), RGETPI(Har)QDWGNRANRGTPTRQEWDCRIS (SEQ ID NO:449), RGETPI(Har)QDWGNRANRGTPTRQEWDARIS (SEQ ID NO:450), RGDpr(Ser)TPT(Har)NGWDVKLSRGTPI(Har)QEW(Har)SL(Nle)NQEW (SEQ ID NO:451), RGTPT(Har)NGWDVKLSRGTPI(Har)QEW(Har)SL(Nle)NQEW (SEQ ID NO:452), RGKTPT(Har)NGWDVKLSRGTPI(Har)QEW(Har)SL(Nle)NQEW (SEQ ID NO:453), RGCTPT(Har)NGWDVKLSRGTPI(Har)QEW(Har)SL(Nle)NQEW (SEQ ID NO:454), RGLys(Me)TPT(Har)NGWDVKLSRGTPI(Har)QEW(Har)SL(Nle)NQEW (SEQ ID NO:455), RGDTPT(Har)NGWDVKLSRGTPI(Har)QEW(Har)SL(Nle)NQEW (SEQ ID NO:456), RGETPT(Har)NGWDVKLSRGTPI(Har)QEW(Har)SL(Nle)NQEW (SEQ ID NO:457), RRLECVYCKQQLLRREVYDFAFRDLC (SEQ ID NO:458), RRLECVYCKQQLLRRRGEVYDFAFRDLC (SEQ ID NO:459), RRRLECVYCKQQLLRRGEVYDFAFRDLC (SEQ ID NO:460), RRRLECVYCKQQLLRRRGEVYDFAFRDLC (SEQ ID NO:461), RRRGLECVYCKQQLLRRRGEVYDFAFRDLC (SEQ ID NO:462), RRGVYDFAFRDLCRRGFAFRDLCIVYR (SEQ ID NO:463), RRGVYDFAFRDLCRRRGGFAFRDLCIVY (SEQ ID NO:464), RRRGVYDFAFRDLCRRGGFAFRDLCIVYR (SEQ ID NO:465), RRRGVYDFAFRDLCRRRGGFAFRDLCIVY (SEQ ID NO:466), RRRGGVYDFAFRDLCRRRGGFAFRDLCIVYR (SEQ ID NO:467), RRGVFDYAFRDINRRGFAYRDINLAYR (SEQ ID NO:468), RRGVYDFAFRDLCRRRGGFAFRDLCIVY (SEQ ID NO:469), RRRGVYDFAFRDLCRRGGFAFRDLCIVYR (SEQ ID NO:470), RRRGVYDFAFRDLCRRRGGFAFRDLCIVY (SEQ ID NO:471), RRRGGVYDFAFRDLCRRRGGFAFRDLCIVYR (SEQ ID NO:472), RRVDIRTLEDLLRRGTLGIVCPIGR (SEQ ID NO:473), RRVDIRTLEDLLRRRGGTLGIVCPIG (SEQ ID NO:474), RRRVDIRTLEDLLRRGGTLGIVCPIGR (SEQ ID NO:475), RRRVDIRTLEDLLRRRGGTLGIVCPIG (SEQ ID NO:476), RRRGVDIRTLEDLLRRRGGTLGIVCPIGR (SEQ ID NO:477), RGNIVPZVVTARRIGDLIVQAV (SEQ ID NO:479), RRNIVPZVVTARRIGDLIVQAV (SEQ ID NO:480), RRRNIVPZVVTARRIGDLIVQAV (SEQ ID NO:481), and RRNIVPZVVTARRRIGDLIVQAV (SEQ ID NO:482).

59. The isolated peptide according to any one of embodiments 1-58, which peptide is not specifically disclosed in any one PCT application with application numbers WO2000N000075, WO2011DK050460, or WO2012DK050010.

60. The isolated peptide according to any one of embodiments 1-59, which peptide is not a peptide selected from RRGYIPLVGAPLGBGRVARALAHGVRV (SEQ ID NO:47), RGYIPLVGAPLGRRVARALAHGVRV (SEQ ID NO:48), RGYIPLVGAPLGRRRVARALAHGVRVR (SEQ ID NO:49), RRGYIPLVGAPLGRRVARALAHGVRV (SEQ ID NO:50), RRGYIPLVGAPLGRRRVARALAHGVRV (SEQ ID NO:51), BRGYIPLVGAPLGRRVARALAHGVRV (SEQ ID NO:52), RRRGYIPLVGAPLGBRVARALAHGVRV (SEQ ID NO:53), RGYIPLVGAPLGKKKVARALAHGVRV (SEQ ID NO:54), RGYIPLVGAPLGRRRVARALAHGVRV (SEQ ID NO:55), KKGYIPLVGAPLGKKVARALAHGVRV (SEQ ID NO:56), WGYIPLVGAPLGRRVARALAHGVRV (SEQ ID NO:57), WWGYIPLVGAPLGRRVARALAHGVRV (SEQ ID NO:58), EEGYIPLVGAPLGEEVARALAHGVRV (SEQ ID NO:59), GGGYIPLVGAPLGGGVARALAHGVRV (SEQ ID NO:60), EEGYIPLVGAPLGRRVARALAHGVRV (SEQ ID NO:61), RRGYIPLVGAPLGLRRVARALAHGVRV (SEQ ID NO:62), WWGYIPLVGAPLGRRVARALAHGVRV (SEQ ID NO:63), WWGYIPLVGAPLGRRRVARALAHGVRV (SEQ ID NO:64), WWGYIPLVGAPLGRVARALAHGVRV (SEQ ID NO:65), RGYIPLVGAPLGRRVARALAHGVRV (SEQ ID NO:66), RRGYLPAVGAPIGBRVIRVIAHGLRL (SEQ ID NO:67), RRGYIPLVGAPLGBRVARALAHGVRV (SEQ ID NO:68), GYIPLVGAPLGGVARALAHGVRV (SEQ ID NO:69), WWGYLPAVGAPIRRVIRVIAHGLRL (SEQ ID NO:70), GYIPLVGAPLGGVARALAHGVRV (SEQ ID NO:71), RRGYIPLVGAPLGBGRVARALAHGVRV (SEQ ID NO:72), RGYIPLVGAPLGRRVARALAHGVRV (SEQ ID NO:73), RGYIPLVGAPLGRRRVARALAHGVRV (SEQ ID NO:74), RRGYIPLVGAPLGRRVARALAHGVRV (SEQ ID NO:75), RRGYIPLVGAPLGRRRVARALAHGVRV (SEQ ID NO:76), BRGYIPLVGAPLGRRVARALAHGVRV (SEQ ID NO:77), RRRGYIPLVGAPLGBRVARALAHGVRV (SEQ ID NO:78), RGYIPLVGAPLGKKKVARALAHGVRV (SEQ ID NO:79), RGYIPLVGAPLGRRRVARALAHGVRV (SEQ ID NO:80), KKGYIPLVGAPLGKKVARALAHGVRV (SEQ ID NO:81), WGYIPLVGAPLGRRVARALAHGVRV (SEQ ID NO:82), WWGYIPLVGAPLGRRVARALAHGVRV (SEQ ID NO:83), RRGYIPLVGAPLGLRRVARALAHGVRV (SEQ ID NO:84), RRNYVTGNIPGBRGITFSIFLIVS (SEQ ID NO:85), WWNYATGNLPGRRCSFSIFLLAL (SEQ ID NO:86), WWNYVTGNIPGBRGITFSIFLIVS (SEQ ID NO:87), WWNYVTGNIPGRRGITFSIFLIVS (SEQ ID NO:88), RRNYATGNLPGRRGCSFSIFLLAL (SEQ ID NO:89), RRVTGNIPGSTYSGBRGITFSIYLIVS (SEQ ID NO:90), RRIRNLGRVIETLTGBRLNleGYIPLIGA (SEQ ID NO:91), RRSRNLGKVIDTLTCBRLMGYIPLVGA (SEQ ID NO:92), SRNLGKVIDTLTCGFADLMGYIPLVGA (SEQ ID NO:93), WWIRNLGRVIETLTRRLNIeGYIPLIGA (SEQ ID NO:94), WWSRNLGKVIDTLTCRRLMGYIPLVGA (SEQ ID NO:95), RRGGGQIIGGNYLIPRBPBIGVRATB (SEQ ID NO:96), GGGQIVGGVYLLPRRGPRLGVRATR (SEQ ID NO:97), RRGGGQIVGGVYLLPRRGPRLGVRATR (SEQ ID NO:98), WWGGGQIVGGVYLLPRRGPRLGVRAT (SEQ ID NO:99), BRLIFLARSALIVRGSVAHKS (SEQ ID NO:100), EDLIFLARSALILRGSVAHKS (SEQ ID NO:101), BRLIFLARSALILBGRSALILRGSVAHK (SEQ ID NO:102), SAYERMCNILKGKFQTAAQRAMM (SEQ ID NO:103), SAYERNleVNILKGKFQTAAQRAVNle (SEQ ID NO:104), BRTAYERNleCNILBRGRFQTVVQBA (SEQ ID NO:105), BRIAYERMCNILLBRGKFQTAAQRA (SEQ ID NO:106), IAYERMCNILKGKFQTAAQRA (SEQ ID NO:107), LFFKCIYRLFKHGLKRGPSTEGVPESM (SEQ ID NO:108), BRRLFFKTITRLFBHGLRRLLSTEGVPNSNle (SEQ ID NO:109), BRGLEPLVIAGILARRGSLVGLLHIVL (SEQ ID NO:110), BRGSDPLVVAASIVRRASIVGILHLIL (SEQ ID NO:111), RNLVPMVATVRRNLVPMVATVB (SEQ ID NO:112), RNLVPMVATVBRRNLVPMVATVB (SEQ ID NO:113), RNIVPNleVVTARRNIVPNleVVTAB (SEQ ID NO:114), PEVIPMFSALSEGATPQDLNTMLN (SEQ ID NO:115), RFIIPXFTALSGGRRALLYGATPYAIG (SEQ ID NO:116), KALGPAATLEEMMTACQGVG (SEQ ID NO:117), RRGPVVHLTLRRRGQAGDDFS (SEQ ID NO:118), RRGPVVHLTLRRRGQAGDDFS (SEQ ID NO:119), RRGPVVHLTLRGRRGQAGDDFS (SEQ ID NO:120), RRLECVYCKQQLLRREVYDFAFRDLC (SEQ ID NO:121), RRGVYDFAFRDLCRRGFAFRDLCIVYR (SEQ ID NO:122), RRGVFDYAFRDINRRGFAYRDINLAYR (SEQ ID NO:123), RRGATPVDLLGARRGALNLCLPMR (SEQ ID NO:124), RRGVTPAGLIGVRRGALQIBLPLR (SEQ ID NO:125), RGYLPAVGAPIGRRRVIRVIAHGLRLR (SEQ ID NO:196), RRSRNLGKVIDTLTCRRLMGYIPLVGA (SEQ ID NO:197), RRIRNLGRVIETLTLNleGYIPLIGARRIRNLGRVIETLTLNleGYIPLIGAR (SEQ ID NO:199), $X^1$-NYVTGNIPG-$X^3$-GITFSIYLIVS; $X^1$-IRNLGRVIETLT-$X^3$-LNleGYIPLIGA; $X^1$-GYLPAVGAPI-$X^3$-VIRVIAHGLRL; $X^1$-GGGQIIGGNYLIP-$X^3$-PBIGVRATB; $X^1$-NYATGNLPG-$X^3$-GCSFSIFLLAL; $X^1$-SRNLGKVIDTLTC-$X^3$-LMGYIPLVGA; $X^1$-GYIPLVGAPL-$X^3$-VARALAHGVRV; $X^1$-GGGQIVGGVYLLP-$X^3$-PRLGVRATR; $X^1$-LTFLVRSVLL$^1$-$X^3$-GSVLIVRGSLVH; $X^1$-TAYERNleCNIL-$X^3$-GRFQTVVQBA; $X^1$-SDPLVVAASIV-$X^3$-ASIVGILHLIL; $X^1$-LIFLARSALIL-$X^3$-SALILRGSVAH; $X^1$-IAYERMCNIL-$X^3$-GKFQTAAQRA; and $X^1$-LEPLVIAGILA-$X^3$-GSLVGLLHIVL; $X^1$-NLVPMVATV-$X^3$-NLVPMATV; $X^1$-GYLPAVGAPIG-$X^3$-VIRVIAHGLRL; $X^1$-IRNLGRVIETLTG-$X^3$-LNleGYIPLIGA; $X^1$-GVYDFAFRDLC-$X^3$-GFAFRDLCIVYR, $X^1$-GVFDYAFRDIN-$X^3$-GFAYRDINLAYR, $X^1$-GATPVDLLGA-$X^3$-GALNLCLPMR, $X^1$-GVTPAGLIGV-$X^3$-GALQIBLPLR, and $X^1$-IRNLGRVIETLTLNleGYIPLIGA-$X^3$-IRNLGRVIETLTLNleGYIPLIGA; optionally with an $X^5$ in the C-terminal of the peptide; wherein $X^1$ and $X^3$ and $X^5$ refers to $X^1$, $X^3$, and $X^5$ of formula II.

61. An isolated multimeric, such as dimeric peptide comprising two or more monomeric peptides, each monomeric peptide independently comprising the following structure

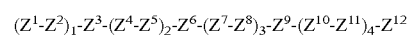

wherein $Z^1$, $Z^4$, and optional $Z^7$ and $Z^{10}$ defines a linear sequence of one, two, or three arginine residues or derivatives thereof optionally followed by a glycine (G) or an alanine (A); $Z^2$, $Z^5$, $Z^8$ and $Z^{11}$ defines an optional amino acid selected from cysteine (C), lysine (K), aspartic acid (D), asparagine (N), glutamic acid (E), glutamine (Q), 2,3-Diaminopropionic acid (Dpr), tryptophan (W), or tyrosine (Y) or a derivative thereof; $Z^3$, and optional $Z^6$, $Z^9$ and $Z^{12}$ defines any chemical moiety, such as a linear amino acid sequence, said monomeric peptides being covalently joined by one or more intermolecular bond.

62. The isolated multimeric, such as dimeric peptide according to embodiment 61, wherein two or more monomeric peptides are identical in sequence.

63. The isolated multimeric, such as dimeric peptide according to embodiment 61, wherein two or more monomeric peptides are different in sequence.

64. The isolated multimeric, such as dimeric peptide according to any of embodiments 61-63, comprising at least two peptides monomers, each peptide monomer independently being as defined in any one of embodiments 1-58.

65. The isolated multimeric, such as dimeric peptide according to any one of embodiments 61-64, wherein one or more peptide strands of the multimeric, such as dimeric peptide has delayed proteolytic degradation in the N-terminal, such as by incorporation of the first 1, 2, or 3 amino acids in the N-terminal in the D-form, or by incorporation of the first 1, 2, or 3 amino acids in the N-terminal in beta or gamma form.

66. The isolated multimeric, such as dimeric peptide according to any one of embodiments 61-65, which multimeric, such as dimeric peptide contain a helper epitope of at least 12 amino acids, such as at least 13, 14, 15 or 17 amino acids, which helper epitope consist of a combined sequence of amino acids, which is a sequence of amino acids from a first specific continuous antigenic peptide sequences, and a sequence of amino acids from at least one second specific continuous antigenic peptide sequence of the same or different protein derived from the same virus, any different virus, or any disease antigen, such as between 2-12 amino acids from the first specific continuous antigenic peptide sequences and 2-12 amino acids from the at least one second specific continuous antigenic antigenic peptide sequence.

67. The isolated multimeric, such as dimeric peptide according to any one of embodiments 61-66, wherein said intermolecular bond is a disulfide (S—S) bond between two Cys residues.

68. The isolated multimeric, such as dimeric peptide according to any one of embodiments 61-67, wherein said intermolecular bond is a thioether bond between a Cys residue in the first monomeric peptide and a modified Lys residue in the at least one second monomeric peptide.

69. The isolated multimeric, such as dimeric peptide according to any one of embodiments 61-68, wherein said intermolecular bond is an oxime bond between a derivatized Lys residue in the first monomeric peptide and a derivatized Ser residue in the at least one second monomeric peptide.

70. The isolated multimeric, such as dimeric peptide according to any one of embodiments 61-69, wherein said intermolecular bond is a peptide bond between a N-methylated Lys side-chain in the first monomeric peptide and the side-chain of an Asp or Glu residue in the at least one second monomeric peptide.

71. The isolated multimeric, such as dimeric peptide according to any one of embodiments 61-70, wherein said intermolecular bond is an oxime bond between an aldehyde moiety, produced by oxidation of a serine residue in the first monomeric peptide and a free aminooxy group of a modified amino acid (aminooxy acid), such as derivatized diaminopropionic acid, Lysine or Ornithine in in the second monomeric peptide 72. The isolated multimeric, such as dimeric peptide according to any one of embodiments 61-71, wherein said monomeric peptides are linked by a polyethylene glycol (PEG) linker, such as through an Asp or a Glu residue in the first monomeric peptide and an Asp or a Glu residue in the at least one second monomeric peptide, or by a polyLys core.

73. The isolated multimeric, such as dimeric peptide according to any one of embodiments 61-72, wherein a C residue in $Z^2$ of the first peptide monomer is linked to an amino acid selected from a K or a C residue in $Z^2$ of the second monomer.

74. The isolated multimeric, such as dimeric peptide according to any one of embodiments 61-73, wherein a K residue in $Z^2$ of the first peptide monomer is linked to an amino acid selected from a C, D or E residue in $Z^2$ of the second monomer.

75. The isolated multimeric, such as dimeric peptide according to any one of embodiments 61-74, wherein a D residue in $Z^2$ of the first peptide monomer is linked to an amino acid selected from a N or Q residue in $Z^2$ of the second monomer.

76. The isolated multimeric, such as dimeric peptide according to any one of embodiments 61-75, wherein a E residue in $Z^2$ of the first peptide monomer is linked to an amino acid selected from a N or Q residue in $Z^2$ of the second monomer.

77. The isolated multimeric, such as dimeric peptide according to any one of embodiments 61-76, wherein a N residue in $Z^2$ of the first peptide monomer is linked to a D or E residue in $Z^2$ of the second monomer.

78. The isolated multimeric, such as dimeric peptide according to any one of embodiments 61-77, wherein a Q residue in $Z^2$ of the first peptide monomer is linked to a D or E residue in $Z^2$ of the second monomer.

79. The isolated multimeric, such as dimeric peptide according to any one of embodiments 61-78, wherein a Dpr(Aao) residue in $Z^2$ of the first peptide monomer is linked to an Dpr(Ser) residue in $Z^2$ of the second monomer.

80. The isolated multimeric, such as dimeric peptide according to any one of embodiments 61-79, wherein a W residue in $Z^2$ of the first $Z^1$-$Z^2$ peptide repeat is linked to an Y residue in $Z^2$ of the second $Z^1$-$Z^2$ peptide repeat.

81. The isolated multimeric, such as dimeric peptide according to any one of embodiments 61-80, wherein a Y residue in $Z^2$ of the first $Z^1$-$Z^2$ peptide repeat is linked to an W residue in $Z^2$ of the second $Z^1$-$Z^2$ peptide repeat.

82. Composition comprising two or more compounds selected from a monomeric peptide is as defined in any one of embodiments 1-60, and an isolated multimeric, such as dimeric peptide as defined in any one of embodiments 61-81.

83. Use of a peptide selected from a monomeric peptide is as defined in any one of embodiments 1-60, and an isolated multimeric, such as dimeric peptide as defined in any one of embodiments 61-81 for inducing an immune response in a subject, such as a humoral or Cell Mediated Immune (CMI) response.

84. An isolated nucleic acid or polynucleotide encoding a peptide according to any one of embodiments 1-61.

85. A vector comprising the nucleic acid or polynucleotide according to embodiment 84.

86. A host cell comprising the vector according to embodiment 85.

87. An immunogenic composition comprising at least one monomeric peptide according to any one of embodiments 1-61, an isolated multimeric, such as dimeric peptide according to any one of embodiments 61-81, a peptide composition according to embodiment 82, the nucleic acid or polynucleotide according to embodiment 84, or the vector according to embodiment 85; in combination with a pharmaceutically acceptable diluent or vehicle and optionally an immunological adjuvant.

88. The immunogenic composition according to embodiment 87 in the form of a vaccine composition.

89. A method for inducing an immune response in a subject against an antigen which comprises administration of at least one monomeric peptide according to any one of embodiments 1-60, an isolated multimeric, such as dimeric peptide according to any one of embodiments 61-79, a peptide composition according to embodiment 82, the nucleic acid or polynucleotide according to embodiment 84, or the vector according to embodiment 85; or the composition according to any one of embodiments 87-88.

90. A method for reducing and/or delaying the pathological effects of a disease antigen, such as an infectious agent in a subject infected with said agent or having said disease caused by said antigen, the method comprising administering an effective amount of at least one monomeric peptide according to any one of embodiments 1-60, an isolated multimeric, such as dimeric peptide according to any one of embodiments 61-81, a peptide composition according to embodiment 82, the nucleic acid or polynucleotide according to embodiment 84, or the vector according to embodiment 85; or the composition according to any one of embodiments 87-88.

91. A peptide according to any one of embodiments 1-81 for use as a medicament.

92. A peptide according to any one of embodiments 1-81 for treating the pathological effects of a disease antigen, such as an infectious agent in a subject infected with said agent or having said disease caused by said antigen.

93. A peptide according to any one of embodiments 1-81 for use in an in vitro assay, such as an ELISA assay, such as for diagnostic purposes.

94. Use of a peptide according to any one of embodiments 1-81 for in vitro assay, such as an ELISA assay, such as for diagnostic purposes.

Sequence list (amino acids in bold represents suitable antigenic sequences that may be used as any of $Z^3$, and optional $Z^6$, $Z^9$ and $Z^{12}$ as defined in formula I of the present invention)

```
SEQ ID NO: 1:
Accession no AF009606; Hepatitis C virus subtype
is polyprotein gene, complete cds.
MSTNPKPQRKTKRNTNRRPQDVKFPGGGQIVGGVYLLPRRGPRL

GVRATRKTSERSQPRGRRQPIPKARRPEGRTWAQPGYPWPLYGNEGCGWAGWLLSPRG

SRPSWGPTDPRRRSRNLGKVIDTLTCGFADLMGYIPLVGAPLGGAARALAHGVRVLED

GVNYATGNLPGCSFSIFLLALLSCLTVPASAYQVRNSSGLYHVTNDCPNSSIVYEAAD

AILHTPGCVPCVREGNASRCWVAVTPTVATRDGKLPTTQLRRHIDLLVGSATLCSALY

VGDLCGSVFLVGQLFTFSPRRHWTTQDCNCSIYPGHITGHRMAWDMMMNWSPTAALVV

AQLLRIPQAIMDMIAGAHWGVLAGIAYFSMVGNWAKVLVVLLLFAGVDAETHVTGGSA

GRTTAGLVGLLTPGAKQNIQLINTNGSWHINSTALNCNESLNTGWLAGLFYQHKFNSS

GCPERLASCRRLTDFAQGWGPISYANGSGLDERPYCWHYPPRPCGIVPAKSVCGPVYC

FTPSPVVVGTTDRSGAPTYSWGANDTDVFVLNNTRPPLGNWFGCTWMNSTGFTKVCGA

PPCVIGGVGNNTLLCPTDCFRKHPEATYSRCGSGPWITPRCMVDYPYRLWHYPCTINY

TIFKVRMYVGGVEHRLEAACNWTRGERCDLEDRDRSELSPLLLSTTQWQVLPCSFTTL

PALSTGLIHLHQNIVDVQYLYGVGSSIASWAIKWEYVVLLFLLLADARVCSCLWMMLL

ISQAEAALENLVILNAASLAGTHGLVSFLVFFCFAWYLKGRWVPGAVYAFYGMWPLLL

LLLALPQRAYALDTEVAASCGGVVLVGLMALTLSPYYKRYISWCMWWLQYFLTRVEAQ

LHVWVPPLNVRGGRDAVILLMCVVHPTLVFDITKLLLAIFGPLWILQASLLKVPYFVR

VQGLLRICALARKIAGGHYVQMAIIKLGALTGTYVYNHLTPLRDWAHNGLRDLAVAVE

PVVFSRMETKLITWGADTAACGDIINGLPVSARRGQEILLGPADGMVSKGWRLLAPIT

AYAQQTRGLLGCIITSLTGRDKNQVEGEVQIVSTATQTFLATCINGVCWTVYHGAGTR

TIASPKGPVIQMYTNVDQDLVGWPAPQGSRSLTPCTCGSSDLYLVTRHADVIPVRRRG

DSRGSLLSPRPISYLKGSSGGPLLCPAGHAVGLFRAAVCTRGVAKAVDFIPVENLETT

MRSPVFTDNSSPPAVPQSFQVAHLHAPTGSGKSTKVPAAYAAQGYKVLVLNPSVAATL

GFGAYMSKAHGVDPNIRTGVRTITTGSPITYSTYGKFLADGGCSGGAYDIIICDECHS

TDATSILGIGTVLDQAETAGARLVVLATATPPGSVTVSHPNIEEVALSTTGEIPFYGK

AIPLEVIKGGRHLIFCHSKKKCDELAAKLVALGINAVAYYRGLDVSVIPTSGDVVVVS

TDALMTGFTGDFDSVIDCNTCVTQTVDFSLDPTFTIETTTLPQDAVSRTQRRGRTGRG

KPGIYRFVAPGERPSGMFDSSVLCECYDAGCAWYELTPAETTVRLRAYMNTPGLPVCQ

DHLEFWEGVFTGLTHIDAHFLSQTKQSGENFPYLVAYQATVCARAQAPPPSWDQMWKC

LIRLKPTLHGPTPLLYRLGAVQNEVTLTHPITKYIMTCMSADLEVVTSTWVLGGVLA

ALAAYCLSTGCVVIVGRIVLSGKPAIIPDREVLYQEFDEMEECSQHLPYIEQGMMLAE
```

-continued

QFKQKALGLLQTASRQAEVITPAVQTNWQKLEVFWAKHMWNFISGIQYLAGLSTLPGN

PAIASLMAFTAAVTSPLTTGQTLLFNILGGWVAAQLAAPGAATAFVGAGLAGAAIGSV

GLGKVLVDILAGYGAGVAGALVAFKIMSGEVPSTEDLVNLLPAILSPGALVVGVVCAA

ILRRHVGPGEGAVQWMNRLIAFASRGNHVSPTHYVPESDAAARVTAILSSLTVTQLLR

RLHQWISSECTTPCSGSWLRDIWDWICEVLSDFKTWLKAKLMPQLPGIPFVSCQRGYR

GVWRGDGIMHTRCHCGAEITGHVKNGTMRIVGPRTCRNMWSGTFPINAYTTGPCTPLP

APNYKFALWRVSAEEYVEIRRVGDFHYVSGMTTDNLKCPCQIPSPEFFTELDGVRLHR

FAPPCKPLLREEVSFRVGLHEYPVGSQLPCEPEPDVAVLTSMLTDPSHITAEAAGRRL

ARGSPPSMASSSASQLSAPSLKATCTANHDSPDAELIEANLLWRQEMGGNITRVESEN

KVVILDSFDPLVAEEDEREVSVPAEILRKSRRFARALPVWARPDYNPPLVETWKKPDY

EPPVVHGCPLPPPRSPPVPPPRKKRTVVLTESTLSTALAELATKSFGSSSTSGITGDN

TTTSSEPAPSGCPPDSDVESYSSMPPLEGEPGDPDLSDGSWSTVSSGADTEDVVCCSM

SYSWTGALVTPCAAEEQKLPINALSNSLLRHHNLVYSTTSRSACQRQKKVTFDRLQVL

DSHYQDVLKEVKAAASKVKANLLSVEEACSLTPPHSAKSKFGYGAKDVRCHARKAVAH

INSVWKDLLEDSVTPIDTTIMAKNEVFCVQPEKGGRKPARLIVFPDLGVRVCEKMALY

DVVSKLPLAVMGSSYGFQYSPGQRVEFLVQAWKSKKTPMGFSYDTRCFDSTVTESDIR

TEEAIYQCCDLDPQARVAIKSLTERLYVGGPLTNSRGENCGYRRCRASGVLTTSCGNT

LTCYIKARAACRAAGLQDCTMLVCGDDLVVICESAGVQEDAASLRAFTEAMTRYSAPP

GDPPQPEYDLELITSCSSNVSVAHDGAGKRVYYLTRDPTTPLARAAWETARHTPVNSW

LGNIIMFAPTLWARMILMTHFFSVLIARDQLEQALNCEIYGACYSIEPLDLPPIIQRL

HGLSAFSLHSYSPGEINRVAACLRKLGVPPLRAWRHRARSVRARLLSRGGRAAICGKY

LFNWAVRTKLKLTPIAAAGRLDLSGWFTAGYSGGDIYHSVSHARPRWFWFCLLLLAAG

VGIYLLPNR

SEQ ID NO: 2:
HCV core protein, H77, Accession AF009606
Genbank number: 2316097
>gi|2316098|gb|AAB66324.1| polyprotein [Hepatitis C virus
subtype 1a]
MSTNPKPQRKTKRNTNRRPQDVKFPGGGQIVGGVYLLPRRGPRLGVRATRKTSERSQPRGRRQPIPKARR

PEGRTWAQPGYPWPLYGNEGCGWAGWLLSPRGSRPSWGPTDPRRRSRNLGKVIDTLTCGFADLMGYIPLVGAPLGGAAR

ALAHGVRVLEDGVNYATGNLPGCSFSIFLLALLSCLTVPASA

SEQ ID NO: 3:
Hepatitis C virus mRNA, complete cds;
ACCESSION M96362 M72423;
Hepatitis C virus subtype 1b
MSTNPKPQRKTKRNTNRRPQDIKFPGGGQIVGGVYLLPRRGPRL

GVRATRKTSERSQPRGRRQPIPKARRPEGRAWAQPGYPWPLYGNEGLGWAGWLLSPRG

SRPSWGPTDPRRKSRNLGKVIDTLTCGFADLMGYIPLVGAPLGGVARALAHGVRVLED

GVNYATGNLPGCSFSIFLLALLSCLTTPVSAYEVRNASGMYHVTNDCSNSSIVYEAAD

MIMHTPGCVPCVREDNSSRCWVALTPTLAARNASVPTTTLRRHVDLLVGVAAFCSAMY

VGDLCGSVFLVSQLFTESPRRHETVQDCNCSIYPGRVSGHRMAWDMMMNWSPTTALVV

SQLLRIPQAVVDMVTGSHWGILAGLAYYSMVGNWAKVLIAMLLFAGVDGTTHVTGGAQ

GRAASSLTSLFSPGPVQHLQLINTNGSWHINRTALSCNDSLNTGFVAALFYKYRFNAS

GCPERLATCRPIDTFAQGWGPITYTEPHDLDQRPYCWHYAPQPCGIVPTLQVCGPVYC

FTPSPVAVGTTDRFGAPTYRWGANETDVLLLNNAGPPQGNWFGCTWMNGTGFTKTCGG

-continued

PPCNIGGVGNNTLTCPTDCFRKHPGATYTKCGSGPWLTPRCLVDYPYRLWHYPCTVNF
TIFKVRMYVGGAEHRLDAACNWTRGERCDLEDRDRSELSPLLLSTTEWQVLPCSFTTL
PALSTGLIHLHQNIVDIQYLYGIGSAVVSFAIKWEYIVLLFLLLADARVCACLWMMLL
VAQAEAALENLVVLNAASVAGAHGILSFIVFFCAAWYIKGRLVPGAAYALYGVWPLLL
LLLALPPRAYAMDREMAASCGGAVFVGLVLLTLSPHYKVFLARFIWWLQYLITRTEAH
LQVWVPPLNVRGGRDAIILLTCVVHPELIFDITKYLLAIFGPLMVLQAGITRVPYFVR
AQGLIRACMLARKVVGGHYVQMVFMKLAALAGTYVYDHLTPLRDWAHTGLRDLAVAVE
PVVFSDMETKVITWGADTAACGDIILALPASARRGKEILLGPADSLEGQGWRLLAPIT
AYSQQTRGLLGCIITSLTGRDKNQVEGEVQVVSTATQSFLATCINGVCWTVFHGAGSK
TLAGPKGPITQMYTNVDQDLVGWPAPPGARSLTPCTCGSSDLYLVTRHADVIPVRRRG
DGRGSLLPPRPVSYLKGSSGGPLLCPSGHAVGILPAAVCTRGVAMAVEFIPVESMETT
MRSPVFTDNPSPPAVPQTFQVAHLHAPTGSGKSTRVPAAYAAQGYKVLVLNPSVAATL
GFGAYMSKAHGIDPNLRTGVRTITTGAPITYSTYGKFLADGGGSGGAYDIIMCDECHS
TDSTTIYGIGTVLDQAETAGARLVVLSTATPPGSVTVPHLNIEEVALSNTGEIPFYGK
AIPIEAIKGGRHLIFCHSKKKCDELAAKLSGLGLNAVAYYRGLDVSVIPTSGDVVVVA
TDALMTGFTGDFDSVIDCNTCVTQTVDFSLDPTFTIETTTVPQDAVSRSQRRGRTGRG
RAGIYRFVTPGERPSGMFDSSVLCECYDAGCAWYELTPAETSVRLRAYLNTPGLPVCQ
DHLEFSEGVFTGLTHIDAHFLSQTKQAGENFPYLVAYQATVCARAQAPPPSWDEMWRC
LIRLKPTLHGPTPLLYRLGAVQNEVTLTHPITKFIMTCMSADLEVVTSTWVLVGGVLA
ALAAYCLTTGSVVIVGRIILSGKPAIIPDREVLYQEFDEMEECASHLPYFEQGMQLAE
QFKQKALGLLQTATKQAEAAAPVVESKWRALETFWAKHMWNFISGIQYLAGLSTLPGN
PAIRSPMAFTASITSPLTTQHTLLFNILGGWVAAQLAPPSAASAFVGAGIAGAAVGTI
GLGKVLVDILAGYGAGVAGALVAFKIMSGEMPSAEDMVNLLPAILSPGALVVGIVCAA
ILRRHVGPGEGAVQWMNRLIAFASRGNHVSPRHYVPESEPAARVTQILSSLTITQLLK
RLHQWINEDCSTPCSSSWLREIWDWICTVLTDFKTWLQSKLLPRLPGVPFFSCQRGYK
GVWRGDGIMHTTCPCGAQITGHVKNGSMRIVGPKTCSNTWYGTFPINAYTTGPCTPSP
APNYSKALWRVAAEEYVEVTRVGDFHYVTGMTTDNVKCPCQVPAPEFFTEVDGVRLHR
YAPACRPLLREEVVFQVGLHQYLVGSQLPCEPEPDVAVLTSMLTDPSHITAETAKRRL
ARGSPPSLASSSASQLSAPSLKATCTTHHDSPDADLIEANLLWRQEMGGNITRVESEN
KVVILDSFDPLRAEDDEGEISVPAEILRKSRKFPPALPIWAPPDYNPPLLESWKDPDY
VPPVVHGCPLPPTKAPPIPPPRRKRTVVLTESTVSSALAELATKTFGSSGSSAIDSGT
ATAPPDQASGDGDRESDVESFSSMPPLEGEPGDPDLSDGSWSTVSEEASEDVVCCSMS
YTWTGALITPCAAEESKLPINPLSNSLLRHHNMVYATTSRSAGLRQKKVTFDRLQVLD
DHYRDVLKEMKAKASTVKAKLLSVEEACKLTPPHSAKSKFGYGAKDVRSLSSRAVTHI
RSVWKDLLEDTETPISTTIMAKNEVFCVQPEKGGRKPARLIVFPDLGVRVCEKMALYD
VVSTLPQAVMGSSYGFQYSPKQRVEFLVNTWKSKKCPMGFSYDTRCFDSTVTENDIRV
EESIYQCCDLAPEAKLAIKSLTERLYIGGPLTNSKGQNCGYRRCRASGVLTTSCGNTL
TCYLKATAACRAAKLRDCTMLVNGDDLVVICESAGTQEDAASLRVFTEAMTRYSAPPG
DPPQPEYDLELITSCSSNVSVAHDASGKRVYYLTRDPTTPLARAAWETARHTPVNSWL
GNIIMYAPTLWARMILMTHFFSILLAQEQLEKTLDCQIYGACYSIEPLDLPQIIERLH
GLSAFSLHSYSPGEINRVASCLRKLGVPPLRAWRHRARSVRAKLLSQGGRAATCGKYL

```
FNWAVRTKLKLTPIPAASRLDLSGWFVAGYSGGDIYHSLSRARPRWFMLCLLLLSVGV

GIYLLPNR
```

SEQ ID NO: 4,
nucleocapsid protein of influenza A virus
```
  1 MASQGTKRSY EQMETSGERQ NATEIRASVG RMVGGIGRFY IQMCTELKLS DHEGRLIQNS

61 ITIERMVLSA FDERRNKYLE EHPSAGKDPK KTGGPIYRRR DGKWMRELIL YDKEEIRRIW

121 RQANNGEDAT AGLTHMMIWH SNLNDATYQR TRALVRTGMD PRMCSLMQGS TLPRRSGAAG

181 AAVKGVGTMV MELIRMIKRG INDRNFWRGE NGRRTRIAYE RMCNILKGKF QTAAQRAMMD

241 QVRESRNPGN AEIEDLIFLA RSALILRGSV AHKSCLPACV YGLAVASGYD FEREGYSLVG

301 IDPFRLLQNS QVFSLIRPNE NPAHKSQLVW MACHSAAFED LRVSSFIRGT RVVPRGQLST

361 RGVQIASNEN METMDSSTLE LRSRYWAIRT RSGGNTNQQR ASAGQISVQP TFSVQRNLPF

421 ERATIMAAFT GNTEGRTSDM RTEIIRMMEN ARPEDVSFQG RGVFELSDEK ATNPIVPSFD

481 MSNEGS
```

SEQ ID NO: 5
>gi|73919153|ref|YP_308840.1| matrix protein 2
[Influenza A virus (A/New York/392/2004(H3N2))]
MSLLTEVETPIRNEWGCRCNDSSDPLVVAASIIGILHLILWILDRLFFKCVYRLEKHGLKRGPSTEGVPE   70

SMREEYRKEQQNAVDADDSHFVSIELE

SEQ ID NO: 6
>gi|73919147|ref|YP_308843.1| nucleocapsid protein
[Influenza A virus (A/New York/392/2004(H3N2))]
```
MASQGTKRSYEQMETDGDRQNATEIRASVGKMIDGIGRFYIQMCTELKLSDHEGRLIQNSLTIEKMVLSA    70

FDERRNKYLEEHPSAGKDPKKTGGPIYRRVDGKWMRELVLYDKEEIRRIWRQANNGEDATAGLTHIMIWH   140

SNLNDATYQRTRALVRTGMDPRMCSLMQGSTLPRRSGAAGAAVKGIGTMVMELIRMVKRGINDRNFWRGE   210
```
NGRKTRSAYERMCNILKGKFQTAAQRAMVDQVRESRNPGNAEIEDLIFLARSALILRGSVAHKSCLPACA   280
```
YGPAVSSGYDFEKEGYSLVGIDPFKLLQNSQIYSLIRPNENPAHKSQLVWMACHSAAFEDLRLLSFIRGT   350

KVSPRGKLSTRGVQIASNENMDNMGSSTLELRSGYWAIRTRSGGNTNQQRASAGQTSVQPTFSVQRNLPF   420

EKSTIMAAFTGNTEGRTSDMRAEIIRMMEGAKPEEVSFRGRGVFELSDEKATNPIVPSFDMSNEGSYFFG   490

DNAEEYDN
--
```

SEQ ID NO: 7
>gi|56583270|ref|NP_040979.2| matrix protein 2
[Influenza A virus (A/Puerto Rico/8/34(H1N1))]
MSLLTEVETPIRNEWGCRCNGSSDPLAIAANIIGILHLILWILDRLFFKCIYRREKYGLKGGPSTEGVPK

SMREEYRKEQQSAVDADDGHFVSIELE

SEQ ID NO: 8
>gi|8486130|ref|NP_040982.1| nucleocapsid protein
[Influenza A virus (A/Puerto Rico/8/34(H1N1))]
```
MASQGTKRSYEQMETDGERQNATEIRASVGKMIGGIGRFYIQMCTELKLSDYEGRLIQNSLTIERMVLSA

FDERRNKYLEEHPSAGKDPKKTGGPIYRRVNGKWMRELILYDKEEIRRIWRQANNGDDATAGLTHMMIWH

SNLNDATYQRTRALVRTGMDPRMCSLMQGSTLPRRSGAAGAAVKGVGTMVMELVRMIKRGINDRNFWRGE
```
NGRKTRIAYERMCNILKGKFQTAAQKAMMDQVRESRDPGNAEFEDLTFLARSALILRGSVAHKSCLPACV
```
YGPAVASGYDFEREGYSLVGIDPFRLLQNSQVYSLIRPNENPAHKSQLVWMACHSAAFEDLRVLSFIKGT

KVVPRGKLSTRGVQIASNENMETMESSTLELRSRYWAIRTRSGGNTNQQRASAGQISIQPTFSVQRNLPF

DRTTVMAAFTGNTEGRTSDMRTEIIRMMESARPEDVSFQGRGVFELSDEKAASPIVPSFDMSNEGSYFFG

DNAEEYDN
--
```

SEQ ID NO: 9
>gi|73912687|ref|YP_308853.1| membrane protein M2

-continued

[Influenza A virus (A/Korea/426/68(H2N2))]
MSLLTEVETPIRNEWGCRCNDSSDPLVVAASIIGILHFILWILDRLFFKCIYRFEKHGLKRGPSTEGVPE

SMREEYRKEQQSAVDADDSHFVSIELE

SEQ ID NO: 10

>gi|73921307|ref|YP_308871.1| nucleoprotein [Influenza A virus (A/Korea/426/68(H2N2))]
MASQGTKRSYEQMETDGERQNATEIRASVGKMIDGIGRFYIQMCTELKLSDYEGRLIQNSLTIERMVLSA

FDERRNKYLEEHPSAGKDPKKTGGPIYKRVDGKWMRELVLYDKEEIRRIWRQANNGDDATAGLTHMMIWH

SNLNDTTYQRTRALVRTGMDPRMCSLMQGSTLPRRSGAAGAAVKGVGTMVMELIRMIKRGINDRNFWRGE

NGRKTRSAYERMCNILKGKFQTAAQRAMMDQVRESRNPGNAEIEDLIFLARSALILRGSVAHKSCLPACV

YGPAIASGYNFEKEGYSLVGIDPFKLLQNSQVYSLIRPNENPAHKSQLVWMACNSAAFEDLRVLSFIRGT

KVSPRGKLSTRGVQIASNENMDTMESSTLELRSRYWAIRTRSGGNTNQQRASAGQISVQPAFSVQRNLPF

DKPTIMAAFTGNTEGRTSDMRAEIIRMMEGAKPEEMSFQGRGVFELSDEKATNPIVPSFDMSNEGSYFFG

DNAEEYDN

SEQ ID NO: 11

>gi|330647|gb|AAA45994.1| pp65 [Human herpesvirus 5]
MASVLGPISGHVLKAVFSRGDTPVLPHETRLLQTGIHVRVSQPSLILVSQYTPDSTPCHRGDNQLQVQHT 70

YFTGSEVENVSVNVHNPTGRSICPSQEPMSIYVYALPLKMLNIPSINVHHYPSAAERKHRHLPVADAVIH 140

ASGKQMWQARLTVSGLAWTRQQNQWKEPDVYYTSAFVFPTKDVALRHVVCAHELVCSMENTRATKMQVIG 210

DQYVKVYLESFCEDVPSGKLFMHVTLGSDVEEDLTMTRNPQPFMRPHERNGFTVLCPKNMIIKPGKISHI 280

MLDVAFTSHEHFGLLCPKSIPGLSISGNLLMNGQQIFLEVQAIRETVELRQYDPVAALFFFDIDLLLQRG 350

PQYSEHPTFTSQYRIQGKLEYRHTWDRHDEGAAQGDDDVWTSGSDSDEELVTTERKTPRVTGGGAMAGAS 420

TSAGRKRKSASSATACTAGVMTRGRLKAESTVAPEEDTDEDSDNEIHNPAVFTWPPWQAGILARNLVPMV 490

ATVQGQNLKYQEFFWDANDIYRIFAELEGVWQPAAQPKRRRHRQDALPGPCIASTPKKHRG 541

SEQ ID NO: 12

>gi|33330937|gb|AAQ10712.1| putative transforming protein E6 [Human papillomavirus type 16]
MHQKRTAMFQDPQERPGKLPQLCTELQTTIHDIILECVYCKQQLLRREVYDFAFRDLCIVYRDGNPYAVC 70

DKCLKFYSKISEYRHYCYSVYGTTLEQQYNKPLCDLLIRCINCQKPLCPEEKQRHLDKKQRFHNIRGRWT 140

GRCMSCCRSSRTRRETQL

SEQ ID NO: 13

>gi|56583270|ref|NP_040979.2| matrix protein 2 [Influenza A virus (A/Puerto Rico/8/34(H1N1))]
MSLLTEVETPIRNEWGCRCNGSSDPLAIAANIIGILHLILWILDRLFFKCIYRRFKYGLKGGPSTEGVPK

SMREEYRKEQQSAVDADDGHFVSIELE

SEQ ID NO: 14

>gi|8486139|ref|NP_040987.1| PB2 protein [Influenza A virus (A/Puerto Rico/8/34(H1N1))]
MERIKELRNLMSQSRTREILTKTTVDHMAIIKKYTSGRQEKNPALRMKWMMAMKYPITADKRITEMIPER

NEQGQTLWSKMNDAGSDRVMVSPLAVTWWNRNGPMTNTVHYPKIYKTYFERVERLKHGTFGPVHFRNQVK

IRRRVDINPGHADLSAKEAQDVIMEVVFPNEVGARILTSESQLTITKEKKEELQDCKISPLMVAYMLERE

LVRKTRFLPVAGGTSSVYIEVLHLTQGTCWEQMYTPGGEVKNDDVDQSLIIAARNIVRRAAVSADPLASL

LEMCHSTQIGGIRMVDILKQNPTEEQAVGICKAAMGLRISSSFSFGGFTFKRTSGSSVKREEEVLTGNLQ

TLKIRVHEGYEEFTMVGRRATAILRKATRRLIQLIVSGRDEQSIAEAIIVAMVFSQEDCMIKAVRGDLNF

VNRANQRLNPMHQLLRHFQKDAKVLFQNWGVEPIDNVMGMIGILPDMTPSIEMSMRGVRISKMGVDEYSS

TERVVVSIDRFLRVRDQRGNVLLSPEEVSETQGTEKLTITYSSSMMWEINGPESVLVNTYQWIIRNWETV

KIQWSQNPTMLYNKMEFEPFQSLVPKAIRGQYSGFVRTLFQQMRDVLGTFDTAQIIKLLPFAAAPPKQSR

MQFSSFTVNVRGSGMRILVRGNSPVFNYNKATKRLTVLGKDAGTLTEDPDEGTAGVESAVLRGFLILGKE

-continued
DRRYGPALSINELSNLAKGEKANVLIGQGDVVLVMKRKRDSSILTDSQTATKRIRMAIN

SEQ ID NO: 15
\>gi|8486137|ref|NP_040986.1| polymerase PA
[Influenza A virus (A/Puerto Rico/8/34(H1N1))]
MEDFVRQCFNPMIVELAEKTMKEYGEDLKIETNKFAAICTHLEVCFMYSDFHFINEQGESIIVELGDPNA

LLKHRFEIIEGRDRTMAWTVVNSICNTTGAEKPKFLPDLYDYKENRFIEIGVTRREVHIYYLEKANKIKS

EKTHIHIFSFTGEEMATKADYTLDEESRARIKTRLFTIRQEMASRGLWDSFRQSERGEETIEERFEITGT

MRKLADQSLPPNFSSLENFRAYVDGFEPNGYIEGKLSQMSKEVNARIEPFLKTTPRPLRLPNGPPCSQRS

KFLLMDALKLSIEDPSHEGEGIPLYDAIKCMRTFFGWKEPNVVKPHEKGINPNYLLSWKQVLAELQDIEN

EEKIPKTKNMKKTSQLKWALGENMAPEKVDFDDCKDVGDLKQYDSDEPELRSLASWIQNEFNKACELTDS

SWIELDEIGEDVAPIEHIASMRRNYFTSEVSHCRATEYIMKGVYINTALLNASCAAMDDFQLIPMISKCR

TKEGRRKTNLYGFIIKGRSHLRNDTDVVNFVSMEFSLTDPRLEPHKWEKYCVLEIGDMLLRSAIGQVSRP

MFLYVRTNGTSKIKMKWGMEMRRCLLQSLQQIESMIEAESSVKEKDMTKEFFENKSETWPIGESPKGVEE

SSIGKVCRTLLAKSVFNSLYASPQLEGFSAESRKLLLIVQALRDNLEPGTFDLGGLYEAIEECLINDPWV

LLNASWFNSFLTHALS

SEQ ID NO: 16
\>gi|8486133|ref|NP_040984.1| nonstructural protein NS1
[Influenza A virus (A/Puerto Rico/8/34(H1N1))]
MDPNTVSSFQVDCFLWHVRKRVADQELGDAPFLDRLRRDQKSLRGRGSTLGLDIETATRAGKQIVERILK

EESDEALKMTMASVPASRYLTDMTLEEMSREWSMLIPKQKVAGPLCIRMDQAIMDKNIILKANFSVIFDR

LETLILLRAFTEEGAIVGEISPLPSLPGHTAEDVKNAVGVLIGGLEWNDNTVRVSETLQRFAWRSSNENG

RPPLTPKQKREMAGTIRSEV

SEQ ID NO: 17
\>gi|8486132|ref|NP_040983.1| nonstructural protein NS2
[Influenza A virus (A/Puerto Rico/8/34(H1N1))]
MDPNTVSSFQDILLRMSKMQLESSSEDLNGMITQFESLKLYRDSLGEAVMRMGDLHSLQNRNEKWREQLG

QKFEEIRWLIEEVRHKLKVTENSFEQITFMQALHLLLEVEQEIRTFSFQLI

SEQ ID NO: 18
\>gi|8486128|ref|NP_040981.1| neuraminidase
[Influenza A virus (A/Puerto Rico/8/34(H1N1))]
MNPNQKIITIGSICLVVGLISLILQIGNIISIWISHSIQTGSQNHTGICNQNIITYKNSTWVKDTTSVIL

TGNSSLCPIRGWAIYSKDNSIRIGSKGDVFVIREPFISCSHLECRTFFLTQGALLNDRHSNGTVKDRSPY

RALMSCPVGEAPSPYNSRFESVAWSASACHDGMGWLTIGISGPDNGAVAVLKYNGIITETIKSWRKKILR

TQESECACVNGSCFTIMTDGPSDGLASYKIFKIEKGKVTKSIELNAPNSHYEECSCYPDTGKVMCVCRDN

WHGSNRPWVSFDQNLDYQIGYICSGVFGDNPRPKDGTGSCGPVYVDGANGVKGFSYRYGNGVWIGRTKSH

SSRHGFEMIWDPNGWTETDSKFSVRQDVVAMTDWSGYSGSFVQHPELTGLDCIRPCFWVELIRGRPKEKT

IWTSASSISFCGVNSDTVDWSWPDGAELPFTIDK

SEQ ID NO: 19
\>gi|8486126|ref|NP_040980.1| haemagglutinin [Influenza A virus
(A/Puerto Rico/8/34(H1N1))]
MKANLLVLLCALAAADADTICIGYHANNSTDTVDTVLEKNVTVTHSVNLLEDSHNGKLCRLKGIAPLQLG

KCNIAGWLLGNPECDPLLPVRSWSYIVETPNSENGICYPGDFIDYEELREQLSSVSSFERFEIFPKESSW

PNHNTTKGVTAACSHAGKSSFYRNLLWLTEKEGSYPKLKNSYVNKKGKEVLVLWGIHHPSNSKDQQNIYQ

NENAYVSVVTSNYNRRFTPEIAERPKVRDQAGRMNYYWTLLKPGDTIIFEANGNLIAPRYAFALSRGFGS

GIITSNASMHECNTKCQTPLGAINSSLPFQNIHPVTIGECPKYVRSAKLRMVTGLRNIPSIQSRGLFGAI

AGFIEGGWTGMIDGWYGYHHQNEQGSGYAADQKSTQNAINGITNKVNSVIEKMNIQFTAVGKEFNKLEKR

MENLNKKVDDGFLDIWTYNAELLVLLENERTLDFHDSNVKNLYEKVKSQLKNNAKEIGNGCFEFYHKCDN

ECMESVRNGTYDYPKYSEESKLNREKVDGVKLESMGIYQILAIYSTVASSLVLLVSLGAISFWMCSNGSL

QCRICI

SEQ ID NO: 20
>gi|8486123|ref|NP_040978.1| matrix protein 1 [Influenza A virus
(A/Puerto Rico/8/34(H1N1))]
MSLLTEVETYVLSIIPSGPLKAEIAQRLEDVFAGKNTDLEVLMEWLKTRPILSPLTKGILGFVFTLTVPS

ERGLQRRRFVQNALNGNGDPNNMDKAVKLYRKLKREITFHGAKEISLSYSAGALASCMGLIYNRMGAVTT

EVAFGLVCATCEQIADSQHRSHRQMVTTTNPLIRHENRMVLASTTAKAMEQMAGSSEQAAEAMEVASQAR

QMVQAMRTIGTHPSSSAGLKNDLLENLQAYQKRMGVQMQRFK

SEQ ID NO: 21
>gi|83031685|ref|YP_418248.1| PB1-F2 protein [Influenza A virus
(A/Puerto Rico/8/34(H1N1))]
MGQEQDTPWILSTGHISTQKRQDGQQTPKLEHRNSTRLMGHCQKTMNQVVMPKQIVYWKQWLSLRNPILV

FLKTRVLKRWRLFSKHE

SEQ ID NO: 22
>gi|8486135|ref|NP_040985.1| polymerase 1 PB1 [Influenza A virus
(A/Puerto Rico/8/34(H1N1))]
MDVNPTLLFLKVPAQNAISTTFPYTGDPPYSHGTGTGYTMDTVNRTHQYSEKARWTTNTETGAPQLNPID

GPLPEDNEPSGYAQTDCVLEAMAFLEESHPGIFENSCIETMEVVQQTRVDKLTQGRQTYDWTLNRNQPAA

TALANTIEVFRSNGLTANESGRLIDFLKDVMESMKKEEMGITTHFQRKRRVRDNMTKKMITQRTIGKRKQ

RLNKRSYLIRALTLNTMTKDAERGKLKRRAIATPGMQIRGFVYFVETLARSICEKLEQSGLPVGGNEKKA

KLANVVRKMMTNSQDTELSLTITGDNTKWNENQNPRMFLAMITYMTRNQPEWFRNVLSIAPIMFSNKMAR

LGKGYMFESKSMKLRTQIPAEMLASIDLKYFNDSTRKKIEKIRPLLIEGTASLSPGMMMGMFNMLSTVLG

VSILNLGQKRYTKTTYWWDGLQSSDDFALIVNAPNHEGIQAGVDRFYRTCKLHGINMSKKKSYINRTGTF

EFTSFFYRYGFVANFSMELPSFGVSGSNESADMSIGVTVIKNNMINNDLGPATAQMALQLFIKDYRYTYR

CHRGDTQIQTRRSFEIKKLWEQTRSKAGLLVSDGGPNLYNIRNLHIPEVCLKWELMDEDYQGRLCNPLNP

FVSHKEIESMNNAVMMPAHGPAKNMEYDAVATTHSWIPKRNRSILNTSQRGVLEDEQMYQRCCNLFEKFF

PSSSYRRPVGISSMVEAMVSRARIDARIDFESGRIKKEEFTEIMKICSTIEELRRQK

SEQ ID NO: 23
>gi|8486130|ref|NP_040982.1| nucleocapsid protein
[Influenza A virus (A/Puerto Rico/8/34(H1N1))]
MASQGTKRSYEQMETDGERQNATEIRASVGKMIGGIGRFYIQMCTELKLSDYEGRLIQNSLTIERMVLSA

FDERRNKYLEEHPSAGKDPKKTGGPIYRRVNGKWMRELILYDKEEIRRIWRQANNGDDATAGLTHMMIWH

SNLNDATYQRTRALVRTGMDPRMCSLMQGSTLPRRSGAAGAAVKGVGTMVMELVRMIKRGINDRNFWRGE

NGRKTRIAYERMCNILKGKFQTAAQKAMMDQVRESRDPGNAEFEDLTFLARSALILRGSVAHKSCLPACV

YGPAVASGYDFEREGYSLVGIDPFRLLQNSQVYSLIRPNENPAHKSQLVWMACHSAAFEDLRVLSFIKGT

KVVPRGKLSTRGVQIASNENMETMESSTLELRSRYWAIRTRSGGNTNQQRASAGQISIQPTFSVQRNLPF

DRTTVMAAFTGNTEGRTSDMRTEIIRMMESARPEDVSFQGRGVFELSDEKAASPIVPSFDMSNEGSYFFG

DNAEEYDN

SEQ ID NO: 24
>gi|73918826|ref|YP_308855.1| polymerase 2 [Influenza A virus
(A/Korea/426/1968(H2N2))]
MERIKELRNLMSQSRTREILTKTTVDHMAIIKKYTSGRQEKNPSLRMKWMMAMKYPITADKRITEMVPER

NEQGQTLWSKMSDAGSDRVMVSPLAVTWWNRNGPMTSTVHYPKIYKTYFEKVERLKHGTFGPVHFRNQVK

IRRRVDINPGHADLSAKEAQDVIMEVVFPNEVGARILTSESQLTITKEKKEELQDCKISPLMVAYMLERE

LVRKTRFLPVAGGTSSVYIEVLHLTQGTCWEQMYTPGGEVRNDDVDQSLIIAARNIVRRAAVSADPLASL

LEMCHSTQIGGTRMVDILRQNPTEEQAVDICKAAMGLRISSSFSFGGFTFKRTSGSSIKREEEVLTGNLQ

TLKIRVHEGYEEFTMVGKRATAILRKATRRLVQLIVSGRDEQSIAEAIIVAMVFSQEDCMIKAVRGDLNF

VNRANQRLNPMHQLLRHFQKDAKVLFQNWGIEHIDNVMGMIGVLPDMTPSTEMSMRGIRVSKMGVDEYSS

-continued

TERVVVSIDRFLRVRDQRGNVLLSPEEVSETQGTEKLTITYSSSMMWEINGPESVLVNTYQWIIRNWETV

KIQWSQNPTMLYNKMEFEPFQSLVPKAIRGQYSGFVRTLFQQMRDVLGTFDTTQIIKLLPFAAAPPKQSR

MQFSSLTVNVRGSGMRILVRGNSPVFNYNKTTKRLTILGKDAGTLTEDPDEGTSGVESAVLRGFLILGKE

DRRYGPALSINELSTLAKGEKANVLIGQGDVVLVMKRKRDSSILTDSQTATKRIRMAIN

SEQ ID NO: 25

>gi|73919145|ref|YP_308850.1| hemagglutinin [Influenza A virus (A/Korea/426/68(H2N2))]

MAIIYLILLFTAVRGDQICIGYHANNSTEKVDTILERNVTVTHAKDILEKTHNGKLCKLNGIPPLELGDC

SIAGWLLGNPECDRLLSVPEWSYIMEKENPRYSLCYPGSFNDYEELKHLLSSVKHFEKVKILPKDRWTQH

TTTGGSWACAVSGKPSFFRNMVWLTRKGSNYPVAKGSYNNTSGEQMLIIWGVHHPNDEAEQRALYQNVGT

YVSVATSTLYKRSIPEIAARPKVNGLGRRMEFSWTLLDMWDTINFESTGNLVAPEYGFKISKRGSSGIMK

TEGTLENCETKCQTPLGAINTTLPFHNVHPLTIGECPKYVKSEKLVLATGLRNVPQIESRGLFGAIAGFI

EGGWQGMVDGWYGYHHSNDQGSGYAADKESTQKAFNGITNKVNSVIEKMNTQFEAVGKEFSNLEKRLENL

NKKMEDGFLDVWTYNAELLVLMENERTLDFHDSNVKNLYDKVRMQLRDNVKELGNGCFEFYHKCDNECMD

SVKNGTYDYPKYEEESKLNRNEIKGVKLSSMGVYQILAIYATVAGSLSLAIMMAGISFWMCSNGSLQCRI

CI

SEQ ID NO: 26

>gi|73912688|ref|YP_308854.1| membrane protein M1 [Influenza A virus (A/Korea/426/68(H2N2))]

MSLLTEVETYVLSIVPSGPLKAEIAQRLEDVFAGKNTDLEALMEWLKTRPILSPLTKGILGFVFTLTVPS

ERGLQRRRFVQNALNGNGDPNNMDRAVKLYRKLKREITFHGAKEVALSYSAGALASCMGLIYNRMGAVTT

EVAFAVVCATCEQIADSQHRSHRQMVTTTNPLIRHENRMVLASTTAKAMEQMAGSSEQAAEAMEVASQAR

QMVQAMRAIGTPPSSSAGLKDDLLENLQAYQKRMGVQMQRFK

SEQ ID NO: 27

>gi|73912687|ref|YP_308853.1| membrane protein M2 [Influenza A virus (A/Korea/426/68(H2N2))]

MSLLTEVETPIRNEWGCRCNDSSDPLVVAASIIGILHFILWILDRLFFKCIYRFFKHGLKRGPSTEGVPE

SMREEYRKEQQSAVDADDSHFVSIELE

SEQ ID NO: 28

>gi|73912685|ref|YP_308852.1| polymerase PA [Influenza A virus (A/Korea/426/68(H2N2))]

MEDFVRQCFNPMIVELAEKAMKEYGEDLKIETNKFAAICTHLEVCFMYSDFHFINEQGESIMVELDDPNA

LLKHRFEIIEGRDRTMAWTVVNSICNTTGAEKPKFLPDLYDYKENRFIEIGVTRREVHIYYLEKANKIKS

ENTHIHIFSFTGEEMATKADYTLDEESRARIKTRLFTIRQEMANRGLWDSFRQSERGEETIEERFEITGT

MRRLADQSLPPNFSCLENFRAYVDGFEPNGYIEGKLSQMSKEVNAKIEPFLKTTPRPIRLPDGPPCFQRS

KFLLMDALKLSIEDPSHEGEGIPLYDAIKCMRTFFGWKEPYIVKPHEKGINPNYLLSWKQVLAELQDIEN

EEKIPRTKNMKKTSQLKWALGENMAPEKVDFDNCRDISDLKQYDSDEPELRSLSSWIQNEFNKACELTDS

IWIELDEIGEDVAPIEHIASMRRNYFTAEVSHCRATEYIMKGVYINTALLNASCAAMDDFQLIPMISKCR

TKEGRRKTNLYGFIIKGRSHLRNDTDVVNFVSMEFSLTDPRLEPHKWEKYCVLEIGDMLLRSAIGQMSRP

MFLYVRTNGTSKIKMKWGMEMRPCLLQSLQQIESMVEAESSVKEKDMTKEFFENKSETWPIGESPKGVEE

GSIGKVCRTLLAKSVFNSLYASPQLEGFSAESRKLLLVVQALRDNLEPGTFDLGGLYEAIEECLINDPWV

LLNASWFNSFLTHALR

SEQ ID NO: 29

>gi|73921833|ref|YP_308877.1| PB1-F2 protein [Influenza A virus (A/Korea/426/68(H2N2))]

MGQEQDTPWTQSTEHINIQKRGSGQQTRKLERPNLTQLMDHYLRTMNQVDMHKQTASWKQWLSLRNHTQE

SLKIRVLKRWKLFNKQEWTN

```
                                                                SEQ ID NO: 30
>gi|73912683|ref|YP_308851.1| PB1 polymerase subunit
[Influenza A virus (A/Korea/426/68(H2N2))]
MDVNPTLLFLKVPAQNAISTTFPYTGDPPYSHGTGTGYTMDTVNRTHQYSEKGKWTTNTETGAPQLNPID

GPLPEDNEPSGYAQTDCVLEAMAFLEESHPGIFENSCLETMEVIQQTRVDKLTQGRQTYDWTLNRNQPAA

TALANTIEVFRSNGLTANESGRLIDFLKDVIESMDKEEMEITTHFQRKRRVRDNMTKKMVTQRTIGKKKQ

RLNKRSYLIRALTLNTMTKDAERGKLKRRAIATPGMQIRGFVHFVETLARNICEKLEQSGLPVGGNEKKA

KLANVVRKMMTNSQDTELSFTITGDNTKWNENQNPRVFLAMITYITRNQPEWFRNVLSIAPIMFSNKMAR

LGKGYMFESKSMKLRTQIPAEMLASIDLKYFNESTRKKIEKIRPLLIDGTVSLSPGMMMGMFNMLSTVLG

VSILNLGQKKYTKTTYWWDGLQSSDDFALIVNAPNHEGIQAGVNRFYRTCKLVGINMSKKKSYINRTGTF

EFTSFFYRYGFVANFSMELPSFGVSGINESADMSIGVTVIKNNMINNDLGPATAQMALQLFIKDYRYTYR

CHRGDTQIQTRRSFELKKLWEQTRSKAGLLVSDGGSNLYNIRNLHIPEVCLKWELMDEDYQGRLCNPLNP

FVSHKEIESVNNAVVMPAHGPAKSMEYDAVATTHSWTPKRNRSILNTSQRGILEDEQMYQKCCNLFEKFF

PSSSYRRPVGISSMVEAMVSRARIDARIDFESGRIKKEEFAEIMKICSTIEELRRQK

SEQ ID NO: 31
>gi|73921567|ref|YP_308869.1| non-structural protein NS2
[Influenza A virus (A/Korea/426/68(H2N2))]
MDSNTVSSFQDILLRMSKMQLGSSSEDLNGMITQFESLKLYRDSLGEAVMRMGDLHSLQNRNGKWREQLG

QKFEEIRWLIEEVRHRLKITENSFEQITFMQALQLLFEVEQEIRTFSFQLI

SEQ ID NO: 32
>gi|73921566|ref|YP_308870.1| non-structural protein NS1
[Influenza A virus (A/Korea/426/68(H2N2))]
MDSNTVSSFQVDCFLWHVRKQVVDQELGDAPFLDRLRRDQKSLRGRGSTLDLDIEAATRVGKQIVERILK

EESDEALKMTMASAPASRYLTDMTIEELSRDWFMLMPKQKVEGPLCIRIDQAIMDKNIMLKANFSVIFDR

LETLILLRAFTEEGAIVGEISPLPSLPGHTIEDVKNAIGVLIGGLEWNDNTVRVSKTLQRFAWRSSNENG

RPPLTPKQKRKMARTIRSKVRRDKMAD

SEQ ID NO: 33
>gi|73921307|ref|YP_308871.1| nucleoprotein [Influenza A virus
(A/Korea/426/68(H2N2))]
MASQGTKRSYEQMETDGERQNATEIRASVGKMIDGIGRFYIQMCTELKLSDYEGRLIQNSLTIERMVLSA

FDERRNKYLEEHPSAGKDPKKTGGPIYKRVDGKWMRELVLYDKEEIRRIWRQANNGDDATAGLTHMMIWH

SNLNDTTYQRTRALVRTGMDPRMCSLMQGSTLPRRSGAAGAAVKGVGTMVMELIRMIKRGINDRNFWRGE

NGRKTRSAYERMCNILKGKFQTAAQRAMMDQVRESRNPGNAEIEDLIFLARSALILRGSVAHKSCLPACV

YGPAIASGYNFEKEGYSLVGIDPFKLLQNSQVYSLIRPNENPAHKSQLVWMACNSAAFEDLRVLSFIRGT

KVSPRGKLSTRGVQIASNENMDTMESSTLELRSRYWAIRTRSGGNTNQQRASAGQISVQPAFSVQRNLPF

DKPTIMAAFTGNTEGRTSDMRAEIIRMMEGAKPEEMSFQGRGVFELSDEKATNPIVPSFDMSNEGSYFFG

DNAEEYDN

SEQ ID NO: 34
>gi|73921304|ref|YP_308872.1| neuraminidase [Influenza A virus
(A/Korea/426/68(H2N2))]
MNPNQKIITIGSVSLTIATVCFLMQIAILVTTVTLHFKQHECDSPASNQVMPCEPIIIERNITEIVYLNN

TTIEKEICPEVVEYRNWSKPQCQITGFAPFSKDNSIRLSAGGDIWVTREPYVSCDPGKCYQFALGQGTTL

DNKHSNDTIHDRIPHRTLLMNELGVPFHLGTRQVCVAWSSSSCHDGKAWLHVCVTGDDKNATASFIYDGR

LMDSIGSWSQNILRTQESECVCINGTCTVVMTDGSASGRADTRILFIEEGKIVHISPLSGSAQHVEECSC

YPRYPDVRCICRDNWKGSNRPVIDINMEDYSIDSSYVCSGLVGDTPRNDDRSSNSNCRNPNNERGNPGVK

GWAFDNGDDVWMGRTISKDLRSGYETFKVIGGWSTPNSKSQINRQVIVDSNNWSGYSGIFSVEGKRCINR

CFYVELIRGRQQETRVWWTSNSIVVFCGTSGTYGTGSWPDGANINFMPI
```

SEQ ID NO: 35

\>gi|73919213|ref|YP_308844.1| nonstructural protein 2
[Influenza A virus (A/New York/392/2004(H3N2))]
MDSNTVSSFQDILLRMSKMQLGSSSEDLNGMITQFESLKIYRDSLGEAVMRMGDLHLLQNRNGKWREQLG

QKFEEIRWLIEEVRHRLKTTENSFEQITFMQALQLLFEVEQEIRTFSFQLI

SEQ ID NO: 36

\>gi|73919212|ref|YP_308845.1| nonstructural protein 1
[Influenza A virus (A/New York/392/2004(H3N2))]
MDSNTVSSFQVDCFLWHIRKQVVDQELSDAPFLDRLRRDQRSLRGRGNTLGLDIKAATHVGKQIVEKILK

EESDEALKMTMVSTPASRYITDMTIEELSRNWFMLMPKQKVEGPLCIRMDQAIMEKNIMLKANFSVIFDR

LETIVLLRAFTEEGAIVGEISPLPSFPGHTIEDVKNAIGVLIGGLEWNDNTVRVSKNLQRFAWRSSNENG

GPPLTPKQKRKMARTARSKV

SEQ ID NO: 37

\>gi|73919207|ref|YP_308839.1| hemagglutinin [Influenza A
virus (A/New York/392/2004(H3N2))]
MKTIIALSYILCLVFAQKLPGNDNSTATLCLGHHAVPNGTIVKTITNDQIEVTNATELVQSSSTGGICDS

PHQILDGENCTLIDALLGDPQCDGFQNKKWDLFVERSKAYSNCYPYDVPDYASLRSLVASSGTLEFNNES

FNWTGVTQNGTSSACKRRSNNSFFSRLNWLTHLKFKYPALNVTMPNNEKFDKLYIWGVHHPGTDNDQISL

YAQASGRITVSTKRSQQTVIPSIGSRPRIRDVPSRISIYWTIVKPGDILLINSTGNLIAPRGYFKIRSGK

SSIMRSDAPIGKCNSECITPNGSIPNDKPFQNVNRITYGACPRYVKQNTLKLATGMRNVPEKQTRGIFGA

IAGFIENGWEGMVDGWYGFRHQNSEGTGQAADLKSTQAAINQINGKLNRLIGKTNEKFHQIEKEFSEVEG

RIQDLEKYVEDTKIDLWSYNAELLVALENQHTIDLTDSEMNKLFERTKKQLRENAEDMGNGCFKIYHKCD

NACIGSIRNGTYDHDVYRDEALNNRFQIKGVELKSGYKDWILWISFAISCFLLCVALLGFIMWACQKGNI

RCNICI

SEQ ID NO: 38

\>gi|73919153|ref|YP_308840.1| matrix protein 2 [Influenza A
virus (A/New York/392/2004(H3N2))]
MSLLTEVETPIRNEWGCRCNDSSDPLVVAASIIGILHLILWILDRLFFKCVYRLFKHGLKRGPSTEGVPE

SMREEYRKEQQNAVDADDSHFVSIELE

SEQ ID NO: 39

\>gi|73919152|ref|YP_308841.1| matrix protein 1 [Influenza A
virus (A/New York/392/2004(H3N2))]
MSLLTEVETYVLSIVPSGPLKAEIAQRLEDVFAGKNTDLEALMEWLKTRPILSPLTKGILGFVFTLTVPS

ERGLQRRRFVQNALNGNGDPNNMDKAVKLYRKLKREITFHGAKEIALSYSAGALASCMGLIYNRMGAVTT

EVAFGLVCATCEQIADSQHRSHRQMVATTNPLIKHENRMVLASTTAKAMEQMAGSSEQAAEAMEIASQAR

QMVQAMRAVGTHPSSSTGLRDDLLENLQTYQKRMGVQMQRFK

SEQ ID NO: 40

\>gi|73919150|ref|YP_308848.1| PB1-F2 protein [Influenza A
virus (A/New York/392/2004(H3N2))]
MEQEQDTPWTQSTEHTNIQRRGSGRQIQKLGHPNSTQLMDHYLRIMSQVDMHKQTVSWRLWPSLKNPTQV

SLRTHALKQWKSFNKQGWTN

SEQ ID NO: 41

\>gi|73919149|ref|YP_308847.1| polymerase PB1 [Influenza A
virus (A/New York/392/2004(H3N2))]
MDVNPTLLFLKVPAQNAISTTFPYTGDPPYSHGTGTGYTMDTVNRTHQYSEKGKWTTNTETGAPQLNPID

GPLPEDNEPSGYAQTDCVLEAMAFLEESHPGIFENSCLETMEVVQQTRVDKLTQGRQTYDWTLNRNQPAA

TALANTIEVFRSNGLTANESGRLIDFLKDVMESMDKEEMEITTHFQRKRRVRDNMTKKMVTQRTIGKKKQ

RVNKRGYLIRALTLNTMTKDAERGKLKRRAIATPGMQIRGFVYFVETLARSICEKLEQSGLPVGGNEKKA

KLANVVRKMMTNSQDTELSFTITGDNTKWNENQNPRMFLAMITYITKNQPEWFRNILSIAPIMFSNKMAR

LGKGYMFESKRMKLRTQIPAEMLASIDLKYFNESTRKKIEKIRPLLIDGTASLSPGMMMGMFNMLSTVLG

VSVLNLGQKKYTKTTYWWDGLQSSDDFALIVNAPNHEGIQAGVDRFYRTCKLVGINMSKKKSYINKTGTF

-continued

```
EFTSFFYRYGFVANFSMELPSFGVSGINESADMSIGVTVIKNNMINNDLGPATAQMALQLFIKDYRYTYR

CHRGDTQIQTRRSFELKKLWDQTQSRAGLLVSDGGPNLYNIRNLHIPEVCLKWELMDENYRGRLCNPLNP

FVSHKEIESVNNAVVMPAHGPAKSMEYDAVATTHSWNPKRNRSILNTSQRGILEDEQMYQKCCNLFEKFF

PSSSYRRPIGISSMVEAMVSRARIDARIDFESGRIKKEEFSEIMKICSTIEELRRQK
```

SEQ ID NO: 42
```
>gi|73919147|ref|YP_308843.1| nucleocapsid protein
[Influenza A virus (A/New York/392/2004(H3N2))]
MASQGTKRSYEQMETDGDRQNATEIRASVGKMIDGIGRFYIQMCTELKLSDHEGRLIQNSLTIEKMVLSA

FDERRNKYLEEHPSAGKDPKKTGGPIYRRVDGKWMRELVLYDKEEIRRIWRQANNGEDATAGLTHIMIWH

SNLNDATYQRTRALVRTGMDPRMCSLMQGSTLPRRSGAAGAAVKGIGTMVMELIRMVKRGINDRNFWRGE

NGRKTRSAYERMCNILKGKFQTAAQRAMVDQVRESRNPGNAEIEDLIFLARSALILRGSVAHKSCLPACA

YGPAVSSGYDFEKEGYSLVGIDPFKLLQNSQIYSLIRPNENPAHKSQLVWMACHSAAFEDLRLLSFIRGT

KVSPRGKLSTRGVQIASNENMDNMGSSTLELRSGYWAIRTRSGGNTNQQRASAGQTSVQPTFSVQRNLPF

EKSTIMAAFTGNTEGRTSDMRAEIIRMMEGAKPEEVSFRGRGVFELSDEKATNPIVPSFDMSNEGSYFFG

DNAEEYDN
```

SEQ ID NO: 43
```
>gi|73919136|ref|YP_308842.1| neuraminidase
[Influenza A virus (A/New York/392/2004(H3N2))]
MNPNQKIITIGSVSLTISTICFFMQIAILITTVTLHFKQYEFNSPPNNQVMLCEPTIIERNITEIVYLTN

TTIEKEMCPKLAEYRNWSKPQCDITGFAPFSKDNSIRLSAGGDIWVTREPYVSCDPDKCYQFALGQGTTL

NNVHSNDTVHDRTPYRTLLMNELGVPFHLGTKQVCIAWSSSSCHDGKAWLHVCVTGDDKNATASFIYNGR

LVDSIVSWSKKILRTQESECVCINGTCTVVMTDGSASGKADTKILFIEEGKIIHTSTLSGSAQHVEECSC

YPRYPGVRCVCRDNWKGSNRPIVDINIKDYSIVSSYVCSGLVGDTPRKNDSSSSHCLDPNNEEGGHGVK

GWAFDDGNDVWMGRTISEKLRSGYETFKVIEGWSKPNSKLQINRQVIVDRGNRSGYSGIFSVEGKSCINR

CFYVELIRGRKEETEVLWTSNSIVVFCGTSGTYGTGSWPDGADINLMPI
```

SEQ ID NO: 44
```
>gi|73919134|ref|YP_308846.1| polymerase PA
[Influenza A virus (A/New York/392/2004(H3N2))]
MEDFVRQCFNPMIVELAEKAMKEYGEDLKIETNKFAAICTHLEVCFMYSDFHFINEQGESIVVELDDPNA

LLKHRFEIIEGRDRTMAWTVVNSICNTTGAEKPKFLPDLYDYKENRFIEIGVTRREVHIYYLEKANKIKS

ENTHIHIFSFTGEEIATKADYTLDEESRARIKTRLFTIRQEMANRGLWDSFRQSERGEETIEEKFEISGT

MRRLADQSLPPKFSCLENFRAYVDGFEPNGCIEGKLSQMSKEVNAKIEPFLKTTPRPIKLPNGPPCYQRS

KFLLMDALKLSIEDPSHEGEGIPLYDAIKCIKTFFGWKEPYIVKPHEKGINSNYLLSWKQVLSELQDIEN

EEKIPRTKNMKKTSQLKWALGENMAPEKVDFDNCRDISDLKQYDSDEPELRSLSSWIQNEFNKACELTDS

IWIELDEIGEDVAPIEYIASMRRNYFTAEVSHCRATEYIMKGVYINTALLNASCAAMDDFQLIPMISKCR

TKEGRRKTNLYGFIIKGRSHLRNDTDVVNFVSMEFSLTDPRLEPHKWEKYCVLEIGDMLLRSAIGQISRP

MFLYVRTNGTSKVKMKWGMEMRRCLLQSLQQIESMIEAESSIKEKDMTKEFFENKSEAWPIGESPKGVEE

GSIGKVCRTLLAKSVFNSLYASPQLEGFSAESRKLLLVVQALRDNLEPGTFDLGGLYEAIEECLINDPWV

LLNASWFNSFLTHALK
```

SEQ ID NO: 45
```
>gi|73919060|ref|YP_308849.1| polymerase PB2
[Influenza A virus (A/New York/392/2004(H3N2))]
MERIKELRNLMSQSRTREILTKTTVDHMAIIKKYTSGRQEKNPSLRMKWMMAMKYPITADKRITEMVPER

NEQGQTLWSKMSDAGSDRVMVSPLAVTWWNRNGPVASTVHYPKVYKTYFDKVERLKHGTFGPVHFRNQVK

IRRRVDINPGHADLSAKEAQDVIMEVVFPNEVGARILTSESQLTITKEKKEELRDCKISPLMVAYMLERE

LVRKTRFLPVAGGTSSIYIEVLHLTQGTCWEQMYTPGGEVRNDDVDQSLIIAARNIVRRAAVSADPLASL
```

LEMCHSTQIGGTRMVDILRQNPTEEQAVDICKAAMGLRISSSFSFGGFTFKRTSGSSVKKEEEVLTGNLQ

TLKIRVHEGYEEFTMVGKRATAILRKATRRLVQLIVSGRDEQSIAEAIIVAMVFSQEDCMIKAVRGDLNF

VNRANQRLNPMHQLLRHFQKDAKVLFQNWGIEHIDSVMGMVGVLPDMTPSTEMSMRGIRVSKMGVDEYSS

TERVVVSIDRFLRVRDQRGNVLLSPEEVSETQGTERLTITYSSSMMWEINGPESVLVNTYQWIIRNWEAV

KIQWSQNPAMLYNKMEFEPFQSLVPKAIRSQYSGFVRTLFQQMRDVLGTFDTTQIIKLLPFAAAPPKQSR

MQFSSLTVNVRGSGMRILVRGNSPVFNYNKTTKRLTILGKDAGTLIEDPDESTSGVESAVLRGFLIIGKE

DRRYGPALSINELSNLAKGEKANVLIGQGDVVLVMKRKRDSSILTDSQTATKRIRMAIN

SEQ ID NO: 46: CMV Protein IE122:
>gi|39841910|gb|AAR31478.1| UL122 [Human herpesvirus 5]
MESSAKRKMDPDNPDEGPSSKVPRPETPVTKATTFLQTMLRKEVNSQLSLGDPLFPELAEESLKTFEQVT

EDCNENPEKDVLAELGDILAQAVNHAGIDSSSTGHTLTTHSCSVSSAPLNKPTPTSVAVTNTPLPGASAT

PELSPRKKPRKTTRPFKVIIKPPVPPAPIMLPLIKQEDIKPEPDFTIQYRNKIIDTAGCIVISDSEEEQG

EEVETRGATASSPSTGSGTPRVTSPTHPLSQMNHPPLPDPLARPDEDSSSSSSSSCSSASDSESESEEMK

CSSGGGASVTSSHHGRGGFGSAASSSLLSCGHQSSGGASTGPRKKKSKRISELDNEKVRNIMKDKNTPFCTPNVQTRRG

RVKIDEVSRMFRNTNRSLEYKNLPFTIPSMHQVLDEAIKACKTMQVNNKGIQIIYTRNHEVKSEVDAVRCRLGTMCNLA

LSTPFLMEHTMPVTHPPEVAQRTADACNEGVKAAWSLKELHTHQLCPRSSDYRNMIIHAATPVDLLGALNLCLPLMQKF

PKQVMVRIFSTNQGGFMLPIYETAAKAYAVGQFEQPTETPPEDLDTLSLAIEAAIQDLRNKSQ

SEQ ID NO: 126:
>gi|4927721|gb|AAD33253.1|AF125673_2 E7
[Human papillomavirus type 16]
MHGDTPTLHEYMLDLQPETTDLYCYEQLNDSSEEEDEIDGPAGQAEPDRAHYNIVTFCCKCDSTLRLCVQ

STHVDIRTLEDLLMGTLGIVCPICSQKP

SEQ ID NO: 200: Influensa M2
>gi|21693176|gb|AAM75162| /Human/M2/H1N1/Puerto
Rico/1934/// matrix protein M2 [Influenza A virus
(A/Puerto Rico/8/34/Mount Sinai(H1N1))]
MSLLTEVETPIRNEWGCRCNGSSDPLAIAANIIGILHLTLWILDRLFFKCIYRRFKYGLKGGPSTEGVPK

SMREEYRKEQQSAVDADDGHFVSIELE

SEQ ID NO: 201: >gi|1906383|gb|AAB50256.1| tat protein
[Human immunodeficiency virus 1]
MEPVDPRLEPWKHPGSQPKTACTNCYCKKCCFHCQVCFITKALGISYGRKKRRQRRRAHQNSQTHQASLS

KQPTSQPRGDPTGPKE

SEQ ID NO: 202: >B.FR.1983.HXB2-LAI-IIIB-BRU (gp120)
MRVKEKYQHLWRWGWRWGTMLLGMLMICSATEKLWVTVYYGVPVWKEATTTLFCASDAKAYDTEVHNVWATHACV

PTDPNPQEVVLVNVTENFNMWKNDMVEQMHEDIISLWDQSLKPCVKLTPLCVSLKCTDLKNDTNTNSSSGRMIME

KGEIKNCSFNISTSIRGKVQKEYAFFYKLDIIPIDNDTTSYKLTSCNTSVITQACPKVSFEPIPIHYCAPAGFAI

LKCNNKTFNGTGPCTNVSTVQCTHGIRPVVSTQLLLNGSLAEEEVVIRSVNFTDNAKTIIVQLNTSVEINCTRPN

NNTRKRIRIQRGPGRAFVTIGKIGNMRQAHCNISRAKWNNTLKQIASKLREQFGNNKTIIFKQSSGGDPEIVTHS

FNCGGEFFYCNSTQLFNSTWFNSTWSTEGSNNTEGSDTITLPCRIKQIINMWQKVGKAMYAPPISGQIRCSSNIT

GLLLTRDGGNSNNESEIFRPGGGDMRDNWRSELYKYKVVKIEPLGVAPTKAKRRVVQREKR

SEQ ID NO: 203: HIV gp41
>B.FR.1983.HXB2-LAI-IIIB-BRU (ACC No. K03455)
AVGIGALFLGFLGAAGSTMGAASMTLTVQARQLLSGIVQQQNNLLRAIEAQQHLLQLTVWGIKQLQARILAVERY

LKDQQLLGIWGCSGKLICTTAVPWNASWSNKSLEQIWNHTTWMEWDREINNYTSLIHSLIEESQNQQEKNEQELL

ELDKWASLWNWFNITNWLWYIKLFIMIVGGLVGLRIVFAVLSIVNRVRQGYSPLSFQTHLPTPRGPDRPEGIEEE

GGERDRDRSIRLVNGSLALIWDDLRSLCLFSYHRLRDLLLIVTRIVELLGRRGWEALKYWWNLLQYWSQELKNSA

VSLLNATAIAVAEGTDRVIEVVQGACRAIRHIPRRIRQGLERILL

SEQ ID NO: 204: >1b._._.AB016785._ (HCV-E1)

-continued

YEVRNVSGVYHVTNDCSNSSIVYGAADMIMHTPGCVPCVRENNSSRCWVALTPTLAARNRSIPTTTIRRHVDLLV

GAAAFCSAMYVGDLCGSVFLVSQLFTFSPRRYETVQDCNCSLYPGHVSGHRMAWDMMMNWSPTAALVVSQLLRIP

QAVVDMVTGAHWGVLAGLAYYSMVGNWAKVLIVMLLFAGVDG

SEQ ID NO: 205: >1b._._.AB016785.AB016785
TTHVTGGQTGRTTLGITAMFAFGPHQKLQLINTNGSWHINRTALNCNDSLNTGFLAALFYARKFNSSGCPERMAS

CRPIDKFVQGWGPITHAVPDNLDQRPYCWHYAPQPCGIIPASQVCGPVYCFTPSPVVVGTTDRFGAPTYTWGENE

TDVLLLNNTRPPQGNWFGCTWMNGTGFAKTCGGPPCNIGGVGNNTLTCPTDCFRKHPEATYTKCGSGPWLTPRCM

VDYPYRLWHYPCTVNFTIFKVRMYVGGVEHRLTAACNWTRGERCDLEDRDRSELSPLLLSTTEWQVLPCSFTTLP

ALSTGLIHLHQNIVDVQYLYGVGSAVVSIVIKWEYILLLFLLLADARVCACLWMMLLIAQAEA

SEQ ID NO: 309: >gi|52139259|ref|YP_081534.1| major
capsid protein [Human herpesvirus 5]
MENWSALELLPKVGIPTDFLTHVKTSAGEEMFEALRIYYGDDPERYNIHFEAIFGTFCNRLEWVYFLTSG

LAAAAHAIKFHDLNKLTTGKMLFHVQVPRVASGAGLPTSRQTTIMVTKYSEKSPITIPFELSAACLTYLR

ETFEGTILDKILNVEAMHTVLRALKNTADAMERGLIHSFLQTLLRKAPPYFVVQTLVENATLARQALNRI

QRSNILQSFKAKMLATLFLLNRTRDRDYVLKFLTRLAEAATDSILDNPTTYTTSSGAKISGVMVSTANVM

QIIMSLLSSHITKETVSAPATYGNFVLSPENAVTAISYHSILADFNSYKAHLTSGQPHLPNDSLSQAGAH

SLTPLSMDVIRLGEKTVIMENLRRVYKNTDTKDPLERNVDLTFFFPVGLYLPEDRGYTTVESKVKLNDTV

RNALPTTAYLLNRDRAVQKIDFVDALKTLCHPVLHEPAPCLQTFTERGPPSEPAMQRLLECRFQQEPMGG

AARRIPHFYRVRREVPRTVNEMKQDFVVTDFYKVGNITLYTELHPFFDFTHCQENSETVALCTPRIVIGN

LPDGLAPGPFHELRTWEIMEHMRLRPPPDYEETLRLFKTTVTSPNYPELCYLVDVLVHGNVDAFLLIRTF

VARCIVNMFHTRQLLVFAHSYALVTLIAEHLADGALPPQLLFHYRNLVAVLRLVTRISALPGLNNGQLAE

EPLSAYVNALHDHRLWPPFVTHLPRNMEGVQVVADRQPLNPANIEARHHGVSDVPRLGAMDADEPLFVDD

YRATDDEWTLQKVFYLCLMPAMTNNRACGLGLNLKTLLVDLFYRPAFLLMPAATAVSTSGTTSKESTSGV

TPEDSIAAQRQAVGEMLTELVEDVATDAHTPLLQACRELFLAVQFVGEHVKVLEVRAPLDHAQRQGLPDF

ISRQHVLYNGCCVVTAPKTLIEYSLPVPFHRFYSNPTICAALSDDIKRYVTEFPHYHRHDGGFPLPTAFA

HEYHNWLRSPFSRYSATCPNVLHSVMTLAAMLYKISPVSLVLQTKAHIHPGFALTAVRTDTFEVDMLLYS

GKSCTSVIINNPIVTKEERDISTTYHVTQNINTVDMGLGYTSNTCVAYVNRVRTDMGVRVQDLFRVFPMN

VYRHDEVDRWIRHAAGVERPQLLDTETISMLTFGSMSERNAAATVHGQKAACELILTPVTMDVNYFKIPN

NPRGRASCMLAVDPYDTEAATKAIYDHREADAQTFAATHNPWASQAGCLSDVLYNTRHRERLGYNSKFYS

PCAQYFNTEEIIAANKTLFKTIDEYLLRAKDCIRGDTDTQYVCVEGTEQLIENPCRLTQEALPILSTTTL

ALMETKLKGGAGAFATSETHFGNYVVGEIIPLQQSMLFNS

SEQ ID NO: 310: >gi|52139266|ref|YP_081541.1|
tegument protein UL16 [Human herpesvirus 5]
MAWRSGLCETDSRTLKQFLQEECMWKLVGKSRKHREYRAVACRSTIFSPEDDGSCILCQLLLFYRDGEWI

LCLCCNGRYQGHYGVGHVHRRRRRICHLPTLYQLSFGGPLGPASIDFLPSFSQVTSSMTCDGITPDVIYE

VCMLVPQDEAKRILVKGHGAMDLTCQKAVTLGGAGAWLLPRPEGYTLFFYILCYDLFTSCGNRCDIPSMT

RLMAAATACGQAGCSFCTDHEGHVDPTGNYVGCTPDMGRCLCYVPCGPMTQSLIHNEEPATFFCESDDAK

YLCAVGSKTAAQVTLGDGLDYHIGVKDSEGRWLPVKTDVWDLVKVEEPVSRMIVCSCPVLKNLVH

SEQ ID NO: 311: >gi|52139212|ref|YP_081485.1|
tegument protein UL26 [Human herpesvirus 5]
MTSRRAPDGGLNLDDFMRRQRGRHLDLPYPRGYTLFVCDVEETILTPRDVEYWKLLVVTQGQLRVIGTIG

LANLFSWDRSVAGVAADGSVLCYEISRENFVVRAADSLPQLLERGLLHSYFEDVERAAQGRLRHGNRSGL

RRDADGQVIRESACYVSRALLRHRVTPGKQEITDAMFEAGNVPSALLP

SEQ ID NO: 312: >gi|52139244|ref|YP_081517.1|
multifunctional expression regulator [Human herpesvirus 5]

-continued

```
MELHSRGRHDAPSLSSLSERERRARRARRFCLDYEPVPRKFRRERSPTSPSTRNGAAASEYHLAEDTVGA

ASHHHRPCVPARRPRYSKDDDTEGDPDHYPPPLPPSSRHALGGTGGHIIMGTAGFRGGHRASSSFKRRVA

ASASVPLNPHYGKSYDNDDGEPHHHGGDSTHLRRRVPSCPTTFGSSHPSSANNHHGSSAGPQQQQMLALI

DDELDAMDEDELQQLSRLIEKKKRARLQRGAASSGTSPSSTSPVYDLQRYTAESLRLAPYPADLKVPTAF

PQDHQPRGRILLSHDELMHTDYLLHIRQQFDWLEEPLLRKLVVEKIFAVYNAPNLHTLLAIIDETLSYMK

YHHLHGLPVNPHDPYLETVGGMRQLLFNKLNNLDLGCILDHQDGWGDHCSTLKRLVKKPGQMSAWLRDDV

CDLQKRPPETFSQPMHRAMAYVCSFSRVAVSLRRRALQVTGTPQFFDQFDTNNAMGTYRCGAVSDLILGA

LQCHECQNEMCELRIQRALAPYRFMIAYCPFDEQSLLDLTVFAGTTTTTASNHATAGGQQRGGDQIHPTD

EQCASMESRTDPATLTAYDKKDREGSHRHPSPMIAAAAPPAQPPSQPQQHYSEGELEEDEDSDDASSQDL

VRATDRHGDTVVYKTTAVPPSPPAPLAGVRSHRGELNLMTPSPSHGGSPPQVPHKQPIIPVQSANGNHST

TATQQQQPPPPPPVPQEDDSVVMRCQTPDYEDMLCYSDDMDD
```

Example 1

Preparation of Dimeric Peptides According to the Invention

Amino acids that link two monomeric peptide sequences are underlined.

Influenza (M2e):

Constructs derived from the extracellular domain on influenza protein M2 (M2e-domain)

Native Domain:

MSLLTEVETPIRNEWGCRCNDSSD

The following sequences was prepared or are under preparation. The different parts, $Z^1$-$Z^7$, are divided by brackets.

```
BI155 dimer
 [RG] [(Dpr(Aoa))] [TPI(Har)QDWGNRAN] [RG] [-] [TPTRQEWDCRIS]
 [RG] [(Dpr(Ser))] [TPT(Har)NGWDVKLS] [RG] [-] [TPI(Har)QEW(Har)SL(Nle)NQEW]
```

This construct links the monomeric peptides via a Dpr(Aoa) in the first peptide to an oxidized by NaIO$_4$ Dpr(Ser) residue in the second.

Dpr(Aoa)=N-α-Fmoc-N-β-(N-t.-Boc-amino-oxyacetyl)-L-diaminopropionic acid

Explanation:

The brackets used in the sequences are meant to indicate the different parts/boxes. For the BI155 monomeric parts, the boxes will have the following amino-acid sequences (A/B monomer):

Part $Z^1$ RG

Part $Z^2$ Dpr(Aoa)/Dpr(Ser)

Part $Z^3$ TPI(Har)QDWGNRAN/TPT(Har)NGWDVKLS

Part $Z^4$ RG

Part $Z^5$ -, means not present in these peptides

Part $Z^6$ TPTRQEWDCRIS/TPI(Har)QEW(Har)SL(Nle)NQEW

Part $Z^7$ not present (optional)

The boxes on part of the other sequences can be found in a

```
BI155-2
  [RG] [(Dpr(Aoa))] [TPI(Har)QDWGNRAN] [RG] [-] [TPTRQEWDARIS]
              |
  [RG] [(Dpr(Ser))] [TPT(Har)NGWDVKLS] [RG] [-] [TPI(Har)QEW(Har)SL(Nle)NQEW]
```

Examples of disulfide linked constructs can be, but are not restricted to, the following linked peptide sequences:

```
BI-155-16
  [RG] [C] [TPI(Har)QDWGNRAN] [RG] [-] [TPTRQEWDARIS]
       |
  [RG] [C] [TPT(Har)NGWDVKLS] [RG] [-] [TPI(Har)QEW(Har)SL(Nle)NQEW]
```

The above disulfide linked constructs may e.g. be synthesised by titration of 2-pyridinesulfenyl (SPyr)-protected cysteine-containing peptides with thiol-unprotected peptides. This has proven to be a superior procedure to selectively generate disulfide-linked peptide heterodimers preventing the formation of homodimers (Schutz A et al., Tetrahedron, Volume 56, Issue 24, 9 Jun. 2000, Pages 3889-3891). Similar dimeric constructs may be made with the other monomeric peptides according to the invention.

```
BI-155-15
  [RG] [C] [TPI(Har)QDWGNRAN] [RG] [-] [TPTRQEWDCRIS]
       |
  [RG] [C] [TPT(Har)NGWDVKLS] [RG] [-] [TPI(Har)QEW(Har)SL(Nle)NQEW]
```

Examples of thio-ester linked constructs can be, but are not restricted to, the following linked peptide sequences:

```
BI-155-3
  [RG] [C] [TPI(Har)QDWGNRAN] [RG] [-] [TPTRQEWDCRIS]
       |
  [RG] [K] [TPT(Har)NGWDVKLS] [RG] [-] [TPI(Har)QEW(Har)SL(Nle)NQEW]
BI-155-4
  [RG] [C] [TPI(Har)QDWGNRAN] [RG] [-] [TPTRQEWDARIS]
       |
  [RG] [K] [TPT(Har)NGWDVKLS] [RG] [-] [TPI(Har)QEW(Har)SL(Nle)NQEW]
BI-155-5
  [RG] [K] [TPI(Har)QDWGNRAN] [RG] [-] [TPTRQEWDCRIS]
       |
  [RG] [C] [TPT(Har)NGWDVKLS] [RG] [-] [TPI(Har)QEW(Har)SL(Nle)NQEW]
BI-155-6
  [RG] [K] [TPI(Har)QDWGNRAN] [RG] [-] [TPTRQEWDARIS]
       |
  [RG] [C] [TPT(Har)NGWDVKLS] [RG] [-] [TPI(Har)QEW(Har)SL(Nle)NQEW]
```

The Cys-Lys linker is typically established in the form of a thioether bond between a cysteine in one peptide and a bromoacetyl derivatized lysine in the other peptide.

Examples of other linked constructs can be, but are not restricted to, the following linked peptide sequences, N-ε-methylated Lys may be linked to Asp or Glu by a side-chain to side-chain peptide bond, wherein the N methylation makes the bond more stable (Lys(Me) refers to an N-ε-methylated Lys residue).

BI-155-7
[RG][(Lys(Me))][TPI(Har)QDWGNRAN][RG][-][TPTRQEWDCRIS]
          |
[RG][D][TPT(Har)NGWDVKLS][RG][-][TPI(Har)QEW(Har)SL(Nle)NQEW]
BI-155-8
[RG][(Lys(Me))][TPI(Har)QDWGNRAN][RG][-][TPTRQEWDCRIS]
          |
[RG][E][TPT(Har)NGWDVKLS][RG][-][TPI(Har)QEW(Har)SL(Nle)NQEW]
BI-155-9
[RG][(Lys(Me))][TPI(Har)QDWGNRAN][RG][-][TPTRQEWDDARIS]
          |
[RG][D][TPT(Har)NGWDVKLS][RG][-][TPI(Har)QEW(Har)SL(Nle)NQEW]
BI-155-10
[RG][(Lys(Me))][TPI(Har)QDWGNRAN][RG][-][TPTRQEWDDARIS]
          |
[RG][E][TPT(Har)NGWDVKLS][RG][-][TPI(Har)QEW(Har)SL(Nle)NQEW]
BI-155-11
[RG][D][TPI(Har)QDWGNRAN][RG][-][TPTRQEWDCRIS]
          |
[RG][(Lys(Me))][TPT(Har)NGWDVKLS][RG][-][TPI(Har)QEW(Har)SL(Nle)NQEW]
BI-155-12
[RG][D][TPI(Har)QDWGNRAN][RG][-][TPTRQEWDARIS]
          |
[RG][(Lys(Me))][TPT(Har)NGWDVKLS][RG][-][TPI(Har)QEW(Har)SL(Nle)NQEW]
BI-155-13
[RG][E][TPI(Har)QDWGNRAN][RG][-][TPTRQEWDCRIS]
          |
[RG][(Lys(Me))][TPT(Har)NGWDVKLS][RG][-][TPI(Har)QEW(Har)SL(Nle)NQEW]
BI-155-14
[RG][E][TPI(Har)QDWGNRAN][RG][-][TPTRQEWDARIS]
          |
[RG][(Lys(Me))][TPT(Har)NGWDVKLS][RG][-][TPI(Har)QEW(Har)SL(Nle)NQEW]

Example 3

Immunological Studies

Rabbit Immunizations

New Zealand White female rabbits (n=3) is immunized intradermally at weeks 0, 2 & 6 with 1 ml of BI400-B vaccine consisting of 500 μg BI400-B in 50% V/V Freund's adjuvant (i.e. Complete Freund's adjuvant used for priming, followed by boostings with Incomplete Freund's adjuvant). Individual blood serum is isolated for ELISA.

Direct ELISA for Human or Rabbit Sera 50-100 μl of BI400-B (pre-incubated in Coating buffer—0.05M $Na_2CO_3$ pH9.6; denoted CB—in cold at 16 μg/ml for each peptide 1-3 days prior to coating) or just CB (background control) is used for coating wells in microtiter plates at 4° C. overnight. The microtiter plates are then washed 3× with washing buffer (PBS+1% v/v Triton-X100; denoted WB), followed by 2 h blocking at room temperature (RT) with 200 μl/well of blocking buffer (PBS+1% w/v BSA). Plates are then washed 3× with WB, followed by 1 h incubation at 37° C. with 50-70 ul/well of added human (or rabbit) sera (serial dilutions ranging from 1:1-1:250 in dilution buffer (PBS+1% v/v Triton-X100+1% w/v BSA; denoted DB)). Plates are then washed 6× with WB, followed by 1 h incubation at RT with 70 μl/well of Alkaline Phosphatase-conjugated Protein G (3 μg/ml in DB; Calbiochem 539305). Plates are then washed 6× with WB, followed by 10-60 min incubation at room temperature with 100 μl/well of 0.3% w/v of Phenophtalein monophosphate (Sigma P-5758). Plates are finally quenched by adding 100 μl/well of Quench solution (0.1M TRIS+0.1M EDTA+0.5M NaOH+0.01% w/v $NaN_3$; pH14), followed by ELISA reader (ASYS UVM 340) at 550 nm.

Example 4

Virus Specific Response by ELISPOT Assay

At day one, PBMC samples from blood donors are thawed, washed with warm medium and incubated in flasks (250000 PBMCs/cm2) for 24 hours at 37° C., 5% CO2 in covering amount of culture media (RPMI 1640 with ultraglutamine, Lonza, BE12-702F701; 10% Foetal Bovine serum (FBS), Fisher Scientific Cat. No. A15-101; Penicillin/Streptomycin, Fisher Scientific Cat. No. P11-010) to allow the cells to recover after thawing. At day two, the cells are added to a Falcon Microtest Tissue Culture plate, 96 well flat bottom, at 500 000 cells per well in a volume of 200 μl total medium. Parallel wells are added the indicated stimuli in duplicate or left with medium as a control for 6 days at 37° C., 5% $CO_2$. After the six day of incubation, 100 μl of the cell suspension are transferred to an ELISPOT (Millipore multiscreen HTS) plate coated with 1 μg/ml native influenza M2e protein. After a 24 hour incubation, the plate is washed four times with PBS+0.05% Tween20, and a fifth time with PBS, 200 μl/well. A mouse Anti-human IgG or IgM biotin (Southern Biotech 9040-08 and 9020-08) is diluted in PBS with 0.5% FBS and incubated for 90 minutes at 37° C. The washing is repeated as described, before 80 μl Streptavidin-Alkaline-Phosphatase (Sigma Aldrich, S289) is added each well and incubated at 60 minutes in the dark, at room temperature. The wells are then washed 2 times with PBS+0.05% Tween20 and 4 times with PBS, 200 μl/well, before the substrate, Vector Blue Alkaline Phosphatase Substrate kit III (Vector Blue, SK-5300) is added and let to develop for 7 minutes at room temperature. The reaction is stopped with running water, the plates let dry and the sport enumerated by an ELISPOT reader (CTL-ImmunoSpot® S5 UV Analyzer).

Virus Specific Response by ELISA

100 µl of antigen as indicated (pre-incubated in Coating buffer—0.05M $Na_2CO_3$ pH9.6; denoted CB—in cold at 8 µg/ml 1-3 days) or just CB (background control) is used for coating wells in microtiter plates at 4° C. The microtiter plates are then washed 3× with washing buffer (PBS+1% v/v Triton-X100; denoted WB), followed by 2 h blocking at room temperature (RT) with 200 µl/well of blocking buffer (PBS+1% w/v BSA). Plates are then washed 3× with WB, followed by 1 h incubation at 37° C. with 50-70 ul/well of added human (or rabbit or sheep) sera (serial dilutions ranging from 1:5-1:250 in dilution buffer (PBS+1% v/v Triton-X100+1% w/v BSA; denoted DB)). Plates are then washed 6× with WB, followed by 1 h incubation at RT with 70 µl/well of Alkaline Phosphatase-conjugated Protein G (3 µg/ml in DB; Calbiochem 539305) or goat anti-mouse IgG biotin (1 µg/ml, Southern Biotech, 1030-08. In case of the goat anti-mouse IgG biotin, the plates are washed one extra step as described, before addition of 100 µl Streptavidin-Alkaline-Phosphatase (1 µg/ml, Sigma Aldrich, S289) and incubated 1 hour at RT. Plates are then washed 6× with WB, followed by 10-60 min incubation at room temperature with 100 µl/well of 0.3% w/v of Phenophtalein monophosphate (Sigma P-5758). Plates are finally quenched by adding 100 µl/well of Quench solution (0.1M TRIS+0.1M EDTA+0.5M NaOH+0.01% w/v $NaN_3$; pH14), followed by a measurement with a ELISA reader (ASYS UVM 340) at 550 nm. The strength of the sera, i.e. the magnitude of the humoral immune response, is then reported as the dilution of sera that result in the described Optical Density (OD) value, or the OD value at the indicated dilution of sera.

Example 5

The peptides according to the invention used in the following examples are synthesized by Schafer-N as c-terminal amides using the Fmoc-strategy of Sheppard, (1978) J. Chem. Soc., Chem. Commun., 539.

BI100-190e, BI100-190f, BI100-260b, BI100-260c, BI100-260d, BI100-260e, and BI100-260f were synthezised by Schafer-N with and without Biotin in the C-terminal tested:

Cell Penetration Assay

A set of peptides were biotinylated on C-terminal, and different combinations of aminoacids, with respect to length and type, were added to the sequence box $Z^1$, $Z^4$ and $Z^7$ in the peptides according to the present invention, formula I. The peptides were tested on cells grown from one individual blood donor.

Schematic diagram of amino acid sequence of the peptides according to the invention (Each Z here defines a sequence of amino acids):

| $Z^1$ | $Z^2$ | $Z^3$ | $Z^4$ | $Z^5$ | $Z^6$ | $Z^7$ |
|---|---|---|---|---|---|---|

Intracellular Staining for Biotinylated Peptides 96-well U-bottom polystyrene plates (NUNC, cat no: 163320) were used for staining of human PBMCs. Briefly, 8 ul of N- or C-terminally biotinylated peptides according to table 1 or table 2 (i.e. 5 mM, 2.5 mM & 1.25 mM tested for each peptide) were incubated at 37° C. for 2 h with 40 ul of PBMC (12.5×106 cells/ml) from blood donors. Cells were then washed 3× with 150 ul of Cellwash (BD, cat no: 349524), followed by resuspension of each cell pellet with 100 ul of Trypsin-EDTA (Sigma, cat no: T4424), then incubated at 37° C. for 5 min. Trypsinated cells were then washed 3× with 150 ul of Cellwash (BD, cat no: 349524), followed by resuspension with BD Cytofix/Cytoperm™ plus (BD, cat no: 554715), then incubated at 4° C. for 20 min according to manufacturer. Cells were then washed 2× with 150 ul PermWash (BD, cat no: 554715). Cells were then stained with Streptavidin-APC (BD, cat no: 554067) & Anti-hCD11c (eBioscience, cat no: 12-0116) according to manufacturer at 4° C. for 30 min aiming to visualize biotinylated peptides & dendritic cells, respectively. Cells were then washed 3× with 150 ul PermWash, followed by resuspension in staining buffer (BD, cat no: 554656) before flow cytometry. Dendritic cells were gated as CD11c+ events outside lymphocyte region (i.e. higher FSC & SSC signals than lymphocytes). 200 000 total cells were acquired on a FACSCanto II flow cytometer with HTS loader, and histograms for both total cells & dendritic cells with respect to peptide-fluorescence (i.e. GeoMean) were prepared.

Extracellular Staining for Biotinylated Peptides 96-well U-bottom polystyrene plates (NUNC, cat no: 163320) were used for staining of human PBMCs. Briefly, 8 ul of N- or C-terminally biotinylated peptides according to table 1 or table 2 (i.e. 5 mM, 2.5 mM & 1.25 mM tested for each peptide; all peptides manufactured by Schafer) were incubated at 37° C. for 2 h with 40 ul of PBMC (12.5×106 cells/ml) from blood donors. Cells were then washed 3× with 150 ul of Cellwash (BD, cat no: 349524), then stained with Streptavidin-APC (BD, cat no: 554067) & Anti-hCD11c (eBioscience, cat no: 12-0116) according to manufacturer at 4° C. for 30 min aiming to visualize biotinylated peptides & dendritic cells, respectively. Cells were then washed 3× with 150 ul of Cellwash (BD, cat no: 349524), followed by resuspension in staining buffer (BD, cat no: 554656) before flow cytometry. Dendritic cells were gated as CD11c+ events outside lymphocyte region (i.e. higher FSC & SSC signals than lymphocytes). 200 000 total cells were acquired on a FACSCanto II flow cytometer with HTS loader, and histograms for both total cells & dendritic cells with respect to peptide-fluorescence (i.e. GeoMean) were prepared.

Example 6

Positive CTL response may alternatively be assayed by ELISPOT assay.

Human IFN-Gamma Cytotoxic T-Cell (CTL) Response by ELISPOT Assay

Briefly, at day 1, PBMC samples from HCV patients were incubated in flasks (430 000 PBMCs/cm2) for 2 h at 37° C., 5% CO2 in covering amount of culture media (RPMI 1640 Fisher Scientific; Cat No. PAAE15-039 supplemented with L-Glutamine, (MedProbe Cat. No. 13E17-605E, 10% Foetal Bovine serum (FBS), Fisher Scientific Cat. No. A15-101) and Penicillin/Streptomycin, (Fisher Scientific Cat. No. P11-010) in order to allow adherence of monocytes. Non-adherent cells were isolated, washed, and frozen in 10% V/V DMSO in FBS until further usage. Adherent cells were carefully washed with culture media, followed by incubation at 37° C. until day 3 in culture media containing 2 µg/ml final concentration of hrGM-CSF (Xiamen amoytop biotech co, cat no: 3004.9090.90) & 1 µg/ml hrIL-4 (Invitrogen, Cat no: PHC0043), and this procedure is then repeated at day 6. At day 7, cultured dendritic cells (5 000-10 000 per well) were added to ELISPOT (Millipore multiscreen HTS) plates coated with 0.5 µg/well anti-human γ Interferon together with thawed autologous non-adherent cells (200 000 per well), antigen samples (1-8 ug/ml final concentration for peptide antigens; 5 ug/ml final concentration for Concanavalin A (Sigma, Cat no: C7275) or PHA (Sigma, Cat no: L2769)) and optionally, anti-Anergy antibodies (0.03-0.05 ug/ml final concentration for both anti-PD-1 (eBioscience, cat no: 16-9989-82) & anti-PD-L1 (eBioscience, cat no: 16-5983-82)). Plates were incubated overnight and spots were developed according to manufacturer. Spots were read on ELISPOT reader (CTL-ImmunoSpot® S5 UV Analyzer).

Example 7

The REVEAL & ProVE® Rapid Epitope Discovery System in Detail

Binding properties to HLA for the ninemers listed are tested for the following HLA-classes: HLA-A1, HLA-A2, HLA-A3, HLA-A11, HLA-A24, HLA-A29, HLA-B7, HLA-B8, HLA-B14, HLA-B15, HLA-B27, HLA-B35, HLA-B40.

The peptides are synthesized as a Prospector PEPscreen®: Custom Peptide Library. Peptides 8-15 amino acids in length are synthesized in 0.5-2 mg quantities with high average purity. Quality control by MALDI-TOF Mass Spectrometry is carried out on 100% of samples.

The REVEAL™ binding assay determined the ability of each candidate peptide to bind to one or more MHC class I alleles and stabilizing the MHC-peptide complex. By comparing the binding to that of high and intermediate affinity T cell epitopes, the most likely immunogenic peptides in a protein sequence can be identified. Detection is based on the presence or absence of the native conformation of the MHC-peptide complex.

Each peptide is given a score relative to the positive control peptide, which is a known T cell epitope. The score of the test peptide is reported quantitatively as a percentage of the signal generated by the positive control peptide, and the peptide is indicated as having a putative pass or fail result. Assay performance is confirmed by including an intermediate control peptide that is known to bind with weaker affinity to the allele under investigation.

Example 8

Intracellular Staining

Peptides as described herein with $Z^3$ and $Z^6$ derived from HCV, Influenza, or CMV are prepared and tested for intracellular staining in an experiment as described above in the "Cell penetration assay".

Average over results from buffy coats from ten donors, normalized to N-biotin for each donor is illustrated in FIGS. 3 and 4.

Example 9

TABLE 10

Peptides used as controls and not part to the invention, but carrying the same epitopes (Z3, Z6, Z9) linked by glycines and serines, for comparison to peptides of the invention. (Z = Norleucine, X = Homoarginine, biotc indicates that a biotinylated lysine residue has been added to the C-terminal).

| Peptide | - | Z3 | - | Z6 | - | Z9 | C-ter tag |
|---|---|---|---|---|---|---|---|
| BI330-72-2-ns-biotc | GS | VITYSIFLIVS | GS | GGNVIGGIYZIPR | | | biotin-NH2 |
| BI330-83-ns-biotc | GS | TANWARVIS | GS | ANWAKVIL | S | NWAKVI | biotin-NH2 |
| BI310-511-ns-biotc | S | GYLPAVGAPI | GS | VIRVIAHGLRL | | | biotin-NH2 |
| BI100-330-ns-biotc | GS | TAYERZCNIL | GS | GLEPLVIAGILA | | | biotin-NH2 |
| BI100-270-ns-biotc | GS | TVIGASZIPLL | GS | TPIXQDWENRAN | | | biotin-NH2 |
| BI100-130-ns-biotc | GS | AAFEEZXITS | GS | VAFEDLXZZSFI | | | biotin-NH2 |

Results

Biotinylated versions of scaffold peptides were tested for intracellular and extracellular uptake. All tested peptides had stronger intracellular and extracellular uptake compared to the control peptide N-biotin (N-bio), as seen from FIGS. 1-2. Also when comparing the uptake of peptides according to the invention to peptides carrying the same epitopes linked by Glycine and Serine residues instead (Table 11), tested peptides according to the invention generally had a higher uptake. Many of the peptides tested show very strong uptake and potentially we are seeing saturation of the cell assay system for these.

Values represent averages over readouts from buffy coats from ten (five) donors and three (four) concentrations of peptide each, normalized by value for N-biotin for each donor for scaffold (non-scaffold) peptides respectively.

TABLE 11

Intracellular and extracellular uptake of peptides of the invention (Bold) compared to peptides containing the same epitopes linked by Gly and Ser residues (non-bold Italics). Median readouts from buffy coats from ten (five) donors and three (four) concentrations of peptide each, normalized by value for N-biotin for each donor for scaffold (non-scaffold) peptides.

| Peptide (biotinylated) | Intracellular Uptake | Extracellular Uptake |
| --- | --- | --- |
| BI100-270 | 2.05 | 20.47 |
| BI100-270b | 3.35 | 16.54 |
| BI100-270c | 2.91 | 9.56 |
| BI100-270d | 5.73 | 4.77 |
| BI100-270e | 10.26 | 3.54 |
| *BI100-270ns* | *1.30* | *1.29* |
| BI100-330 | 70.36 | 655.35 |
| BI100-330b | 76.42 | 744.11 |
| BI100-330c | 880.85 | 244.29 |
| BI100-330d | 80.82 | 592.82 |
| BI100-330e | 23.89 | 529.05 |
| *BI100-330ns* | *1.82* | *416.04* |
| BI310-511 | 22.62 | 227.46 |
| BI310-511b | 67.29 | 466.71 |
| BI310-511c | 31.83 | 203.62 |
| BI310-511d | 70.64 | 267.15 |
| BI310-511e | 44.59 | 473.80 |
| BI310-511f | 26.85 | 178.61 |
| BI310-511g | 66.74 | 171.31 |
| *BI310-511ns* | *3.85* | *4.56* |
| BI330-83 | 194.69 | 364.04 |
| BI330-83b | 120.10 | 518.60 |
| BI330-83c | 154.43 | 435.66 |
| BI330-83d | 52.14 | 267.38 |
| *BI330-83ns* | *63.51* | *380.25* |

Example 10

Effect of Peptide Based Influenza Vaccine in Protection of HLA A2 Mice Against Influenza Virus Challenge C57/B6/Tg HLA A2 mice (n=10 mice per group) were immunized week 0 and week 2 by subcutaneous administration (2×50 µl; each side of base of tail), of a solution containing 50 µg of each peptide, or 0.07 µg HA of inactivated influenza A/PR8 (H1N1) virus given as vaccine control.

At week 4 the mice was infected with live influenza virus in order to measure the immune response to viral infection. The challenge was done with a mouse adapted strain of influenza A at a dose of $1 \times 10^5 TCID_{50}$/mouse which is enough to reliably infect the animals without mortality as determined by titration in the same mouse strain. The animals were then monitored for 7 days by weight loss at the start of challenge and daily from day three before they were sacrificed and serum collected. Individual serum for mice in all groups were collected before start of experiment, and day of sacrifice.

TABLE 12

| Group | Treatment |
| --- | --- |
| 1 | Vaccinate with peptides + adjuvant Provax (week 0, 2) |
| 2 | Vaccinate with peptides + adjuvant ISA 51 (week 0, 2) |
| 3 | Vaccinate with inactivated conventional vaccine (week 0, 2) |
| 4 | Naïve mice. |

TABLE 13

| | Survival (n) | | | |
| --- | --- | --- | --- | --- |
| | | Day | | |
| Group | 1-4 | 5 | 6 | 7 |
| 1 Peptide, Provax | 10 | 10 | 10 | 7 |
| 2 Peptide, ISA 51 | 10 | 10 | 10 | 9 |
| 3 PR8 | 10 | 9 | 9 | 6 |
| 4 Naïve | 10 | 10 | 10 | 8 |

Results

Following the weight loss after challenge a clear protective effect is seen for both groups receiving the peptide vaccine with either ISA51 or Provax as adjuvant, as compared to the standard inactivated viral vaccine, PR8, or naïve mice (FIG. 5).

The invention claimed is:

1. An isolated monomeric peptide comprising the following structure $Z^1$-$Z^2$-$Z^3$-$Z^4$-$Z^6$-$Z^7$-$Z^9$ wherein $Z^1$, $Z^4$, and optional $Z^7$ defines a linear sequence of one, two, or three arginine residues or derivatives thereof optionally followed by a glycine (G); $Z^2$ defines an optional amino acid selected from 2,3-Diaminopropionic acid (Dpr), Cysteine, Lysine, Aspartic acid, and Glutamic acid, or a derivative thereof; $Z^3$ selected from the group consisting of GGQLIGGIYLIPG (SEQ ID NO:313), VITYSIFLIVS (SEQ ID NO:314), TANWARVIS (SEQ ID NO:315), GYLPAVGAPI (SEQ ID NO:316), NIVP(Nle)VVTA (SEQ ID NO:317), VTPADLIGA (SEQ ID NO:318), PRPEGYTLFF (SEQ ID NO:319), LPYPRGYTLFV (SEQ ID NO:320), ETILTPRDV (SEQ ID NO:321), SSTSPVYDL (SEQ ID NO:322), TAYER(Nle)CNIL (SEQ ID NO:323), TVIGAS(Nle)IPLL (SEQ ID NO:324), AAFEE(Nle)(Har)ITS (SEQ ID NO:325), GLEPLVIAGILA (SEQ ID NO:326), TAFLVRNVA (SEQ ID NO:327), TPI(Har)QDWGNRAN (SEQ ID NO:328), TPT(Har)NGWDVKLS (SEQ ID NO:329), LECVYCKQQLL (SEQ ID NO:330), GVYDFAFRDLC (SEQ ID NO:331), GVFDYAFRDIN (SEQ ID NO:332), and VDIRTLEDLL (SEQ ID NO:333); wherein $Z^6$ is selected from the group consisting of EVYDFAFRDLC (SEQ ID NO:334), GFAFRDLCIVY (SEQ ID NO:335), GFAYRDINLAY (SEQ ID NO:336), GTLGIVCPIG (SEQ ID NO:337), GLEPLVIAGILA (SEQ ID NO:338), TPI(Har)QDWENRAN (SEQ ID NO:339), VAFEDL(Har)(Nle)(Nle)SFI (SEQ ID NO:340), RFQTVVQBA (SEQ ID NO:341), GSLVGLLHIVL (SEQ ID NO:342), SIARSVTI(Nle)(Har)ASVVH (SEQ ID NO:343), TPTRQEWDCRIS (SEQ ID NO:344), TPTRQEWDARIS (SEQ ID NO:345), TPI(Har)QEW(Har)SL(Nle)NQEW (SEQ ID NO:346), IGDLIVAQV (SEQ ID NO:347), QYNPVAV(Nle)F (SEQ ID NO:348), GYTLFFTS (SEQ ID NO:349), GYTLFVSD (SEQ ID NO:350), NTL(Nle)TPRDV (SEQ ID NO:351), SSTSPVYNL (SEQ ID NO:352), VITFSIYLIVS (SEQ ID NO:353), GGNVIGGIY(Nle)IPR (SEQ ID NO:354), ANWAKVIL (SEQ ID NO:355), VIRVIAHGLRL (SEQ ID NO:356), and IGDLIVQAV (SEQ ID NO:478); and wherein optional $Z^9$ is NWAKVI, wherein Nle is Norleucine and Har is homoarginine.

2. An isolated dimeric or multimeric peptide comprising two or more covalently joined monomeric peptides, each monomeric peptide independently comprising the following structure $Z^1$-$Z^2$-$Z^3$-$Z^4$-$Z^6$-$Z^7$-$Z^9$ wherein $Z^1$, $Z^4$, and optional $Z^7$ defines a linear sequence of one, two, or three arginine residues or derivatives thereof optionally followed by a glycine (G); $Z^2$ defines an optional amino acid selected from 2,3-Diaminopropionic acid (Dpr), Cysteine, Lysine, Aspartic acid and Glutamic acid, or a derivative thereof; wherein $Z^3$ is selected from the group consisting of GGQLIGGIYLIPG (SEQ ID NO:313), VITYSIFLIVS (SEQ ID NO:314), TANWARVIS (SEQ ID NO:315), GYLPAVGAPI (SEQ ID NO:316), NIVP(Nle)VVTA (SEQ ID NO:317), VTPADLIGA (SEQ ID NO:318), PRPEGYTLFF (SEQ ID NO:319), LPYPRGYTLFV (SEQ ID NO:320), ETILTPRDV (SEQ ID NO:321), SSTSPVYDL (SEQ ID NO:322), TAYER(Nle)CNIL (SEQ ID NO:323), TVIGAS(Nle)IPLL (SEQ ID NO:324), AAFEE(Nle)(Har)ITS (SEQ ID NO:325), GLEPLVIAGILA (SEQ ID NO:326), TAFLVRNVA (SEQ ID NO:327), TPI(Har)QDWGNRAN (SEQ ID NO:328), TPT(Har)NGWDVKLS (SEQ ID NO:329), LECVYCKQQLL (SEQ ID NO:330), GVYDFAFRDLC (SEQ ID NO:331), GVFDYAFRDIN (SEQ ID NO:332), and VDIRTLEDLL (SEQ ID NO:333); wherein $Z^6$ is selected from the group consisting of EVYDFAFRDLC (SEQ ID NO:334), GFAFRDLCIVY (SEQ ID NO:335), GFAYRDINLAY (SEQ ID NO:336), GTLGIVCPIG (SEQ ID NO:337), GLEPLVIAGILA (SEQ ID NO:338), TPI(Har)QDWENRAN (SEQ ID NO:339), VAFEDL(Har)(Nle)(NLE)SFI (SEQ ID NO:340), RFQTVVQBA (SEQ ID NO:341), GSLVGLLHIVL (SEQ ID NO:342), SIARSVTI(Nle)(Har)ASVVH (SEQ ID NO:343), TPTRQEWDCRIS (SEQ ID NO:344), TPTRQEWDARIS (SEQ ID NO:345), TPI(Har)QEW(Har)SL(Nle)NQEW (SEQ ID NO:346), IGDLIVAQV (SEQ ID NO:347), QYN-PVAV(Nle)F (SEQ ID NO:348), GYTLFFTS (SEQ ID NO:349), GYTLFVSD (SEQ ID NO:350), NTL(Nle)T-PRDV (SEQ ID NO:351), SSTSPVYNL (SEQ ID NO:352), VITFSIYLIVS (SEQ ID NO:353), GGNVIGGIY(Nle)IPR (SEQ ID NO:354), ANWAKVIL (SEQ ID NO:355), VIRVI-AHGLRL (SEQ ID NO:356), and IGDLIVQAV (SEQ ID NO:478); and wherein optional $Z^9$ is NWAKVI, wherein Nle is Norleucine and Har is homoarginine.

3. The isolated dimeric or multimeric peptide according to claim 2, wherein two or more monomeric peptides are different in sequence.

4. A composition comprising two or more compounds selected from a monomeric peptide is as defined in claim 1, and an isolated dimeric or multimeric peptide comprising two or more covalently joined monomeric peptides, each monomeric peptide independently comprising the following structure $Z^1$-$Z^2$-$Z^3$-$Z^4$-$Z^6$-$Z^7$-$Z^9$ wherein $Z^1$, $Z^4$, and optional $Z^7$ defines a linear sequence of one, two, or three arginine residues or derivatives thereof optionally followed by a glycine (G); $Z^2$ defines an optional amino acid selected from 2,3-Diaminopropionic acid (Dpr), Cysteine, Lysine, Aspartic acid and Glutamic acid, or a derivative thereof; wherein $Z^3$ is selected from the group consisting of GGQLIGGIYLIPG (SEQ ID NO:313), VITYSIFLIVS (SEQ ID NO:314), TANWARVIS (SEQ ID NO:315), GYLPAVGAPI (SEQ ID NO:316), NIVP(Nle)VVTA (SEQ ID NO:317), VTPADLIGA (SEQ ID NO:318), PRPEGYTLFF (SEQ ID NO:319), LPYPRGYTLFV (SEQ ID NO:320), ETILTPRDV (SEQ ID NO:321), SST-SPVYDL (SEQ ID NO:322), TAYER(Nle)CNIL (SEQ ID NO:323), TVIGAS(Nle)IPLL (SEQ ID NO:324), AAFEE(Nle)(Har)ITS (SEQ ID NO:325), GLEPLVIAGILA (SEQ ID NO:326), TAFLVRNVA (SEQ ID NO:327), TPI(Har)QDWGNRAN (SEQ ID NO:328), TPT(Har)NGWDVKLS (SEQ ID NO:329), LECVYCKQQLL (SEQ ID NO:330), GVYDFAFRDLC (SEQ ID NO:331), GVFDYAFRDIN (SEQ ID NO:332), and VDIRTLEDLL (SEQ ID NO:333); wherein $Z^6$ is selected from the group consisting of EVYD-FAFRDLC (SEQ ID NO:334), GFAFRDLCIVY (SEQ ID NO:335), GFAYRDINLAY (SEQ ID NO:336), GTL-GIVCPIG (SEQ ID NO:337), GLEPLVIAGILA (SEQ ID NO:338), TPI(Har)QDWENRAN (SEQ ID NO:339), VAFEDL(Har)(Nle)(Nle)SFI (SEQ ID NO:340), RFQTV-VQBA (SEQ ID NO:341), GSLVGLLHIVL (SEQ ID NO:342), SIARSVTI(Nle)(Har)ASVVH (SEQ ID NO:343), TPTRQEWDCRIS (SEQ ID NO:344), TPTRQEWDARIS (SEQ ID NO:345), TPI(Har)QEW(Har)SL(Nle)NQEW (SEQ ID NO:346), IGDLIVAQV (SEQ ID NO:347), QYN-PVAV(Nle)F (SEQ ID NO:348), GYTLFFTS (SEQ ID NO:349), GYTLFVSD (SEQ ID NO:350), NTL(Nle)T-PRVD (SEQ ID NO:351), SSTSPVYNL (SEQ ID NO:352), VITFSIYLIVS (SEQ ID NO:353), GGNVIGGIY(Nle)IPR (SEQ ID NO:354), ANWAKVIL (SEQ ID NO:355), VIRVI-AHGLRL (SEQ ID NO:356), and IGDLIVQAV (SEQ ID NO:478); and wherein optional $Z^9$ is NWAKVI, wherein Nle is Norleucine and Har is homoarginine.

5. An immunogenic composition comprising
at least one monomeric peptide according to claim 1, and
an isolated dimeric or multimeric peptide comprising two or more covalently joined monomeric peptides, each monomeric peptide independently comprising the following structure $Z^1$-$Z^2$-$Z^3$-$Z^4$-$Z^6$-$Z^7$-$Z^9$ wherein $Z^1$, $Z^4$, and optional $Z^7$ defines a linear sequence of one, two, or three arginine residues or derivatives thereof optionally followed by a glycine (G); $Z^2$ defines an optional amino acid selected from 2,3-Diaminopropionic acid (Dpr), Cysteine, Lysine, Aspartic acid and Glutamic acid, or a derivative thereof; wherein $Z^3$ is selected from the group consisting of GGQLIGGIYLIPG (SEQ ID NO:313), VITYSIFLIVS (SEQ ID NO:314), TANWARVIS (SEQ ID NO:315), GYLPAVGAPI (SEQ ID NO:316), NIVP(Nle) VVTA (SEQ ID NO:317), VTPADLIGA (SEQ ID NO:318), PRPEGYTLFF (SEQ ID NO:319), LPYPRGYTLFV (SEQ ID NO:320), ETILTPRDV (SEQ ID NO:321), SST-SPVYDL (SEQ ID NO:322), TAYER(Nle)CNIL (SEQ ID NO:323), TVIGAS(Nle)IPLL (SEQ ID NO:324), AAFEE (Nle)(Har)ITS (SEQ ID NO:325), GLEPLVIAGILA (SEQ ID NO:326), TAFLVRNVA (SEQ ID NO:327), TPI(Har) QDWGNRAN (SEQ ID NO:328), TPT(Har)NGWDVKLS (SEQ ID NO:329), LECVYCKQQLL (SEQ ID NO:330), GVYDFAFRDLC (SEQ ID NO:331), GVFDYAFRDIN (SEQ ID NO:332), and VDIRTLEDLL (SEQ ID NO:333); wherein $Z^6$ is selected from the group consisting of EVYD-FAFRDLC (SEQ ID NO:334), GFAFRDLCIVY (SEQ ID NO:335), GFAYRDINLAY (SEQ ID NO:336), GTL-GIVCPIG (SEQ ID NO:337), GLEPLVIAGILA (SEQ ID NO:338), TPI(Har)QDWENRAN (SEQ ID NO:339), VAFEDL(Har)(Nle)(Nle)SFI (SEQ ID NO:340), RFQTV-VQBA (SEQ ID NO:341), GSLVGLLHIVL (SEQ ID NO:342), SIARSVTI(Nle)(Har)ASVVH (SEQ ID NO:343), TPTRQEWDCRIS (SEQ ID NO:344), TPTRQEWDARIS (SEQ ID NO:345), TPI(Har)QEW(Har)SL(Nle)NQEW (SEQ ID NO:346), IGDLIVAQV (SEQ ID NO:347), QYN-PVAV(Nle)F (SEQ ID NO:348), GYTLFFTS (SEQ ID NO:349), GYTLFVSD (SEQ ID NO:350), NTL(Nle)T-PRDV (SEQ ID NO:351), SSTSPVYNL (SEQ ID NO:352), VITFSIYLIVS (SEQ ID NO:353), GGNVIGGIY(Nle)IPR (SEQ ID NO:354), ANWAKVIL (SEQ ID NO:355), VIRVI-AHGLRL (SEQ ID NO:356), and IGDLIVQAV (SEQ ID NO:478); and wherein optional $Z^9$ is NWAKVI, wherein Nle is Norleucine and Har is homoarginine.

6. The immunogenic composition according to claim 5 in the form of a vaccine composition.

7. A method for inducing an immune response in a subject against an antigen which comprises administration of
at least one monomeric peptide according to claim 1,
an isolated dimeric or multimeric peptide comprising two or more covalently joined monomeric peptides, each monomeric peptide independently comprising the following structure $Z^1$-$Z^2$-$Z^3$-$Z^4$-$Z^6$-$Z^7$-$Z^9$ wherein $Z^1$, $Z^4$, and optional $Z^7$ defines a linear sequence of one, two, or three arginine residues or derivatives thereof optionally followed by a glycine (G); $Z^2$ defines an optional amino acid selected from 2,3-Diaminopropionic acid (Dpr), Cysteine, Lysine, Aspartic acid, and Glutamic acid, or a derivative thereof; wherein $Z^3$ is selected from the group consisting of GGQLIGGI-YLIPG (SEQ ID NO:313), VITYSIFLIVS (SEQ ID NO:314), TANWARVIS (SEQ ID NO:315), GYLPAV-GAPI (SEQ ID NO:316), NIVP(Nle)VVTA (SEQ ID NO:317), VTPADLIGA (SEQ ID NO:318), PRP-EGYTLFF (SEQ ID NO:319), LPYPRGYTLFV (SEQ ID NO:320), ETILTPRDV (SEQ ID NO:321), SST-SPVYDL (SEQ ID NO:322), TAYER(Nle)CNIL (SEQ ID NO:323), TVIGAS(Nle)IPLL (SEQ ID NO:324), AAFEE(Nle)(Har)ITS (SEQ ID NO:325), GLEPLVI-AGILA (SEQ ID NO:326), TAFLVRNVA (SEQ ID NO:327), TPI(Har)QDWGNRAN (SEQ ID NO:328), TPT(Har)NGWDVKLS (SEQ ID NO:329), LECVYCKQQLL (SEQ ID NO:330), GVYDFAFRDLC (SEQ ID NO:331), GVFDYAFRDIN (SEQ ID NO:332), and VDIRTLEDLL (SEQ ID NO:333); wherein $Z^6$ is selected from the group consisting of EVYDFAFRDLC (SEQ ID NO:334), GFAFRDLCIVY (SEQ ID NO:335), GFAYRDINLAY (SEQ ID NO:336), GTLGIVCPIG (SEQ ID NO:337), GLEPLVIAGILA (SEQ ID NO:338), TPI(Har)QDWENRAN (SEQ ID NO:339), VAFEDL(Har)(Nle)(Nle)SFI (SEQ ID NO:340), RFQTVVQBA (SEQ ID NO:341), GSLVGLLHIVL (SEQ ID NO:342), SIARSVTI(Nle)(Har)ASVVH (SEQ ID NO:343), TPTRQEWDCRIS (SEQ ID NO:344), TPTRQEWDARIS (SEQ ID NO:345), TPI(Har)QEW(Har)SL(Nle)NQEW (SEQ ID NO:346), IGDLIVAQV (SEQ ID NO:347), QYNPVAV(Nle)F (SEQ ID NO:348), GYTLFFTS (SEQ ID NO:349), GYTLFVSD (SEQ ID NO:350), NTL(Nle)TPRDV (SEQ ID NO:351), SSTSPVYNL (SEQ ID NO:352), VITFSIYLIVS (SEQ ID NO:353), GGNVIGGIY(Nle)IPR (SEQ ID NO:354), ANWAKVIL (SEQ ID NO:355), VIRVIAHGLRL (SEQ ID NO:356), and IGDLIVQAV (SEQ ID NO:478); and wherein optional $Z^9$ is NWAKVI, wherein Nle is Norleucine and Har is homoarginine, a peptide composition comprising two or more compounds selected from a monomeric peptide is as defined in claim 1, and an isolated dimeric or multimericpeptide comprising two or more monomeric peptides, each monomeric peptide independently comprising the following structure $Z^1$-$Z^2$-$Z^3$-$Z^4$-$Z^6$-$Z^7$-$Z^9$ wherein $Z^1$, $Z^4$, and optional $Z^7$ defines a linear sequence of one, two, or three arginine residues or derivatives thereof optionally followed by a glycine (G); $Z^2$ defines an optional amino acid selected from 2,3-Diaminopropionic acid (Dpr), Cysteine, Lysine, Aspartic acid, and Glutamic acid, or a derivative thereof; wherein $Z^3$ is selected from the group consisting of GGQLIGGIYLIPG (SEQ ID NO:313), VITYSIFLIVS (SEQ ID NO:314), TANWARVIS (SEQ ID NO:315), GYLPAVGAPI (SEQ ID NO:316), NIVP(Nle)VVTA (SEQ ID NO:317), VTPADLIGA (SEQ ID NO:318), PRPEGYTLFF (SEQ ID NO:319), LPYPRGYTLFV (SEQ ID NO:320), ETILTPRDV (SEQ ID NO:321), SSTSPVYDL (SEQ ID NO:322), TAYER(Nle)CNIL (SEQ ID NO:323), TVIGAS(Nle)IPLL (SEQ ID NO:324), AAFEE(Nle)(Har)ITS (SEQ ID NO:325), GLEPLVIAGILA (SEQ ID NO:326), TAFLVRNVA (SEQ ID NO:327), TPI(Har)QDWGNRAN (SEQ ID NO:328), TPT(Har)NGWDVKLS (SEQ ID NO:329), LECVYCKQQLL (SEQ ID NO:330), GVYDFAFRDLC (SEQ ID NO:331), GVFDYAFRDIN (SEQ ID NO:332), and VDIRTLEDLL (SEQ ID NO:333); wherein $Z^6$ is selected from the group consisting of EVYDFAFRDLC (SEQ ID NO:334), GFAFRDLCIVY (SEQ ID NO:335), GFAYRDINLAY (SEQ ID NO:336), GTLGIVCPIG (SEQ ID NO:337), GLEPLVIAGILA (SEQ ID NO:338), TPI(Har)QDWENRAN (SEQ ID NO:339), VAFEDL(Har)(Nle)SFI (SEQ ID NO:340), RFQTVVQBA (SEQ ID NO:341), GSLVGLLHIVL (SEQ ID NO:342), SIARSVTI(Nle)(Har)ASVVH (SEQ ID NO:343), TPTRQEWDCRIS (SEQ ID NO:344), TPTRQEWDARIS (SEQ ID NO:345), TPI(Har)QEW(Har)SL(Nle)NQEW (SEQ ID NO:346), IGDLIVAQV (SEQ ID NO:347), QYNPVAV(Nle)F (SEQ ID NO:348), GYTLFFTS (SEQ ID NO:349), GYTLFVSD (SEQ ID NO:350), NTL(Nle)TPRDV (SEQ ID NO:351), SSTSPVYNL (SEQ ID NO:352), VITFSIYLIVS (SEQ ID NO:353), GGNVIGGIY(Nle)IPR (SEQ ID NO:354), ANWAKVIL (SEQ ID NO:355), VIRVIAHGLRL (SEQ ID NO:356), and IGDLIVQAV (SEQ ID NO:478); and wherein optional $Z^9$ is NWAKVI, wherein Nle is Norleucine and Har is homoarginine.

8. A peptide according to claim 1, a peptide composition comprising two or more compounds selected from a monomeric peptide is as defined in claim 1, and an isolated dimeric or multimeric dimeric peptide comprising two or more covalently joined monomeric peptides, each monomeric peptide independently comprising the following structure $Z^1$-$Z^2$-$Z^3$-$Z^4$-$Z^6$-$Z^7$-$Z^9$ wherein $Z^1$, $Z^4$, and optional $Z^7$ defines a linear sequence of one, two, or three arginine residues or derivatives thereof optionally followed by a glycine (G); $Z^2$ defines an optional amino acid selected from 2,3-Diaminopropionic acid (Dpr), Cysteine, Lysine, Aspartic acid and Glutamic acid, or a derivative thereof; wherein $Z^3$ is selected from the group consisting of GGQLIGGIYLIPG (SEQ ID NO:313), VITYSIFLIVS (SEQ ID NO:314), TANWARVIS (SEQ ID NO:315), GYLPAVGAPI (SEQ ID NO:316), NIVP(Nle)VVTA (SEQ ID NO:317), VTPADLIGA (SEQ ID NO:318), PRPEGYTLFF (SEQ ID NO:319), LPYPRGYTLFV (SEQ ID NO:320), ETILTPRDV (SEQ ID NO:321), SSTSPVYDL (SEQ ID NO:322), TAYER(Nle)CNIL (SEQ ID NO:323), TVIGAS(Nle)IPLL (SEQ ID NO:324), AAFEE(Nle)(Har)ITS (SEQ ID NO:325), GLEPLVIAGILA (SEQ ID NO:326), TAFLVRNVA (SEQ ID NO:327), TPI(Har)QDWGNRAN (SEQ ID NO:328), TPT(Har)NGWDVKLS (SEQ ID NO:329), LECVYCKQQLL (SEQ ID NO:330), GVYDFAFRDLC (SEQ ID NO:331), GVFDYAFRDIN (SEQ ID NO:332), and VDIRTLEDLL (SEQ ID NO:333); wherein $Z^6$ is selected from the group consisting of EVYDFAFRDLC (SEQ ID NO:334), GFAFRDLCIVY (SEQ ID NO:335), GFAYRDINLAY (SEQ ID NO:336), GTLGIVCPIG (SEQ ID NO:337), GLEPLVIAGILA (SEQ ID NO:338), TPI(Har)QDWENRAN (SEQ ID NO:339), VAFEDL(Har)(Nle)SFI (SEQ ID NO:340), RFQTVVQBA (SEQ ID NO:341), GSLVGLLHIVL (SEQ ID NO:342), SIARSVTI(Nle)(Har)ASVVH (SEQ ID NO:343), TPTRQEWDCRIS (SEQ ID NO:344), TPTRQEWDARIS (SEQ ID NO:345), TPI(Har)QEW(Har)SL(Nle)NQEW (SEQ ID NO:346), IGDLIVAQV (SEQ ID NO:347), QYNPVAV(Nle)F (SEQ ID NO:348), GYTLFFTS (SEQ ID NO:349), GYTLFVSD (SEQ ID NO:350), NTL(Nle)TPRDV (SEQ ID NO:351), SSTSPVYNL (SEQ ID NO:352), VITFSIYLIVS (SEQ ID NO:353), GGNVIGGIY(Nle)IPR (SEQ ID NO:354), ANWAKVIL (SEQ ID NO:355), VIRVIAHGLRL (SEQ ID NO:356), and IGDLIVQAV (SEQ ID NO:478); and wherein optional $Z^9$ is NWAKVI, for use as a medicament, wherein Nle is Norleucine and Har is homoarginine.

9. A peptide according to claim 1, a peptide composition comprising two or more compounds selected from a monomeric peptide is as defined in claim 1, and an isolated dimeric or multimeric peptide comprising two or more covalently joined monomeric peptides, each monomeric peptide independently comprising the following structure $Z^1$-$Z^2$-$Z^3$-$Z^4$-$Z^6$-$Z^7$-$Z^9$ wherein $Z^1$, $Z^4$, and optional $Z^7$ defines a linear sequence of one, two, or three arginine residues or derivatives thereof optionally followed by a glycine (G); $Z^2$ defines an optional amino acid selected from 2,3-Diaminopropionic acid (Dpr), Cysteine, Lysine, Aspartic acid and Glutamic acid, or a derivative thereof; wherein $Z^3$ is selected from the group consisting of GGQLIGGIYLIPG (SEQ ID NO:313), VITYSIFLIVS (SEQ ID NO:314), TANWARVIS (SEQ ID NO:315), GYLPAVGAPI (SEQ ID NO:316), NIVP(Nle)VVTA (SEQ ID NO:317), VTPADLIGA (SEQ ID NO:318), PRPEGYTLFF (SEQ ID NO:319), LPYPRGYTLFV (SEQ ID NO:320), ETILTPRDV (SEQ ID NO:321), SSTSPVYDL (SEQ ID NO:322), TAYER(Nle)CNIL (SEQ ID NO:323), TVIGA(Nle)IPLL (SEQ ID NO:324), AAFEE(Nle)(Har)ITS (SEQ ID NO:325), GLEPLVIAGILA (SEQ ID NO:326), TAFLVRNVA (SEQ ID NO:327), TPI(Har)QDWGNRAN (SEQ ID NO:328), TPT(Har)NGWDVKLS (SEQ ID NO:329), LECVYCKQQLL (SEQ ID NO:330), GVYDFAFRDLC (SEQ ID NO:331), GVFDYAFRDIN (SEQ ID NO:332), and VDIRTLEDLL (SEQ ID NO:333); wherein $Z^6$ is selected from the group consisting of EVYDFAFRDLC (SEQ ID NO:334), GFAFRDLCIVY (SEQ ID NO:335), GFAYRDINLAY (SEQ ID NO:336), GTLGIVCPIG (SEQ ID NO:337), GLEPLVIAGILA (SEQ ID NO:338), TPI(Har)QDWENRAN (SEQ ID NO:339), VAFEDL(Har)(Nle)(Nle)SFI (SEQ ID NO:340), RFQTVVQBA (SEQ ID NO:341), GSLVGLLHIVL (SEQ ID NO:342), SIARSVTI(Nle)(Har)ASVVH (SEQ ID NO:343), TPTRQEWDCRIS (SEQ ID NO:344), TPTRQEWDARIS (SEQ ID NO:345), TPI(Har)QEW(Har)SL(Nle)NQEW (SEQ ID NO:346), IGDLIVAQV (SEQ ID NO:347), QYNPVAV(Nle)F (SEQ ID NO:348), GYTLFFTS (SEQ ID NO:349), GYTLFVSD (SEQ ID NO:350), NTL(Nle)TPRDV (SEQ ID NO:351), SSTSPVYNL (SEQ ID NO:352), VITFSIYLIVS (SEQ ID NO:353), GGNVIGGIY(Nle)IPR (SEQ ID NO:354), ANWAKVIL (SEQ ID NO:355), VIRVIAHGLRL (SEQ ID NO:356), and IGDLIVQAV (SEQ ID NO:478); and wherein optional $Z^9$ is NWAKVI, for treating the pathological effects of a disease antigen wherein Nle is Norleucine, and Har is homoar

SEQUENCE LISTING

```
<160> NUMBER OF SEQ ID NOS: 486

<210> SEQ ID NO 1
<211> LENGTH: 3011
<212> TYPE: PRT
<213> ORGANISM: Hepatitis C virus

<400> SEQUENCE: 1

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
```

```
                65                  70                  75                  80
Tyr Pro Trp Pro Leu Tyr Gly Asn Glu Gly Cys Gly Trp Ala Gly Trp
                    85                  90                  95
Leu Leu Ser Pro Arg Gly Ser Arg Pro Ser Trp Gly Pro Thr Asp Pro
                    100                 105                 110
Arg Arg Arg Ser Arg Asn Leu Gly Lys Val Ile Asp Thr Leu Thr Cys
                    115                 120                 125
Gly Phe Ala Asp Leu Met Gly Tyr Ile Pro Leu Val Gly Ala Pro Leu
130                 135                 140
Gly Gly Ala Ala Arg Ala Leu Ala His Gly Val Arg Val Leu Glu Asp
145                 150                 155                 160
Gly Val Asn Tyr Ala Thr Gly Asn Leu Pro Gly Cys Ser Phe Ser Ile
                    165                 170                 175
Phe Leu Leu Ala Leu Leu Ser Cys Leu Thr Val Pro Ala Ser Ala Tyr
                    180                 185                 190
Gln Val Arg Asn Ser Ser Gly Leu Tyr His Val Thr Asn Asp Cys Pro
                    195                 200                 205
Asn Ser Ser Ile Val Tyr Glu Ala Ala Asp Ala Ile Leu His Thr Pro
210                 215                 220
Gly Cys Val Pro Cys Val Arg Glu Gly Asn Ala Ser Arg Cys Trp Val
225                 230                 235                 240
Ala Val Thr Pro Thr Val Ala Thr Arg Asp Gly Lys Leu Pro Thr Thr
                    245                 250                 255
Gln Leu Arg Arg His Ile Asp Leu Leu Val Gly Ser Ala Thr Leu Cys
                    260                 265                 270
Ser Ala Leu Tyr Val Gly Asp Leu Cys Gly Ser Val Phe Leu Val Gly
                    275                 280                 285
Gln Leu Phe Thr Phe Ser Pro Arg Arg His Trp Thr Thr Gln Asp Cys
                    290                 295                 300
Asn Cys Ser Ile Tyr Pro Gly His Ile Thr Gly His Arg Met Ala Trp
305                 310                 315                 320
Asp Met Met Met Asn Trp Ser Pro Thr Ala Ala Leu Val Val Ala Gln
                    325                 330                 335
Leu Leu Arg Ile Pro Gln Ala Ile Met Asp Met Ile Ala Gly Ala His
                    340                 345                 350
Trp Gly Val Leu Ala Gly Ile Ala Tyr Phe Ser Met Val Gly Asn Trp
                    355                 360                 365
Ala Lys Val Leu Val Val Leu Leu Leu Phe Ala Gly Val Asp Ala Glu
                    370                 375                 380
Thr His Val Thr Gly Gly Ser Ala Gly Arg Thr Thr Ala Gly Leu Val
385                 390                 395                 400
Gly Leu Leu Thr Pro Gly Ala Lys Gln Asn Ile Gln Leu Ile Asn Thr
                    405                 410                 415
Asn Gly Ser Trp His Ile Asn Ser Thr Ala Leu Asn Cys Asn Glu Ser
                    420                 425                 430
Leu Asn Thr Gly Trp Leu Ala Gly Leu Phe Tyr Gln His Lys Phe Asn
                    435                 440                 445
Ser Ser Gly Cys Pro Glu Arg Leu Ala Ser Cys Arg Arg Leu Thr Asp
                    450                 455                 460
Phe Ala Gln Gly Trp Gly Pro Ile Ser Tyr Ala Asn Gly Ser Gly Leu
465                 470                 475                 480
Asp Glu Arg Pro Tyr Cys Trp His Tyr Pro Arg Pro Cys Gly Ile
                    485                 490                 495
```

```
Val Pro Ala Lys Ser Val Cys Gly Pro Val Tyr Cys Phe Thr Pro Ser
            500                 505                 510
Pro Val Val Gly Thr Thr Asp Arg Ser Gly Ala Pro Thr Tyr Ser
            515                 520                 525
Trp Gly Ala Asn Asp Thr Asp Val Phe Val Leu Asn Asn Thr Arg Pro
            530                 535                 540
Pro Leu Gly Asn Trp Phe Gly Cys Thr Trp Met Asn Ser Thr Gly Phe
545                 550                 555                 560
Thr Lys Val Cys Gly Ala Pro Pro Cys Val Ile Gly Val Gly Asn
            565                 570                 575
Asn Thr Leu Leu Cys Pro Thr Asp Cys Phe Arg Lys His Pro Glu Ala
            580                 585                 590
Thr Tyr Ser Arg Cys Gly Ser Gly Pro Trp Ile Thr Pro Arg Cys Met
            595                 600                 605
Val Asp Tyr Pro Tyr Arg Leu Trp His Tyr Pro Cys Thr Ile Asn Tyr
            610                 615                 620
Thr Ile Phe Lys Val Arg Met Tyr Val Gly Gly Val Glu His Arg Leu
625                 630                 635                 640
Glu Ala Ala Cys Asn Trp Thr Arg Gly Glu Arg Cys Asp Leu Glu Asp
            645                 650                 655
Arg Asp Arg Ser Glu Leu Ser Pro Leu Leu Leu Ser Thr Thr Gln Trp
            660                 665                 670
Gln Val Leu Pro Cys Ser Phe Thr Thr Leu Pro Ala Leu Ser Thr Gly
            675                 680                 685
Leu Ile His Leu His Gln Asn Ile Val Asp Val Gln Tyr Leu Tyr Gly
            690                 695                 700
Val Gly Ser Ser Ile Ala Ser Trp Ala Ile Lys Trp Glu Tyr Val Val
705                 710                 715                 720
Leu Leu Phe Leu Leu Leu Ala Asp Ala Arg Val Cys Ser Cys Leu Trp
            725                 730                 735
Met Met Leu Leu Ile Ser Gln Ala Glu Ala Ala Leu Glu Asn Leu Val
            740                 745                 750
Ile Leu Asn Ala Ala Ser Leu Ala Gly Thr His Gly Leu Val Ser Phe
            755                 760                 765
Leu Val Phe Phe Cys Phe Ala Trp Tyr Leu Lys Gly Arg Trp Val Pro
            770                 775                 780
Gly Ala Val Tyr Ala Phe Tyr Gly Met Trp Pro Leu Leu Leu Leu Leu
785                 790                 795                 800
Leu Ala Leu Pro Gln Arg Ala Tyr Ala Leu Asp Thr Glu Val Ala Ala
            805                 810                 815
Ser Cys Gly Gly Val Val Leu Val Gly Leu Met Ala Leu Thr Leu Ser
            820                 825                 830
Pro Tyr Tyr Lys Arg Tyr Ile Ser Trp Cys Met Trp Trp Leu Gln Tyr
            835                 840                 845
Phe Leu Thr Arg Val Glu Ala Gln Leu His Val Trp Val Pro Pro Leu
            850                 855                 860
Asn Val Arg Gly Gly Arg Asp Ala Val Ile Leu Leu Met Cys Val Val
865                 870                 875                 880
His Pro Thr Leu Val Phe Asp Ile Thr Lys Leu Leu Leu Ala Ile Phe
            885                 890                 895
Gly Pro Leu Trp Ile Leu Gln Ala Ser Leu Leu Lys Val Pro Tyr Phe
            900                 905                 910
```

```
Val Arg Val Gln Gly Leu Leu Arg Ile Cys Ala Leu Ala Arg Lys Ile
        915                 920                 925

Ala Gly Gly His Tyr Val Gln Met Ala Ile Ile Lys Leu Gly Ala Leu
        930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Arg Met Glu Thr Lys Leu Ile Thr Trp Gly Ala Asp Thr Ala Ala
        980                 985                 990

Cys Gly Asp Ile Ile Asn Gly Leu Pro Val Ser Ala Arg Arg Gly Gln
        995                 1000                1005

Glu Ile Leu Leu Gly Pro Ala Asp Gly Met Val Ser Lys Gly Trp
        1010                1015                1020

Arg Leu Leu Ala Pro Ile Thr Ala Tyr Ala Gln Gln Thr Arg Gly
        1025                1030                1035

Leu Leu Gly Cys Ile Ile Thr Ser Leu Thr Gly Arg Asp Lys Asn
        1040                1045                1050

Gln Val Glu Gly Glu Val Gln Ile Val Ser Thr Ala Thr Gln Thr
        1055                1060                1065

Phe Leu Ala Thr Cys Ile Asn Gly Val Cys Trp Thr Val Tyr His
        1070                1075                1080

Gly Ala Gly Thr Arg Thr Ile Ala Ser Pro Lys Gly Pro Val Ile
        1085                1090                1095

Gln Met Tyr Thr Asn Val Asp Gln Asp Leu Val Gly Trp Pro Ala
        1100                1105                1110

Pro Gln Gly Ser Arg Ser Leu Thr Pro Cys Thr Cys Gly Ser Ser
        1115                1120                1125

Asp Leu Tyr Leu Val Thr Arg His Ala Asp Val Ile Pro Val Arg
        1130                1135                1140

Arg Arg Gly Asp Ser Arg Gly Ser Leu Leu Ser Pro Arg Pro Ile
        1145                1150                1155

Ser Tyr Leu Lys Gly Ser Ser Gly Gly Pro Leu Leu Cys Pro Ala
        1160                1165                1170

Gly His Ala Val Gly Leu Phe Arg Ala Ala Val Cys Thr Arg Gly
        1175                1180                1185

Val Ala Lys Ala Val Asp Phe Ile Pro Val Glu Asn Leu Glu Thr
        1190                1195                1200

Thr Met Arg Ser Pro Val Phe Thr Asp Asn Ser Ser Pro Pro Ala
        1205                1210                1215

Val Pro Gln Ser Phe Gln Val Ala His Leu His Ala Pro Thr Gly
        1220                1225                1230

Ser Gly Lys Ser Thr Lys Val Pro Ala Ala Tyr Ala Ala Gln Gly
        1235                1240                1245

Tyr Lys Val Leu Val Leu Asn Pro Ser Val Ala Ala Thr Leu Gly
        1250                1255                1260

Phe Gly Ala Tyr Met Ser Lys Ala His Gly Val Asp Pro Asn Ile
        1265                1270                1275

Arg Thr Gly Val Arg Thr Ile Thr Thr Gly Ser Pro Ile Thr Tyr
        1280                1285                1290

Ser Thr Tyr Gly Lys Phe Leu Ala Asp Gly Gly Cys Ser Gly Gly
        1295                1300                1305

Ala Tyr Asp Ile Ile Ile Cys Asp Glu Cys His Ser Thr Asp Ala
```

-continued

```
            1310                1315                1320
Thr Ser Ile Leu Gly Ile Gly Thr Val Leu Asp Gln Ala Glu Thr
        1325                1330                1335
Ala Gly Ala Arg Leu Val Val Leu Ala Thr Ala Thr Pro Pro Gly
        1340                1345                1350
Ser Val Thr Val Ser His Pro Asn Ile Glu Glu Val Ala Leu Ser
        1355                1360                1365
Thr Thr Gly Glu Ile Pro Phe Tyr Gly Lys Ala Ile Pro Leu Glu
        1370                1375                1380
Val Ile Lys Gly Gly Arg His Leu Ile Phe Cys His Ser Lys Lys
        1385                1390                1395
Lys Cys Asp Glu Leu Ala Ala Lys Leu Val Ala Leu Gly Ile Asn
        1400                1405                1410
Ala Val Ala Tyr Tyr Arg Gly Leu Asp Val Ser Val Ile Pro Thr
        1415                1420                1425
Ser Gly Asp Val Val Val Ser Thr Asp Ala Leu Met Thr Gly
        1430                1435                1440
Phe Thr Gly Asp Phe Asp Ser Val Ile Asp Cys Asn Thr Cys Val
        1445                1450                1455
Thr Gln Thr Val Asp Phe Ser Leu Asp Pro Thr Phe Thr Ile Glu
        1460                1465                1470
Thr Thr Thr Leu Pro Gln Asp Ala Val Ser Arg Thr Gln Arg Arg
        1475                1480                1485
Gly Arg Thr Gly Arg Gly Lys Pro Gly Ile Tyr Arg Phe Val Ala
        1490                1495                1500
Pro Gly Glu Arg Pro Ser Gly Met Phe Asp Ser Ser Val Leu Cys
        1505                1510                1515
Glu Cys Tyr Asp Ala Gly Cys Ala Trp Tyr Glu Leu Thr Pro Ala
        1520                1525                1530
Glu Thr Thr Val Arg Leu Arg Ala Tyr Met Asn Thr Pro Gly Leu
        1535                1540                1545
Pro Val Cys Gln Asp His Leu Glu Phe Trp Glu Gly Val Phe Thr
        1550                1555                1560
Gly Leu Thr His Ile Asp Ala His Phe Leu Ser Gln Thr Lys Gln
        1565                1570                1575
Ser Gly Glu Asn Phe Pro Tyr Leu Val Ala Tyr Gln Ala Thr Val
        1580                1585                1590
Cys Ala Arg Ala Gln Ala Pro Pro Pro Ser Trp Asp Gln Met Trp
        1595                1600                1605
Lys Cys Leu Ile Arg Leu Lys Pro Thr Leu His Gly Pro Thr Pro
        1610                1615                1620
Leu Leu Tyr Arg Leu Gly Ala Val Gln Asn Glu Val Thr Leu Thr
        1625                1630                1635
His Pro Ile Thr Lys Tyr Ile Met Thr Cys Met Ser Ala Asp Leu
        1640                1645                1650
Glu Val Val Thr Ser Thr Trp Val Leu Val Gly Gly Val Leu Ala
        1655                1660                1665
Ala Leu Ala Ala Tyr Cys Leu Ser Thr Gly Cys Val Val Ile Val
        1670                1675                1680
Gly Arg Ile Val Leu Ser Gly Lys Pro Ala Ile Ile Pro Asp Arg
        1685                1690                1695
Glu Val Leu Tyr Gln Glu Phe Asp Glu Met Glu Glu Cys Ser Gln
        1700                1705                1710
```

His Leu Pro Tyr Ile Glu Gln Gly Met Met Leu Ala Glu Gln Phe
    1715                1720                1725

Lys Gln Lys Ala Leu Gly Leu Leu Gln Thr Ala Ser Arg Gln Ala
    1730                1735                1740

Glu Val Ile Thr Pro Ala Val Gln Thr Asn Trp Gln Lys Leu Glu
    1745                1750                1755

Val Phe Trp Ala Lys His Met Trp Asn Phe Ile Ser Gly Ile Gln
    1760                1765                1770

Tyr Leu Ala Gly Leu Ser Thr Leu Pro Gly Asn Pro Ala Ile Ala
    1775                1780                1785

Ser Leu Met Ala Phe Thr Ala Ala Val Thr Ser Pro Leu Thr Thr
    1790                1795                1800

Gly Gln Thr Leu Leu Phe Asn Ile Leu Gly Gly Trp Val Ala Ala
    1805                1810                1815

Gln Leu Ala Ala Pro Gly Ala Ala Thr Ala Phe Val Gly Ala Gly
    1820                1825                1830

Leu Ala Gly Ala Ala Ile Gly Ser Val Gly Leu Gly Lys Val Leu
    1835                1840                1845

Val Asp Ile Leu Ala Gly Tyr Gly Ala Gly Val Ala Gly Ala Leu
    1850                1855                1860

Val Ala Phe Lys Ile Met Ser Gly Glu Val Pro Ser Thr Glu Asp
    1865                1870                1875

Leu Val Asn Leu Leu Pro Ala Ile Leu Ser Pro Gly Ala Leu Val
    1880                1885                1890

Val Gly Val Val Cys Ala Ala Ile Leu Arg Arg His Val Gly Pro
    1895                1900                1905

Gly Glu Gly Ala Val Gln Trp Met Asn Arg Leu Ile Ala Phe Ala
    1910                1915                1920

Ser Arg Gly Asn His Val Ser Pro Thr His Tyr Val Pro Glu Ser
    1925                1930                1935

Asp Ala Ala Ala Arg Val Thr Ala Ile Leu Ser Ser Leu Thr Val
    1940                1945                1950

Thr Gln Leu Leu Arg Arg Leu His Gln Trp Ile Ser Ser Glu Cys
    1955                1960                1965

Thr Thr Pro Cys Ser Gly Ser Trp Leu Arg Asp Ile Trp Asp Trp
    1970                1975                1980

Ile Cys Glu Val Leu Ser Asp Phe Lys Thr Trp Leu Lys Ala Lys
    1985                1990                1995

Leu Met Pro Gln Leu Pro Gly Ile Pro Phe Val Ser Cys Gln Arg
    2000                2005                2010

Gly Tyr Arg Gly Val Trp Arg Gly Asp Gly Ile Met His Thr Arg
    2015                2020                2025

Cys His Cys Gly Ala Glu Ile Thr Gly His Val Lys Asn Gly Thr
    2030                2035                2040

Met Arg Ile Val Gly Pro Arg Thr Cys Arg Asn Met Trp Ser Gly
    2045                2050                2055

Thr Phe Pro Ile Asn Ala Tyr Thr Thr Gly Pro Cys Thr Pro Leu
    2060                2065                2070

Pro Ala Pro Asn Tyr Lys Phe Ala Leu Trp Arg Val Ser Ala Glu
    2075                2080                2085

Glu Tyr Val Glu Ile Arg Arg Val Gly Asp Phe His Tyr Val Ser
    2090                2095                2100

```
Gly Met Thr Thr Asp Asn Leu Lys Cys Pro Cys Gln Ile Pro Ser
    2105                2110                2115

Pro Glu Phe Phe Thr Glu Leu Asp Gly Val Arg Leu His Arg Phe
    2120                2125                2130

Ala Pro Pro Cys Lys Pro Leu Leu Arg Glu Val Ser Phe Arg
    2135                2140                2145

Val Gly Leu His Glu Tyr Pro Val Gly Ser Gln Leu Pro Cys Glu
    2150                2155                2160

Pro Glu Pro Asp Val Ala Val Leu Thr Ser Met Leu Thr Asp Pro
    2165                2170                2175

Ser His Ile Thr Ala Glu Ala Ala Gly Arg Arg Leu Ala Arg Gly
    2180                2185                2190

Ser Pro Pro Ser Met Ala Ser Ser Ser Ala Ser Gln Leu Ser Ala
    2195                2200                2205

Pro Ser Leu Lys Ala Thr Cys Thr Ala Asn His Asp Ser Pro Asp
    2210                2215                2220

Ala Glu Leu Ile Glu Ala Asn Leu Leu Trp Arg Gln Glu Met Gly
    2225                2230                2235

Gly Asn Ile Thr Arg Val Glu Ser Glu Asn Lys Val Val Ile Leu
    2240                2245                2250

Asp Ser Phe Asp Pro Leu Val Ala Glu Glu Asp Glu Arg Glu Val
    2255                2260                2265

Ser Val Pro Ala Glu Ile Leu Arg Lys Ser Arg Arg Phe Ala Arg
    2270                2275                2280

Ala Leu Pro Val Trp Ala Arg Pro Asp Tyr Asn Pro Pro Leu Val
    2285                2290                2295

Glu Thr Trp Lys Lys Pro Asp Tyr Glu Pro Pro Val Val His Gly
    2300                2305                2310

Cys Pro Leu Pro Pro Arg Ser Pro Pro Val Pro Pro Pro Arg
    2315                2320                2325

Lys Lys Arg Thr Val Val Leu Thr Glu Ser Thr Leu Ser Thr Ala
    2330                2335                2340

Leu Ala Glu Leu Ala Thr Lys Ser Phe Gly Ser Ser Ser Thr Ser
    2345                2350                2355

Gly Ile Thr Gly Asp Asn Thr Thr Thr Ser Ser Glu Pro Ala Pro
    2360                2365                2370

Ser Gly Cys Pro Pro Asp Ser Asp Val Glu Ser Tyr Ser Ser Met
    2375                2380                2385

Pro Pro Leu Glu Gly Glu Pro Gly Asp Pro Asp Leu Ser Asp Gly
    2390                2395                2400

Ser Trp Ser Thr Val Ser Ser Gly Ala Asp Thr Glu Asp Val Val
    2405                2410                2415

Cys Cys Ser Met Ser Tyr Ser Trp Thr Gly Ala Leu Val Thr Pro
    2420                2425                2430

Cys Ala Ala Glu Glu Gln Lys Leu Pro Ile Asn Ala Leu Ser Asn
    2435                2440                2445

Ser Leu Leu Arg His His Asn Leu Val Tyr Ser Thr Thr Ser Arg
    2450                2455                2460

Ser Ala Cys Gln Arg Gln Lys Lys Val Thr Phe Asp Arg Leu Gln
    2465                2470                2475

Val Leu Asp Ser His Tyr Gln Asp Val Leu Lys Glu Val Lys Ala
    2480                2485                2490

Ala Ala Ser Lys Val Lys Ala Asn Leu Leu Ser Val Glu Glu Ala
```

```
                    2495                2500                2505

Cys Ser Leu Thr Pro Pro His Ser Ala Lys Ser Lys Phe Gly Tyr
        2510                2515                2520

Gly Ala Lys Asp Val Arg Cys His Ala Arg Lys Ala Val Ala His
    2525                2530                2535

Ile Asn Ser Val Trp Lys Asp Leu Leu Glu Asp Ser Val Thr Pro
    2540                2545                2550

Ile Asp Thr Thr Ile Met Ala Lys Asn Glu Val Phe Cys Val Gln
    2555                2560                2565

Pro Glu Lys Gly Gly Arg Lys Pro Ala Arg Leu Ile Val Phe Pro
    2570                2575                2580

Asp Leu Gly Val Arg Val Cys Glu Lys Met Ala Leu Tyr Asp Val
    2585                2590                2595

Val Ser Lys Leu Pro Leu Ala Val Met Gly Ser Ser Tyr Gly Phe
    2600                2605                2610

Gln Tyr Ser Pro Gly Gln Arg Val Glu Phe Leu Gln Ala Trp
    2615                2620                2625

Lys Ser Lys Lys Thr Pro Met Gly Phe Ser Tyr Asp Thr Arg Cys
    2630                2635                2640

Phe Asp Ser Thr Val Thr Glu Ser Asp Ile Arg Thr Glu Glu Ala
    2645                2650                2655

Ile Tyr Gln Cys Cys Asp Leu Asp Pro Gln Ala Arg Val Ala Ile
    2660                2665                2670

Lys Ser Leu Thr Glu Arg Leu Tyr Val Gly Gly Pro Leu Thr Asn
    2675                2680                2685

Ser Arg Gly Glu Asn Cys Gly Tyr Arg Arg Cys Arg Ala Ser Gly
    2690                2695                2700

Val Leu Thr Thr Ser Cys Gly Asn Thr Leu Thr Cys Tyr Ile Lys
    2705                2710                2715

Ala Arg Ala Ala Cys Arg Ala Ala Gly Leu Gln Asp Cys Thr Met
    2720                2725                2730

Leu Val Cys Gly Asp Asp Leu Val Val Ile Cys Glu Ser Ala Gly
    2735                2740                2745

Val Gln Glu Asp Ala Ala Ser Leu Arg Ala Phe Thr Glu Ala Met
    2750                2755                2760

Thr Arg Tyr Ser Ala Pro Pro Gly Asp Pro Pro Gln Pro Glu Tyr
    2765                2770                2775

Asp Leu Glu Leu Ile Thr Ser Cys Ser Ser Asn Val Ser Val Ala
    2780                2785                2790

His Asp Gly Ala Gly Lys Arg Val Tyr Tyr Leu Thr Arg Asp Pro
    2795                2800                2805

Thr Thr Pro Leu Ala Arg Ala Ala Trp Glu Thr Ala Arg His Thr
    2810                2815                2820

Pro Val Asn Ser Trp Leu Gly Asn Ile Ile Met Phe Ala Pro Thr
    2825                2830                2835

Leu Trp Ala Arg Met Ile Leu Met Thr His Phe Phe Ser Val Leu
    2840                2845                2850

Ile Ala Arg Asp Gln Leu Glu Gln Ala Leu Asn Cys Glu Ile Tyr
    2855                2860                2865

Gly Ala Cys Tyr Ser Ile Glu Pro Leu Asp Leu Pro Pro Ile Ile
    2870                2875                2880

Gln Arg Leu His Gly Leu Ser Ala Phe Ser Leu His Ser Tyr Ser
    2885                2890                2895
```

```
Pro Gly Glu Ile Asn Arg Val Ala Ala Cys Leu Arg Lys Leu Gly
    2900            2905                2910
Val Pro Pro Leu Arg Ala Trp Arg His Arg Ala Arg Ser Val Arg
    2915            2920                2925
Ala Arg Leu Leu Ser Arg Gly Gly Arg Ala Ala Ile Cys Gly Lys
    2930            2935                2940
Tyr Leu Phe Asn Trp Ala Val Arg Thr Lys Leu Lys Leu Thr Pro
    2945            2950                2955
Ile Ala Ala Ala Gly Arg Leu Asp Leu Ser Gly Trp Phe Thr Ala
    2960            2965                2970
Gly Tyr Ser Gly Gly Asp Ile Tyr His Ser Val Ser His Ala Arg
    2975            2980                2985
Pro Arg Trp Phe Trp Phe Cys Leu Leu Leu Leu Ala Ala Gly Val
    2990            2995                3000
Gly Ile Tyr Leu Leu Pro Asn Arg
    3005            3010

<210> SEQ ID NO 2
<211> LENGTH: 191
<212> TYPE: PRT
<213> ORGANISM: Hepatitis C virus

<400> SEQUENCE: 2

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
            180                 185                 190

<210> SEQ ID NO 3
<211> LENGTH: 3010
<212> TYPE: PRT
<213> ORGANISM: Hepatitis C virus

<400> SEQUENCE: 3

Met Ser Thr Asn Pro Lys Pro Gln Arg Lys Thr Lys Arg Asn Thr Asn
1               5                   10                  15
```

```
Arg Arg Pro Gln Asp Ile Lys Phe Pro Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
50                  55                  60

Ile Pro Lys Ala Arg Arg Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Lys Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Thr Pro Val Ser Ala Tyr
            180                 185                 190

Glu Val Arg Asn Ala Ser Gly Met Tyr His Val Thr Asn Asp Cys Ser
            195                 200                 205

Asn Ser Ser Ile Val Tyr Glu Ala Ala Asp Met Ile Met His Thr Pro
210                 215                 220

Gly Cys Val Pro Cys Val Arg Glu Asp Asn Ser Ser Arg Cys Trp Val
225                 230                 235                 240

Ala Leu Thr Pro Thr Leu Ala Ala Arg Asn Ala Ser Val Pro Thr Thr
                245                 250                 255

Thr Leu Arg Arg His Val Asp Leu Leu Val Gly Val Ala Ala Phe Cys
            260                 265                 270

Ser Ala Met Tyr Val Gly Asp Leu Cys Gly Ser Val Phe Leu Val Ser
            275                 280                 285

Gln Leu Phe Thr Phe Ser Pro Arg Arg His Glu Thr Val Gln Asp Cys
290                 295                 300

Asn Cys Ser Ile Tyr Pro Gly Arg Val Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Val Asp Met Val Thr Gly Ser His
            340                 345                 350

Trp Gly Ile Leu Ala Gly Leu Ala Tyr Tyr Ser Met Val Gly Asn Trp
            355                 360                 365

Ala Lys Val Leu Ile Ala Met Leu Leu Phe Ala Gly Val Asp Gly Thr
            370                 375                 380

Thr His Val Thr Gly Gly Ala Gln Gly Arg Ala Ala Ser Ser Leu Thr
385                 390                 395                 400

Ser Leu Phe Ser Pro Gly Pro Val Gln His Leu Gln Leu Ile Asn Thr
                405                 410                 415

Asn Gly Ser Trp His Ile Asn Arg Thr Ala Leu Ser Cys Asn Asp Ser
            420                 425                 430
```

```
Leu Asn Thr Gly Phe Val Ala Leu Phe Tyr Lys Tyr Arg Phe Asn
            435                 440                 445

Ala Ser Gly Cys Pro Glu Arg Leu Ala Thr Cys Arg Pro Ile Asp Thr
450                 455                 460

Phe Ala Gln Gly Trp Gly Pro Ile Thr Tyr Thr Glu Pro His Asp Leu
465                 470                 475                 480

Asp Gln Arg Pro Tyr Cys Trp His Tyr Ala Pro Gln Pro Cys Gly Ile
                485                 490                 495

Val Pro Thr Leu Gln Val Cys Gly Pro Val Tyr Cys Phe Thr Pro Ser
            500                 505                 510

Pro Val Ala Val Gly Thr Thr Asp Arg Phe Gly Ala Pro Thr Tyr Arg
            515                 520                 525

Trp Gly Ala Asn Glu Thr Asp Val Leu Leu Asn Asn Ala Gly Pro
530                 535                 540

Pro Gln Gly Asn Trp Phe Gly Cys Thr Trp Met Asn Gly Thr Gly Phe
545                 550                 555                 560

Thr Lys Thr Cys Gly Gly Pro Pro Cys Asn Ile Gly Gly Val Gly Asn
                565                 570                 575

Asn Thr Leu Thr Cys Pro Thr Asp Cys Phe Arg Lys His Pro Gly Ala
            580                 585                 590

Thr Tyr Thr Lys Cys Gly Ser Gly Pro Trp Leu Thr Pro Arg Cys Leu
            595                 600                 605

Val Asp Tyr Pro Tyr Arg Leu Trp His Tyr Pro Cys Thr Val Asn Phe
            610                 615                 620

Thr Ile Phe Lys Val Arg Met Tyr Val Gly Gly Ala Glu His Arg Leu
625                 630                 635                 640

Asp Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Glu Trp
                660                 665                 670

Gln Val Leu Pro Cys Ser Phe Thr Thr Leu Pro Ala Leu Ser Thr Gly
            675                 680                 685

Leu Ile His Leu His Gln Asn Ile Val Asp Ile Gln Tyr Leu Tyr Gly
            690                 695                 700

Ile Gly Ser Ala Val Val Ser Phe Ala Ile Lys Trp Glu Tyr Ile Val
705                 710                 715                 720

Leu Leu Phe Leu Leu Leu Ala Asp Ala Arg Val Cys Ala Cys Leu Trp
                725                 730                 735

Met Met Leu Leu Val Ala Gln Ala Glu Ala Ala Leu Glu Asn Leu Val
            740                 745                 750

Val Leu Asn Ala Ala Ser Val Ala Gly Ala His Gly Ile Leu Ser Phe
            755                 760                 765

Ile Val Phe Phe Cys Ala Ala Trp Tyr Ile Lys Gly Arg Leu Val Pro
            770                 775                 780

Gly Ala Ala Tyr Ala Leu Tyr Gly Val Trp Pro Leu Leu Leu Leu Leu
785                 790                 795                 800

Leu Ala Leu Pro Pro Arg Ala Tyr Ala Met Asp Arg Glu Met Ala Ala
                805                 810                 815

Ser Cys Gly Gly Ala Val Phe Val Gly Leu Val Leu Leu Thr Leu Ser
                820                 825                 830

Pro His Tyr Lys Val Phe Leu Ala Arg Phe Ile Trp Trp Leu Gln Tyr
            835                 840                 845

Leu Ile Thr Arg Thr Glu Ala His Leu Gln Val Trp Val Pro Pro Leu
```

-continued

```
            850                 855                 860
Asn Val Arg Gly Gly Arg Asp Ala Ile Ile Leu Leu Thr Cys Val Val
865                 870                 875                 880

His Pro Glu Leu Ile Phe Asp Ile Thr Lys Tyr Leu Leu Ala Ile Phe
                    885                 890                 895

Gly Pro Leu Met Val Leu Gln Ala Gly Ile Thr Arg Val Pro Tyr Phe
                900                 905                 910

Val Arg Ala Gln Gly Leu Ile Arg Ala Cys Met Leu Ala Arg Lys Val
            915                 920                 925

Val Gly Gly His Tyr Val Gln Met Val Phe Met Lys Leu Ala Ala Leu
        930                 935                 940

Ala Gly Thr Tyr Val Tyr Asp His Leu Thr Pro Leu Arg Asp Trp Ala
945                 950                 955                 960

His Thr Gly Leu Arg Asp Leu Ala Val Ala Val Glu Pro Val Val Phe
                    965                 970                 975

Ser Asp Met Glu Thr Lys Val Ile Thr Trp Gly Ala Asp Thr Ala Ala
                980                 985                 990

Cys Gly Asp Ile Ile Leu Ala Leu  Pro Ala Ser Ala Arg  Arg Gly Lys
            995                 1000                1005

Glu Ile  Leu Leu Gly Pro Ala  Asp Ser Leu Glu Gly  Gln Gly Trp
    1010                1015                1020

Arg Leu  Leu Ala Pro Ile Thr  Ala Tyr Ser Gln Gln  Thr Arg Gly
    1025                1030                1035

Leu Leu  Gly Cys Ile Ile Thr  Ser Leu Thr Gly Arg  Asp Lys Asn
    1040                1045                1050

Gln Val  Glu Gly Glu Val Gln  Val Val Ser Thr Ala  Thr Gln Ser
    1055                1060                1065

Phe Leu  Ala Thr Cys Ile Asn  Gly Val Cys Trp Thr  Val Phe His
    1070                1075                1080

Gly Ala  Gly Ser Lys Thr Leu  Ala Gly Pro Lys Gly  Pro Ile Thr
    1085                1090                1095

Gln Met  Tyr Thr Asn Val Asp  Gln Asp Leu Val Gly  Trp Pro Ala
    1100                1105                1110

Pro Pro  Gly Ala Arg Ser Leu  Thr Pro Cys Thr Cys  Gly Ser Ser
    1115                1120                1125

Asp Leu  Tyr Leu Val Thr Arg  His Ala Asp Val Ile  Pro Val Arg
    1130                1135                1140

Arg Arg  Gly Asp Gly Arg Gly  Ser Leu Leu Pro Arg  Pro Val
    1145                1150                1155

Ser Tyr  Leu Lys Gly Ser Ser  Gly Gly Pro Leu Leu  Cys Pro Ser
    1160                1165                1170

Gly His  Ala Val Gly Ile Leu  Pro Ala Ala Val Cys  Thr Arg Gly
    1175                1180                1185

Val Ala  Met Ala Val Glu Phe  Ile Pro Val Glu Ser  Met Glu Thr
    1190                1195                1200

Thr Met  Arg Ser Pro Val Phe  Thr Asp Asn Pro Ser  Pro Pro Ala
    1205                1210                1215

Val Pro  Gln Thr Phe Gln Val  Ala His Leu His Ala  Pro Thr Gly
    1220                1225                1230

Ser Gly  Lys Ser Thr Arg Val  Pro Ala Ala Tyr Ala  Ala Gln Gly
    1235                1240                1245

Tyr Lys  Val Leu Val Leu Asn  Pro Ser Val Ala Ala  Thr Leu Gly
    1250                1255                1260
```

-continued

```
Phe Gly Ala Tyr Met Ser Lys Ala His Gly Ile Asp Pro Asn Leu
    1265                1270                1275

Arg Thr Gly Val Arg Thr Ile Thr Thr Gly Ala Pro Ile Thr Tyr
    1280                1285                1290

Ser Thr Tyr Gly Lys Phe Leu Ala Asp Gly Gly Ser Gly Gly
    1295                1300                1305

Ala Tyr Asp Ile Ile Met Cys Asp Glu Cys His Ser Thr Asp Ser
    1310                1315                1320

Thr Thr Ile Tyr Gly Ile Gly Thr Val Leu Asp Gln Ala Glu Thr
    1325                1330                1335

Ala Gly Ala Arg Leu Val Val Leu Ser Thr Ala Thr Pro Pro Gly
    1340                1345                1350

Ser Val Thr Val Pro His Leu Asn Ile Glu Glu Val Ala Leu Ser
    1355                1360                1365

Asn Thr Gly Glu Ile Pro Phe Tyr Gly Lys Ala Ile Pro Ile Glu
    1370                1375                1380

Ala Ile Lys Gly Gly Arg His Leu Ile Phe Cys His Ser Lys Lys
    1385                1390                1395

Lys Cys Asp Glu Leu Ala Ala Lys Leu Ser Gly Leu Gly Leu Asn
    1400                1405                1410

Ala Val Ala Tyr Tyr Arg Gly Leu Asp Val Ser Val Ile Pro Thr
    1415                1420                1425

Ser Gly Asp Val Val Val Ala Thr Asp Ala Leu Met Thr Gly
    1430                1435                1440

Phe Thr Gly Asp Phe Asp Ser Val Ile Asp Cys Asn Thr Cys Val
    1445                1450                1455

Thr Gln Thr Val Asp Phe Ser Leu Asp Pro Thr Phe Thr Ile Glu
    1460                1465                1470

Thr Thr Thr Val Pro Gln Asp Ala Val Ser Arg Ser Gln Arg Arg
    1475                1480                1485

Gly Arg Thr Gly Arg Gly Arg Ala Gly Ile Tyr Arg Phe Val Thr
    1490                1495                1500

Pro Gly Glu Arg Pro Ser Gly Met Phe Asp Ser Ser Val Leu Cys
    1505                1510                1515

Glu Cys Tyr Asp Ala Gly Cys Ala Trp Tyr Glu Leu Thr Pro Ala
    1520                1525                1530

Glu Thr Ser Val Arg Leu Arg Ala Tyr Leu Asn Thr Pro Gly Leu
    1535                1540                1545

Pro Val Cys Gln Asp His Leu Glu Phe Ser Glu Gly Val Phe Thr
    1550                1555                1560

Gly Leu Thr His Ile Asp Ala His Phe Leu Ser Gln Thr Lys Gln
    1565                1570                1575

Ala Gly Glu Asn Phe Pro Tyr Leu Val Ala Tyr Gln Ala Thr Val
    1580                1585                1590

Cys Ala Arg Ala Gln Ala Pro Pro Pro Ser Trp Asp Glu Met Trp
    1595                1600                1605

Arg Cys Leu Ile Arg Leu Lys Pro Thr Leu His Gly Pro Thr Pro
    1610                1615                1620

Leu Leu Tyr Arg Leu Gly Ala Val Gln Asn Glu Val Thr Leu Thr
    1625                1630                1635

His Pro Ile Thr Lys Phe Ile Met Thr Cys Met Ser Ala Asp Leu
    1640                1645                1650
```

```
Glu Val Val Thr Ser Thr Trp Val Leu Val Gly Gly Val Leu Ala
    1655                1660                1665

Ala Leu Ala Ala Tyr Cys Leu Thr Thr Gly Ser Val Val Ile Val
    1670                1675                1680

Gly Arg Ile Ile Leu Ser Gly Lys Pro Ala Ile Ile Pro Asp Arg
    1685                1690                1695

Glu Val Leu Tyr Gln Glu Phe Asp Glu Met Glu Glu Cys Ala Ser
    1700                1705                1710

His Leu Pro Tyr Phe Glu Gln Gly Met Gln Leu Ala Glu Gln Phe
    1715                1720                1725

Lys Gln Lys Ala Leu Gly Leu Leu Gln Thr Ala Thr Lys Gln Ala
    1730                1735                1740

Glu Ala Ala Ala Pro Val Val Glu Ser Lys Trp Arg Ala Leu Glu
    1745                1750                1755

Thr Phe Trp Ala Lys His Met Trp Asn Phe Ile Ser Gly Ile Gln
    1760                1765                1770

Tyr Leu Ala Gly Leu Ser Thr Leu Pro Gly Asn Pro Ala Ile Arg
    1775                1780                1785

Ser Pro Met Ala Phe Thr Ala Ser Ile Thr Ser Pro Leu Thr Thr
    1790                1795                1800

Gln His Thr Leu Leu Phe Asn Ile Leu Gly Gly Trp Val Ala Ala
    1805                1810                1815

Gln Leu Ala Pro Pro Ser Ala Ala Ser Ala Phe Val Gly Ala Gly
    1820                1825                1830

Ile Ala Gly Ala Ala Val Gly Thr Ile Gly Leu Gly Lys Val Leu
    1835                1840                1845

Val Asp Ile Leu Ala Gly Tyr Gly Ala Gly Val Ala Gly Ala Leu
    1850                1855                1860

Val Ala Phe Lys Ile Met Ser Gly Glu Met Pro Ser Ala Glu Asp
    1865                1870                1875

Met Val Asn Leu Leu Pro Ala Ile Leu Ser Pro Gly Ala Leu Val
    1880                1885                1890

Val Gly Ile Val Cys Ala Ala Ile Leu Arg Arg His Val Gly Pro
    1895                1900                1905

Gly Glu Gly Ala Val Gln Trp Met Asn Arg Leu Ile Ala Phe Ala
    1910                1915                1920

Ser Arg Gly Asn His Val Ser Pro Arg His Tyr Val Pro Glu Ser
    1925                1930                1935

Glu Pro Ala Ala Arg Val Thr Gln Ile Leu Ser Ser Leu Thr Ile
    1940                1945                1950

Thr Gln Leu Leu Lys Arg Leu His Gln Trp Ile Asn Glu Asp Cys
    1955                1960                1965

Ser Thr Pro Cys Ser Ser Ser Trp Leu Arg Glu Ile Trp Asp Trp
    1970                1975                1980

Ile Cys Thr Val Leu Thr Asp Phe Lys Thr Trp Leu Gln Ser Lys
    1985                1990                1995

Leu Leu Pro Arg Leu Pro Gly Val Pro Phe Phe Ser Cys Gln Arg
    2000                2005                2010

Gly Tyr Lys Gly Val Trp Arg Gly Asp Gly Ile Met His Thr Thr
    2015                2020                2025

Cys Pro Cys Gly Ala Gln Ile Thr Gly His Val Lys Asn Gly Ser
    2030                2035                2040

Met Arg Ile Val Gly Pro Lys Thr Cys Ser Asn Thr Trp Tyr Gly
```

-continued

```
            2045                2050                2055
Thr Phe Pro Ile Asn Ala Tyr Thr Thr Gly Pro Cys Thr Pro Ser
        2060                2065                2070
Pro Ala Pro Asn Tyr Ser Lys Ala Leu Trp Arg Val Ala Ala Glu
        2075                2080                2085
Glu Tyr Val Glu Val Thr Arg Val Gly Asp Phe His Tyr Val Thr
        2090                2095                2100
Gly Met Thr Thr Asp Asn Val Lys Cys Pro Cys Gln Val Pro Ala
        2105                2110                2115
Pro Glu Phe Phe Thr Glu Val Asp Gly Val Arg Leu His Arg Tyr
        2120                2125                2130
Ala Pro Ala Cys Arg Pro Leu Leu Arg Glu Glu Val Val Phe Gln
        2135                2140                2145
Val Gly Leu His Gln Tyr Leu Val Gly Ser Gln Leu Pro Cys Glu
        2150                2155                2160
Pro Glu Pro Asp Val Ala Val Leu Thr Ser Met Leu Thr Asp Pro
        2165                2170                2175
Ser His Ile Thr Ala Glu Thr Ala Lys Arg Arg Leu Ala Arg Gly
        2180                2185                2190
Ser Pro Pro Ser Leu Ala Ser Ser Ser Ala Ser Gln Leu Ser Ala
        2195                2200                2205
Pro Ser Leu Lys Ala Thr Cys Thr Thr His His Asp Ser Pro Asp
        2210                2215                2220
Ala Asp Leu Ile Glu Ala Asn Leu Leu Trp Arg Gln Glu Met Gly
        2225                2230                2235
Gly Asn Ile Thr Arg Val Glu Ser Glu Asn Lys Val Val Ile Leu
        2240                2245                2250
Asp Ser Phe Asp Pro Leu Arg Ala Glu Asp Glu Gly Glu Ile
        2255                2260                2265
Ser Val Pro Ala Glu Ile Leu Arg Lys Ser Arg Lys Phe Pro Pro
        2270                2275                2280
Ala Leu Pro Ile Trp Ala Pro Pro Asp Tyr Asn Pro Pro Leu Leu
        2285                2290                2295
Glu Ser Trp Lys Asp Pro Asp Tyr Val Pro Pro Val Val His Gly
        2300                2305                2310
Cys Pro Leu Pro Pro Thr Lys Ala Pro Pro Ile Pro Pro Pro Arg
        2315                2320                2325
Arg Lys Arg Thr Val Val Leu Thr Glu Ser Thr Val Ser Ser Ala
        2330                2335                2340
Leu Ala Glu Leu Ala Thr Lys Thr Phe Gly Ser Ser Gly Ser Ser
        2345                2350                2355
Ala Ile Asp Ser Gly Thr Ala Thr Ala Pro Pro Asp Gln Ala Ser
        2360                2365                2370
Gly Asp Gly Asp Arg Glu Ser Asp Val Glu Ser Phe Ser Ser Met
        2375                2380                2385
Pro Pro Leu Glu Gly Glu Pro Gly Asp Pro Asp Leu Ser Asp Gly
        2390                2395                2400
Ser Trp Ser Thr Val Ser Glu Glu Ala Ser Glu Asp Val Val Cys
        2405                2410                2415
Cys Ser Met Ser Tyr Thr Trp Thr Gly Ala Leu Ile Thr Pro Cys
        2420                2425                2430
Ala Ala Glu Glu Ser Lys Leu Pro Ile Asn Pro Leu Ser Asn Ser
        2435                2440                2445
```

-continued

```
Leu Leu Arg His His Asn Met Val Tyr Ala Thr Thr Ser Arg Ser
    2450            2455                2460

Ala Gly Leu Arg Gln Lys Lys Val Thr Phe Asp Arg Leu Gln Val
    2465            2470                2475

Leu Asp Asp His Tyr Arg Asp Val Leu Lys Glu Met Lys Ala Lys
    2480            2485                2490

Ala Ser Thr Val Lys Ala Lys Leu Leu Ser Val Glu Glu Ala Cys
    2495            2500                2505

Lys Leu Thr Pro Pro His Ser Ala Lys Ser Lys Phe Gly Tyr Gly
    2510            2515                2520

Ala Lys Asp Val Arg Ser Leu Ser Ser Arg Ala Val Thr His Ile
    2525            2530                2535

Arg Ser Val Trp Lys Asp Leu Leu Glu Asp Thr Glu Thr Pro Ile
    2540            2545                2550

Ser Thr Thr Ile Met Ala Lys Asn Glu Val Phe Cys Val Gln Pro
    2555            2560                2565

Glu Lys Gly Gly Arg Lys Pro Ala Arg Leu Ile Val Phe Pro Asp
    2570            2575                2580

Leu Gly Val Arg Val Cys Glu Lys Met Ala Leu Tyr Asp Val Val
    2585            2590                2595

Ser Thr Leu Pro Gln Ala Val Met Gly Ser Ser Tyr Gly Phe Gln
    2600            2605                2610

Tyr Ser Pro Lys Gln Arg Val Glu Phe Leu Val Asn Thr Trp Lys
    2615            2620                2625

Ser Lys Lys Cys Pro Met Gly Phe Ser Tyr Asp Thr Arg Cys Phe
    2630            2635                2640

Asp Ser Thr Val Thr Glu Asn Asp Ile Arg Val Glu Glu Ser Ile
    2645            2650                2655

Tyr Gln Cys Cys Asp Leu Ala Pro Glu Ala Lys Leu Ala Ile Lys
    2660            2665                2670

Ser Leu Thr Glu Arg Leu Tyr Ile Gly Gly Pro Leu Thr Asn Ser
    2675            2680                2685

Lys Gly Gln Asn Cys Gly Tyr Arg Arg Cys Arg Ala Ser Gly Val
    2690            2695                2700

Leu Thr Thr Ser Cys Gly Asn Thr Leu Thr Cys Tyr Leu Lys Ala
    2705            2710                2715

Thr Ala Ala Cys Arg Ala Ala Lys Leu Arg Asp Cys Thr Met Leu
    2720            2725                2730

Val Asn Gly Asp Asp Leu Val Val Ile Cys Glu Ser Ala Gly Thr
    2735            2740                2745

Gln Glu Asp Ala Ala Ser Leu Arg Val Phe Thr Glu Ala Met Thr
    2750            2755                2760

Arg Tyr Ser Ala Pro Pro Gly Asp Pro Pro Gln Pro Glu Tyr Asp
    2765            2770                2775

Leu Glu Leu Ile Thr Ser Cys Ser Ser Asn Val Ser Val Ala His
    2780            2785                2790

Asp Ala Ser Gly Lys Arg Val Tyr Tyr Leu Thr Arg Asp Pro Thr
    2795            2800                2805

Thr Pro Leu Ala Arg Ala Ala Trp Glu Thr Ala Arg His Thr Pro
    2810            2815                2820

Val Asn Ser Trp Leu Gly Asn Ile Ile Met Tyr Ala Pro Thr Leu
    2825            2830                2835
```

```
Trp Ala Arg Met Ile Leu Met Thr His Phe Phe Ser Ile Leu Leu
    2840            2845            2850

Ala Gln Glu Gln Leu Glu Lys Thr Leu Asp Cys Gln Ile Tyr Gly
    2855            2860            2865

Ala Cys Tyr Ser Ile Glu Pro Leu Asp Leu Pro Gln Ile Ile Glu
    2870            2875            2880

Arg Leu His Gly Leu Ser Ala Phe Ser Leu His Ser Tyr Ser Pro
    2885            2890            2895

Gly Glu Ile Asn Arg Val Ala Ser Cys Leu Arg Lys Leu Gly Val
    2900            2905            2910

Pro Pro Leu Arg Ala Trp Arg His Arg Ala Arg Ser Val Arg Ala
    2915            2920            2925

Lys Leu Leu Ser Gln Gly Gly Arg Ala Ala Thr Cys Gly Lys Tyr
    2930            2935            2940

Leu Phe Asn Trp Ala Val Arg Thr Lys Leu Lys Leu Thr Pro Ile
    2945            2950            2955

Pro Ala Ala Ser Arg Leu Asp Leu Ser Gly Trp Phe Val Ala Gly
    2960            2965            2970

Tyr Ser Gly Gly Asp Ile Tyr His Ser Leu Ser Arg Ala Arg Pro
    2975            2980            2985

Arg Trp Phe Met Leu Cys Leu Leu Leu Ser Val Gly Val Gly
    2990            2995            3000

Ile Tyr Leu Leu Pro Asn Arg
    3005            3010

<210> SEQ ID NO 4
<211> LENGTH: 486
<212> TYPE: PRT
<213> ORGANISM: influenza A virus

<400> SEQUENCE: 4

Met Ala Ser Gln Gly Thr Lys Arg Ser Tyr Glu Gln Met Glu Thr Ser
1               5                   10                  15

Gly Glu Arg Gln Asn Ala Thr Glu Ile Arg Ala Ser Val Gly Arg Met
                20                  25                  30

Val Gly Gly Ile Gly Arg Phe Tyr Ile Gln Met Cys Thr Glu Leu Lys
            35                  40                  45

Leu Ser Asp His Glu Gly Arg Leu Ile Gln Asn Ser Ile Thr Ile Glu
        50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Arg Asp Gly Lys Trp Met Arg Glu Leu Ile Leu Tyr Asp
                100                 105                 110

Lys Glu Glu Ile Arg Arg Ile Trp Arg Gln Ala Asn Asn Gly Glu Asp
            115                 120                 125

Ala Thr Ala Gly Leu Thr His Met Met Ile Trp His Ser Asn Leu Asn
        130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
                180                 185                 190
```

```
Leu Ile Arg Met Ile Lys Arg Gly Ile Asn Asp Arg Asn Phe Trp Arg
            195                 200                 205

Gly Glu Asn Gly Arg Arg Thr Arg Ile Ala Tyr Glu Arg Met Cys Asn
        210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Ala Ser Gly
        275                 280                 285

Tyr Asp Phe Glu Arg Glu Gly Tyr Ser Leu Val Gly Ile Asp Pro Phe
        290                 295                 300

Arg Leu Leu Gln Asn Ser Gln Val Phe Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Thr Arg Val
            340                 345                 350

Val Pro Arg Gly Gln Leu Ser Thr Arg Gly Val Gln Ile Ala Ser Asn
        355                 360                 365

Glu Asn Met Glu Thr Met Asp Ser Ser Thr Leu Glu Leu Arg Ser Arg
        370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
            420                 425                 430

Thr Glu Gly Arg Thr Ser Asp Met Arg Thr Glu Ile Ile Arg Met Met
        435                 440                 445

Glu Asn Ala Arg Pro Glu Asp Val Ser Phe Gln Gly Arg Gly Val Phe
        450                 455                 460

Glu Leu Ser Asp Glu Lys Ala Thr Asn Pro Ile Val Pro Ser Phe Asp
465                 470                 475                 480

Met Ser Asn Glu Gly Ser
                485

<210> SEQ ID NO 5
<211> LENGTH: 97
<212> TYPE: PRT
<213> ORGANISM: influenza A virus

<400> SEQUENCE: 5

Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Val Ala Ala Ser Ile
            20                  25                  30

Ile Gly Ile Leu His Leu Ile Leu Trp Ile Leu Asp Arg Leu Phe Phe
        35                  40                  45

Lys Cys Val Tyr Arg Leu Phe Lys His Gly Leu Lys Arg Gly Pro Ser
    50                  55                  60

Thr Glu Gly Val Pro Glu Ser Met Arg Glu Glu Tyr Arg Lys Glu Gln
```

```
                    65                  70                  75                  80
Gln Asn Ala Val Asp Ala Asp Ser His Phe Val Ser Ile Glu Leu
                85                  90                  95

Glu

<210> SEQ ID NO 6
<211> LENGTH: 498
<212> TYPE: PRT
<213> ORGANISM: influenza A virus

<400> SEQUENCE: 6

Met Ala Ser Gln Gly Thr Lys Arg Ser Tyr Glu Gln Met Glu Thr Asp
1               5                   10                  15

Gly Asp Arg Gln Asn Ala Thr Glu Ile Arg Ala Ser Val Gly Lys Met
                20                  25                  30

Ile Asp Gly Ile Gly Arg Phe Tyr Ile Gln Met Cys Thr Glu Leu Lys
            35                  40                  45

Leu Ser Asp His Glu Gly Arg Leu Ile Gln Asn Ser Leu Thr Ile Glu
        50                  55                  60

Lys Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asp Gly Lys Trp Met Arg Glu Leu Val Leu Tyr Asp
                100                 105                 110

Lys Glu Glu Ile Arg Arg Ile Trp Arg Gln Ala Asn Asn Gly Glu Asp
            115                 120                 125

Ala Thr Ala Gly Leu Thr His Ile Met Ile Trp His Ser Asn Leu Asn
130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Ile Gly Thr Met Val Met Glu
                180                 185                 190

Leu Ile Arg Met Val Lys Arg Gly Ile Asn Asp Arg Asn Phe Trp Arg
            195                 200                 205

Gly Glu Asn Gly Arg Lys Thr Arg Ser Ala Tyr Glu Arg Met Cys Asn
        210                 215                 220

Ile Leu Lys Gly Lys Phe Gln Thr Ala Ala Gln Arg Ala Met Val Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
                260                 265                 270

Lys Ser Cys Leu Pro Ala Cys Ala Tyr Gly Pro Ala Val Ser Ser Gly
            275                 280                 285

Tyr Asp Phe Glu Lys Glu Gly Tyr Ser Leu Val Gly Ile Asp Pro Phe
        290                 295                 300

Lys Leu Leu Gln Asn Ser Gln Ile Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Leu Leu Ser Phe Ile Arg Gly Thr Lys Val
```

```
                340             345             350
Ser Pro Arg Gly Lys Leu Ser Thr Arg Gly Val Gln Ile Ala Ser Asn
            355                 360                 365

Glu Asn Met Asp Asn Met Gly Ser Ser Thr Leu Glu Leu Arg Ser Gly
        370                 375                 380

Tyr Trp Ala Ile Arg Thr Arg Ser Gly Gly Asn Thr Asn Gln Gln Arg
385                 390                 395                 400

Ala Ser Ala Gly Gln Thr Ser Val Gln Pro Thr Phe Ser Val Gln Arg
                405                 410                 415

Asn Leu Pro Phe Glu Lys Ser Thr Ile Met Ala Ala Phe Thr Gly Asn
            420                 425                 430

Thr Glu Gly Arg Thr Ser Asp Met Arg Ala Glu Ile Ile Arg Met Met
        435                 440                 445

Glu Gly Ala Lys Pro Glu Glu Val Ser Phe Arg Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 7
<211> LENGTH: 97
<212> TYPE: PRT
<213> ORGANISM: influenza A virus

<400> SEQUENCE: 7

Met Ser Leu Leu Thr Glu Val Glu Thr Pro Ile Arg Asn Glu Trp Gly
1               5                   10                  15

Cys Arg Cys Asn Gly Ser Ser Asp Pro Leu Ala Ile Ala Ala Asn Ile
            20                  25                  30

Ile Gly Ile Leu His Leu Ile Leu Trp Ile Leu Asp Arg Leu Phe Phe
        35                  40                  45

Lys Cys Ile Tyr Arg Arg Phe Lys Tyr Gly Leu Lys Gly Gly Pro Ser
    50                  55                  60

Thr Glu Gly Val Pro Lys Ser Met Arg Glu Glu Tyr Arg Lys Glu Gln
65                  70                  75                  80

Gln Ser Ala Val Asp Ala Asp Asp Gly His Phe Val Ser Ile Glu Leu
                85                  90                  95

Glu

<210> SEQ ID NO 8
<211> LENGTH: 498
<212> TYPE: PRT
<213> ORGANISM: influenza A virus

<400> SEQUENCE: 8

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60
```

```
Arg Met Val Leu Ser Ala Phe Asp Glu Arg Arg Asn Lys Tyr Leu Glu
 65                  70                  75                  80

Glu His Pro Ser Ala Gly Lys Asp Pro Lys Lys Thr Gly Gly Pro Ile
                 85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Gly Asp Asp
            115                 120                 125

Ala Thr Ala Gly Leu Thr His Met Met Ile Trp His Ser Asn Leu Asn
130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
                180                 185                 190

Leu Val Arg Met Ile Lys Arg Gly Ile Asn Asp Arg Asn Phe Trp Arg
            195                 200                 205

Gly Glu Asn Gly Arg Lys Thr Arg Ile Ala Tyr Glu Arg Met Cys Asn
210                 215                 220

Ile Leu Lys Gly Lys Phe Gln Thr Ala Ala Gln Lys Ala Met Met Asp
225                 230                 235                 240

Gln Val Arg Glu Ser Arg Asp Pro Gly Asn Ala Glu Phe Glu Asp Leu
                245                 250                 255

Thr Phe Leu Ala Arg Ser Ala Leu Ile Leu Arg Gly Ser Val Ala His
                260                 265                 270

Lys Ser Cys Leu Pro Ala Cys Val Tyr Gly Pro Ala Val Ala Ser Gly
            275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Ser Phe Ile Lys Gly Thr Lys Val
            340                 345                 350

Val Pro Arg Gly Lys Leu Ser Thr Arg Gly Val Gln Ile Ala Ser Asn
        355                 360                 365

Glu Asn Met Glu Thr Met Glu Ser Ser Thr Leu Glu Leu Arg Ser Arg
370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Val Met Ala Ala Phe Thr Gly Asn
            420                 425                 430

Thr Glu Gly Arg Thr Ser Asp Met Arg Thr Glu Ile Ile Arg Met Met
            435                 440                 445

Glu Ser Ala Arg Pro Glu Asp Val Ser Phe Gln Gly Arg Gly Val Phe
            450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
```

```
                       485              490              495

Asp Asn

<210> SEQ ID NO 9
<211> LENGTH: 97
<212> TYPE: PRT
<213> ORGANISM: influenza A virus

<400> SEQUENCE: 9

Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Val Ala Ala Ser Ile
            20                  25                  30

Ile Gly Ile Leu His Phe Ile Leu Trp Ile Leu Asp Arg Leu Phe Phe
        35                  40                  45

Lys Cys Ile Tyr Arg Phe Phe Lys His Gly Leu Lys Arg Gly Pro Ser
    50                  55                  60

Thr Glu Gly Val Pro Glu Ser Met Arg Glu Glu Tyr Arg Lys Glu Gln
65                  70                  75                  80

Gln Ser Ala Val Asp Ala Asp Asp Ser His Phe Val Ser Ile Glu Leu
                85                  90                  95

Glu

<210> SEQ ID NO 10
<211> LENGTH: 498
<212> TYPE: PRT
<213> ORGANISM: influenza A virus

<400> SEQUENCE: 10

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Asp Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Lys Arg Val Asp Gly Lys Trp Met Arg Glu Leu Val Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205
```

```
Gly Glu Asn Gly Arg Lys Thr Arg Ser Ala Tyr Glu Arg Met Cys Asn
            210                 215                 220
Ile Leu Lys Gly Lys Phe Gln Thr Ala Ala Gln Arg Ala Met Met Asp
225                 230                 235                 240
Gln Val Arg Glu Ser Arg Asn Pro Gly Asn Ala Glu Ile Glu Asp Leu
                245                 250                 255
Ile Phe Leu Ala Arg Ser Ala Leu Ile Leu Arg Gly Ser Val Ala His
            260                 265                 270
Lys Ser Cys Leu Pro Ala Cys Val Tyr Gly Pro Ala Ile Ala Ser Gly
        275                 280                 285
Tyr Asn Phe Glu Lys Glu Gly Tyr Ser Leu Val Gly Ile Asp Pro Phe
    290                 295                 300
Lys Leu Leu Gln Asn Ser Gln Val Tyr Ser Leu Ile Arg Pro Asn Glu
305                 310                 315                 320
Asn Pro Ala His Lys Ser Gln Leu Val Trp Met Ala Cys Asn Ser Ala
                325                 330                 335
Ala Phe Glu Asp Leu Arg Val Leu Ser Phe Ile Arg Gly Thr Lys Val
            340                 345                 350
Ser Pro Arg Gly Lys Leu Ser Thr Arg Gly Val Gln Ile Ala Ser Asn
        355                 360                 365
Glu Asn Met Asp Thr Met Glu Ser Ser Thr Leu Glu Leu Arg Ser Arg
    370                 375                 380
Tyr Trp Ala Ile Arg Thr Arg Ser Gly Gly Asn Thr Asn Gln Gln Arg
385                 390                 395                 400
Ala Ser Ala Gly Gln Ile Ser Val Gln Pro Ala Phe Ser Val Gln Arg
                405                 410                 415
Asn Leu Pro Phe Asp Lys Pro Thr Ile Met Ala Ala Phe Thr Gly Asn
            420                 425                 430
Thr Glu Gly Arg Thr Ser Asp Met Arg Ala Glu Ile Ile Arg Met Met
        435                 440                 445
Glu Gly Ala Lys Pro Glu Glu Met Ser Phe Gln Gly Arg Gly Val Phe
    450                 455                 460
Glu Leu Ser Asp Glu Lys Ala Thr Asn Pro Ile Val Pro Ser Phe Asp
465                 470                 475                 480
Met Ser Asn Glu Gly Ser Tyr Phe Phe Gly Asp Asn Ala Glu Glu Tyr
                485                 490                 495
Asp Asn

<210> SEQ ID NO 11
<211> LENGTH: 551
<212> TYPE: PRT
<213> ORGANISM: Human herpesvirus 5

<400> SEQUENCE: 11

Met Ala Ser Val Leu Gly Pro Ile Ser Gly His Val Leu Lys Ala Val
1               5                   10                  15
Phe Ser Arg Gly Asp Thr Pro Val Leu Pro His Glu Thr Arg Leu Leu
            20                  25                  30
Gln Thr Gly Ile His Val Arg Val Ser Gln Pro Ser Leu Ile Leu Val
        35                  40                  45
Ser Gln Tyr Thr Pro Asp Ser Thr Pro Cys His Arg Gly Asp Asn Gln
    50                  55                  60
Leu Gln Val Gln His Thr Tyr Phe Thr Gly Ser Glu Val Glu Asn Val
65                  70                  75                  80
```

-continued

```
Ser Val Asn Val His Asn Pro Thr Gly Arg Ser Ile Cys Pro Ser Gln
             85                  90                  95
Glu Pro Met Ser Ile Tyr Val Tyr Ala Leu Pro Leu Lys Met Leu Asn
            100                 105                 110
Ile Pro Ser Ile Asn Val His His Tyr Pro Ser Ala Ala Glu Arg Lys
            115                 120                 125
His Arg His Leu Pro Val Ala Asp Ala Val Ile His Ala Ser Gly Lys
            130                 135                 140
Gln Met Trp Gln Ala Arg Leu Thr Val Ser Gly Leu Ala Trp Thr Arg
145                 150                 155                 160
Gln Gln Asn Gln Trp Lys Glu Pro Asp Val Tyr Tyr Thr Ser Ala Phe
                165                 170                 175
Val Phe Pro Thr Lys Asp Val Ala Leu Arg His Val Val Cys Ala His
            180                 185                 190
Glu Leu Val Cys Ser Met Glu Asn Thr Arg Ala Thr Lys Met Gln Val
            195                 200                 205
Ile Gly Asp Gln Tyr Val Lys Val Tyr Leu Ser Phe Cys Glu Asp
            210                 215                 220
Val Pro Ser Gly Lys Leu Phe Met His Val Thr Leu Gly Ser Asp Val
225                 230                 235                 240
Glu Glu Asp Leu Thr Met Thr Arg Asn Pro Gln Pro Phe Met Arg Pro
            245                 250                 255
His Glu Arg Asn Gly Phe Thr Val Leu Cys Pro Lys Asn Met Ile Ile
            260                 265                 270
Lys Pro Gly Lys Ile Ser His Ile Met Leu Asp Val Ala Phe Thr Ser
            275                 280                 285
His Glu His Phe Gly Leu Leu Cys Pro Lys Ser Ile Pro Gly Leu Ser
            290                 295                 300
Ile Ser Gly Asn Leu Leu Met Asn Gly Gln Gln Ile Phe Leu Glu Val
305                 310                 315                 320
Gln Ala Ile Arg Glu Thr Val Glu Leu Arg Gln Tyr Asp Pro Val Ala
                325                 330                 335
Ala Leu Phe Phe Phe Asp Ile Asp Leu Leu Gln Arg Gly Pro Gln
            340                 345                 350
Tyr Ser Glu His Pro Thr Phe Thr Ser Gln Tyr Arg Ile Gln Gly Lys
            355                 360                 365
Leu Glu Tyr Arg His Thr Trp Asp Arg His Asp Glu Gly Ala Ala Gln
            370                 375                 380
Gly Asp Asp Asp Val Trp Thr Ser Gly Ser Asp Ser Asp Glu Glu Leu
385                 390                 395                 400
Val Thr Thr Glu Arg Lys Thr Pro Arg Val Thr Gly Gly Ala Met
                405                 410                 415
Ala Gly Ala Ser Thr Ser Ala Gly Arg Lys Arg Lys Ser Ala Ser Ser
            420                 425                 430
Ala Thr Ala Cys Thr Ala Gly Val Met Thr Arg Gly Arg Leu Lys Ala
            435                 440                 445
Glu Ser Thr Val Ala Pro Glu Glu Asp Thr Asp Glu Asp Ser Asp Asn
            450                 455                 460
Glu Ile His Asn Pro Ala Val Phe Thr Trp Pro Trp Gln Ala Gly
465                 470                 475                 480
Ile Leu Ala Arg Asn Leu Val Pro Met Val Ala Thr Val Gln Gly Gln
                485                 490                 495
Asn Leu Lys Tyr Gln Glu Phe Phe Trp Asp Ala Asn Asp Ile Tyr Arg
```

```
                500             505             510
Ile Phe Ala Glu Leu Glu Gly Val Trp Gln Pro Ala Ala Gln Pro Lys
            515                 520             525

Arg Arg Arg His Arg Gln Asp Ala Leu Pro Gly Pro Cys Ile Ala Ser
            530                 535             540

Thr Pro Lys Lys His Arg Gly
545                 550

<210> SEQ ID NO 12
<211> LENGTH: 158
<212> TYPE: PRT
<213> ORGANISM: Human papillomavirus type 16

<400> SEQUENCE: 12

Met His Gln Lys Arg Thr Ala Met Phe Gln Asp Pro Gln Glu Arg Pro
1               5                   10                  15

Gly Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Val Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
130                 135                 140

Ser Cys Cys Arg Ser Ser Arg Thr Arg Arg Glu Thr Gln Leu
145                 150                 155

<210> SEQ ID NO 13
<211> LENGTH: 97
<212> TYPE: PRT
<213> ORGANISM: Influenza A virus

<400> SEQUENCE: 13

Met Ser Leu Leu Thr Glu Val Glu Thr Pro Ile Arg Asn Glu Trp Gly
1               5                   10                  15

Cys Arg Cys Asn Gly Ser Ser Asp Pro Leu Ala Ile Ala Ala Asn Ile
            20                  25                  30

Ile Gly Ile Leu His Leu Ile Leu Trp Ile Leu Asp Arg Leu Phe Phe
        35                  40                  45

Lys Cys Ile Tyr Arg Arg Phe Lys Tyr Gly Leu Lys Gly Gly Pro Ser
50                  55                  60

Thr Glu Gly Val Pro Lys Ser Met Arg Glu Glu Tyr Arg Lys Glu Gln
65                  70                  75                  80

Gln Ser Ala Val Asp Ala Asp Asp Gly His Phe Val Ser Ile Glu Leu
                85                  90                  95

Glu

<210> SEQ ID NO 14
```

```
<211> LENGTH: 759
<212> TYPE: PRT
<213> ORGANISM: Influenza A virus

<400> SEQUENCE: 14

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Thr
    50                  55                  60

Glu Met Ile Pro Glu Arg Asn Glu Gln Gly Gln Thr Leu Trp Ser Lys
65                  70                  75                  80

Met Asn Asp Ala Gly Ser Asp Arg Val Met Val Ser Pro Leu Ala Val
                85                  90                  95

Thr Trp Trp Asn Arg Asn Gly Pro Met Thr Asn Thr Val His Tyr Pro
            100                 105                 110

Lys Ile Tyr Lys Thr Tyr Phe Glu Arg Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Lys Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Lys Gln Asn Pro Thr Glu
    290                 295                 300

Glu Gln Ala Val Gly Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Val Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
```

```
            385                 390                 395                 400
Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
                420                 425                 430

Gln Leu Leu Arg His Phe Gln Lys Asp Ala Lys Val Leu Phe Gln Asn
                435                 440                 445

Trp Gly Val Glu Pro Ile Asp Asn Val Met Gly Met Ile Gly Ile Leu
            450                 455                 460

Pro Asp Met Thr Pro Ser Ile Glu Met Ser Met Arg Gly Val Arg Ile
465                 470                 475                 480

Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Val Leu
                500                 505                 510

Leu Ser Pro Glu Glu Val Ser Glu Thr Gln Gly Thr Glu Lys Leu Thr
            515                 520                 525

Ile Thr Tyr Ser Ser Ser Met Met Trp Glu Ile Asn Gly Pro Glu Ser
            530                 535                 540

Val Leu Val Asn Thr Tyr Gln Trp Ile Ile Arg Asn Trp Glu Thr Val
545                 550                 555                 560

Lys Ile Gln Trp Ser Gln Asn Pro Thr Met Leu Tyr Asn Lys Met Glu
                565                 570                 575

Phe Glu Pro Phe Gln Ser Leu Val Pro Lys Ala Ile Arg Gly Gln Tyr
                580                 585                 590

Ser Gly Phe Val Arg Thr Leu Phe Gln Gln Met Arg Asp Val Leu Gly
            595                 600                 605

Thr Phe Asp Thr Ala Gln Ile Ile Lys Leu Leu Pro Phe Ala Ala Ala
            610                 615                 620

Pro Pro Lys Gln Ser Arg Met Gln Phe Ser Ser Phe Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
                660                 665                 670

Gly Thr Leu Thr Glu Asp Pro Asp Glu Gly Thr Ala Gly Val Glu Ser
            675                 680                 685

Ala Val Leu Arg Gly Phe Leu Ile Leu Gly Lys Glu Asp Arg Arg Tyr
            690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
                740                 745                 750

Arg Ile Arg Met Ala Ile Asn
        755

<210> SEQ ID NO 15
<211> LENGTH: 716
<212> TYPE: PRT
<213> ORGANISM: Influenza A virus

<400> SEQUENCE: 15
```

-continued

```
Met Glu Asp Phe Val Arg Gln Cys Phe Asn Pro Met Ile Val Glu Leu
1               5                   10                  15

Ala Glu Lys Thr Met Lys Glu Tyr Gly Glu Asp Leu Lys Ile Glu Thr
            20                  25                  30

Asn Lys Phe Ala Ala Ile Cys Thr His Leu Glu Val Cys Phe Met Tyr
            35                  40                  45

Ser Asp Phe His Phe Ile Asn Glu Gln Gly Glu Ser Ile Ile Val Glu
50                  55                  60

Leu Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
            85                  90                  95

Thr Thr Gly Ala Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
            115                 120                 125

Ile Tyr Tyr Leu Glu Lys Ala Asn Lys Ile Lys Ser Glu Lys Thr His
130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
            165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
            195                 200                 205

Gly Thr Met Arg Lys Leu Ala Asp Gln Ser Leu Pro Pro Asn Phe Ser
210                 215                 220

Ser Leu Glu Asn Phe Arg Ala Tyr Val Asp Gly Phe Glu Pro Asn Gly
225                 230                 235                 240

Tyr Ile Glu Gly Lys Leu Ser Gln Met Ser Lys Glu Val Asn Ala Arg
            245                 250                 255

Ile Glu Pro Phe Leu Lys Thr Thr Pro Arg Pro Leu Arg Leu Pro Asn
            260                 265                 270

Gly Pro Pro Cys Ser Gln Arg Ser Lys Phe Leu Leu Met Asp Ala Leu
            275                 280                 285

Lys Leu Ser Ile Glu Asp Pro Ser His Glu Gly Gly Ile Pro Leu
290                 295                 300

Tyr Asp Ala Ile Lys Cys Met Arg Thr Phe Phe Gly Trp Lys Glu Pro
305                 310                 315                 320

Asn Val Val Lys Pro His Glu Lys Gly Ile Asn Pro Asn Tyr Leu Leu
            325                 330                 335

Ser Trp Lys Gln Val Leu Ala Glu Leu Gln Asp Ile Glu Asn Glu Glu
            340                 345                 350

Lys Ile Pro Lys Thr Lys Asn Met Lys Lys Thr Ser Gln Leu Lys Trp
            355                 360                 365

Ala Leu Gly Glu Asn Met Ala Pro Glu Lys Val Asp Phe Asp Asp Cys
370                 375                 380

Lys Asp Val Gly Asp Leu Lys Gln Tyr Asp Ser Asp Glu Pro Glu Leu
385                 390                 395                 400

Arg Ser Leu Ala Ser Trp Ile Gln Asn Glu Phe Asn Lys Ala Cys Glu
            405                 410                 415

Leu Thr Asp Ser Ser Trp Ile Glu Leu Asp Glu Ile Gly Glu Asp Val
```

```
                420              425                430
Ala Pro Ile Glu His Ile Ala Ser Met Arg Arg Asn Tyr Phe Thr Ser
            435                 440                 445

Glu Val Ser His Cys Arg Ala Thr Glu Tyr Ile Met Lys Gly Val Tyr
        450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
530                 535                 540

Ile Gly Asp Met Leu Leu Arg Ser Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Lys Gly Val Glu Glu Ser Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
        690                 695                 700

Ser Trp Phe Asn Ser Phe Leu Thr His Ala Leu Ser
705                 710                 715

<210> SEQ ID NO 16
<211> LENGTH: 230
<212> TYPE: PRT
<213> ORGANISM: Influenza A virus

<400> SEQUENCE: 16

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80
```

```
Met Ala Ser Val Pro Ala Ser Arg Tyr Leu Thr Asp Met Thr Leu Glu
                 85                  90                  95

Glu Met Ser Arg Glu Trp Ser Met Leu Ile Pro Lys Gln Lys Val Ala
            100                 105                 110

Gly Pro Leu Cys Ile Arg Met Asp Gln Ala Ile Met Asp Lys Asn Ile
            115                 120                 125

Ile Leu Lys Ala Asn Phe Ser Val Ile Phe Asp Arg Leu Glu Thr Leu
        130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Ala Glu Asp Val Lys Asn
                165                 170                 175

Ala Val Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
            195                 200                 205

Asn Gly Arg Pro Pro Leu Thr Pro Lys Gln Lys Arg Glu Met Ala Gly
            210                 215                 220

Thr Ile Arg Ser Glu Val
225                 230

<210> SEQ ID NO 17
<211> LENGTH: 121
<212> TYPE: PRT
<213> ORGANISM: Influenza A virus

<400> SEQUENCE: 17

Met Asp Pro Asn Thr Val Ser Ser Phe Gln Asp Ile Leu Leu Arg Met
1               5                   10                  15

Ser Lys Met Gln Leu Glu Ser Ser Glu Asp Leu Asn Gly Met Ile
            20                  25                  30

Thr Gln Phe Glu Ser Leu Lys Leu Tyr Arg Asp Ser Leu Gly Glu Ala
        35                  40                  45

Val Met Arg Met Gly Asp Leu His Ser Leu Gln Asn Arg Asn Glu Lys
    50                  55                  60

Trp Arg Glu Gln Leu Gly Gln Lys Phe Glu Glu Ile Arg Trp Leu Ile
65                  70                  75                  80

Glu Glu Val Arg His Lys Leu Lys Val Thr Glu Asn Ser Phe Glu Gln
                85                  90                  95

Ile Thr Phe Met Gln Ala Leu His Leu Leu Leu Glu Val Glu Gln Glu
            100                 105                 110

Ile Arg Thr Phe Ser Phe Gln Leu Ile
        115                 120

<210> SEQ ID NO 18
<211> LENGTH: 454
<212> TYPE: PRT
<213> ORGANISM: Influenza A virus

<400> SEQUENCE: 18

Met Asn Pro Asn Gln Lys Ile Ile Thr Ile Gly Ser Ile Cys Leu Val
1               5                   10                  15

Val Gly Leu Ile Ser Leu Ile Leu Gln Ile Gly Asn Ile Ile Ser Ile
            20                  25                  30

Trp Ile Ser His Ser Ile Gln Thr Gly Ser Gln Asn His Thr Gly Ile
        35                  40                  45
```

```
Cys Asn Gln Asn Ile Ile Thr Tyr Lys Asn Ser Thr Trp Val Lys Asp
     50                  55                  60

Thr Thr Ser Val Ile Leu Thr Gly Asn Ser Ser Leu Cys Pro Ile Arg
 65                  70                  75                  80

Gly Trp Ala Ile Tyr Ser Lys Asp Asn Ser Ile Arg Ile Gly Ser Lys
                 85                  90                  95

Gly Asp Val Phe Val Ile Arg Glu Pro Phe Ile Ser Cys Ser His Leu
                100                 105                 110

Glu Cys Arg Thr Phe Phe Leu Thr Gln Gly Ala Leu Leu Asn Asp Arg
            115                 120                 125

His Ser Asn Gly Thr Val Lys Asp Arg Ser Pro Tyr Arg Ala Leu Met
130                 135                 140

Ser Cys Pro Val Gly Glu Ala Pro Ser Pro Tyr Asn Ser Arg Phe Glu
145                 150                 155                 160

Ser Val Ala Trp Ser Ala Ser Ala Cys His Asp Gly Met Gly Trp Leu
                165                 170                 175

Thr Ile Gly Ile Ser Gly Pro Asp Asn Gly Ala Val Ala Val Leu Lys
                180                 185                 190

Tyr Asn Gly Ile Ile Thr Glu Thr Ile Lys Ser Trp Arg Lys Lys Ile
        195                 200                 205

Leu Arg Thr Gln Glu Ser Glu Cys Ala Cys Val Asn Gly Ser Cys Phe
210                 215                 220

Thr Ile Met Thr Asp Gly Pro Ser Asp Gly Leu Ala Ser Tyr Lys Ile
225                 230                 235                 240

Phe Lys Ile Glu Lys Gly Lys Val Thr Lys Ser Ile Glu Leu Asn Ala
                245                 250                 255

Pro Asn Ser His Tyr Glu Glu Cys Ser Cys Tyr Pro Asp Thr Gly Lys
                260                 265                 270

Val Met Cys Val Cys Arg Asp Asn Trp His Gly Ser Asn Arg Pro Trp
            275                 280                 285

Val Ser Phe Asp Gln Asn Leu Asp Tyr Gln Ile Gly Tyr Ile Cys Ser
290                 295                 300

Gly Val Phe Gly Asp Asn Pro Arg Pro Lys Asp Gly Thr Gly Ser Cys
305                 310                 315                 320

Gly Pro Val Tyr Val Asp Gly Ala Asn Gly Val Lys Gly Phe Ser Tyr
                325                 330                 335

Arg Tyr Gly Asn Gly Val Trp Ile Gly Arg Thr Lys Ser His Ser Ser
                340                 345                 350

Arg His Gly Phe Glu Met Ile Trp Asp Pro Asn Gly Trp Thr Glu Thr
            355                 360                 365

Asp Ser Lys Phe Ser Val Arg Gln Asp Val Val Ala Met Thr Asp Trp
370                 375                 380

Ser Gly Tyr Ser Gly Ser Phe Val Gln His Pro Glu Leu Thr Gly Leu
385                 390                 395                 400

Asp Cys Ile Arg Pro Cys Phe Trp Val Glu Leu Ile Arg Gly Arg Pro
                405                 410                 415

Lys Glu Lys Thr Ile Trp Thr Ser Ala Ser Ser Ile Ser Phe Cys Gly
                420                 425                 430

Val Asn Ser Asp Thr Val Asp Trp Ser Trp Pro Asp Gly Ala Glu Leu
            435                 440                 445

Pro Phe Thr Ile Asp Lys
450
```

```
<210> SEQ ID NO 19
<211> LENGTH: 566
<212> TYPE: PRT
<213> ORGANISM: Influenza A virus

<400> SEQUENCE: 19

Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Thr Lys Gly Val Thr Ala Ala Cys Ser His Ala Gly Lys Ser Ser
145                 150                 155                 160

Phe Tyr Arg Asn Leu Leu Trp Leu Thr Glu Lys Glu Gly Ser Tyr Pro
                165                 170                 175

Lys Leu Lys Asn Ser Tyr Val Asn Lys Lys Gly Lys Glu Val Leu Val
            180                 185                 190

Leu Trp Gly Ile His His Pro Ser Asn Ser Lys Asp Gln Gln Asn Ile
        195                 200                 205

Tyr Gln Asn Glu Asn Ala Tyr Val Ser Val Val Thr Ser Asn Tyr Asn
    210                 215                 220

Arg Arg Phe Thr Pro Glu Ile Ala Glu Arg Pro Lys Val Arg Asp Gln
225                 230                 235                 240

Ala Gly Arg Met Asn Tyr Tyr Trp Thr Leu Leu Lys Pro Gly Asp Thr
                245                 250                 255

Ile Ile Phe Glu Ala Asn Gly Asn Leu Ile Ala Pro Arg Tyr Ala Phe
            260                 265                 270

Ala Leu Ser Arg Gly Phe Gly Ser Gly Ile Ile Thr Ser Asn Ala Ser
        275                 280                 285

Met His Glu Cys Asn Thr Lys Cys Gln Thr Pro Leu Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Arg Ser Ala Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380
```

```
Thr Gln Asn Ala Ile Asn Gly Ile Thr Asn Lys Val Asn Ser Val Ile
385                 390                 395                 400

Glu Lys Met Asn Ile Gln Phe Thr Ala Val Gly Lys Glu Phe Asn Lys
            405                 410                 415

Leu Glu Lys Arg Met Glu Asn Leu Asn Lys Lys Val Asp Asp Gly Phe
        420                 425                 430

Leu Asp Ile Trp Thr Tyr Asn Ala Glu Leu Leu Val Leu Leu Glu Asn
                435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asp Asn Glu Cys Met Glu Ser Val
            485                 490                 495

Arg Asn Gly Thr Tyr Asp Tyr Pro Lys Tyr Ser Glu Glu Ser Lys Leu
        500                 505                 510

Asn Arg Glu Lys Val Asp Gly Val Lys Leu Glu Ser Met Gly Ile Tyr
    515                 520                 525

Gln Ile Leu Ala Ile Tyr Ser Thr Val Ala Ser Ser Leu Val Leu Leu
530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 20
<211> LENGTH: 252
<212> TYPE: PRT
<213> ORGANISM: Influenza A virus

<400> SEQUENCE: 20

Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Val Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
            85                  90                  95

Val Lys Leu Tyr Arg Lys Leu Lys Arg Glu Ile Thr Phe His Gly Ala
        100                 105                 110

Lys Glu Ile Ser Leu Ser Tyr Ser Ala Gly Ala Leu Ala Ser Cys Met
    115                 120                 125

Gly Leu Ile Tyr Asn Arg Met Gly Ala Val Thr Thr Glu Val Ala Phe
130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
            165                 170                 175

Asn Arg Met Val Leu Ala Ser Thr Thr Ala Lys Ala Met Glu Gln Met
        180                 185                 190
```

```
Ala Gly Ser Ser Glu Gln Ala Ala Glu Ala Met Glu Val Ala Ser Gln
        195                 200                 205

Ala Arg Gln Met Val Gln Ala Met Arg Thr Ile Gly Thr His Pro Ser
        210                 215                 220

Ser Ser Ala Gly Leu Lys Asn Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 21
<211> LENGTH: 87
<212> TYPE: PRT
<213> ORGANISM: Influenza A virus

<400> SEQUENCE: 21

Met Gly Gln Glu Gln Asp Thr Pro Trp Ile Leu Ser Thr Gly His Ile
1               5                   10                  15

Ser Thr Gln Lys Arg Gln Asp Gly Gln Gln Thr Pro Lys Leu Glu His
            20                  25                  30

Arg Asn Ser Thr Arg Leu Met Gly His Cys Gln Lys Thr Met Asn Gln
        35                  40                  45

Val Val Met Pro Lys Gln Ile Val Tyr Trp Lys Gln Trp Leu Ser Leu
    50                  55                  60

Arg Asn Pro Ile Leu Val Phe Leu Lys Thr Arg Val Leu Lys Arg Trp
65                  70                  75                  80

Arg Leu Phe Ser Lys His Glu
                85

<210> SEQ ID NO 22
<211> LENGTH: 757
<212> TYPE: PRT
<213> ORGANISM: Influenza A virus

<400> SEQUENCE: 22

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Ala Arg Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Ile Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Lys Lys
                165                 170                 175
```

```
Glu Glu Met Gly Ile Thr Thr His Phe Gln Arg Lys Arg Val Arg
            180                 185                 190

Asp Asn Met Thr Lys Lys Met Ile Thr Gln Arg Thr Ile Gly Lys Arg
        195                 200                 205

Lys Gln Arg Leu Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Leu Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Met Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
    370                 375                 380

Thr Arg Lys Lys Ile Glu Lys Ile Arg Pro Leu Leu Ile Glu Gly Thr
385                 390                 395                 400

Ala Ser Leu Ser Pro Gly Met Met Gly Met Phe Asn Met Leu Ser
                405                 410                 415

Thr Val Leu Gly Val Ser Ile Leu Asn Leu Gly Gln Lys Arg Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu His Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ser Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Ile
                565                 570                 575

Lys Lys Leu Trp Glu Gln Thr Arg Ser Lys Ala Gly Leu Leu Val Ser
            580                 585                 590
```

```
Asp Gly Gly Pro Asn Leu Tyr Asn Ile Arg Asn Leu His Ile Pro Glu
            595                 600                 605

Val Cys Leu Lys Trp Glu Leu Met Asp Glu Asp Tyr Gln Gly Arg Leu
610                 615                 620

Cys Asn Pro Leu Asn Pro Phe Val Ser His Lys Glu Ile Glu Ser Met
625                 630                 635                 640

Asn Asn Ala Val Met Met Pro Ala His Gly Pro Ala Lys Asn Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Val Leu Glu Asp Glu Gln Met
        675                 680                 685

Tyr Gln Arg Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Thr Glu Ile Met Lys Ile Cys Ser Thr Ile Glu Glu
            740                 745                 750

Leu Arg Arg Gln Lys
        755

<210> SEQ ID NO 23
<211> LENGTH: 498
<212> TYPE: PRT
<213> ORGANISM: Influenza A virus

<400> SEQUENCE: 23

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205
```

```
Gly Glu Asn Gly Arg Lys Thr Arg Ile Ala Tyr Glu Arg Met Cys Asn
        210                 215                 220

Ile Leu Lys Gly Lys Phe Gln Thr Ala Ala Gln Lys Ala Met Met Asp
225                 230                 235                 240

Gln Val Arg Glu Ser Arg Asp Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
        290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Ser Phe Ile Lys Gly Thr Lys Val
            340                 345                 350

Val Pro Arg Gly Lys Leu Ser Thr Arg Gly Val Gln Ile Ala Ser Asn
        355                 360                 365

Glu Asn Met Glu Thr Met Glu Ser Ser Thr Leu Glu Leu Arg Ser Arg
370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Val Met Ala Ala Phe Thr Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 24
<211> LENGTH: 759
<212> TYPE: PRT
<213> ORGANISM: Influenza A virus

<400> SEQUENCE: 24

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
                20                  25                  30

Lys Tyr Thr Ser Gly Arg Gln Glu Lys Asn Pro Ser Leu Arg Met Lys
            35                  40                  45

Trp Met Met Ala Met Lys Tyr Pro Ile Thr Ala Asp Lys Arg Ile Thr
        50                  55                  60

Glu Met Val Pro Glu Arg Asn Glu Gln Gly Gln Thr Leu Trp Ser Lys
65                  70                  75                  80
```

```
Met Ser Asp Ala Gly Ser Asp Arg Val Met Val Ser Pro Leu Ala Val
             85                  90                  95

Thr Trp Trp Asn Arg Asn Gly Pro Met Thr Ser Thr Val His Tyr Pro
            100                 105                 110

Lys Ile Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
                180                 185                 190

Leu Gln Asp Cys Lys Ile Ser Pro Leu Met Val Ala Tyr Met Leu Glu
                195                 200                 205

Arg Glu Leu Val Arg Lys Thr Arg Phe Leu Pro Val Ala Gly Gly Thr
210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Val Arg Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
            275                 280                 285

Ile Gly Gly Thr Arg Met Val Asp Ile Leu Arg Gln Asn Pro Thr Glu
            290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Ile Lys Arg Glu Glu Val Leu Thr Gly Asn Leu Gln Thr Leu
            340                 345                 350

Lys Ile Arg Val His Glu Gly Tyr Glu Glu Phe Thr Met Val Gly Lys
            355                 360                 365

Arg Ala Thr Ala Ile Leu Arg Lys Ala Thr Arg Arg Leu Val Gln Leu
            370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
                420                 425                 430

Gln Leu Leu Arg His Phe Gln Lys Asp Ala Lys Val Leu Phe Gln Asn
            435                 440                 445

Trp Gly Ile Glu His Ile Asp Asn Val Met Gly Met Ile Gly Val Leu
    450                 455                 460

Pro Asp Met Thr Pro Ser Thr Glu Met Ser Met Arg Gly Ile Arg Val
465                 470                 475                 480

Ser Lys Met Gly Val Asp Glu Tyr Ser Ser Thr Glu Arg Val Val Val
            485                 490                 495
```

```
Ser Ile Asp Arg Phe Leu Arg Val Arg Asp Gln Arg Gly Asn Val Leu
                500                 505                 510

Leu Ser Pro Glu Glu Val Ser Glu Thr Gln Gly Thr Glu Lys Leu Thr
            515                 520                 525

Ile Thr Tyr Ser Ser Ser Met Met Trp Glu Ile Asn Gly Pro Glu Ser
        530                 535                 540

Val Leu Val Asn Thr Tyr Gln Trp Ile Ile Arg Asn Trp Glu Thr Val
545                 550                 555                 560

Lys Ile Gln Trp Ser Gln Asn Pro Thr Met Leu Tyr Asn Lys Met Glu
                565                 570                 575

Phe Glu Pro Phe Gln Ser Leu Val Pro Lys Ala Ile Arg Gly Gln Tyr
            580                 585                 590

Ser Gly Phe Val Arg Thr Leu Phe Gln Gln Met Arg Asp Val Leu Gly
        595                 600                 605

Thr Phe Asp Thr Thr Gln Ile Ile Lys Leu Leu Pro Phe Ala Ala Ala
        610                 615                 620

Pro Pro Lys Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Thr Thr Lys Arg Leu Thr Ile Leu Gly Lys Asp Ala
                660                 665                 670

Gly Thr Leu Thr Glu Asp Pro Asp Glu Gly Thr Ser Gly Val Glu Ser
            675                 680                 685

Ala Val Leu Arg Gly Phe Leu Ile Leu Gly Lys Glu Asp Arg Arg Tyr
        690                 695                 700

Gly Pro Ala Leu Ser Ile Asn Glu Leu Ser Thr Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
                740                 745                 750

Arg Ile Arg Met Ala Ile Asn
            755

<210> SEQ ID NO 25
<211> LENGTH: 562
<212> TYPE: PRT
<213> ORGANISM: Influenza A virus

<400> SEQUENCE: 25

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
                20                  25                  30

Thr Ile Leu Glu Arg Asn Val Thr Val Thr His Ala Lys Asp Ile Leu
            35                  40                  45

Glu Lys Thr His Asn Gly Lys Leu Cys Lys Leu Asn Gly Ile Pro Pro
        50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Tyr Ser Leu Cys Tyr Pro Gly Ser Phe Asn Asp
                100                 105                 110
```

```
Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
130                 135                 140

Gly Ser Trp Ala Cys Ala Val Ser Gly Lys Pro Ser Phe Phe Arg Asn
145                 150                 155                 160

Met Val Trp Leu Thr Arg Lys Gly Ser Asn Tyr Pro Val Ala Lys Gly
                165                 170                 175

Ser Tyr Asn Asn Thr Ser Gly Glu Gln Met Leu Ile Ile Trp Gly Val
                180                 185                 190

His His Pro Asn Asp Glu Ala Glu Gln Arg Ala Leu Tyr Gln Asn Val
                195                 200                 205

Gly Thr Tyr Val Ser Val Ala Thr Ser Thr Leu Tyr Lys Arg Ser Ile
        210                 215                 220

Pro Glu Ile Ala Ala Arg Pro Lys Val Asn Gly Leu Gly Arg Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Val Ala Pro Glu Tyr Gly Phe Lys Ile Ser Lys
                260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
        290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
                340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
        370                 375                 380

Phe Asn Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Lys Arg
                405                 410                 415

Leu Glu Asn Leu Asn Lys Lys Met Glu Asp Gly Phe Leu Asp Val Trp
                420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
450                 455                 460

Gln Leu Arg Asp Asn Val Lys Glu Leu Gly Asn Gly Cys Phe Glu Phe
465                 470                 475                 480

Tyr His Lys Cys Asp Asn Glu Cys Met Asp Ser Val Lys Asn Gly Thr
                485                 490                 495

Tyr Asp Tyr Pro Lys Tyr Glu Glu Ser Lys Leu Asn Arg Asn Glu
        500                 505                 510

Ile Lys Gly Val Lys Leu Ser Ser Met Gly Val Tyr Gln Ile Leu Ala
        515                 520                 525
```

Ile Tyr Ala Thr Val Ala Gly Ser Leu Ser Leu Ala Ile Met Met Ala
        530                 535                 540

Gly Ile Ser Phe Trp Met Cys Ser Asn Gly Ser Leu Gln Cys Arg Ile
545                 550                 555                 560

Cys Ile

<210> SEQ ID NO 26
<211> LENGTH: 252
<212> TYPE: PRT
<213> ORGANISM: Influenza A virus

<400> SEQUENCE: 26

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Arg Lys Leu Lys Arg Glu Ile Thr Phe His Gly Ala
            100                 105                 110

Lys Glu Val Ala Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Ala Val Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Ala Ile Gly Thr Pro Pro Ser
    210                 215                 220

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 27
<211> LENGTH: 97
<212> TYPE: PRT
<213> ORGANISM: Influenza A virus

<400> SEQUENCE: 27

Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Val Ala Ala Ser Ile
            20                  25                  30

Ile Gly Ile Leu His Phe Ile Leu Trp Ile Leu Asp Arg Leu Phe Phe

```
            35                  40                  45
Lys Cys Ile Tyr Arg Phe Phe Lys His Gly Leu Lys Arg Gly Pro Ser
     50                  55                  60
Thr Glu Gly Val Pro Glu Ser Met Arg Glu Glu Tyr Arg Lys Glu Gln
 65                  70                  75                  80
Gln Ser Ala Val Asp Ala Asp Ser His Phe Val Ser Ile Glu Leu
                 85                  90                  95
Glu

<210> SEQ ID NO 28
<211> LENGTH: 716
<212> TYPE: PRT
<213> ORGANISM: Influenza A virus

<400> SEQUENCE: 28

Met Glu Asp Phe Val Arg Gln Cys Phe Asn Pro Met Ile Val Glu Leu
 1               5                  10                  15
Ala Glu Lys Ala Met Lys Glu Tyr Gly Glu Asp Leu Lys Ile Glu Thr
                 20                  25                  30
Asn Lys Phe Ala Ala Ile Cys Thr His Leu Glu Val Cys Phe Met Tyr
             35                  40                  45
Ser Asp Phe His Phe Ile Asn Glu Gln Gly Glu Ser Ile Met Val Glu
     50                  55                  60
Leu Asp Asp Pro Asn Ala Leu Leu Lys His Arg Phe Glu Ile Ile Glu
 65                  70                  75                  80
Gly Arg Asp Arg Thr Met Ala Trp Thr Val Val Asn Ser Ile Cys Asn
                 85                  90                  95
Thr Thr Gly Ala Glu Lys Pro Lys Phe Leu Pro Asp Leu Tyr Asp Tyr
            100                 105                 110
Lys Glu Asn Arg Phe Ile Glu Ile Gly Val Thr Arg Arg Glu Val His
            115                 120                 125
Ile Tyr Tyr Leu Glu Lys Ala Asn Lys Ile Lys Ser Glu Asn Thr His
        130                 135                 140
Ile His Ile Phe Ser Phe Thr Gly Glu Glu Met Ala Thr Lys Ala Asp
145                 150                 155                 160
Tyr Thr Leu Asp Glu Glu Ser Arg Ala Arg Ile Lys Thr Arg Leu Phe
                165                 170                 175
Thr Ile Arg Gln Glu Met Ala Asn Arg Gly Leu Trp Asp Ser Phe Arg
            180                 185                 190
Gln Ser Glu Arg Gly Glu Glu Thr Ile Glu Glu Arg Phe Glu Ile Thr
            195                 200                 205
Gly Thr Met Arg Arg Leu Ala Asp Gln Ser Leu Pro Pro Asn Phe Ser
        210                 215                 220
Cys Leu Glu Asn Phe Arg Ala Tyr Val Asp Gly Phe Glu Pro Asn Gly
225                 230                 235                 240
Tyr Ile Glu Gly Lys Leu Ser Gln Met Ser Lys Glu Val Asn Ala Lys
                245                 250                 255
Ile Glu Pro Phe Leu Lys Thr Thr Pro Arg Pro Ile Arg Leu Pro Asp
            260                 265                 270
Gly Pro Pro Cys Phe Gln Arg Ser Lys Phe Leu Leu Met Asp Ala Leu
            275                 280                 285
Lys Leu Ser Ile Glu Asp Pro Ser His Glu Gly Glu Gly Ile Pro Leu
        290                 295                 300
Tyr Asp Ala Ile Lys Cys Met Arg Thr Phe Phe Gly Trp Lys Glu Pro
```

```
                305                 310                 315                 320
Tyr Ile Val Lys Pro His Glu Lys Gly Ile Asn Pro Asn Tyr Leu Leu
                    325                 330                 335

Ser Trp Lys Gln Val Leu Ala Glu Leu Gln Asp Ile Glu Asn Glu Glu
                    340                 345                 350

Lys Ile Pro Arg Thr Lys Asn Met Lys Lys Thr Ser Gln Leu Lys Trp
                    355                 360                 365

Ala Leu Gly Glu Asn Met Ala Pro Glu Lys Val Asp Phe Asp Asn Cys
            370                 375                 380

Arg Asp Ile Ser Asp Leu Lys Gln Tyr Asp Ser Asp Glu Pro Glu Leu
385                 390                 395                 400

Arg Ser Leu Ser Ser Trp Ile Gln Asn Glu Phe Asn Lys Ala Cys Glu
                    405                 410                 415

Leu Thr Asp Ser Ile Trp Ile Glu Leu Asp Glu Ile Gly Glu Asp Val
                420                 425                 430

Ala Pro Ile Glu His Ile Ala Ser Met Arg Arg Asn Tyr Phe Thr Ala
            435                 440                 445

Glu Val Ser His Cys Arg Ala Thr Glu Tyr Ile Met Lys Gly Val Tyr
            450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                    485                 490                 495

Lys Thr Asn Leu Tyr Gly Phe Ile Ile Lys Gly Arg Ser His Leu Arg
                500                 505                 510

Asn Asp Thr Asp Val Val Asn Phe Val Ser Met Glu Phe Ser Leu Thr
            515                 520                 525

Asp Pro Arg Leu Glu Pro His Lys Trp Glu Lys Tyr Cys Val Leu Glu
            530                 535                 540

Ile Gly Asp Met Leu Leu Arg Ser Ala Ile Gly Gln Met Ser Arg Pro
545                 550                 555                 560

Met Phe Leu Tyr Val Arg Thr Asn Gly Thr Ser Lys Ile Lys Met Lys
                    565                 570                 575

Trp Gly Met Glu Met Arg Pro Cys Leu Leu Gln Ser Leu Gln Gln Ile
                580                 585                 590

Glu Ser Met Val Glu Ala Glu Ser Ser Val Lys Glu Lys Asp Met Thr
            595                 600                 605

Lys Glu Phe Phe Glu Asn Lys Ser Glu Thr Trp Pro Ile Gly Glu Ser
            610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                    645                 650                 655

Gly Phe Ser Ala Glu Ser Arg Lys Leu Leu Val Val Gln Ala Leu
                660                 665                 670

Arg Asp Asn Leu Glu Pro Gly Thr Phe Asp Leu Gly Gly Leu Tyr Glu
            675                 680                 685

Ala Ile Glu Glu Cys Leu Ile Asn Asp Pro Trp Val Leu Leu Asn Ala
            690                 695                 700

Ser Trp Phe Asn Ser Phe Leu Thr His Ala Leu Arg
705                 710                 715

<210> SEQ ID NO 29
```

<211> LENGTH: 90
<212> TYPE: PRT
<213> ORGANISM: Influenza A virus

<400> SEQUENCE: 29

Met Gly Gln Glu Gln Asp Thr Pro Trp Thr Gln Ser Thr Glu His Ile
1               5                   10                  15

Asn Ile Gln Lys Arg Gly Ser Gly Gln Gln Thr Arg Lys Leu Glu Arg
            20                  25                  30

Pro Asn Leu Thr Gln Leu Met Asp His Tyr Leu Arg Thr Met Asn Gln
        35                  40                  45

Val Asp Met His Lys Gln Thr Ala Ser Trp Lys Gln Trp Leu Ser Leu
    50                  55                  60

Arg Asn His Thr Gln Glu Ser Leu Lys Ile Arg Val Leu Lys Arg Trp
65                  70                  75                  80

Lys Leu Phe Asn Lys Gln Glu Trp Thr Asn
                85                  90

<210> SEQ ID NO 30
<211> LENGTH: 757
<212> TYPE: PRT
<213> ORGANISM: Influenza A virus

<400> SEQUENCE: 30

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Ile Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Ile Glu Ser Met Asp Lys
                165                 170                 175

Glu Glu Met Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Leu Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val His Phe Val Glu
                245                 250                 255

Thr Leu Ala Arg Asn Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Val Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Glu Ser
    370                 375                 380

Thr Arg Lys Lys Ile Glu Lys Ile Arg Pro Leu Leu Ile Asp Gly Thr
385                 390                 395                 400

Val Ser Leu Ser Pro Gly Met Met Met Gly Met Phe Asn Met Leu Ser
                405                 410                 415

Thr Val Leu Gly Val Ser Ile Leu Asn Leu Gly Gln Lys Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asn
    450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Glu Gln Thr Arg Ser Lys Ala Gly Leu Leu Val Ser
            580                 585                 590

Asp Gly Gly Ser Asn Leu Tyr Asn Ile Arg Asn Leu His Ile Pro Glu
        595                 600                 605

Val Cys Leu Lys Trp Glu Leu Met Asp Glu Asp Tyr Gln Gly Arg Leu
    610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Thr Pro Lys Arg Asn Arg
            660                 665                 670

```
Ser Ile Leu Asn Thr Ser Gln Arg Gly Ile Leu Glu Asp Glu Gln Met
            675                 680                 685
Tyr Gln Lys Cys Cys Asn Leu Phe Glu Lys Phe Phe Pro Ser Ser Ser
        690                 695                 700
Tyr Arg Arg Pro Val Gly Ile Ser Ser Met Val Glu Ala Met Val Ser
705                 710                 715                 720
Arg Ala Arg Ile Asp Ala Arg Ile Asp Phe Glu Ser Gly Arg Ile Lys
                725                 730                 735
Lys Glu Glu Phe Ala Glu Ile Met Lys Ile Cys Ser Thr Ile Glu Glu
            740                 745                 750
Leu Arg Arg Gln Lys
        755

<210> SEQ ID NO 31
<211> LENGTH: 121
<212> TYPE: PRT
<213> ORGANISM: Influenza A virus

<400> SEQUENCE: 31

Met Asp Ser Asn Thr Val Ser Ser Phe Gln Asp Ile Leu Leu Arg Met
1               5                   10                  15
Ser Lys Met Gln Leu Gly Ser Ser Glu Asp Leu Asn Gly Met Ile
            20                  25                  30
Thr Gln Phe Glu Ser Leu Lys Leu Tyr Arg Asp Ser Leu Gly Glu Ala
        35                  40                  45
Val Met Arg Met Gly Asp Leu His Ser Leu Gln Asn Arg Asn Gly Lys
50                  55                  60
Trp Arg Glu Gln Leu Gly Gln Lys Phe Glu Glu Ile Arg Trp Leu Ile
65                  70                  75                  80
Glu Glu Val Arg His Arg Leu Lys Ile Thr Glu Asn Ser Phe Glu Gln
                85                  90                  95
Ile Thr Phe Met Gln Ala Leu Gln Leu Leu Phe Glu Val Glu Gln Glu
            100                 105                 110
Ile Arg Thr Phe Ser Phe Gln Leu Ile
        115                 120

<210> SEQ ID NO 32
<211> LENGTH: 237
<212> TYPE: PRT
<213> ORGANISM: Influenza A virus

<400> SEQUENCE: 32

Met Asp Ser Asn Thr Val Ser Ser Phe Gln Val Asp Cys Phe Leu Trp
1               5                   10                  15
His Val Arg Lys Gln Val Val Asp Gln Glu Leu Gly Asp Ala Pro Phe
            20                  25                  30
Leu Asp Arg Leu Arg Arg Asp Gln Lys Ser Leu Arg Gly Arg Gly Ser
        35                  40                  45
Thr Leu Asp Leu Asp Ile Glu Ala Ala Thr Arg Val Gly Lys Gln Ile
50                  55                  60
Val Glu Arg Ile Leu Lys Glu Glu Ser Asp Glu Ala Leu Lys Met Thr
65                  70                  75                  80
Met Ala Ser Ala Pro Ala Ser Arg Tyr Leu Thr Asp Met Thr Ile Glu
                85                  90                  95
Glu Leu Ser Arg Asp Trp Phe Met Leu Met Pro Lys Gln Lys Val Glu
            100                 105                 110
```

-continued

```
Gly Pro Leu Cys Ile Arg Ile Asp Gln Ala Ile Met Asp Lys Asn Ile
            115                 120                 125

Met Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Ile Glu Asp Val Lys Asn
                165                 170                 175

Ala Ile Gly Val Leu Ile Gly Gly Leu Glu Trp Asn Asp Asn Thr Val
            180                 185                 190

Arg Val Ser Lys Thr Leu Gln Arg Phe Ala Trp Arg Ser Ser Asn Glu
        195                 200                 205

Asn Gly Arg Pro Pro Leu Thr Pro Lys Gln Lys Arg Lys Met Ala Arg
    210                 215                 220

Thr Ile Arg Ser Lys Val Arg Arg Asp Lys Met Ala Asp
225                 230                 235

<210> SEQ ID NO 33
<211> LENGTH: 498
<212> TYPE: PRT
<213> ORGANISM: Influenza A virus

<400> SEQUENCE: 33

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Asp Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Lys Arg Val Asp Gly Lys Trp Met Arg Glu Leu Val Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Lys Thr Arg Ser Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255
```

-continued

```
Ile Phe Leu Ala Arg Ser Ala Leu Ile Leu Arg Gly Ser Val Ala His
            260                 265                 270

Lys Ser Cys Leu Pro Ala Cys Val Tyr Gly Pro Ala Ile Ala Ser Gly
        275                 280                 285

Tyr Asn Phe Glu Lys Glu Gly Tyr Ser Leu Val Gly Ile Asp Pro Phe
        290                 295                 300

Lys Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys Asn Ser Ala
            325                 330                 335

Ala Phe Glu Asp Leu Arg Val Leu Ser Phe Ile Arg Gly Thr Lys Val
            340                 345                 350

Ser Pro Arg Gly Lys Leu Ser Thr Arg Gly Val Gln Ile Ala Ser Asn
            355                 360                 365

Glu Asn Met Asp Thr Met Glu Ser Ser Thr Leu Glu Leu Arg Ser Arg
        370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Ala Phe Ser Val Gln Arg
            405                 410                 415

Asn Leu Pro Phe Asp Lys Pro Thr Ile Met Ala Ala Phe Thr Gly Asn
            420                 425                 430

Thr Glu Gly Arg Thr Ser Asp Met Arg Ala Glu Ile Ile Arg Met Met
        435                 440                 445

Glu Gly Ala Lys Pro Glu Glu Met Ser Phe Gln Gly Arg Gly Val Phe
            450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
            485                 490                 495

Asp Asn

<210> SEQ ID NO 34
<211> LENGTH: 469
<212> TYPE: PRT
<213> ORGANISM: Influenza A virus

<400> SEQUENCE: 34

Met Asn Pro Asn Gln Lys Ile Ile Thr Ile Gly Ser Val Ser Leu Thr
1               5                   10                  15

Ile Ala Thr Val Cys Phe Leu Met Gln Ile Ala Ile Leu Val Thr Thr
            20                  25                  30

Val Thr Leu His Phe Lys Gln His Glu Cys Asp Ser Pro Ala Ser Asn
        35                  40                  45

Gln Val Met Pro Cys Glu Pro Ile Ile Ile Glu Arg Asn Ile Thr Glu
    50                  55                  60

Ile Val Tyr Leu Asn Asn Thr Thr Ile Glu Lys Glu Ile Cys Pro Glu
65                  70                  75                  80

Val Val Glu Tyr Arg Asn Trp Ser Lys Pro Gln Cys Gln Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Gly Lys
        115                 120                 125
```

```
Cys Tyr Gln Phe Ala Leu Gly Gln Gly Thr Thr Leu Asp Asn Lys His
        130                 135                 140

Ser Asn Asp Thr Ile His Asp Arg Ile Pro His Arg Thr Leu Leu Met
145                 150                 155                 160

Asn Glu Leu Gly Val Pro Phe His Leu Gly Thr Arg Gln Val Cys Val
                165                 170                 175

Ala Trp Ser Ser Ser Cys His Asp Gly Lys Ala Trp Leu His Val
            180                 185                 190

Cys Val Thr Gly Asp Asp Lys Asn Ala Thr Ala Ser Phe Ile Tyr Asp
            195                 200                 205

Gly Arg Leu Met Asp Ser Ile Gly Ser Trp Ser Gln Asn Ile Leu Arg
        210                 215                 220

Thr Gln Glu Ser Glu Cys Val Cys Ile Asn Gly Thr Cys Thr Val Val
225                 230                 235                 240

Met Thr Asp Gly Ser Ala Ser Gly Arg Ala Asp Thr Arg Ile Leu Phe
                245                 250                 255

Ile Glu Glu Gly Lys Ile Val His Ile Ser Pro Leu Ser Gly Ser Ala
            260                 265                 270

Gln His Val Glu Glu Cys Ser Cys Tyr Pro Arg Tyr Pro Asp Val Arg
        275                 280                 285

Cys Ile Cys Arg Asp Asn Trp Lys Gly Ser Asn Arg Pro Val Ile Asp
290                 295                 300

Ile Asn Met Glu Asp Tyr Ser Ile Asp Ser Ser Tyr Val Cys Ser Gly
305                 310                 315                 320

Leu Val Gly Asp Thr Pro Arg Asn Asp Asp Arg Ser Ser Asn Ser Asn
                325                 330                 335

Cys Arg Asn Pro Asn Asn Glu Arg Gly Asn Pro Gly Val Lys Gly Trp
            340                 345                 350

Ala Phe Asp Asn Gly Asp Asp Val Trp Met Gly Arg Thr Ile Ser Lys
        355                 360                 365

Asp Leu Arg Ser Gly Tyr Glu Thr Phe Lys Val Ile Gly Gly Trp Ser
    370                 375                 380

Thr Pro Asn Ser Lys Ser Gln Ile Asn Arg Gln Val Ile Val Asp Ser
385                 390                 395                 400

Asn Asn Trp Ser Gly Tyr Ser Gly Ile Phe Ser Val Glu Gly Lys Arg
                405                 410                 415

Cys Ile Asn Arg Cys Phe Tyr Val Glu Leu Ile Arg Gly Arg Gln Gln
            420                 425                 430

Glu Thr Arg Val Trp Trp Thr Ser Asn Ser Ile Val Val Phe Cys Gly
        435                 440                 445

Thr Ser Gly Thr Tyr Gly Thr Gly Ser Trp Pro Asp Gly Ala Asn Ile
    450                 455                 460

Asn Phe Met Pro Ile
465

<210> SEQ ID NO 35
<211> LENGTH: 121
<212> TYPE: PRT
<213> ORGANISM: Influenza A virus

<400> SEQUENCE: 35

Met Asp Ser Asn Thr Val Ser Ser Phe Gln Asp Ile Leu Leu Arg Met
1               5                   10                  15

Ser Lys Met Gln Leu Gly Ser Ser Ser Glu Asp Leu Asn Gly Met Ile
```

```
                    20                  25                  30

Thr Gln Phe Glu Ser Leu Lys Ile Tyr Arg Asp Ser Leu Gly Glu Ala
            35                  40                  45

Val Met Arg Met Gly Asp Leu His Leu Leu Gln Asn Arg Asn Gly Lys
    50                  55                  60

Trp Arg Glu Gln Leu Gly Gln Lys Phe Glu Ile Arg Trp Leu Ile
65                  70                  75                  80

Glu Glu Val Arg His Arg Leu Lys Thr Thr Glu Asn Ser Phe Glu Gln
                85                  90                  95

Ile Thr Phe Met Gln Ala Leu Gln Leu Leu Phe Glu Val Glu Gln Glu
            100                 105                 110

Ile Arg Thr Phe Ser Phe Gln Leu Ile
            115                 120

<210> SEQ ID NO 36
<211> LENGTH: 230
<212> TYPE: PRT
<213> ORGANISM: Influenza A virus

<400> SEQUENCE: 36

Met Asp Ser Asn Thr Val Ser Ser Phe Gln Val Asp Cys Phe Leu Trp
1               5                   10                  15

His Ile Arg Lys Gln Val Val Asp Gln Glu Leu Ser Asp Ala Pro Phe
            20                  25                  30

Leu Asp Arg Leu Arg Arg Asp Gln Arg Ser Leu Arg Gly Arg Gly Asn
        35                  40                  45

Thr Leu Gly Leu Asp Ile Lys Ala Ala Thr His Val Gly Lys Gln Ile
    50                  55                  60

Val Glu Lys Ile Leu Lys Glu Glu Ser Asp Glu Ala Leu Lys Met Thr
65                  70                  75                  80

Met Val Ser Thr Pro Ala Ser Arg Tyr Ile Thr Asp Met Thr Ile Glu
                85                  90                  95

Glu Leu Ser Arg Asn Trp Phe Met Leu Met Pro Lys Gln Lys Val Glu
            100                 105                 110

Gly Pro Leu Cys Ile Arg Met Asp Gln Ala Ile Met Glu Lys Asn Ile
        115                 120                 125

Met Leu Lys Ala Asn Phe Ser Val Ile Phe Asp Arg Leu Glu Thr Ile
    130                 135                 140

Val Leu Leu Arg Ala Phe Thr Glu Glu Gly Ala Ile Val Gly Glu Ile
145                 150                 155                 160

Ser Pro Leu Pro Ser Phe Pro Gly His Thr Ile Glu Asp Val Lys Asn
                165                 170                 175

Ala Ile Gly Val Leu Ile Gly Gly Leu Glu Trp Asn Asp Asn Thr Val
            180                 185                 190

Arg Val Ser Lys Asn Leu Gln Arg Phe Ala Trp Arg Ser Ser Asn Glu
        195                 200                 205

Asn Gly Gly Pro Pro Leu Thr Pro Lys Gln Lys Arg Lys Met Ala Arg
    210                 215                 220

Thr Ala Arg Ser Lys Val
225                 230

<210> SEQ ID NO 37
<211> LENGTH: 566
<212> TYPE: PRT
<213> ORGANISM: Influenza A virus
```

<400> SEQUENCE: 37

```
Met Lys Thr Ile Ile Ala Leu Ser Tyr Ile Leu Cys Leu Val Phe Ala
1               5                   10                  15
Gln Lys Leu Pro Gly Asn Asp Asn Ser Thr Ala Thr Leu Cys Leu Gly
            20                  25                  30
His His Ala Val Pro Asn Gly Thr Ile Val Lys Thr Ile Thr Asn Asp
        35                  40                  45
Gln Ile Glu Val Thr Asn Ala Thr Glu Leu Val Gln Ser Ser Ser Thr
50                  55                  60
Gly Gly Ile Cys Asp Ser Pro His Gln Ile Leu Asp Gly Glu Asn Cys
65                  70                  75                  80
Thr Leu Ile Asp Ala Leu Leu Gly Asp Pro Gln Cys Asp Gly Phe Gln
                85                  90                  95
Asn Lys Lys Trp Asp Leu Phe Val Glu Arg Ser Lys Ala Tyr Ser Asn
            100                 105                 110
Cys Tyr Pro Tyr Asp Val Pro Asp Tyr Ala Ser Leu Arg Ser Leu Val
        115                 120                 125
Ala Ser Ser Gly Thr Leu Glu Phe Asn Asn Glu Ser Phe Asn Trp Thr
130                 135                 140
Gly Val Thr Gln Asn Gly Thr Ser Ser Ala Cys Lys Arg Arg Ser Asn
145                 150                 155                 160
Asn Ser Phe Phe Ser Arg Leu Asn Trp Leu Thr His Leu Lys Phe Lys
                165                 170                 175
Tyr Pro Ala Leu Asn Val Thr Met Pro Asn Asn Glu Lys Phe Asp Lys
            180                 185                 190
Leu Tyr Ile Trp Gly Val His His Pro Gly Thr Asp Asn Asp Gln Ile
        195                 200                 205
Ser Leu Tyr Ala Gln Ala Ser Gly Arg Ile Thr Val Ser Thr Lys Arg
210                 215                 220
Ser Gln Gln Thr Val Ile Pro Ser Ile Gly Ser Arg Pro Arg Ile Arg
225                 230                 235                 240
Asp Val Pro Ser Arg Ile Ser Ile Tyr Trp Thr Ile Val Lys Pro Gly
                245                 250                 255
Asp Ile Leu Leu Ile Asn Ser Thr Gly Asn Leu Ile Ala Pro Arg Gly
            260                 265                 270
Tyr Phe Lys Ile Arg Ser Gly Lys Ser Ser Ile Met Arg Ser Asp Ala
        275                 280                 285
Pro Ile Gly Lys Cys Asn Ser Glu Cys Ile Thr Pro Asn Gly Ser Ile
290                 295                 300
Pro Asn Asp Lys Pro Phe Gln Asn Val Asn Arg Ile Thr Tyr Gly Ala
305                 310                 315                 320
Cys Pro Arg Tyr Val Lys Gln Asn Thr Leu Lys Leu Ala Thr Gly Met
                325                 330                 335
Arg Asn Val Pro Glu Lys Gln Thr Arg Gly Ile Phe Gly Ala Ile Ala
            340                 345                 350
Gly Phe Ile Glu Asn Gly Trp Glu Gly Met Val Asp Gly Trp Tyr Gly
        355                 360                 365
Phe Arg His Gln Asn Ser Glu Gly Thr Gly Gln Ala Ala Asp Leu Lys
370                 375                 380
Ser Thr Gln Ala Ala Ile Asn Gln Ile Asn Gly Lys Leu Asn Arg Leu
385                 390                 395                 400
Ile Gly Lys Thr Asn Glu Lys Phe His Gln Ile Glu Lys Glu Phe Ser
                405                 410                 415
```

```
Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
            435                 440                 445

Asn Gln His Thr Ile Asp Leu Thr Asp Ser Glu Met Asn Lys Leu Phe
            450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
            485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
            530                 535                 540

Val Ala Leu Leu Gly Phe Ile Met Trp Ala Cys Gln Lys Gly Asn Ile
545                 550                 555                 560

Arg Cys Asn Ile Cys Ile
            565

<210> SEQ ID NO 38
<211> LENGTH: 97
<212> TYPE: PRT
<213> ORGANISM: Influenza A virus

<400> SEQUENCE: 38

Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Val Ala Ala Ser Ile
            20                  25                  30

Ile Gly Ile Leu His Leu Ile Leu Trp Ile Leu Asp Arg Leu Phe Phe
        35                  40                  45

Lys Cys Val Tyr Arg Leu Phe Lys His Gly Leu Lys Arg Gly Pro Ser
    50                  55                  60

Thr Glu Gly Val Pro Glu Ser Met Arg Glu Glu Tyr Arg Lys Glu Gln
65                  70                  75                  80

Gln Asn Ala Val Asp Ala Asp Asp Ser His Phe Val Ser Ile Glu Leu
                85                  90                  95

Glu

<210> SEQ ID NO 39
<211> LENGTH: 252
<212> TYPE: PRT
<213> ORGANISM: Influenza A virus

<400> SEQUENCE: 39

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
            35                  40                  45

Arg Pro Ile Leu Ser Pro Leu Thr Lys Gly Ile Leu Gly Phe Val Phe
        50                  55                  60
```

Thr Leu Thr Val Pro Ser Glu Arg Gly Leu Gln Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ala Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Ala Thr Thr Asn Pro Leu Ile Lys His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Ile Ala Ser Gln
        195                 200                 205

Ala Arg Gln Met Val Gln Ala Met Arg Ala Val Gly Thr His Pro Ser
    210                 215                 220

Ser Ser Thr Gly Leu Arg Asp Asp Leu Leu Glu Asn Leu Gln Thr Tyr
225                 230                 235                 240

Gln Lys Arg Met Gly Val Gln Met Gln Arg Phe Lys
                245                 250

<210> SEQ ID NO 40
<211> LENGTH: 90
<212> TYPE: PRT
<213> ORGANISM: Influenza A virus

<400> SEQUENCE: 40

Met Glu Gln Glu Gln Asp Thr Pro Trp Thr Gln Ser Thr Glu His Thr
1               5                   10                  15

Asn Ile Gln Arg Arg Gly Ser Gly Arg Gln Ile Gln Lys Leu Gly His
            20                  25                  30

Pro Asn Ser Thr Gln Leu Met Asp His Tyr Leu Arg Ile Met Ser Gln
        35                  40                  45

Val Asp Met His Lys Gln Thr Val Ser Trp Arg Leu Trp Pro Ser Leu
    50                  55                  60

Lys Asn Pro Thr Gln Val Ser Leu Arg Thr His Ala Leu Lys Gln Trp
65                  70                  75                  80

Lys Ser Phe Asn Lys Gln Gly Trp Thr Asn
                85                  90

<210> SEQ ID NO 41
<211> LENGTH: 757
<212> TYPE: PRT
<213> ORGANISM: Influenza A virus

<400> SEQUENCE: 41

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

```
Tyr Ser Glu Lys Gly Lys Trp Thr Thr Asn Thr Glu Thr Gly Ala Pro
    50              55                  60

Gln Leu Asn Pro Ile Asp Gly Pro Leu Pro Glu Asp Asn Glu Pro Ser
65              70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Met Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
            195                 200                 205

Lys Gln Arg Val Asn Lys Arg Gly Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
        260                 265                 270

Val Gly Gly Asn Glu Lys Lys Ala Lys Leu Ala Asn Val Val Arg Lys
    275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Lys Asn Gln Pro Glu Trp Phe Arg Asn Ile
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Arg Met Lys Leu Arg Thr Gln Ile
            355                 360                 365

Pro Ala Glu Met Leu Ala Ser Ile Asp Leu Lys Tyr Phe Asn Glu Ser
    370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Val Leu Asn Leu Gly Gln Lys Lys Tyr Thr
            420                 425                 430

Lys Thr Thr Tyr Trp Trp Asp Gly Leu Gln Ser Ser Asp Asp Phe Ala
            435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
```

```
                    465                 470                 475                 480
Lys Ser Tyr Ile Asn Lys Thr Gly Thr Phe Glu Phe Thr Ser Phe
                485                 490                 495

Tyr Arg Tyr Gly Phe Val Ala Asn Phe Ser Met Glu Leu Pro Ser Phe
                500                 505                 510

Gly Val Ser Gly Ile Asn Glu Ser Ala Asp Met Ser Ile Gly Val Thr
                515                 520                 525

Val Ile Lys Asn Asn Met Ile Asn Asn Asp Leu Gly Pro Ala Thr Ala
                530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Asp Gln Thr Gln Ser Arg Ala Gly Leu Leu Val Ser
                580                 585                 590

Asp Gly Gly Pro Asn Leu Tyr Asn Ile Arg Asn Leu His Ile Pro Glu
                595                 600                 605

Val Cys Leu Lys Trp Glu Leu Met Asp Glu Asn Tyr Arg Gly Arg Leu
610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Asn Pro Lys Arg Asn Arg
                660                 665                 670

Ser Ile Leu Asn Thr Ser Gln Arg Gly Ile Leu Glu Asp Glu Gln Met
                675                 680                 685

Tyr Gln Lys Cys Cys Asn Leu Phe Glu Lys Phe Phe Pro Ser Ser Ser
                690                 695                 700

Tyr Arg Arg Pro Ile Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ser Glu Ile Met Lys Ile Cys Ser Thr Ile Glu Glu
                740                 745                 750

Leu Arg Arg Gln Lys
                755

<210> SEQ ID NO 42
<211> LENGTH: 498
<212> TYPE: PRT
<213> ORGANISM: Influenza A virus

<400> SEQUENCE: 42

Met Ala Ser Gln Gly Thr Lys Arg Ser Tyr Glu Gln Met Glu Thr Asp
1                   5                   10                  15

Gly Asp Arg Gln Asn Ala Thr Glu Ile Arg Ala Ser Val Gly Lys Met
                20                  25                  30

Ile Asp Gly Ile Gly Arg Phe Tyr Ile Gln Met Cys Thr Glu Leu Lys
                35                  40                  45

Leu Ser Asp His Glu Gly Arg Leu Ile Gln Asn Ser Leu Thr Ile Glu
                50                  55                  60

Lys Met Val Leu Ser Ala Phe Asp Glu Arg Arg Asn Lys Tyr Leu Glu
65                  70                  75                  80
```

```
Glu His Pro Ser Ala Gly Lys Asp Pro Lys Thr Gly Gly Pro Ile
                85              90              95

Tyr Arg Arg Val Asp Gly Lys Trp Met Arg Glu Leu Val Leu Tyr Asp
            100             105             110

Lys Glu Glu Ile Arg Arg Ile Trp Arg Gln Ala Asn Asn Gly Glu Asp
            115             120             125

Ala Thr Ala Gly Leu Thr His Ile Met Ile Trp His Ser Asn Leu Asn
    130             135             140

Asp Ala Thr Tyr Gln Arg Thr Arg Ala Leu Val Arg Thr Gly Met Asp
145             150             155             160

Pro Arg Met Cys Ser Leu Met Gln Gly Ser Thr Leu Pro Arg Arg Ser
                165             170             175

Gly Ala Ala Gly Ala Ala Val Lys Gly Ile Gly Thr Met Val Met Glu
            180             185             190

Leu Ile Arg Met Val Lys Arg Gly Ile Asn Asp Arg Asn Phe Trp Arg
            195             200             205

Gly Glu Asn Gly Arg Lys Thr Arg Ser Ala Tyr Glu Arg Met Cys Asn
    210             215             220

Ile Leu Lys Gly Lys Phe Gln Thr Ala Ala Gln Arg Ala Met Val Asp
225             230             235             240

Gln Val Arg Glu Ser Arg Asn Pro Gly Asn Ala Glu Ile Glu Asp Leu
                245             250             255

Ile Phe Leu Ala Arg Ser Ala Leu Ile Leu Arg Gly Ser Val Ala His
            260             265             270

Lys Ser Cys Leu Pro Ala Cys Ala Tyr Gly Pro Ala Val Ser Ser Gly
            275             280             285

Tyr Asp Phe Glu Lys Glu Gly Tyr Ser Leu Val Gly Ile Asp Pro Phe
    290             295             300

Lys Leu Leu Gln Asn Ser Gln Ile Tyr Ser Leu Ile Arg Pro Asn Glu
305             310             315             320

Asn Pro Ala His Lys Ser Gln Leu Val Trp Met Ala Cys His Ser Ala
                325             330             335

Ala Phe Glu Asp Leu Arg Leu Leu Ser Phe Ile Arg Gly Thr Lys Val
            340             345             350

Ser Pro Arg Gly Lys Leu Ser Thr Arg Gly Val Gln Ile Ala Ser Asn
            355             360             365

Glu Asn Met Asp Asn Met Gly Ser Ser Thr Leu Glu Leu Arg Ser Gly
    370             375             380

Tyr Trp Ala Ile Arg Thr Arg Ser Gly Gly Asn Thr Asn Gln Gln Arg
385             390             395             400

Ala Ser Ala Gly Gln Thr Ser Val Gln Pro Thr Phe Ser Val Gln Arg
                405             410             415

Asn Leu Pro Phe Glu Lys Ser Thr Ile Met Ala Ala Phe Thr Gly Asn
            420             425             430

Thr Glu Gly Arg Thr Ser Asp Met Arg Ala Glu Ile Ile Arg Met Met
            435             440             445

Glu Gly Ala Lys Pro Glu Glu Val Ser Phe Arg Gly Arg Gly Val Phe
    450             455             460

Glu Leu Ser Asp Glu Lys Ala Thr Asn Pro Ile Val Pro Ser Phe Asp
465             470             475             480

Met Ser Asn Glu Gly Ser Tyr Phe Phe Gly Asp Asn Ala Glu Glu Tyr
                485             490             495

Asp Asn
```

<210> SEQ ID NO 43
<211> LENGTH: 469
<212> TYPE: PRT
<213> ORGANISM: Influenza A virus

<400> SEQUENCE: 43

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Met Cys Pro Lys
65                  70                  75                  80

Leu Ala Glu Tyr Arg Asn Trp Ser Lys Pro Gln Cys Asp Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
    130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Val Thr Gly Asp Asp Lys Asn Ala Thr Ala Ser Phe Ile Tyr Asn
        195                 200                 205

Gly Arg Leu Val Asp Ser Ile Val Ser Trp Ser Lys Lys Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Ile His Thr Ser Thr Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300

Ile Asn Ile Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
        355                 360                 365

Lys Leu Arg Ser Gly Tyr Glu Thr Phe Lys Val Ile Glu Gly Trp Ser

```
                370               375               380
Lys Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
                420                 425                 430

Glu Thr Glu Val Leu Trp Thr Ser Asn Ser Ile Val Phe Cys Gly
                435                 440                 445

Thr Ser Gly Thr Tyr Gly Thr Gly Ser Trp Pro Asp Gly Ala Asp Ile
450                 455                 460

Asn Leu Met Pro Ile
465

<210> SEQ ID NO 44
<211> LENGTH: 716
<212> TYPE: PRT
<213> ORGANISM: Influenza A virus

<400> SEQUENCE: 44

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Leu Lys Ile Glu Thr
                20                  25                  30

Asn Lys Phe Ala Ala Ile Cys Thr His Leu Glu Val Cys Phe Met Tyr
            35                  40                  45

Ser Asp Phe His Phe Ile Asn Glu Gln Gly Glu Ser Ile Val Val Glu
        50                  55                  60

Leu Asp Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
                100                 105                 110

Lys Glu Asn Arg Phe Ile Glu Ile Gly Val Thr Arg Arg Glu Val His
            115                 120                 125

Ile Tyr Tyr Leu Glu Lys Ala Asn Lys Ile Lys Ser Glu Asn Thr His
        130                 135                 140

Ile His Ile Phe Ser Phe Thr Gly Glu Glu Ile Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Asn Arg Gly Leu Trp Asp Ser Phe Arg
                180                 185                 190

Gln Ser Glu Arg Gly Glu Glu Thr Ile Glu Glu Lys Phe Glu Ile Ser
            195                 200                 205

Gly Thr Met Arg Arg Leu Ala Asp Gln Ser Leu Pro Pro Lys Phe Ser
        210                 215                 220

Cys Leu Glu Asn Phe Arg Ala Tyr Val Asp Gly Phe Glu Pro Asn Gly
225                 230                 235                 240

Cys Ile Glu Gly Lys Leu Ser Gln Met Ser Lys Glu Val Asn Ala Lys
                245                 250                 255

Ile Glu Pro Phe Leu Lys Thr Thr Pro Arg Pro Ile Lys Leu Pro Asn
                260                 265                 270
```

-continued

```
Gly Pro Pro Cys Tyr Gln Arg Ser Lys Phe Leu Leu Met Asp Ala Leu
            275                 280                 285

Lys Leu Ser Ile Glu Asp Pro Ser His Glu Gly Glu Gly Ile Pro Leu
        290                 295                 300

Tyr Asp Ala Ile Lys Cys Ile Lys Thr Phe Phe Gly Trp Lys Glu Pro
305                 310                 315                 320

Tyr Ile Val Lys Pro His Glu Lys Gly Ile Asn Ser Asn Tyr Leu Leu
                325                 330                 335

Ser Trp Lys Gln Val Leu Ser Glu Leu Gln Asp Ile Glu Asn Glu Glu
            340                 345                 350

Lys Ile Pro Arg Thr Lys Asn Met Lys Lys Thr Ser Gln Leu Lys Trp
        355                 360                 365

Ala Leu Gly Glu Asn Met Ala Pro Glu Lys Val Asp Phe Asp Asn Cys
    370                 375                 380

Arg Asp Ile Ser Asp Leu Lys Gln Tyr Asp Ser Asp Glu Pro Glu Leu
385                 390                 395                 400

Arg Ser Leu Ser Ser Trp Ile Gln Asn Glu Phe Asn Lys Ala Cys Glu
                405                 410                 415

Leu Thr Asp Ser Ile Trp Ile Glu Leu Asp Glu Ile Gly Glu Asp Val
            420                 425                 430

Ala Pro Ile Glu Tyr Ile Ala Ser Met Arg Arg Asn Tyr Phe Thr Ala
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Leu Arg Ser Ala Ile Gly Gln Ile Ser Arg Pro
545                 550                 555                 560

Met Phe Leu Tyr Val Arg Thr Asn Gly Thr Ser Lys Val Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ile Lys Glu Lys Asp Met Thr
        595                 600                 605

Lys Glu Phe Phe Glu Asn Lys Ser Glu Ala Trp Pro Ile Gly Glu Ser
    610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Val Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
```

```
                690                 695                 700
Ser Trp Phe Asn Ser Phe Leu Thr His Ala Leu Lys
705                 710                 715

<210> SEQ ID NO 45
<211> LENGTH: 759
<212> TYPE: PRT
<213> ORGANISM: Influenza A virus

<400> SEQUENCE: 45

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ser Leu Arg Met Lys
        35                  40                  45

Trp Met Met Ala Met Lys Tyr Pro Ile Thr Ala Asp Lys Arg Ile Thr
    50                  55                  60

Glu Met Val Pro Glu Arg Asn Glu Gln Gly Gln Thr Leu Trp Ser Lys
65                  70                  75                  80

Met Ser Asp Ala Gly Ser Asp Arg Val Met Val Ser Pro Leu Ala Val
                85                  90                  95

Thr Trp Trp Asn Arg Asn Gly Pro Val Ala Ser Thr Val His Tyr Pro
            100                 105                 110

Lys Val Tyr Lys Thr Tyr Phe Asp Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Arg Asp Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Ile Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Thr Arg Met Val Asp Ile Leu Arg Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Lys Glu Glu Glu Val Leu Thr Gly Asn Leu Gln Thr Leu
            340                 345                 350
```

-continued

```
Lys Ile Arg Val His Glu Gly Tyr Glu Glu Phe Thr Met Val Gly Lys
            355                 360                 365
Arg Ala Thr Ala Ile Leu Arg Lys Ala Thr Arg Leu Val Gln Leu
370                 375                 380
Ile Val Ser Gly Arg Asp Glu Gln Ser Ile Ala Glu Ala Ile Ile Val
385                 390                 395                 400
Ala Met Val Phe Ser Gln Glu Asp Cys Met Ile Lys Ala Val Arg Gly
                405                 410                 415
Asp Leu Asn Phe Val Asn Arg Ala Asn Gln Arg Leu Asn Pro Met His
                420                 425                 430
Gln Leu Leu Arg His Phe Gln Lys Asp Ala Lys Val Leu Phe Gln Asn
            435                 440                 445
Trp Gly Ile Glu His Ile Asp Ser Val Met Gly Met Val Gly Val Leu
450                 455                 460
Pro Asp Met Thr Pro Ser Thr Glu Met Ser Met Arg Gly Ile Arg Val
465                 470                 475                 480
Ser Lys Met Gly Val Asp Glu Tyr Ser Ser Thr Glu Arg Val Val Val
                485                 490                 495
Ser Ile Asp Arg Phe Leu Arg Val Arg Asp Gln Arg Gly Asn Val Leu
                500                 505                 510
Leu Ser Pro Glu Glu Val Ser Glu Thr Gln Gly Thr Glu Arg Leu Thr
            515                 520                 525
Ile Thr Tyr Ser Ser Ser Met Met Trp Glu Ile Asn Gly Pro Glu Ser
            530                 535                 540
Val Leu Val Asn Thr Tyr Gln Trp Ile Ile Arg Asn Trp Glu Ala Val
545                 550                 555                 560
Lys Ile Gln Trp Ser Gln Asn Pro Ala Met Leu Tyr Asn Lys Met Glu
                565                 570                 575
Phe Glu Pro Phe Gln Ser Leu Val Pro Lys Ala Ile Arg Ser Gln Tyr
                580                 585                 590
Ser Gly Phe Val Arg Thr Leu Phe Gln Gln Met Arg Asp Val Leu Gly
            595                 600                 605
Thr Phe Asp Thr Thr Gln Ile Ile Lys Leu Leu Pro Phe Ala Ala Ala
610                 615                 620
Pro Pro Lys Gln Ser Arg Met Gln Phe Ser Ser Leu Thr Val Asn Val
625                 630                 635                 640
Arg Gly Ser Gly Met Arg Ile Leu Val Arg Gly Asn Ser Pro Val Phe
                645                 650                 655
Asn Tyr Asn Lys Thr Thr Lys Arg Leu Thr Ile Leu Gly Lys Asp Ala
                660                 665                 670
Gly Thr Leu Ile Glu Asp Pro Asp Glu Ser Thr Ser Gly Val Glu Ser
            675                 680                 685
Ala Val Leu Arg Gly Phe Leu Ile Ile Gly Lys Glu Asp Arg Arg Tyr
690                 695                 700
Gly Pro Ala Leu Ser Ile Asn Glu Leu Ser Asn Leu Ala Lys Gly Glu
705                 710                 715                 720
Lys Ala Asn Val Leu Ile Gly Gln Gly Asp Val Val Leu Val Met Lys
                725                 730                 735
Arg Lys Arg Asp Ser Ser Ile Leu Thr Asp Ser Gln Thr Ala Thr Lys
                740                 745                 750
Arg Ile Arg Met Ala Ile Asn
                755
```

<210> SEQ ID NO 46
<211> LENGTH: 580
<212> TYPE: PRT
<213> ORGANISM: CMV virus

<400> SEQUENCE: 46

```
Met Glu Ser Ser Ala Lys Arg Lys Met Asp Pro Asp Asn Pro Asp Glu
1               5                   10                  15

Gly Pro Ser Ser Lys Val Pro Arg Pro Glu Thr Pro Val Thr Lys Ala
            20                  25                  30

Thr Thr Phe Leu Gln Thr Met Leu Arg Lys Glu Val Asn Ser Gln Leu
        35                  40                  45

Ser Leu Gly Asp Pro Leu Phe Pro Glu Leu Ala Glu Glu Ser Leu Lys
    50                  55                  60

Thr Phe Glu Gln Val Thr Glu Asp Cys Asn Glu Asn Pro Glu Lys Asp
65                  70                  75                  80

Val Leu Ala Glu Leu Gly Asp Ile Leu Ala Gln Ala Val Asn His Ala
                85                  90                  95

Gly Ile Asp Ser Ser Thr Gly His Thr Leu Thr Thr His Ser Cys
            100                 105                 110

Ser Val Ser Ser Ala Pro Leu Asn Lys Pro Thr Pro Thr Ser Val Ala
        115                 120                 125

Val Thr Asn Thr Pro Leu Pro Gly Ala Ser Ala Thr Pro Glu Leu Ser
    130                 135                 140

Pro Arg Lys Lys Pro Arg Lys Thr Thr Arg Pro Phe Lys Val Ile Ile
145                 150                 155                 160

Lys Pro Pro Val Pro Ala Pro Ile Met Leu Pro Leu Ile Lys Gln
                165                 170                 175

Glu Asp Ile Lys Pro Glu Pro Asp Phe Thr Ile Gln Tyr Arg Asn Lys
            180                 185                 190

Ile Ile Asp Thr Ala Gly Cys Ile Val Ile Ser Asp Ser Glu Glu Glu
        195                 200                 205

Gln Gly Glu Glu Val Glu Thr Arg Gly Ala Thr Ala Ser Ser Pro Ser
    210                 215                 220

Thr Gly Ser Gly Thr Pro Arg Val Thr Ser Pro Thr His Pro Leu Ser
225                 230                 235                 240

Gln Met Asn His Pro Pro Leu Pro Asp Pro Leu Ala Arg Pro Asp Glu
                245                 250                 255

Asp Ser Ser Ser Ser Ser Ser Cys Ser Ser Ala Ser Asp Ser
            260                 265                 270

Glu Ser Glu Ser Glu Glu Met Lys Cys Ser Ser Gly Gly Ala Ser
    275                 280                 285

Val Thr Ser Ser His His Gly Arg Gly Gly Phe Gly Ser Ala Ala Ser
    290                 295                 300

Ser Ser Leu Leu Ser Cys Gly His Gln Ser Ser Gly Gly Ala Ser Thr
305                 310                 315                 320

Gly Pro Arg Lys Lys Ser Lys Arg Ile Ser Glu Leu Asp Asn Glu
                325                 330                 335

Lys Val Arg Asn Ile Met Lys Asp Lys Asn Thr Pro Phe Cys Thr Pro
            340                 345                 350

Asn Val Gln Thr Arg Arg Gly Arg Val Lys Ile Asp Glu Val Ser Arg
        355                 360                 365

Met Phe Arg Asn Thr Asn Arg Ser Leu Glu Tyr Lys Asn Leu Pro Phe
    370                 375                 380
```

```
Thr Ile Pro Ser Met His Gln Val Leu Asp Glu Ala Ile Lys Ala Cys
385                 390                 395                 400

Lys Thr Met Gln Val Asn Asn Lys Gly Ile Gln Ile Ile Tyr Thr Arg
            405                 410                 415

Asn His Glu Val Lys Ser Glu Val Asp Ala Val Arg Cys Arg Leu Gly
            420                 425                 430

Thr Met Cys Asn Leu Ala Leu Ser Thr Pro Phe Leu Met Glu His Thr
            435                 440                 445

Met Pro Val Thr His Pro Pro Glu Val Ala Gln Arg Thr Ala Asp Ala
            450                 455                 460

Cys Asn Glu Gly Val Lys Ala Ala Trp Ser Leu Lys Glu Leu His Thr
465                 470                 475                 480

His Gln Leu Cys Pro Arg Ser Ser Asp Tyr Arg Asn Met Ile Ile His
            485                 490                 495

Ala Ala Thr Pro Val Asp Leu Leu Gly Ala Leu Asn Leu Cys Leu Pro
            500                 505                 510

Leu Met Gln Lys Phe Pro Lys Gln Val Met Val Arg Ile Phe Ser Thr
            515                 520                 525

Asn Gln Gly Gly Phe Met Leu Pro Ile Tyr Glu Thr Ala Ala Lys Ala
            530                 535                 540

Tyr Ala Val Gly Gln Phe Glu Gln Pro Thr Glu Thr Pro Pro Glu Asp
545                 550                 555                 560

Leu Asp Thr Leu Ser Leu Ala Ile Glu Ala Ile Gln Asp Leu Arg
                565                 570                 575

Asn Lys Ser Gln
            580

<210> SEQ ID NO 47
<211> LENGTH: 27
<212> TYPE: PRT
<213> ORGANISM: Artificial
<220> FEATURE:
<223> OTHER INFORMATION: Artificial peptide sequence derived from
      antigen

<400> SEQUENCE: 47

Arg Arg Gly Tyr Ile Pro Leu Val Gly Ala Pro Leu Gly Asx Gly Arg
1               5                   10                  15

Val Ala Arg Ala Leu Ala His Gly Val Arg Val
            20                  25

<210> SEQ ID NO 48
<211> LENGTH: 25
<212> TYPE: PRT
<213> ORGANISM: Artificial
<220> FEATURE:
<223> OTHER INFORMATION: Artificial peptide sequence derived from
      antigen

<400> SEQUENCE: 48

Arg Gly Tyr Ile Pro Leu Val Gly Ala Pro Leu Gly Arg Arg Val Ala
1               5                   10                  15

Arg Ala Leu Ala His Gly Val Arg Val
            20                  25

<210> SEQ ID NO 49
<211> LENGTH: 27
<212> TYPE: PRT
<213> ORGANISM: Artificial
<220> FEATURE:
```

```
<223> OTHER INFORMATION: Artificial peptide sequence derived from
      antigen

<400> SEQUENCE: 49

Arg Gly Tyr Ile Pro Leu Val Gly Ala Pro Leu Gly Arg Arg Val
1               5                   10                  15

Ala Arg Ala Leu Ala His Gly Val Arg Val Arg
            20                  25

<210> SEQ ID NO 50
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 50

Arg Arg Gly Tyr Ile Pro Leu Val Gly Ala Pro Leu Gly Arg Val
1               5                   10                  15

Ala Arg Ala Leu Ala His Gly Val Arg Val
            20                  25

<210> SEQ ID NO 51
<211> LENGTH: 27
<212> TYPE: PRT
<213> ORGANISM: Artificial
<220> FEATURE:
<223> OTHER INFORMATION: Artificial peptide sequence derived from
      antigen

<400> SEQUENCE: 51

Arg Arg Gly Tyr Ile Pro Leu Val Gly Ala Pro Leu Gly Arg Arg
1               5                   10                  15

Val Ala Arg Ala Leu Ala His Gly Val Arg Val
            20                  25

<210> SEQ ID NO 52
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 52

Asx Arg Gly Tyr Ile Pro Leu Val Gly Ala Pro Leu Gly Arg Arg Val
1               5                   10                  15

Ala Arg Ala Leu Ala His Gly Val Arg Val
            20                  25

<210> SEQ ID NO 53
<211> LENGTH: 27
<212> TYPE: PRT
<213> ORGANISM: Artificial
<220> FEATURE:
<223> OTHER INFORMATION: Artificial peptide sequence derived from
      antigen

<400> SEQUENCE: 53

Arg Arg Arg Gly Tyr Ile Pro Leu Val Gly Ala Pro Leu Gly Asx Arg
1               5                   10                  15

Val Ala Arg Ala Leu Ala His Gly Val Arg Val
            20                  25
```

<210> SEQ ID NO 54
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 54

Arg Gly Tyr Ile Pro Leu Val Gly Ala Pro Leu Gly Lys Lys Lys Val
1               5                   10                  15

Ala Arg Ala Leu Ala His Gly Val Arg Val
            20                  25

<210> SEQ ID NO 55
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 55

Arg Gly Tyr Ile Pro Leu Val Gly Ala Pro Leu Gly Arg Arg Arg Val
1               5                   10                  15

Ala Arg Ala Leu Ala His Gly Val Arg Val
            20                  25

<210> SEQ ID NO 56
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 56

Lys Lys Gly Tyr Ile Pro Leu Val Gly Ala Pro Leu Gly Lys Lys Val
1               5                   10                  15

Ala Arg Ala Leu Ala His Gly Val Arg Val
            20                  25

<210> SEQ ID NO 57
<211> LENGTH: 25
<212> TYPE: PRT
<213> ORGANISM: Artificial
<220> FEATURE:
<223> OTHER INFORMATION: Artificial peptide sequence derived from
      antigen

<400> SEQUENCE: 57

Trp Gly Tyr Ile Pro Leu Val Gly Ala Pro Leu Gly Arg Arg Val Ala
1               5                   10                  15

Arg Ala Leu Ala His Gly Val Arg Val
            20                  25

<210> SEQ ID NO 58
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 58

```
Trp Trp Gly Tyr Ile Pro Leu Val Gly Ala Pro Leu Gly Arg Arg Val
1               5                   10                  15

Ala Arg Ala Leu Ala His Gly Val Arg Val
            20                  25
```

<210> SEQ ID NO 59
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 59

```
Glu Glu Gly Tyr Ile Pro Leu Val Gly Ala Pro Leu Gly Glu Glu Val
1               5                   10                  15

Ala Arg Ala Leu Ala His Gly Val Arg Val
            20                  25
```

<210> SEQ ID NO 60
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 60

```
Gly Gly Gly Tyr Ile Pro Leu Val Gly Ala Pro Leu Gly Gly Gly Val
1               5                   10                  15

Ala Arg Ala Leu Ala His Gly Val Arg Val
            20                  25
```

<210> SEQ ID NO 61
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 61

```
Glu Glu Gly Tyr Ile Pro Leu Val Gly Ala Pro Leu Gly Arg Arg Val
1               5                   10                  15

Ala Arg Ala Leu Ala His Gly Val Arg Val
            20                  25
```

<210> SEQ ID NO 62
<211> LENGTH: 27
<212> TYPE: PRT
<213> ORGANISM: Artificial
<220> FEATURE:
<223> OTHER INFORMATION: Artificial peptide sequence derived from
      antigen

<400> SEQUENCE: 62

```
Arg Arg Gly Tyr Ile Pro Leu Val Gly Ala Pro Leu Gly Leu Arg Arg
1               5                   10                  15

Val Ala Arg Ala Leu Ala His Gly Val Arg Val
            20                  25
```

<210> SEQ ID NO 63
<211> LENGTH: 26
<212> TYPE: PRT
<213> ORGANISM: Artificial

-continued

```
<220> FEATURE:
<223> OTHER INFORMATION: Artificial peptide sequence derived from
      antigen

<400> SEQUENCE: 63

Trp Trp Gly Tyr Ile Pro Leu Val Gly Ala Pro Leu Gly Arg Arg Val
1               5                   10                  15

Ala Arg Ala Leu Ala His Gly Val Arg Val
            20                  25

<210> SEQ ID NO 64
<211> LENGTH: 27
<212> TYPE: PRT
<213> ORGANISM: Artificial
<220> FEATURE:
<223> OTHER INFORMATION: Artificial peptide sequence derived from
      antigen

<400> SEQUENCE: 64

Trp Trp Gly Tyr Ile Pro Leu Val Gly Ala Pro Leu Gly Arg Arg Arg
1               5                   10                  15

Val Ala Arg Ala Leu Ala His Gly Val Arg Val
            20                  25

<210> SEQ ID NO 65
<211> LENGTH: 25
<212> TYPE: PRT
<213> ORGANISM: Artificial
<220> FEATURE:
<223> OTHER INFORMATION: Artificial peptide sequence derived from
      antigen

<400> SEQUENCE: 65

Trp Trp Gly Tyr Ile Pro Leu Val Gly Ala Pro Leu Gly Arg Val Ala
1               5                   10                  15

Arg Ala Leu Ala His Gly Val Arg Val
            20                  25

<210> SEQ ID NO 66
<211> LENGTH: 25
<212> TYPE: PRT
<213> ORGANISM: Artificial
<220> FEATURE:
<223> OTHER INFORMATION: Artificial peptide sequence derived from
      antigen

<400> SEQUENCE: 66

Arg Gly Tyr Ile Pro Leu Val Gly Ala Pro Leu Gly Arg Arg Val Ala
1               5                   10                  15

Arg Ala Leu Ala His Gly Val Arg Val
            20                  25

<210> SEQ ID NO 67
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 67

Arg Arg Gly Tyr Leu Pro Ala Val Gly Ala Pro Ile Gly Asx Arg Val
1               5                   10                  15

Ile Arg Val Ile Ala His Gly Leu Arg Leu
            20                  25
```

```
<210> SEQ ID NO 68
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 68

Arg Arg Gly Tyr Ile Pro Leu Val Gly Ala Pro Leu Gly Asx Arg Val
1               5                   10                  15

Ala Arg Ala Leu Ala His Gly Val Arg Val
            20                  25

<210> SEQ ID NO 69
<211> LENGTH: 23
<212> TYPE: PRT
<213> ORGANISM: Artificial
<220> FEATURE:
<223> OTHER INFORMATION: Artificial peptide sequence derived from
      antigen

<400> SEQUENCE: 69

Gly Tyr Ile Pro Leu Val Gly Ala Pro Leu Gly Gly Val Ala Arg Ala
1               5                   10                  15

Leu Ala His Gly Val Arg Val
            20

<210> SEQ ID NO 70
<211> LENGTH: 25
<212> TYPE: PRT
<213> ORGANISM: Artificial
<220> FEATURE:
<223> OTHER INFORMATION: Artificial peptide sequence derived from
      antigen

<400> SEQUENCE: 70

Trp Trp Gly Tyr Leu Pro Ala Val Gly Ala Pro Ile Arg Arg Val Ile
1               5                   10                  15

Arg Val Ile Ala His Gly Leu Arg Leu
            20                  25

<210> SEQ ID NO 71
<211> LENGTH: 23
<212> TYPE: PRT
<213> ORGANISM: Artificial
<220> FEATURE:
<223> OTHER INFORMATION: Artificial peptide sequence derived from
      antigen

<400> SEQUENCE: 71

Gly Tyr Ile Pro Leu Val Gly Ala Pro Leu Gly Gly Val Ala Arg Ala
1               5                   10                  15

Leu Ala His Gly Val Arg Val
            20

<210> SEQ ID NO 72
<211> LENGTH: 27
<212> TYPE: PRT
<213> ORGANISM: Artificial
<220> FEATURE:
<223> OTHER INFORMATION: Artificial peptide sequence derived from
      antigen

<400> SEQUENCE: 72
```

Arg Arg Gly Tyr Ile Pro Leu Val Gly Ala Pro Leu Gly Asx Gly Arg
1               5                   10                  15

Val Ala Arg Ala Leu Ala His Gly Val Arg Val
            20                  25

<210> SEQ ID NO 73
<211> LENGTH: 25
<212> TYPE: PRT
<213> ORGANISM: Artificial
<220> FEATURE:
<223> OTHER INFORMATION: Artificial peptide sequence derived from
      antigen

<400> SEQUENCE: 73

Arg Gly Tyr Ile Pro Leu Val Gly Ala Pro Leu Gly Arg Arg Val Ala
1               5                   10                  15

Arg Ala Leu Ala His Gly Val Arg Val
            20                  25

<210> SEQ ID NO 74
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 74

Arg Gly Tyr Ile Pro Leu Val Gly Ala Pro Leu Gly Arg Arg Arg Val
1               5                   10                  15

Ala Arg Ala Leu Ala His Gly Val Arg Val
            20                  25

<210> SEQ ID NO 75
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 75

Arg Arg Gly Tyr Ile Pro Leu Val Gly Ala Pro Leu Gly Arg Arg Val
1               5                   10                  15

Ala Arg Ala Leu Ala His Gly Val Arg Val
            20                  25

<210> SEQ ID NO 76
<211> LENGTH: 27
<212> TYPE: PRT
<213> ORGANISM: Artificial
<220> FEATURE:
<223> OTHER INFORMATION: Artificial peptide sequence derived from
      antigen

<400> SEQUENCE: 76

Arg Arg Gly Tyr Ile Pro Leu Val Gly Ala Pro Leu Gly Arg Arg Arg
1               5                   10                  15

Val Ala Arg Ala Leu Ala His Gly Val Arg Val
            20                  25

<210> SEQ ID NO 77
<211> LENGTH: 26
<212> TYPE: PRT

<213> ORGANISM: Artificial
<220> FEATURE:
<223> OTHER INFORMATION: Artificial peptide sequence derived from
      antigen

<400> SEQUENCE: 77

Asx Arg Gly Tyr Ile Pro Leu Val Gly Ala Pro Leu Gly Arg Arg Val
1               5                   10                  15

Ala Arg Ala Leu Ala His Gly Val Arg Val
            20                  25

<210> SEQ ID NO 78
<211> LENGTH: 27
<212> TYPE: PRT
<213> ORGANISM: Artificial
<220> FEATURE:
<223> OTHER INFORMATION: Artificial peptide sequence derived from
      antigen

<400> SEQUENCE: 78

Arg Arg Arg Gly Tyr Ile Pro Leu Val Gly Ala Pro Leu Gly Asx Arg
1               5                   10                  15

Val Ala Arg Ala Leu Ala His Gly Val Arg Val
            20                  25

<210> SEQ ID NO 79
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 79

Arg Gly Tyr Ile Pro Leu Val Gly Ala Pro Leu Gly Lys Lys Lys Val
1               5                   10                  15

Ala Arg Ala Leu Ala His Gly Val Arg Val
            20                  25

<210> SEQ ID NO 80
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 80

Arg Gly Tyr Ile Pro Leu Val Gly Ala Pro Leu Gly Arg Arg Arg Val
1               5                   10                  15

Ala Arg Ala Leu Ala His Gly Val Arg Val
            20                  25

<210> SEQ ID NO 81
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 81

Lys Lys Gly Tyr Ile Pro Leu Val Gly Ala Pro Leu Gly Lys Lys Val
1               5                   10                  15

Ala Arg Ala Leu Ala His Gly Val Arg Val

```
            20                  25

<210> SEQ ID NO 82
<211> LENGTH: 25
<212> TYPE: PRT
<213> ORGANISM: Artificial
<220> FEATURE:
<223> OTHER INFORMATION: Artificial peptide sequence derived from
      antigen

<400> SEQUENCE: 82

Trp Gly Tyr Ile Pro Leu Val Gly Ala Pro Leu Gly Arg Arg Val Ala
1               5                   10                  15

Arg Ala Leu Ala His Gly Val Arg Val
            20                  25

<210> SEQ ID NO 83
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 83

Trp Trp Gly Tyr Ile Pro Leu Val Gly Ala Pro Leu Gly Arg Arg Val
1               5                   10                  15

Ala Arg Ala Leu Ala His Gly Val Arg Val
            20                  25

<210> SEQ ID NO 84
<211> LENGTH: 27
<212> TYPE: PRT
<213> ORGANISM: Artificial
<220> FEATURE:
<223> OTHER INFORMATION: Artificial peptide sequence derived from
      antigen

<400> SEQUENCE: 84

Arg Arg Gly Tyr Ile Pro Leu Val Gly Ala Pro Leu Gly Leu Arg Arg
1               5                   10                  15

Val Ala Arg Ala Leu Ala His Gly Val Arg Val
            20                  25

<210> SEQ ID NO 85
<211> LENGTH: 24
<212> TYPE: PRT
<213> ORGANISM: Artificial
<220> FEATURE:
<223> OTHER INFORMATION: Artificial peptide sequence derived from
      antigen

<400> SEQUENCE: 85

Arg Arg Asn Tyr Val Thr Gly Asn Ile Pro Gly Asx Arg Gly Ile Thr
1               5                   10                  15

Phe Ser Ile Phe Leu Ile Val Ser
            20

<210> SEQ ID NO 86
<211> LENGTH: 23
<212> TYPE: PRT
<213> ORGANISM: Artificial
<220> FEATURE:
<223> OTHER INFORMATION: Artificial peptide sequence derived from
      antigen
```

-continued

```
<400> SEQUENCE: 86

Trp Trp Asn Tyr Ala Thr Gly Asn Leu Pro Gly Arg Arg Cys Ser Phe
1               5                   10                  15

Ser Ile Phe Leu Leu Ala Leu
            20

<210> SEQ ID NO 87
<211> LENGTH: 24
<212> TYPE: PRT
<213> ORGANISM: Artificial
<220> FEATURE:
<223> OTHER INFORMATION: Artificial peptide sequence derived from
      antigen

<400> SEQUENCE: 87

Trp Trp Asn Tyr Val Thr Gly Asn Ile Pro Gly Asx Arg Gly Ile Thr
1               5                   10                  15

Phe Ser Ile Phe Leu Ile Val Ser
            20

<210> SEQ ID NO 88
<211> LENGTH: 24
<212> TYPE: PRT
<213> ORGANISM: Artificial
<220> FEATURE:
<223> OTHER INFORMATION: Artificial peptide sequence derived from
      antigen

<400> SEQUENCE: 88

Trp Trp Asn Tyr Val Thr Gly Asn Ile Pro Gly Arg Arg Gly Ile Thr
1               5                   10                  15

Phe Ser Ile Phe Leu Ile Val Ser
            20

<210> SEQ ID NO 89
<211> LENGTH: 24
<212> TYPE: PRT
<213> ORGANISM: Artificial
<220> FEATURE:
<223> OTHER INFORMATION: Artificial peptide sequence derived from
      antigen

<400> SEQUENCE: 89

Arg Arg Asn Tyr Ala Thr Gly Asn Leu Pro Gly Arg Arg Gly Cys Ser
1               5                   10                  15

Phe Ser Ile Phe Leu Leu Ala Leu
            20

<210> SEQ ID NO 90
<211> LENGTH: 27
<212> TYPE: PRT
<213> ORGANISM: Artificial
<220> FEATURE:
<223> OTHER INFORMATION: Artificial peptide sequence derived from
      antigen

<400> SEQUENCE: 90

Arg Arg Val Thr Gly Asn Ile Pro Gly Ser Thr Tyr Ser Gly Asx Arg
1               5                   10                  15

Gly Ile Thr Phe Ser Ile Tyr Leu Ile Val Ser
            20                  25

<210> SEQ ID NO 91
<211> LENGTH: 27
```

```
<212> TYPE: PRT
<213> ORGANISM: Artificial
<220> FEATURE:
<223> OTHER INFORMATION: Artificial peptide sequence derived from
      antigen

<400> SEQUENCE: 91

Arg Arg Ile Arg Asn Leu Gly Arg Val Ile Glu Thr Leu Thr Gly Asx
1               5                   10                  15

Arg Leu Glx Gly Tyr Ile Pro Leu Ile Gly Ala
            20                  25

<210> SEQ ID NO 92
<211> LENGTH: 27
<212> TYPE: PRT
<213> ORGANISM: Artificial
<220> FEATURE:
<223> OTHER INFORMATION: Artificial peptide sequence derived from
      antigen

<400> SEQUENCE: 92

Arg Arg Ser Arg Asn Leu Gly Lys Val Ile Asp Thr Leu Thr Cys Asx
1               5                   10                  15

Arg Leu Met Gly Tyr Ile Pro Leu Val Gly Ala
            20                  25

<210> SEQ ID NO 93
<211> LENGTH: 27
<212> TYPE: PRT
<213> ORGANISM: Artificial
<220> FEATURE:
<223> OTHER INFORMATION: Artificial peptide sequence derived from
      antigen

<400> SEQUENCE: 93

Ser Arg Asn Leu Gly Lys Val Ile Asp Thr Leu Thr Cys Gly Phe Ala
1               5                   10                  15

Asp Leu Met Gly Tyr Ile Pro Leu Val Gly Ala
            20                  25

<210> SEQ ID NO 94
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 94

Trp Trp Ile Arg Asn Leu Gly Arg Val Ile Glu Thr Leu Thr Arg Arg
1               5                   10                  15

Leu Glx Gly Tyr Ile Pro Leu Ile Gly Ala
            20                  25

<210> SEQ ID NO 95
<211> LENGTH: 27
<212> TYPE: PRT
<213> ORGANISM: Artificial
<220> FEATURE:
<223> OTHER INFORMATION: Artificial peptide sequence derived from
      antigen

<400> SEQUENCE: 95

Trp Trp Ser Arg Asn Leu Gly Lys Val Ile Asp Thr Leu Thr Cys Arg
1               5                   10                  15
```

```
Arg Leu Met Gly Tyr Ile Pro Leu Val Gly Ala
            20                  25

<210> SEQ ID NO 96
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 96

Arg Arg Gly Gly Gly Gln Ile Ile Gly Gly Asn Tyr Leu Ile Pro Arg
1               5                   10                  15

Asx Pro Asx Ile Gly Val Arg Ala Thr Asx
            20                  25

<210> SEQ ID NO 97
<211> LENGTH: 25
<212> TYPE: PRT
<213> ORGANISM: Artificial
<220> FEATURE:
<223> OTHER INFORMATION: Artificial peptide sequence derived from
      antigen

<400> SEQUENCE: 97

Gly Gly Gly Gln Ile Val Gly Gly Val Tyr Leu Leu Pro Arg Arg Gly
1               5                   10                  15

Pro Arg Leu Gly Val Arg Ala Thr Arg
            20                  25

<210> SEQ ID NO 98
<211> LENGTH: 27
<212> TYPE: PRT
<213> ORGANISM: Artificial
<220> FEATURE:
<223> OTHER INFORMATION: Artificial peptide sequence derived from
      antigen

<400> SEQUENCE: 98

Arg Arg Gly Gly Gly Gln Ile Val Gly Gly Val Tyr Leu Leu Pro Arg
1               5                   10                  15

Arg Gly Pro Arg Leu Gly Val Arg Ala Thr Arg
            20                  25

<210> SEQ ID NO 99
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 99

Trp Trp Gly Gly Gly Gln Ile Val Gly Gly Val Tyr Leu Leu Pro Arg
1               5                   10                  15

Arg Gly Pro Arg Leu Gly Val Arg Ala Thr
            20                  25

<210> SEQ ID NO 100
<211> LENGTH: 21
<212> TYPE: PRT
<213> ORGANISM: Artificial
<220> FEATURE:
<223> OTHER INFORMATION: Artificial peptide sequence derived from
      antigen
```

```
<400> SEQUENCE: 100

Asx Arg Leu Ile Phe Leu Ala Arg Ser Ala Leu Ile Val Arg Gly Ser
1               5                   10                  15

Val Ala His Lys Ser
            20

<210> SEQ ID NO 101
<211> LENGTH: 21
<212> TYPE: PRT
<213> ORGANISM: Artificial
<220> FEATURE:
<223> OTHER INFORMATION: Artificial peptide sequence derived from
      antigen

<400> SEQUENCE: 101

Glu Asp Leu Ile Phe Leu Ala Arg Ser Ala Leu Ile Leu Arg Gly Ser
1               5                   10                  15

Val Ala His Lys Ser
            20

<210> SEQ ID NO 102
<211> LENGTH: 28
<212> TYPE: PRT
<213> ORGANISM: Artificial
<220> FEATURE:
<223> OTHER INFORMATION: Artificial peptide sequence derived from
      antigen

<400> SEQUENCE: 102

Asx Arg Leu Ile Phe Leu Ala Arg Ser Ala Leu Ile Leu Asx Gly Arg
1               5                   10                  15

Ser Ala Leu Ile Leu Arg Gly Ser Val Ala His Lys
            20                  25

<210> SEQ ID NO 103
<211> LENGTH: 23
<212> TYPE: PRT
<213> ORGANISM: Artificial
<220> FEATURE:
<223> OTHER INFORMATION: Artificial peptide sequence derived from
      antigen

<400> SEQUENCE: 103

Ser Ala Tyr Glu Arg Met Cys Asn Ile Leu Lys Gly Lys Phe Gln Thr
1               5                   10                  15

Ala Ala Gln Arg Ala Met Met
            20

<210> SEQ ID NO 104
<211> LENGTH: 23
<212> TYPE: PRT
<213> ORGANISM: Artificial
<220> FEATURE:
<223> OTHER INFORMATION: Artificial peptide sequence derived from
      antigen

<400> SEQUENCE: 104

Ser Ala Tyr Glu Arg Glx Val Asn Ile Leu Lys Gly Lys Phe Gln Thr
1               5                   10                  15

Ala Ala Gln Arg Ala Val Glx
            20

<210> SEQ ID NO 105
```

```
<211> LENGTH: 24
<212> TYPE: PRT
<213> ORGANISM: Artificial
<220> FEATURE:
<223> OTHER INFORMATION: Artificial peptide sequence derived from
      antigen

<400> SEQUENCE: 105

Asx Arg Thr Ala Tyr Glu Arg Glx Cys Asn Ile Leu Asx Arg Gly Arg
1               5                   10                  15

Phe Gln Thr Val Val Gln Asx Ala
            20

<210> SEQ ID NO 106
<211> LENGTH: 25
<212> TYPE: PRT
<213> ORGANISM: Artificial
<220> FEATURE:
<223> OTHER INFORMATION: Artificial peptide sequence derived from
      antigen

<400> SEQUENCE: 106

Asx Arg Ile Ala Tyr Glu Arg Met Cys Asn Ile Leu Leu Asx Arg Gly
1               5                   10                  15

Lys Phe Gln Thr Ala Ala Gln Arg Ala
            20                  25

<210> SEQ ID NO 107
<211> LENGTH: 21
<212> TYPE: PRT
<213> ORGANISM: Artificial
<220> FEATURE:
<223> OTHER INFORMATION: Artificial peptide sequence derived from
      antigen

<400> SEQUENCE: 107

Ile Ala Tyr Glu Arg Met Cys Asn Ile Leu Lys Gly Lys Phe Gln Thr
1               5                   10                  15

Ala Ala Gln Arg Ala
            20

<210> SEQ ID NO 108
<211> LENGTH: 27
<212> TYPE: PRT
<213> ORGANISM: Artificial
<220> FEATURE:
<223> OTHER INFORMATION: Artificial peptide sequence derived from
      antigen

<400> SEQUENCE: 108

Leu Phe Phe Lys Cys Ile Tyr Arg Leu Phe Lys His Gly Leu Lys Arg
1               5                   10                  15

Gly Pro Ser Thr Glu Gly Val Pro Glu Ser Met
            20                  25

<210> SEQ ID NO 109
<211> LENGTH: 30
<212> TYPE: PRT
<213> ORGANISM: Artificial
<220> FEATURE:
<223> OTHER INFORMATION: Artificial peptide sequence derived from
      antigen

<400> SEQUENCE: 109

Asx Arg Arg Leu Phe Phe Lys Thr Ile Thr Arg Leu Phe Asx His Gly
1               5                   10                  15
```

Leu Arg Arg Leu Leu Ser Thr Glu Gly Val Pro Asn Ser Glx
            20                  25                  30

<210> SEQ ID NO 110
<211> LENGTH: 27
<212> TYPE: PRT
<213> ORGANISM: Artificial
<220> FEATURE:
<223> OTHER INFORMATION: Artificial peptide sequence derived from
      antigen

<400> SEQUENCE: 110

Asx Arg Gly Leu Glu Pro Leu Val Ile Ala Gly Ile Leu Ala Arg Arg
1               5                   10                  15

Gly Ser Leu Val Gly Leu Leu His Ile Val Leu
            20                  25

<210> SEQ ID NO 111
<211> LENGTH: 27
<212> TYPE: PRT
<213> ORGANISM: Artificial
<220> FEATURE:
<223> OTHER INFORMATION: Artificial peptide sequence derived from
      antigen

<400> SEQUENCE: 111

Asx Arg Gly Ser Asp Pro Leu Val Val Ala Ala Ser Ile Val Arg Arg
1               5                   10                  15

Ala Ser Ile Val Gly Ile Leu His Leu Ile Leu
            20                  25

<210> SEQ ID NO 112
<211> LENGTH: 22
<212> TYPE: PRT
<213> ORGANISM: Artificial
<220> FEATURE:
<223> OTHER INFORMATION: Artificial peptide sequence derived from
      antigen

<400> SEQUENCE: 112

Arg Asn Leu Val Pro Met Val Ala Thr Val Arg Arg Asn Leu Val Pro
1               5                   10                  15

Met Val Ala Thr Val Asx
            20

<210> SEQ ID NO 113
<211> LENGTH: 23
<212> TYPE: PRT
<213> ORGANISM: Artificial
<220> FEATURE:
<223> OTHER INFORMATION: Artificial peptide sequence derived from
      antigen

<400> SEQUENCE: 113

Arg Asn Leu Val Pro Met Val Ala Thr Val Asx Arg Arg Asn Leu Val
1               5                   10                  15

Pro Met Val Ala Thr Val Asx
            20

<210> SEQ ID NO 114
<211> LENGTH: 22
<212> TYPE: PRT
<213> ORGANISM: Artificial
<220> FEATURE:
<223> OTHER INFORMATION: Artificial peptide sequence derived from antigen

<400> SEQUENCE: 114

Arg Asn Ile Val Pro Glx Val Val Thr Ala Arg Arg Asn Ile Val Pro
1               5                   10                  15

Glx Val Val Thr Ala Asx
            20

<210> SEQ ID NO 115
<211> LENGTH: 24
<212> TYPE: PRT
<213> ORGANISM: Artificial
<220> FEATURE:
<223> OTHER INFORMATION: Artificial peptide sequence derived from
      antigen

<400> SEQUENCE: 115

Pro Glu Val Ile Pro Met Phe Ser Ala Leu Ser Glu Gly Ala Thr Pro
1               5                   10                  15

Gln Asp Leu Asn Thr Met Leu Asn
            20

<210> SEQ ID NO 116
<211> LENGTH: 27
<212> TYPE: PRT
<213> ORGANISM: Artificial
<220> FEATURE:
<223> OTHER INFORMATION: Artificial peptide sequence derived from
      antigen
<220> FEATURE:
<221> NAME/KEY: misc_feature
<222> LOCATION: (6)..(6)
<223> OTHER INFORMATION: Xaa can be any naturally occurring amino acid

<400> SEQUENCE: 116

Arg Phe Ile Ile Pro Xaa Phe Thr Ala Leu Ser Gly Gly Arg Arg Ala
1               5                   10                  15

Leu Leu Tyr Gly Ala Thr Pro Tyr Ala Ile Gly
            20                  25

<210> SEQ ID NO 117
<211> LENGTH: 20
<212> TYPE: PRT
<213> ORGANISM: Artificial
<220> FEATURE:
<223> OTHER INFORMATION: Artificial peptide sequence derived from
      antigen

<400> SEQUENCE: 117

Lys Ala Leu Gly Pro Ala Ala Thr Leu Glu Glu Met Met Thr Ala Cys
1               5                   10                  15

Gln Gly Val Gly
            20

<210> SEQ ID NO 118
<211> LENGTH: 21
<212> TYPE: PRT
<213> ORGANISM: Artificial
<220> FEATURE:
<223> OTHER INFORMATION: Artificial peptide sequence derived from
      antigen

<400> SEQUENCE: 118

Arg Arg Gly Pro Val Val His Leu Thr Leu Arg Arg Gly Gln Ala
1               5                   10                  15

```
Gly Asp Asp Phe Ser
        20

<210> SEQ ID NO 119
<211> LENGTH: 21
<212> TYPE: PRT
<213> ORGANISM: Artificial
<220> FEATURE:
<223> OTHER INFORMATION: Artificial peptide sequence derived from
      antigen

<400> SEQUENCE: 119

Arg Arg Gly Pro Val Val His Leu Thr Leu Arg Arg Arg Gly Gln Ala
1               5                   10                  15

Gly Asp Asp Phe Ser
        20

<210> SEQ ID NO 120
<211> LENGTH: 22
<212> TYPE: PRT
<213> ORGANISM: Artificial
<220> FEATURE:
<223> OTHER INFORMATION: Artificial peptide sequence derived from
      antigen

<400> SEQUENCE: 120

Arg Arg Gly Pro Val Val His Leu Thr Leu Arg Gly Arg Arg Gly Gln
1               5                   10                  15

Ala Gly Asp Asp Phe Ser
        20

<210> SEQ ID NO 121
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 121

Arg Arg Leu Glu Cys Val Tyr Cys Lys Gln Gln Leu Leu Arg Arg Glu
1               5                   10                  15

Val Tyr Asp Phe Ala Phe Arg Asp Leu Cys
        20                  25

<210> SEQ ID NO 122
<211> LENGTH: 27
<212> TYPE: PRT
<213> ORGANISM: Artificial
<220> FEATURE:
<223> OTHER INFORMATION: Artificial peptide sequence derived from
      antigen

<400> SEQUENCE: 122

Arg Arg Gly Val Tyr Asp Phe Ala Phe Arg Asp Leu Cys Arg Arg Gly
1               5                   10                  15

Phe Ala Phe Arg Asp Leu Cys Ile Val Tyr Arg
        20                  25

<210> SEQ ID NO 123
<211> LENGTH: 27
<212> TYPE: PRT
<213> ORGANISM: Artificial
<220> FEATURE:
<223> OTHER INFORMATION: Artificial peptide sequence derived from
      antigen
```

<400> SEQUENCE: 123

Arg Arg Gly Val Phe Asp Tyr Ala Phe Arg Asp Ile Asn Arg Gly
1               5                   10                  15

Phe Ala Tyr Arg Asp Ile Asn Leu Ala Tyr Arg
            20                  25

<210> SEQ ID NO 124
<211> LENGTH: 24
<212> TYPE: PRT
<213> ORGANISM: Artificial
<220> FEATURE:
<223> OTHER INFORMATION: Artificial peptide sequence derived from
      antigen

<400> SEQUENCE: 124

Arg Arg Gly Ala Thr Pro Val Asp Leu Leu Gly Ala Arg Gly Ala
1               5                   10                  15

Leu Asn Leu Cys Leu Pro Met Arg
            20

<210> SEQ ID NO 125
<211> LENGTH: 24
<212> TYPE: PRT
<213> ORGANISM: Artificial
<220> FEATURE:
<223> OTHER INFORMATION: Artificial peptide sequence derived from
      antigen

<400> SEQUENCE: 125

Arg Arg Gly Val Thr Pro Ala Gly Leu Ile Gly Val Arg Gly Ala
1               5                   10                  15

Leu Gln Ile Asx Leu Pro Leu Arg
            20

<210> SEQ ID NO 126
<211> LENGTH: 98
<212> TYPE: PRT
<213> ORGANISM: Human papillomavirus type 16

<400> SEQUENCE: 126

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 127
<211> LENGTH: 11
<212> TYPE: PRT
<213> ORGANISM: Artificial
<220> FEATURE:
<223> OTHER INFORMATION: Artificial peptide sequence derived from
      antigen

<400> SEQUENCE: 127

Gly Tyr Ile Pro Leu Val Gly Ala Pro Leu Gly
1               5                   10

<210> SEQ ID NO 128
<211> LENGTH: 11
<212> TYPE: PRT
<213> ORGANISM: Artificial
<220> FEATURE:
<223> OTHER INFORMATION: Artificial peptide sequence derived from
      antigen

<400> SEQUENCE: 128

Gly Tyr Leu Pro Ala Val Gly Ala Pro Ile Gly
1               5                   10

<210> SEQ ID NO 129
<211> LENGTH: 10
<212> TYPE: PRT
<213> ORGANISM: Artificial
<220> FEATURE:
<223> OTHER INFORMATION: Artificial peptide sequence derived from
      antigen

<400> SEQUENCE: 129

Gly Tyr Leu Pro Ala Val Gly Ala Pro Ile
1               5                   10

<210> SEQ ID NO 130
<211> LENGTH: 9
<212> TYPE: PRT
<213> ORGANISM: Artificial
<220> FEATURE:
<223> OTHER INFORMATION: Artificial peptide sequence derived from
      antigen

<400> SEQUENCE: 130

Asn Tyr Val Thr Gly Asn Ile Pro Gly
1               5

<210> SEQ ID NO 131
<211> LENGTH: 9
<212> TYPE: PRT
<213> ORGANISM: Artificial
<220> FEATURE:
<223> OTHER INFORMATION: Artificial peptide sequence derived from
      antigen

<400> SEQUENCE: 131

Asn Tyr Ala Thr Gly Asn Leu Pro Gly
1               5

<210> SEQ ID NO 132
<211> LENGTH: 9
<212> TYPE: PRT
<213> ORGANISM: Artificial
<220> FEATURE:
<223> OTHER INFORMATION: Artificial peptide sequence derived from
      antigen

<400> SEQUENCE: 132

Asn Tyr Ala Thr Gly Asn Leu Pro Gly
1               5

<210> SEQ ID NO 133
<211> LENGTH: 11

```
<212> TYPE: PRT
<213> ORGANISM: Artificial
<220> FEATURE:
<223> OTHER INFORMATION: Artificial peptide sequence derived from
      antigen

<400> SEQUENCE: 133

Val Thr Gly Asn Ile Pro Gly Ser Thr Tyr Ser
1               5                   10

<210> SEQ ID NO 134
<211> LENGTH: 13
<212> TYPE: PRT
<213> ORGANISM: Artificial
<220> FEATURE:
<223> OTHER INFORMATION: Artificial peptide sequence derived from
      antigen

<400> SEQUENCE: 134

Ile Arg Asn Leu Gly Arg Val Ile Glu Thr Leu Thr Gly
1               5                   10

<210> SEQ ID NO 135
<211> LENGTH: 13
<212> TYPE: PRT
<213> ORGANISM: Artificial
<220> FEATURE:
<223> OTHER INFORMATION: Artificial peptide sequence derived from
      antigen

<400> SEQUENCE: 135

Ser Arg Asn Leu Gly Lys Val Ile Asp Thr Leu Thr Cys
1               5                   10

<210> SEQ ID NO 136
<211> LENGTH: 12
<212> TYPE: PRT
<213> ORGANISM: Artificial
<220> FEATURE:
<223> OTHER INFORMATION: Artificial peptide sequence derived from
      antigen

<400> SEQUENCE: 136

Ile Arg Asn Leu Gly Arg Val Ile Glu Thr Leu Thr
1               5                   10

<210> SEQ ID NO 137
<211> LENGTH: 13
<212> TYPE: PRT
<213> ORGANISM: Artificial
<220> FEATURE:
<223> OTHER INFORMATION: Artificial peptide sequence derived from
      antigen

<400> SEQUENCE: 137

Gly Gly Gly Gln Ile Ile Gly Gly Asn Tyr Leu Ile Pro
1               5                   10

<210> SEQ ID NO 138
<211> LENGTH: 13
<212> TYPE: PRT
<213> ORGANISM: Artificial
<220> FEATURE:
<223> OTHER INFORMATION: Artificial peptide sequence derived from
      antigen

<400> SEQUENCE: 138

Gly Gly Gly Gln Ile Val Gly Gly Val Tyr Leu Leu Pro
```

<210> SEQ ID NO 139
<211> LENGTH: 11
<212> TYPE: PRT
<213> ORGANISM: Artificial
<220> FEATURE:
<223> OTHER INFORMATION: Artificial peptide sequence derived from
      antigen

<400> SEQUENCE: 139

Leu Ile Phe Leu Ala Arg Ser Ala Leu Ile Val
1               5                   10

<210> SEQ ID NO 140
<211> LENGTH: 11
<212> TYPE: PRT
<213> ORGANISM: Artificial
<220> FEATURE:
<223> OTHER INFORMATION: Artificial peptide sequence derived from
      antigen

<400> SEQUENCE: 140

Leu Ile Phe Leu Ala Arg Ser Ala Leu Ile Leu
1               5                   10

<210> SEQ ID NO 141
<211> LENGTH: 11
<212> TYPE: PRT
<213> ORGANISM: Artificial
<220> FEATURE:
<223> OTHER INFORMATION: Artificial peptide sequence derived from
      antigen

<400> SEQUENCE: 141

Leu Ile Phe Leu Ala Arg Ser Ala Leu Ile Leu
1               5                   10

<210> SEQ ID NO 142
<211> LENGTH: 10
<212> TYPE: PRT
<213> ORGANISM: Artificial
<220> FEATURE:
<223> OTHER INFORMATION: Artificial peptide sequence derived from
      antigen

<400> SEQUENCE: 142

Ser Ala Tyr Glu Arg Met Cys Asn Ile Leu
1               5                   10

<210> SEQ ID NO 143
<211> LENGTH: 10
<212> TYPE: PRT
<213> ORGANISM: Artificial
<220> FEATURE:
<223> OTHER INFORMATION: Artificial peptide sequence derived from
      antigen

<400> SEQUENCE: 143

Ser Ala Tyr Glu Arg Glx Val Asn Ile Leu
1               5                   10

<210> SEQ ID NO 144
<211> LENGTH: 10
<212> TYPE: PRT
<213> ORGANISM: Artificial
<220> FEATURE:
<223> OTHER INFORMATION: Artificial peptide sequence derived from antigen

<400> SEQUENCE: 144

Thr Ala Tyr Glu Arg Glx Cys Asn Ile Leu
1               5                   10

<210> SEQ ID NO 145
<211> LENGTH: 10
<212> TYPE: PRT
<213> ORGANISM: Artificial
<220> FEATURE:
<223> OTHER INFORMATION: Artificial peptide sequence derived from
      antigen

<400> SEQUENCE: 145

Ile Ala Tyr Glu Arg Met Cys Asn Ile Leu
1               5                   10

<210> SEQ ID NO 146
<211> LENGTH: 10
<212> TYPE: PRT
<213> ORGANISM: Artificial
<220> FEATURE:
<223> OTHER INFORMATION: Artificial peptide sequence derived from
      antigen

<400> SEQUENCE: 146

Ile Ala Tyr Glu Arg Met Cys Asn Ile Leu
1               5                   10

<210> SEQ ID NO 147
<211> LENGTH: 14
<212> TYPE: PRT
<213> ORGANISM: Artificial
<220> FEATURE:
<223> OTHER INFORMATION: Artificial peptide sequence derived from
      antigen

<400> SEQUENCE: 147

Leu Phe Phe Lys Cys Ile Tyr Arg Leu Phe Lys His Gly Leu
1               5                   10

<210> SEQ ID NO 148
<211> LENGTH: 14
<212> TYPE: PRT
<213> ORGANISM: Artificial
<220> FEATURE:
<223> OTHER INFORMATION: Artificial peptide sequence derived from
      antigen

<400> SEQUENCE: 148

Leu Phe Phe Lys Thr Ile Thr Arg Leu Phe Asx His Gly Leu
1               5                   10

<210> SEQ ID NO 149
<211> LENGTH: 12
<212> TYPE: PRT
<213> ORGANISM: Artificial
<220> FEATURE:
<223> OTHER INFORMATION: Artificial peptide sequence derived from
      antigen

<400> SEQUENCE: 149

Gly Leu Glu Pro Leu Val Ile Ala Gly Ile Leu Ala
1               5                   10

<210> SEQ ID NO 150

```
<211> LENGTH: 12
<212> TYPE: PRT
<213> ORGANISM: Artificial
<220> FEATURE:
<223> OTHER INFORMATION: Artificial peptide sequence derived from
      antigen

<400> SEQUENCE: 150

Gly Ser Asp Pro Leu Val Val Ala Ala Ser Ile Val
1               5                   10

<210> SEQ ID NO 151
<211> LENGTH: 9
<212> TYPE: PRT
<213> ORGANISM: Artificial
<220> FEATURE:
<223> OTHER INFORMATION: Artificial peptide sequence derived from
      antigen

<400> SEQUENCE: 151

Asn Leu Val Pro Met Val Ala Thr Val
1               5

<210> SEQ ID NO 152
<211> LENGTH: 9
<212> TYPE: PRT
<213> ORGANISM: Artificial
<220> FEATURE:
<223> OTHER INFORMATION: Artificial peptide sequence derived from
      antigen

<400> SEQUENCE: 152

Asn Leu Val Pro Met Val Ala Thr Val
1               5

<210> SEQ ID NO 153
<211> LENGTH: 9
<212> TYPE: PRT
<213> ORGANISM: Artificial
<220> FEATURE:
<223> OTHER INFORMATION: Artificial peptide sequence derived from
      antigen

<400> SEQUENCE: 153

Asn Ile Val Pro Glx Val Val Thr Ala
1               5

<210> SEQ ID NO 154
<211> LENGTH: 11
<212> TYPE: PRT
<213> ORGANISM: Artificial
<220> FEATURE:
<223> OTHER INFORMATION: Artificial peptide sequence derived from
      antigen

<400> SEQUENCE: 154

Pro Glu Val Ile Pro Met Phe Ser Ala Leu Ser
1               5                   10

<210> SEQ ID NO 155
<211> LENGTH: 11
<212> TYPE: PRT
<213> ORGANISM: Artificial
<220> FEATURE:
<223> OTHER INFORMATION: Artificial peptide sequence derived from
      antigen
<220> FEATURE:
<221> NAME/KEY: misc_feature
<222> LOCATION: (5)..(5)
```

<223> OTHER INFORMATION: Xaa can be any naturally occurring amino acid

<400> SEQUENCE: 155

Phe Ile Ile Pro Xaa Phe Thr Ala Leu Ser Gly
1               5                   10

<210> SEQ ID NO 156
<211> LENGTH: 8
<212> TYPE: PRT
<213> ORGANISM: Artificial
<220> FEATURE:
<223> OTHER INFORMATION: Artificial peptide sequence derived from
      antigen

<400> SEQUENCE: 156

Ala Leu Gly Pro Ala Ala Thr Leu
1               5

<210> SEQ ID NO 157
<211> LENGTH: 8
<212> TYPE: PRT
<213> ORGANISM: Artificial
<220> FEATURE:
<223> OTHER INFORMATION: Artificial peptide sequence derived from
      antigen

<400> SEQUENCE: 157

Gly Pro Val Val His Leu Thr Leu
1               5

<210> SEQ ID NO 158
<211> LENGTH: 11
<212> TYPE: PRT
<213> ORGANISM: Artificial
<220> FEATURE:
<223> OTHER INFORMATION: Artificial peptide sequence derived from
      antigen

<400> SEQUENCE: 158

Leu Glu Cys Val Tyr Cys Lys Gln Gln Leu Leu
1               5                   10

<210> SEQ ID NO 159
<211> LENGTH: 11
<212> TYPE: PRT
<213> ORGANISM: Artificial
<220> FEATURE:
<223> OTHER INFORMATION: Artificial peptide sequence derived from
      antigen

<400> SEQUENCE: 159

Gly Val Tyr Asp Phe Ala Phe Arg Asp Leu Cys
1               5                   10

<210> SEQ ID NO 160
<211> LENGTH: 11
<212> TYPE: PRT
<213> ORGANISM: Artificial
<220> FEATURE:
<223> OTHER INFORMATION: Artificial peptide sequence derived from
      antigen

<400> SEQUENCE: 160

Gly Val Phe Asp Tyr Ala Phe Arg Asp Ile Asn
1               5                   10

<210> SEQ ID NO 161

```
<211> LENGTH: 10
<212> TYPE: PRT
<213> ORGANISM: Artificial
<220> FEATURE:
<223> OTHER INFORMATION: Artificial peptide sequence derived from
      antigen

<400> SEQUENCE: 161

Gly Ala Thr Pro Val Asp Leu Leu Gly Ala
1               5                   10

<210> SEQ ID NO 162
<211> LENGTH: 10
<212> TYPE: PRT
<213> ORGANISM: Artificial
<220> FEATURE:
<223> OTHER INFORMATION: Artificial peptide sequence derived from
      antigen

<400> SEQUENCE: 162

Gly Val Thr Pro Ala Gly Leu Ile Gly Val
1               5                   10

<210> SEQ ID NO 163
<211> LENGTH: 11
<212> TYPE: PRT
<213> ORGANISM: Artificial
<220> FEATURE:
<223> OTHER INFORMATION: Artificial peptide sequence derived from
      antigen

<400> SEQUENCE: 163

Val Ala Arg Ala Leu Ala His Gly Val Arg Val
1               5                   10

<210> SEQ ID NO 164
<211> LENGTH: 11
<212> TYPE: PRT
<213> ORGANISM: Artificial
<220> FEATURE:
<223> OTHER INFORMATION: Artificial peptide sequence derived from
      antigen

<400> SEQUENCE: 164

Val Ile Arg Val Ile Ala His Gly Leu Arg Leu
1               5                   10

<210> SEQ ID NO 165
<211> LENGTH: 11
<212> TYPE: PRT
<213> ORGANISM: Artificial
<220> FEATURE:
<223> OTHER INFORMATION: Artificial peptide sequence derived from
      antigen

<400> SEQUENCE: 165

Gly Ile Thr Phe Ser Ile Phe Leu Ile Val Ser
1               5                   10

<210> SEQ ID NO 166
<211> LENGTH: 10
<212> TYPE: PRT
<213> ORGANISM: Artificial
<220> FEATURE:
<223> OTHER INFORMATION: Artificial peptide sequence derived from
      antigen

<400> SEQUENCE: 166
```

```
Cys Ser Phe Ser Ile Phe Leu Leu Ala Leu
1               5                   10
```

<210> SEQ ID NO 167
<211> LENGTH: 11
<212> TYPE: PRT
<213> ORGANISM: Artificial
<220> FEATURE:
<223> OTHER INFORMATION: Artificial peptide sequence derived from
      antigen

<400> SEQUENCE: 167

```
Gly Cys Ser Phe Ser Ile Phe Leu Leu Ala Leu
1               5                   10
```

<210> SEQ ID NO 168
<211> LENGTH: 11
<212> TYPE: PRT
<213> ORGANISM: Artificial
<220> FEATURE:
<223> OTHER INFORMATION: Artificial peptide sequence derived from
      antigen

<400> SEQUENCE: 168

```
Gly Ile Thr Phe Ser Ile Tyr Leu Ile Val Ser
1               5                   10
```

<210> SEQ ID NO 169
<211> LENGTH: 10
<212> TYPE: PRT
<213> ORGANISM: Artificial
<220> FEATURE:
<223> OTHER INFORMATION: Artificial peptide sequence derived from
      antigen

<400> SEQUENCE: 169

```
Leu Glx Gly Tyr Ile Pro Leu Ile Gly Ala
1               5                   10
```

<210> SEQ ID NO 170
<211> LENGTH: 10
<212> TYPE: PRT
<213> ORGANISM: Artificial
<220> FEATURE:
<223> OTHER INFORMATION: Artificial peptide sequence derived from
      antigen

<400> SEQUENCE: 170

```
Leu Met Gly Tyr Ile Pro Leu Val Gly Ala
1               5                   10
```

<210> SEQ ID NO 171
<211> LENGTH: 10
<212> TYPE: PRT
<213> ORGANISM: Artificial
<220> FEATURE:
<223> OTHER INFORMATION: Artificial peptide sequence derived from
      antigen

<400> SEQUENCE: 171

```
Leu Glx Gly Tyr Ile Pro Leu Ile Gly Ala
1               5                   10
```

<210> SEQ ID NO 172
<211> LENGTH: 9
<212> TYPE: PRT
<213> ORGANISM: Artificial
<220> FEATURE:

```
<223> OTHER INFORMATION: Artificial peptide sequence derived from
      antigen

<400> SEQUENCE: 172

Pro Asx Ile Gly Val Arg Ala Thr Asx
1               5

<210> SEQ ID NO 173
<211> LENGTH: 10
<212> TYPE: PRT
<213> ORGANISM: Artificial
<220> FEATURE:
<223> OTHER INFORMATION: Artificial peptide sequence derived from
      antigen

<400> SEQUENCE: 173

Gly Pro Arg Leu Gly Val Arg Ala Thr Arg
1               5                   10

<210> SEQ ID NO 174
<211> LENGTH: 9
<212> TYPE: PRT
<213> ORGANISM: Artificial
<220> FEATURE:
<223> OTHER INFORMATION: Artificial peptide sequence derived from
      antigen

<400> SEQUENCE: 174

Gly Pro Arg Leu Gly Val Arg Ala Thr
1               5

<210> SEQ ID NO 175
<211> LENGTH: 8
<212> TYPE: PRT
<213> ORGANISM: Artificial
<220> FEATURE:
<223> OTHER INFORMATION: Artificial peptide sequence derived from
      antigen

<400> SEQUENCE: 175

Arg Gly Ser Val Ala His Lys Ser
1               5

<210> SEQ ID NO 176
<211> LENGTH: 12
<212> TYPE: PRT
<213> ORGANISM: Artificial
<220> FEATURE:
<223> OTHER INFORMATION: Artificial peptide sequence derived from
      antigen

<400> SEQUENCE: 176

Ser Ala Leu Ile Leu Arg Gly Ser Val Ala His Lys
1               5                   10

<210> SEQ ID NO 177
<211> LENGTH: 10
<212> TYPE: PRT
<213> ORGANISM: Artificial
<220> FEATURE:
<223> OTHER INFORMATION: Artificial peptide sequence derived from
      antigen

<400> SEQUENCE: 177

Phe Gln Thr Ala Ala Gln Arg Ala Met Met
1               5                   10
```

```
<210> SEQ ID NO 178
<211> LENGTH: 10
<212> TYPE: PRT
<213> ORGANISM: Artificial
<220> FEATURE:
<223> OTHER INFORMATION: Artificial peptide sequence derived from
      antigen

<400> SEQUENCE: 178

Phe Gln Thr Ala Ala Gln Arg Ala Val Glx
1               5                   10

<210> SEQ ID NO 179
<211> LENGTH: 8
<212> TYPE: PRT
<213> ORGANISM: Artificial
<220> FEATURE:
<223> OTHER INFORMATION: Artificial peptide sequence derived from
      antigen

<400> SEQUENCE: 179

Phe Gln Thr Val Val Gln Asx Ala
1               5

<210> SEQ ID NO 180
<211> LENGTH: 8
<212> TYPE: PRT
<213> ORGANISM: Artificial
<220> FEATURE:
<223> OTHER INFORMATION: Artificial peptide sequence derived from
      antigen

<400> SEQUENCE: 180

Phe Gln Thr Ala Ala Gln Arg Ala
1               5

<210> SEQ ID NO 181
<211> LENGTH: 11
<212> TYPE: PRT
<213> ORGANISM: Artificial
<220> FEATURE:
<223> OTHER INFORMATION: Artificial peptide sequence derived from
      antigen

<400> SEQUENCE: 181

Gly Pro Ser Thr Glu Gly Val Pro Glu Ser Met
1               5                   10

<210> SEQ ID NO 182
<211> LENGTH: 11
<212> TYPE: PRT
<213> ORGANISM: Artificial
<220> FEATURE:
<223> OTHER INFORMATION: Artificial peptide sequence derived from
      antigen

<400> SEQUENCE: 182

Leu Leu Ser Thr Glu Gly Val Pro Asn Ser Glx
1               5                   10

<210> SEQ ID NO 183
<211> LENGTH: 11
<212> TYPE: PRT
<213> ORGANISM: Artificial
<220> FEATURE:
<223> OTHER INFORMATION: Artificial peptide sequence derived from
      antigen

<400> SEQUENCE: 183
```

```
Gly Ser Leu Val Gly Leu Leu His Ile Val Leu
1               5                   10

<210> SEQ ID NO 184
<211> LENGTH: 11
<212> TYPE: PRT
<213> ORGANISM: Artificial
<220> FEATURE:
<223> OTHER INFORMATION: Artificial peptide sequence derived from
      antigen

<400> SEQUENCE: 184

Ala Ser Ile Val Gly Ile Leu His Leu Ile Leu
1               5                   10

<210> SEQ ID NO 185
<211> LENGTH: 9
<212> TYPE: PRT
<213> ORGANISM: Artificial
<220> FEATURE:
<223> OTHER INFORMATION: Artificial peptide sequence derived from
      antigen

<400> SEQUENCE: 185

Asn Leu Val Pro Met Val Ala Thr Val
1               5

<210> SEQ ID NO 186
<211> LENGTH: 9
<212> TYPE: PRT
<213> ORGANISM: Artificial
<220> FEATURE:
<223> OTHER INFORMATION: Artificial peptide sequence derived from
      antigen

<400> SEQUENCE: 186

Asn Ile Val Pro Glx Val Val Thr Ala
1               5

<210> SEQ ID NO 187
<211> LENGTH: 10
<212> TYPE: PRT
<213> ORGANISM: Artificial
<220> FEATURE:
<223> OTHER INFORMATION: Artificial peptide sequence derived from
      antigen

<400> SEQUENCE: 187

Thr Pro Gln Asp Leu Asn Thr Met Leu Asn
1               5                   10

<210> SEQ ID NO 188
<211> LENGTH: 12
<212> TYPE: PRT
<213> ORGANISM: Artificial
<220> FEATURE:
<223> OTHER INFORMATION: Artificial peptide sequence derived from
      antigen

<400> SEQUENCE: 188

Ala Leu Leu Tyr Gly Ala Thr Pro Tyr Ala Ile Gly
1               5                   10

<210> SEQ ID NO 189
<211> LENGTH: 9
<212> TYPE: PRT
<213> ORGANISM: Artificial
```

```
<220> FEATURE:
<223> OTHER INFORMATION: Artificial peptide sequence derived from
      antigen

<400> SEQUENCE: 189

Met Met Thr Ala Cys Gln Gly Val Gly
1               5

<210> SEQ ID NO 190
<211> LENGTH: 8
<212> TYPE: PRT
<213> ORGANISM: Artificial
<220> FEATURE:
<223> OTHER INFORMATION: Artificial peptide sequence derived from
      antigen

<400> SEQUENCE: 190

Gly Gln Ala Gly Asp Asp Phe Ser
1               5

<210> SEQ ID NO 191
<211> LENGTH: 11
<212> TYPE: PRT
<213> ORGANISM: Artificial
<220> FEATURE:
<223> OTHER INFORMATION: Artificial peptide sequence derived from
      antigen

<400> SEQUENCE: 191

Glu Val Tyr Asp Phe Ala Phe Arg Asp Leu Cys
1               5                   10

<210> SEQ ID NO 192
<211> LENGTH: 11
<212> TYPE: PRT
<213> ORGANISM: Artificial
<220> FEATURE:
<223> OTHER INFORMATION: Artificial peptide sequence derived from
      antigen

<400> SEQUENCE: 192

Gly Phe Ala Phe Arg Asp Leu Cys Ile Val Tyr
1               5                   10

<210> SEQ ID NO 193
<211> LENGTH: 11
<212> TYPE: PRT
<213> ORGANISM: Artificial
<220> FEATURE:
<223> OTHER INFORMATION: Artificial peptide sequence derived from
      antigen

<400> SEQUENCE: 193

Gly Phe Ala Tyr Arg Asp Ile Asn Leu Ala Tyr
1               5                   10

<210> SEQ ID NO 194
<211> LENGTH: 9
<212> TYPE: PRT
<213> ORGANISM: Artificial
<220> FEATURE:
<223> OTHER INFORMATION: Artificial peptide sequence derived from
      antigen

<400> SEQUENCE: 194

Gly Ala Leu Asn Leu Cys Leu Pro Met
1               5
```

<210> SEQ ID NO 195
<211> LENGTH: 9
<212> TYPE: PRT
<213> ORGANISM: Artificial
<220> FEATURE:
<223> OTHER INFORMATION: Artificial peptide sequence derived from
      antigen

<400> SEQUENCE: 195

Gly Ala Leu Gln Ile Asx Leu Pro Leu
1               5

<210> SEQ ID NO 196
<211> LENGTH: 27
<212> TYPE: PRT
<213> ORGANISM: Artificial Sequence
<220> FEATURE:
<223> OTHER INFORMATION: Artificial peptide sequence derived from
      antigen

<400> SEQUENCE: 196

Arg Gly Tyr Leu Pro Ala Val Gly Ala Pro Ile Gly Arg Arg Arg Val
1               5                   10                  15

Ile Arg Val Ile Ala His Gly Leu Arg Leu Arg
            20                  25

<210> SEQ ID NO 197
<211> LENGTH: 27
<212> TYPE: PRT
<213> ORGANISM: Artificial Sequence
<220> FEATURE:
<223> OTHER INFORMATION: Artificial peptide sequence derived from
      antigen

<400> SEQUENCE: 197

Arg Arg Ser Arg Asn Leu Gly Lys Val Ile Asp Thr Leu Thr Cys Arg
1               5                   10                  15

Arg Leu Met Gly Tyr Ile Pro Leu Val Gly Ala
            20                  25

<210> SEQ ID NO 198
<211> LENGTH: 22
<212> TYPE: PRT
<213> ORGANISM: Artificial Sequence
<220> FEATURE:
<223> OTHER INFORMATION: Artificial peptide sequence derived from
      antigen

<400> SEQUENCE: 198

Ile Arg Asn Leu Gly Arg Val Ile Glu Thr Leu Thr Leu Glx Gly Tyr
1               5                   10                  15

Ile Pro Leu Ile Gly Ala
            20

<210> SEQ ID NO 199
<211> LENGTH: 49
<212> TYPE: PRT
<213> ORGANISM: Artificial Sequence
<220> FEATURE:
<223> OTHER INFORMATION: Artificial peptide sequence derived from
      antigen

<400> SEQUENCE: 199

Arg Arg Ile Arg Asn Leu Gly Arg Val Ile Glu Thr Leu Thr Leu Glx
1               5                   10                  15

```
Gly Tyr Ile Pro Leu Ile Gly Ala Arg Arg Ile Arg Asn Leu Gly Arg
            20                  25                  30

Val Ile Glu Thr Leu Thr Leu Glx Gly Tyr Ile Pro Leu Ile Gly Ala
            35                  40                  45

Arg
```

<210> SEQ ID NO 200
<211> LENGTH: 97
<212> TYPE: PRT
<213> ORGANISM: Influenza A virus

<400> SEQUENCE: 200

```
Met Ser Leu Leu Thr Glu Val Glu Thr Pro Ile Arg Asn Glu Trp Gly
1               5                   10                  15

Cys Arg Cys Asn Gly Ser Ser Asp Pro Leu Ala Ile Ala Ala Asn Ile
            20                  25                  30

Ile Gly Ile Leu His Leu Thr Leu Trp Ile Leu Asp Arg Leu Phe Phe
            35                  40                  45

Lys Cys Ile Tyr Arg Arg Phe Lys Tyr Gly Leu Lys Gly Gly Pro Ser
        50                  55                  60

Thr Glu Gly Val Pro Lys Ser Met Arg Glu Glu Tyr Arg Lys Glu Gln
65                  70                  75                  80

Gln Ser Ala Val Asp Ala Asp Asp Gly His Phe Val Ser Ile Glu Leu
                85                  90                  95

Glu
```

<210> SEQ ID NO 201
<211> LENGTH: 86
<212> TYPE: PRT
<213> ORGANISM: HIV

<400> SEQUENCE: 201

```
Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
            35                  40                  45

Arg Lys Lys Arg Arg Gln Arg Arg Ala His Gln Asn Ser Gln Thr
        50                  55                  60

His Gln Ala Ser Leu Ser Lys Gln Pro Thr Ser Gln Pro Arg Gly Asp
65                  70                  75                  80

Pro Thr Gly Pro Lys Glu
                85
```

<210> SEQ ID NO 202
<211> LENGTH: 511
<212> TYPE: PRT
<213> ORGANISM: HIV

<400> SEQUENCE: 202

```
Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
            35                  40                  45
```

```
Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Val Val Ile
            260                 265                 270

Arg Ser Val Asn Phe Thr Asp Asn Ala Lys Thr Ile Ile Val Gln Leu
        275                 280                 285

Asn Thr Ser Val Glu Ile Asn Cys Thr Arg Pro Asn Asn Asn Thr Arg
290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
        355                 360                 365

Pro Glu Ile Val Thr His Ser Phe Asn Cys Gly Gly Glu Phe Phe Tyr
370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
        435                 440                 445

Ile Thr Gly Leu Leu Leu Thr Arg Asp Gly Gly Asn Ser Asn Asn Glu
450                 455                 460

Ser Glu Ile Phe Arg Pro Gly Gly Gly Asp Met Arg Asp Asn Trp Arg
```

```
                    465                 470                 475                 480
Ser Glu Leu Tyr Lys Tyr Lys Val Val Lys Ile Glu Pro Leu Gly Val
                        485                 490                 495

Ala Pro Thr Lys Ala Lys Arg Val Val Gln Arg Glu Lys Arg
                        500                 505                 510

<210> SEQ ID NO 203
<211> LENGTH: 345
<212> TYPE: PRT
<213> ORGANISM: HIV

<400> SEQUENCE: 203

Ala Val Gly Ile Gly Ala Leu Phe Leu Gly Phe Leu Gly Ala Ala Gly
1               5                   10                  15

Ser Thr Met Gly Ala Ala Ser Met Thr Leu Thr Val Gln Ala Arg Gln
                20                  25                  30

Leu Leu Ser Gly Ile Val Gln Gln Gln Asn Asn Leu Leu Arg Ala Ile
            35                  40                  45

Glu Ala Gln Gln His Leu Leu Gln Leu Thr Val Trp Gly Ile Lys Gln
        50                  55                  60

Leu Gln Ala Arg Ile Leu Ala Val Glu Arg Tyr Leu Lys Asp Gln Gln
65                  70                  75                  80

Leu Leu Gly Ile Trp Gly Cys Ser Gly Lys Leu Ile Cys Thr Thr Ala
                85                  90                  95

Val Pro Trp Asn Ala Ser Trp Ser Asn Lys Ser Leu Glu Gln Ile Trp
                100                 105                 110

Asn His Thr Thr Trp Met Glu Trp Asp Arg Glu Ile Asn Asn Tyr Thr
            115                 120                 125

Ser Leu Ile His Ser Leu Ile Glu Glu Ser Gln Asn Gln Gln Glu Lys
        130                 135                 140

Asn Glu Gln Glu Leu Leu Glu Leu Asp Lys Trp Ala Ser Leu Trp Asn
145                 150                 155                 160

Trp Phe Asn Ile Thr Asn Trp Leu Trp Tyr Ile Lys Leu Phe Ile Met
                165                 170                 175

Ile Val Gly Gly Leu Val Gly Leu Arg Ile Val Phe Ala Val Leu Ser
                180                 185                 190

Ile Val Asn Arg Val Arg Gln Gly Tyr Ser Pro Leu Ser Phe Gln Thr
            195                 200                 205

His Leu Pro Thr Pro Arg Gly Pro Asp Arg Pro Glu Gly Ile Glu Glu
        210                 215                 220

Glu Gly Gly Glu Arg Asp Arg Asp Arg Ser Ile Arg Leu Val Asn Gly
225                 230                 235                 240

Ser Leu Ala Leu Ile Trp Asp Asp Leu Arg Ser Leu Cys Leu Phe Ser
                245                 250                 255

Tyr His Arg Leu Arg Asp Leu Leu Leu Ile Val Thr Arg Ile Val Glu
                260                 265                 270

Leu Leu Gly Arg Arg Gly Trp Glu Ala Leu Lys Tyr Trp Trp Asn Leu
            275                 280                 285

Leu Gln Tyr Trp Ser Gln Glu Leu Lys Asn Ser Ala Val Ser Leu Leu
        290                 295                 300

Asn Ala Thr Ala Ile Ala Val Ala Glu Gly Thr Asp Arg Val Ile Glu
305                 310                 315                 320

Val Val Gln Gly Ala Cys Arg Ala Ile Arg His Ile Pro Arg Arg Ile
                325                 330                 335
```

Arg Gln Gly Leu Glu Arg Ile Leu Leu
        340                 345

<210> SEQ ID NO 204
<211> LENGTH: 192
<212> TYPE: PRT
<213> ORGANISM: HCV

<400> SEQUENCE: 204

Tyr Glu Val Arg Asn Val Ser Gly Val Tyr His Val Thr Asn Asp Cys
1               5                   10                  15

Ser Asn Ser Ser Ile Val Tyr Gly Ala Ala Asp Met Ile Met His Thr
            20                  25                  30

Pro Gly Cys Val Pro Cys Val Arg Glu Asn Asn Ser Ser Arg Cys Trp
        35                  40                  45

Val Ala Leu Thr Pro Thr Leu Ala Ala Arg Asn Arg Ser Ile Pro Thr
    50                  55                  60

Thr Thr Ile Arg Arg His Val Asp Leu Leu Val Gly Ala Ala Ala Phe
65                  70                  75                  80

Cys Ser Ala Met Tyr Val Gly Asp Leu Cys Gly Ser Val Phe Leu Val
                85                  90                  95

Ser Gln Leu Phe Thr Phe Ser Pro Arg Arg Tyr Glu Thr Val Gln Asp
            100                 105                 110

Cys Asn Cys Ser Leu Tyr Pro Gly His Val Ser Gly His Arg Met Ala
        115                 120                 125

Trp Asp Met Met Met Asn Trp Ser Pro Thr Ala Ala Leu Val Val Ser
    130                 135                 140

Gln Leu Leu Arg Ile Pro Gln Ala Val Val Asp Met Val Thr Gly Ala
145                 150                 155                 160

His Trp Gly Val Leu Ala Gly Leu Ala Tyr Tyr Ser Met Val Gly Asn
                165                 170                 175

Trp Ala Lys Val Leu Ile Val Met Leu Leu Phe Ala Gly Val Asp Gly
            180                 185                 190

<210> SEQ ID NO 205
<211> LENGTH: 363
<212> TYPE: PRT
<213> ORGANISM: HCV

<400> SEQUENCE: 205

Thr Thr His Val Thr Gly Gly Gln Thr Gly Arg Thr Thr Leu Gly Ile
1               5                   10                  15

Thr Ala Met Phe Ala Phe Gly Pro His Gln Lys Leu Gln Leu Ile Asn
            20                  25                  30

Thr Asn Gly Ser Trp His Ile Asn Arg Thr Ala Leu Asn Cys Asn Asp
        35                  40                  45

Ser Leu Asn Thr Gly Phe Leu Ala Ala Leu Phe Tyr Ala Arg Lys Phe
    50                  55                  60

Asn Ser Ser Gly Cys Pro Glu Arg Met Ala Ser Cys Arg Pro Ile Asp
65                  70                  75                  80

Lys Phe Val Gln Gly Trp Gly Pro Ile Thr His Ala Val Pro Asp Asn
                85                  90                  95

Leu Asp Gln Arg Pro Tyr Cys Trp His Tyr Ala Pro Gln Pro Cys Gly
            100                 105                 110

Ile Ile Pro Ala Ser Gln Val Cys Gly Pro Val Tyr Cys Phe Thr Pro
        115                 120                 125

Ser Pro Val Val Gly Thr Thr Asp Arg Phe Gly Ala Pro Thr Tyr
            130                 135                 140

Thr Trp Gly Glu Asn Glu Thr Asp Val Leu Leu Asn Asn Thr Arg
145                 150                 155                 160

Pro Pro Gln Gly Asn Trp Phe Gly Cys Thr Trp Met Asn Gly Thr Gly
                165                 170                 175

Phe Ala Lys Thr Cys Gly Gly Pro Pro Cys Asn Ile Gly Gly Val Gly
                180                 185                 190

Asn Asn Thr Leu Thr Cys Pro Thr Asp Cys Phe Arg Lys His Pro Glu
                195                 200                 205

Ala Thr Tyr Thr Lys Cys Gly Ser Gly Pro Trp Leu Thr Pro Arg Cys
            210                 215                 220

Met Val Asp Tyr Pro Tyr Arg Leu Trp His Tyr Pro Cys Thr Val Asn
225                 230                 235                 240

Phe Thr Ile Phe Lys Val Arg Met Tyr Val Gly Gly Val Glu His Arg
                245                 250                 255

Leu Thr Ala Ala Cys Asn Trp Thr Arg Gly Glu Arg Cys Asp Leu Glu
                260                 265                 270

Asp Arg Asp Arg Ser Glu Leu Ser Pro Leu Leu Leu Ser Thr Thr Glu
            275                 280                 285

Trp Gln Val Leu Pro Cys Ser Phe Thr Thr Leu Pro Ala Leu Ser Thr
            290                 295                 300

Gly Leu Ile His Leu His Gln Asn Ile Val Asp Val Gln Tyr Leu Tyr
305                 310                 315                 320

Gly Val Gly Ser Ala Val Val Ser Ile Val Ile Lys Trp Glu Tyr Ile
                325                 330                 335

Leu Leu Leu Phe Leu Leu Leu Ala Asp Ala Arg Val Cys Ala Cys Leu
                340                 345                 350

Trp Met Met Leu Leu Ile Ala Gln Ala Glu Ala
            355                 360

<210> SEQ ID NO 206
<211> LENGTH: 4
<212> TYPE: PRT
<213> ORGANISM: Artificial Sequence
<220> FEATURE:
<223> OTHER INFORMATION: Artificial peptide sequence

<400> SEQUENCE: 206

Trp Trp Gly Cys
1

<210> SEQ ID NO 207
<211> LENGTH: 4
<212> TYPE: PRT
<213> ORGANISM: Artificial Sequence
<220> FEATURE:
<223> OTHER INFORMATION: Artificial peptide sequence

<400> SEQUENCE: 207

Arg Arg Glx Cys
1

<210> SEQ ID NO 208
<211> LENGTH: 4
<212> TYPE: PRT
<213> ORGANISM: Artificial Sequence
<220> FEATURE:
<223> OTHER INFORMATION: Artificial peptide sequence

```
<400> SEQUENCE: 208

Trp Trp Gln Cys
1

<210> SEQ ID NO 209
<211> LENGTH: 5
<212> TYPE: PRT
<213> ORGANISM: Artificial Sequence
<220> FEATURE:
<223> OTHER INFORMATION: Artificial peptide sequence

<400> SEQUENCE: 209

Trp Asp Trp Gly Cys
1               5

<210> SEQ ID NO 210
<211> LENGTH: 4
<212> TYPE: PRT
<213> ORGANISM: Artificial Sequence
<220> FEATURE:
<223> OTHER INFORMATION: Artificial peptide sequence

<400> SEQUENCE: 210

Cys Gly Gly Gly
1

<210> SEQ ID NO 211
<211> LENGTH: 4
<212> TYPE: PRT
<213> ORGANISM: Artificial Sequence
<220> FEATURE:
<223> OTHER INFORMATION: Artificial peptide sequence

<400> SEQUENCE: 211

Gly Cys Gly Gly
1

<210> SEQ ID NO 212
<211> LENGTH: 5
<212> TYPE: PRT
<213> ORGANISM: Artificial Sequence
<220> FEATURE:
<223> OTHER INFORMATION: Artificial peptide sequence

<400> SEQUENCE: 212

Gly Gly Cys Gly Gly
1               5

<210> SEQ ID NO 213
<211> LENGTH: 5
<212> TYPE: PRT
<213> ORGANISM: Artificial Sequence
<220> FEATURE:
<223> OTHER INFORMATION: Artificial peptide sequence

<400> SEQUENCE: 213

Cys Gly Gly Lys Gly
1               5

<210> SEQ ID NO 214
<211> LENGTH: 6
<212> TYPE: PRT
<213> ORGANISM: Artificial Sequence
<220> FEATURE:
<223> OTHER INFORMATION: Artificial peptide sequence

<400> SEQUENCE: 214
```

Cys Gly Gly Lys Gly Gly
1               5

<210> SEQ ID NO 215
<211> LENGTH: 5
<212> TYPE: PRT
<213> ORGANISM: Artificial Sequence
<220> FEATURE:
<223> OTHER INFORMATION: Artificial peptide sequence

<400> SEQUENCE: 215

Gly Gly Lys Gly Gly
1               5

<210> SEQ ID NO 216
<211> LENGTH: 9
<212> TYPE: PRT
<213> ORGANISM: Artificial Sequence
<220> FEATURE:
<223> OTHER INFORMATION: Artificial peptide sequence

<400> SEQUENCE: 216

Ser Leu Leu Thr Glu Val Glu Thr Pro
1               5

<210> SEQ ID NO 217
<211> LENGTH: 9
<212> TYPE: PRT
<213> ORGANISM: Artificial Sequence
<220> FEATURE:
<223> OTHER INFORMATION: Artificial peptide sequence

<400> SEQUENCE: 217

Ser Leu Glx Thr Asp Ile Glu Thr Pro
1               5

<210> SEQ ID NO 218
<211> LENGTH: 5
<212> TYPE: PRT
<213> ORGANISM: Artificial Sequence
<220> FEATURE:
<223> OTHER INFORMATION: Artificial peptide sequence

<400> SEQUENCE: 218

Thr Asp Ile Glu Thr
1               5

<210> SEQ ID NO 219
<211> LENGTH: 5
<212> TYPE: PRT
<213> ORGANISM: Artificial Sequence
<220> FEATURE:
<223> OTHER INFORMATION: Artificial peptide sequence

<400> SEQUENCE: 219

Cys Ser Leu Leu Thr
1               5

<210> SEQ ID NO 220
<211> LENGTH: 12
<212> TYPE: PRT
<213> ORGANISM: Artificial Sequence
<220> FEATURE:
<223> OTHER INFORMATION: Artificial peptide sequence

<400> SEQUENCE: 220

```
Ser Leu Leu Thr Glu Val Gln Thr Pro Ile Arg Asn
1               5                   10

<210> SEQ ID NO 221
<211> LENGTH: 12
<212> TYPE: PRT
<213> ORGANISM: Artificial Sequence
<220> FEATURE:
<223> OTHER INFORMATION: Artificial peptide sequence

<400> SEQUENCE: 221

Thr Pro Ile Arg Ser Glu Trp Gly Cys Arg Ser Asn
1               5                   10

<210> SEQ ID NO 222
<211> LENGTH: 6
<212> TYPE: PRT
<213> ORGANISM: Artificial Sequence
<220> FEATURE:
<223> OTHER INFORMATION: Artificial peptide sequence

<400> SEQUENCE: 222

Ile Asp Thr Pro Ile Arg
1               5

<210> SEQ ID NO 223
<211> LENGTH: 5
<212> TYPE: PRT
<213> ORGANISM: Artificial Sequence
<220> FEATURE:
<223> OTHER INFORMATION: Artificial peptide sequence

<400> SEQUENCE: 223

Ala Lys Arg Arg Val
1               5

<210> SEQ ID NO 224
<211> LENGTH: 5
<212> TYPE: PRT
<213> ORGANISM: Artificial Sequence
<220> FEATURE:
<223> OTHER INFORMATION: Artificial peptide sequence

<400> SEQUENCE: 224

Ile Glu Glu Glu Gly
1               5

<210> SEQ ID NO 225
<211> LENGTH: 6
<212> TYPE: PRT
<213> ORGANISM: Artificial Sequence
<220> FEATURE:
<223> OTHER INFORMATION: Artificial peptide sequence

<400> SEQUENCE: 225

Ala Lys Arg Arg Val Val
1               5

<210> SEQ ID NO 226
<211> LENGTH: 5
<212> TYPE: PRT
<213> ORGANISM: Artificial Sequence
<220> FEATURE:
<223> OTHER INFORMATION: Artificial peptide sequence

<400> SEQUENCE: 226

Asp Gln Gln Leu Leu
```

```
1               5

<210> SEQ ID NO 227
<211> LENGTH: 6
<212> TYPE: PRT
<213> ORGANISM: Artificial Sequence
<220> FEATURE:
<223> OTHER INFORMATION: Artificial peptide sequence

<400> SEQUENCE: 227

Ala Glu Glu Glu Val Val
1               5

<210> SEQ ID NO 228
<211> LENGTH: 5
<212> TYPE: PRT
<213> ORGANISM: Artificial Sequence
<220> FEATURE:
<223> OTHER INFORMATION: Artificial peptide sequence

<400> SEQUENCE: 228

Gly Ile Glu Glu Glu
1               5

<210> SEQ ID NO 229
<211> LENGTH: 11
<212> TYPE: PRT
<213> ORGANISM: Artificial Sequence
<220> FEATURE:
<223> OTHER INFORMATION: Artificial peptide sequence

<400> SEQUENCE: 229

Ile Glu Glu Glu Gly Gly Arg Asp Arg Asp Arg
1               5                   10

<210> SEQ ID NO 230
<211> LENGTH: 8
<212> TYPE: PRT
<213> ORGANISM: Artificial Sequence
<220> FEATURE:
<223> OTHER INFORMATION: Artificial peptide sequence

<400> SEQUENCE: 230

Cys Ala Lys Arg Arg Val Val Cys
1               5

<210> SEQ ID NO 231
<211> LENGTH: 12
<212> TYPE: PRT
<213> ORGANISM: Artificial Sequence
<220> FEATURE:
<223> OTHER INFORMATION: Artificial peptide sequence

<400> SEQUENCE: 231

Ile Glu Glu Glu Gly Gly Glu Arg Asp Arg Asp Arg
1               5                   10

<210> SEQ ID NO 232
<211> LENGTH: 11
<212> TYPE: PRT
<213> ORGANISM: Artificial Sequence
<220> FEATURE:
<223> OTHER INFORMATION: Artificial peptide sequence

<400> SEQUENCE: 232

Ile Glu Glu Glu Gly Gly Gln Asp Arg Asp Arg
1               5                   10
```

```
<210> SEQ ID NO 233
<211> LENGTH: 12
<212> TYPE: PRT
<213> ORGANISM: Artificial Sequence
<220> FEATURE:
<223> OTHER INFORMATION: Artificial peptide sequence

<400> SEQUENCE: 233

Ile Glu Glu Glu Gly Gly Glu Gln Asp Arg Asp Arg
1               5                   10

<210> SEQ ID NO 234
<211> LENGTH: 10
<212> TYPE: PRT
<213> ORGANISM: Artificial Sequence
<220> FEATURE:
<223> OTHER INFORMATION: Artificial peptide sequence

<400> SEQUENCE: 234

Glu Glu Glu Ile Gly Gly Arg Asp Arg Asp
1               5                   10

<210> SEQ ID NO 235
<211> LENGTH: 7
<212> TYPE: PRT
<213> ORGANISM: Artificial Sequence
<220> FEATURE:
<223> OTHER INFORMATION: Artificial peptide sequence

<400> SEQUENCE: 235

Arg Leu Glu Pro Trp Lys His
1               5

<210> SEQ ID NO 236
<211> LENGTH: 5
<212> TYPE: PRT
<213> ORGANISM: Artificial Sequence
<220> FEATURE:
<223> OTHER INFORMATION: Artificial peptide sequence

<400> SEQUENCE: 236

Phe His Ser Gln Val
1               5

<210> SEQ ID NO 237
<211> LENGTH: 10
<212> TYPE: PRT
<213> ORGANISM: Artificial Sequence
<220> FEATURE:
<223> OTHER INFORMATION: Artificial peptide sequence

<400> SEQUENCE: 237

Phe Ile Thr Lys Gly Leu Gly Ile Ser Tyr
1               5                   10

<210> SEQ ID NO 238
<211> LENGTH: 9
<212> TYPE: PRT
<213> ORGANISM: Artificial Sequence
<220> FEATURE:
<223> OTHER INFORMATION: Artificial peptide sequence

<400> SEQUENCE: 238

Leu Leu Ala Asp Ala Arg Val Cys Ser
1               5
```

<210> SEQ ID NO 239
<211> LENGTH: 10
<212> TYPE: PRT
<213> ORGANISM: Artificial Sequence
<220> FEATURE:
<223> OTHER INFORMATION: Artificial peptide sequence

<400> SEQUENCE: 239

Gly Val Glx Ala Gly Ile Ala Tyr Phe Ser
1               5                   10

<210> SEQ ID NO 240
<211> LENGTH: 6
<212> TYPE: PRT
<213> ORGANISM: Artificial Sequence
<220> FEATURE:
<223> OTHER INFORMATION: Artificial peptide sequence

<400> SEQUENCE: 240

Val Glu Thr Pro Ile Arg
1               5

<210> SEQ ID NO 241
<211> LENGTH: 7
<212> TYPE: PRT
<213> ORGANISM: Artificial Sequence
<220> FEATURE:
<223> OTHER INFORMATION: Artificial peptide sequence

<400> SEQUENCE: 241

Val Glu Thr Pro Ile Arg Asn
1               5

<210> SEQ ID NO 242
<211> LENGTH: 5
<212> TYPE: PRT
<213> ORGANISM: Artificial Sequence
<220> FEATURE:
<223> OTHER INFORMATION: Artificial peptide sequence

<400> SEQUENCE: 242

Ser Asn Asp Ser Ser
1               5

<210> SEQ ID NO 243
<211> LENGTH: 8
<212> TYPE: PRT
<213> ORGANISM: Artificial Sequence
<220> FEATURE:
<223> OTHER INFORMATION: Artificial peptide sequence

<400> SEQUENCE: 243

Thr Pro Ile Asx Gln Asp Trp Gly
1               5

<210> SEQ ID NO 244
<211> LENGTH: 12
<212> TYPE: PRT
<213> ORGANISM: Artificial Sequence
<220> FEATURE:
<223> OTHER INFORMATION: Artificial peptide sequence

<400> SEQUENCE: 244

Ala Lys Arg Arg Val Val Gln Arg Glu Lys Arg Ala
1               5                   10

```
<210> SEQ ID NO 245
<211> LENGTH: 10
<212> TYPE: PRT
<213> ORGANISM: Artificial Sequence
<220> FEATURE:
<223> OTHER INFORMATION: Artificial peptide sequence

<400> SEQUENCE: 245

Ile Glu Glu Glu Gly Gly Glu Arg Asp Arg
1               5                   10

<210> SEQ ID NO 246
<211> LENGTH: 6
<212> TYPE: PRT
<213> ORGANISM: Artificial Sequence
<220> FEATURE:
<223> OTHER INFORMATION: Artificial peptide sequence

<400> SEQUENCE: 246

Ala Glu Glu Glu Ile Val
1               5

<210> SEQ ID NO 247
<211> LENGTH: 5
<212> TYPE: PRT
<213> ORGANISM: Artificial Sequence
<220> FEATURE:
<223> OTHER INFORMATION: Artificial peptide sequence

<400> SEQUENCE: 247

Arg Asp Arg Asp Arg
1               5

<210> SEQ ID NO 248
<211> LENGTH: 6
<212> TYPE: PRT
<213> ORGANISM: Artificial Sequence
<220> FEATURE:
<223> OTHER INFORMATION: Artificial peptide sequence

<400> SEQUENCE: 248

Glu Arg Asp Arg Asp Arg
1               5

<210> SEQ ID NO 249
<211> LENGTH: 12
<212> TYPE: PRT
<213> ORGANISM: Artificial Sequence
<220> FEATURE:
<223> OTHER INFORMATION: Artificial peptide sequence

<400> SEQUENCE: 249

Ala Lys Arg Arg Val Val Glu Arg Glu Lys Arg Ala
1               5                   10

<210> SEQ ID NO 250
<211> LENGTH: 5
<212> TYPE: PRT
<213> ORGANISM: Artificial Sequence
<220> FEATURE:
<223> OTHER INFORMATION: Artificial peptide sequence

<400> SEQUENCE: 250

Gln Asp Arg Asp Arg
1               5

<210> SEQ ID NO 251
```

```
<211> LENGTH: 6
<212> TYPE: PRT
<213> ORGANISM: Artificial Sequence
<220> FEATURE:
<223> OTHER INFORMATION: Artificial peptide sequence

<400> SEQUENCE: 251

Glu Gln Asp Arg Asp Arg
1               5

<210> SEQ ID NO 252
<211> LENGTH: 5
<212> TYPE: PRT
<213> ORGANISM: Artificial Sequence
<220> FEATURE:
<223> OTHER INFORMATION: Artificial peptide sequence

<400> SEQUENCE: 252

Arg Asp Arg Asp Gln
1               5

<210> SEQ ID NO 253
<211> LENGTH: 7
<212> TYPE: PRT
<213> ORGANISM: Artificial Sequence
<220> FEATURE:
<223> OTHER INFORMATION: Artificial peptide sequence

<400> SEQUENCE: 253

Gly Ser Gln Pro Lys Thr Ala
1               5

<210> SEQ ID NO 254
<211> LENGTH: 13
<212> TYPE: PRT
<213> ORGANISM: Artificial Sequence
<220> FEATURE:
<223> OTHER INFORMATION: Artificial peptide sequence

<400> SEQUENCE: 254

Phe Ile Thr Lys Gly Leu Gly Ile Ser Tyr Gly Arg Lys
1               5                   10

<210> SEQ ID NO 255
<211> LENGTH: 9
<212> TYPE: PRT
<213> ORGANISM: Artificial Sequence
<220> FEATURE:
<223> OTHER INFORMATION: Artificial peptide sequence

<400> SEQUENCE: 255

Leu Leu Ala Asp Ala Arg Val Ser Ala
1               5

<210> SEQ ID NO 256
<211> LENGTH: 10
<212> TYPE: PRT
<213> ORGANISM: Artificial Sequence
<220> FEATURE:
<223> OTHER INFORMATION: Artificial peptide sequence

<400> SEQUENCE: 256

Gly Val Leu Ala Gly Ile Ala Tyr Tyr Ser
1               5                   10

<210> SEQ ID NO 257
<211> LENGTH: 8
```

```
<212> TYPE: PRT
<213> ORGANISM: Artificial Sequence
<220> FEATURE:
<223> OTHER INFORMATION: Artificial peptide sequence

<400> SEQUENCE: 257

Thr Pro Ile Arg Asn Glu Trp Gly
1               5

<210> SEQ ID NO 258
<211> LENGTH: 8
<212> TYPE: PRT
<213> ORGANISM: Artificial Sequence
<220> FEATURE:
<223> OTHER INFORMATION: Artificial peptide sequence

<400> SEQUENCE: 258

Ser Glu Trp Gly Ser Arg Ser Asn
1               5

<210> SEQ ID NO 259
<211> LENGTH: 10
<212> TYPE: PRT
<213> ORGANISM: Artificial Sequence
<220> FEATURE:
<223> OTHER INFORMATION: Artificial peptide sequence

<400> SEQUENCE: 259

Ser Leu Glx Thr Asp Ile Glu Thr Pro Gly
1               5                   10

<210> SEQ ID NO 260
<211> LENGTH: 7
<212> TYPE: PRT
<213> ORGANISM: Artificial Sequence
<220> FEATURE:
<223> OTHER INFORMATION: Artificial peptide sequence

<400> SEQUENCE: 260

Gln Arg Glu Lys Arg Ala Val
1               5

<210> SEQ ID NO 261
<211> LENGTH: 5
<212> TYPE: PRT
<213> ORGANISM: Artificial Sequence
<220> FEATURE:
<223> OTHER INFORMATION: Artificial peptide sequence

<400> SEQUENCE: 261

Gln Arg Glu Lys Arg
1               5

<210> SEQ ID NO 262
<211> LENGTH: 6
<212> TYPE: PRT
<213> ORGANISM: Artificial Sequence
<220> FEATURE:
<223> OTHER INFORMATION: Artificial peptide sequence

<400> SEQUENCE: 262

Ile Glu Glu Glu Gly Gly
1               5

<210> SEQ ID NO 263
<211> LENGTH: 6
<212> TYPE: PRT
```

```
<213> ORGANISM: Artificial Sequence
<220> FEATURE:
<223> OTHER INFORMATION: Artificial peptide sequence

<400> SEQUENCE: 263

Glu Arg Glu Lys Arg Ala
1               5

<210> SEQ ID NO 264
<211> LENGTH: 6
<212> TYPE: PRT
<213> ORGANISM: Artificial Sequence
<220> FEATURE:
<223> OTHER INFORMATION: Artificial peptide sequence

<400> SEQUENCE: 264

Gln Arg Glu Lys Arg Ala
1               5

<210> SEQ ID NO 265
<211> LENGTH: 5
<212> TYPE: PRT
<213> ORGANISM: Artificial Sequence
<220> FEATURE:
<223> OTHER INFORMATION: Artificial peptide sequence

<400> SEQUENCE: 265

Glu Arg Asp Arg Asp
1               5

<210> SEQ ID NO 266
<211> LENGTH: 5
<212> TYPE: PRT
<213> ORGANISM: Artificial Sequence
<220> FEATURE:
<223> OTHER INFORMATION: Artificial peptide sequence

<400> SEQUENCE: 266

His Pro Gly Ser Gln
1               5

<210> SEQ ID NO 267
<211> LENGTH: 25
<212> TYPE: PRT
<213> ORGANISM: Artificial Sequence
<220> FEATURE:
<223> OTHER INFORMATION: Artificial peptide sequence

<400> SEQUENCE: 267

Cys Gly Gly Ala Lys Arg Arg Val Val Gly Gly Ala Lys Arg Arg Val
1               5                   10                  15

Val Gly Gln Arg Glu Lys Arg Ala Val
            20                  25

<210> SEQ ID NO 268
<211> LENGTH: 31
<212> TYPE: PRT
<213> ORGANISM: Artificial Sequence
<220> FEATURE:
<223> OTHER INFORMATION: Artificial peptide sequence

<400> SEQUENCE: 268

Cys Gly Gly Gly Asp Gln Gln Leu Leu Gly Gly Ala Glu Glu Glu Ile
1               5                   10                  15

Val Gly Gly Ile Glu Glu Glu Gly Gly Glu Arg Asp Arg Asp Arg
            20                  25                  30
```

```
<210> SEQ ID NO 269
<211> LENGTH: 24
<212> TYPE: PRT
<213> ORGANISM: Artificial Sequence
<220> FEATURE:
<223> OTHER INFORMATION: Artificial peptide sequence

<400> SEQUENCE: 269

Cys Gly Gly Ala Lys Arg Arg Val Val Gly Gly Ala Lys Arg Arg Val
1               5                   10                  15

Val Gly Gly Gln Arg Glu Lys Arg
            20

<210> SEQ ID NO 270
<211> LENGTH: 25
<212> TYPE: PRT
<213> ORGANISM: Artificial Sequence
<220> FEATURE:
<223> OTHER INFORMATION: Artificial peptide sequence

<400> SEQUENCE: 270

Cys Gly Gly Gly Asp Gln Gln Leu Leu Gly Gly Ala Glu Glu Glu Ile
1               5                   10                  15

Val Gly Gly Ile Glu Glu Glu Gly Gly
            20                  25

<210> SEQ ID NO 271
<211> LENGTH: 16
<212> TYPE: PRT
<213> ORGANISM: Artificial Sequence
<220> FEATURE:
<223> OTHER INFORMATION: Artificial peptide sequence

<400> SEQUENCE: 271

Cys Gly Gly Ala Glu Glu Glu Val Val Gly Gly Asp Gln Gln Leu Leu
1               5                   10                  15

<210> SEQ ID NO 272
<211> LENGTH: 18
<212> TYPE: PRT
<213> ORGANISM: Artificial Sequence
<220> FEATURE:
<223> OTHER INFORMATION: Artificial peptide sequence

<400> SEQUENCE: 272

Gly Cys Gly Gly Ala Lys Arg Arg Val Val Gly Gly Ala Lys Arg Arg
1               5                   10                  15

Val Val

<210> SEQ ID NO 273
<211> LENGTH: 31
<212> TYPE: PRT
<213> ORGANISM: Artificial Sequence
<220> FEATURE:
<223> OTHER INFORMATION: Artificial peptide sequence

<400> SEQUENCE: 273

Gly Ala Lys Arg Arg Val Val Gly Gly Cys Gly Gly Ala Lys Arg Arg
1               5                   10                  15

Val Val Gln Arg Glu Lys Arg Ala Gly Glu Arg Glu Lys Arg Ala
            20                  25                  30

<210> SEQ ID NO 274
```

```
<211> LENGTH: 23
<212> TYPE: PRT
<213> ORGANISM: Artificial Sequence
<220> FEATURE:
<223> OTHER INFORMATION: Artificial peptide sequence

<400> SEQUENCE: 274

Gly Lys Gly Gly Ile Glu Glu Glu Gly Gly Arg Asp Arg Asp Arg Gly
1               5                   10                  15

Gly Glu Gln Asp Arg Asp Arg
            20

<210> SEQ ID NO 275
<211> LENGTH: 31
<212> TYPE: PRT
<213> ORGANISM: Artificial Sequence
<220> FEATURE:
<223> OTHER INFORMATION: Artificial peptide sequence

<400> SEQUENCE: 275

Gly Ala Lys Arg Arg Val Val Gly Gly Cys Gly Gly Ala Lys Arg Arg
1               5                   10                  15

Val Val Gln Arg Glu Lys Arg Ala Gly Glu Arg Glu Lys Arg Ala
            20                  25                  30

<210> SEQ ID NO 276
<211> LENGTH: 23
<212> TYPE: PRT
<213> ORGANISM: Artificial Sequence
<220> FEATURE:
<223> OTHER INFORMATION: Artificial peptide sequence

<400> SEQUENCE: 276

Gly Lys Gly Gly Ile Glu Glu Glu Gly Gly Glu Arg Asp Arg Asp Arg
1               5                   10                  15

Gly Gly Gln Asp Arg Asp Arg
            20

<210> SEQ ID NO 277
<211> LENGTH: 31
<212> TYPE: PRT
<213> ORGANISM: Artificial Sequence
<220> FEATURE:
<223> OTHER INFORMATION: Artificial peptide sequence

<400> SEQUENCE: 277

Gly Ala Lys Arg Arg Val Val Gly Gly Cys Gly Gly Ala Lys Arg Arg
1               5                   10                  15

Val Val Glu Arg Glu Lys Arg Ala Gly Gln Arg Glu Lys Arg Ala
            20                  25                  30

<210> SEQ ID NO 278
<211> LENGTH: 22
<212> TYPE: PRT
<213> ORGANISM: Artificial Sequence
<220> FEATURE:
<223> OTHER INFORMATION: Artificial peptide sequence

<400> SEQUENCE: 278

Gly Lys Gly Gly Ile Glu Glu Glu Gly Gly Gln Asp Arg Asp Arg Gly
1               5                   10                  15

Gly Arg Asp Arg Asp Arg
            20
```

```
<210> SEQ ID NO 279
<211> LENGTH: 31
<212> TYPE: PRT
<213> ORGANISM: Artificial Sequence
<220> FEATURE:
<223> OTHER INFORMATION: Artificial peptide sequence

<400> SEQUENCE: 279

Gly Ala Lys Arg Arg Val Val Gly Gly Cys Gly Gly Ala Lys Arg Arg
1               5                   10                  15

Val Val Glu Arg Glu Lys Arg Ala Gly Gln Arg Glu Lys Arg Ala
            20                  25                  30

<210> SEQ ID NO 280
<211> LENGTH: 23
<212> TYPE: PRT
<213> ORGANISM: Artificial Sequence
<220> FEATURE:
<223> OTHER INFORMATION: Artificial peptide sequence

<400> SEQUENCE: 280

Gly Lys Gly Gly Ile Glu Glu Glu Gly Glu Gln Asp Arg Asp Arg
1               5                   10                  15

Gly Gly Glu Arg Asp Arg Asp
            20

<210> SEQ ID NO 281
<211> LENGTH: 31
<212> TYPE: PRT
<213> ORGANISM: Artificial Sequence
<220> FEATURE:
<223> OTHER INFORMATION: Artificial peptide sequence

<400> SEQUENCE: 281

Gly Ala Lys Arg Arg Val Val Gly Gly Ser Gly Gly Ala Lys Arg Arg
1               5                   10                  15

Val Val Gln Arg Glu Lys Arg Ala Gly Glu Arg Glu Lys Arg Ala
            20                  25                  30

<210> SEQ ID NO 282
<211> LENGTH: 16
<212> TYPE: PRT
<213> ORGANISM: Artificial Sequence
<220> FEATURE:
<223> OTHER INFORMATION: Artificial peptide sequence

<400> SEQUENCE: 282

Arg Arg Gly Asn Trp Ala Lys Val Leu Lys Asn Trp Ala Lys Val Ile
1               5                   10                  15

<210> SEQ ID NO 283
<211> LENGTH: 21
<212> TYPE: PRT
<213> ORGANISM: Artificial Sequence
<220> FEATURE:
<223> OTHER INFORMATION: Artificial peptide sequence

<400> SEQUENCE: 283

Arg Arg Gly Leu Leu Ala Asp Ala Arg Val Gly Cys Gly Ser Gly Ala
1               5                   10                  15

Asp Arg Val Cys Ser
            20

<210> SEQ ID NO 284
<211> LENGTH: 16
```

```
<212> TYPE: PRT
<213> ORGANISM: Artificial Sequence
<220> FEATURE:
<223> OTHER INFORMATION: Artificial peptide sequence
<220> FEATURE:
<221> NAME/KEY: MISC_FEATURE
<222> LOCATION: (10)..(10)
<223> OTHER INFORMATION: X at position 10 is Dpr

<400> SEQUENCE: 284

Arg Arg Gly Asn Trp Ala Lys Val Leu Xaa Asn Trp Ala Lys Val Ile
1               5                   10                  15

<210> SEQ ID NO 285
<211> LENGTH: 21
<212> TYPE: PRT
<213> ORGANISM: Artificial Sequence
<220> FEATURE:
<223> OTHER INFORMATION: Artificial peptide sequence
<220> FEATURE:
<221> NAME/KEY: MISC_FEATURE
<222> LOCATION: (12)..(12)
<223> OTHER INFORMATION: X in position 12 is Dpr(Ser)

<400> SEQUENCE: 285

Arg Arg Gly Leu Leu Ala Asp Ala Arg Val Gly Xaa Gly Ser Gly Ala
1               5                   10                  15

Asp Arg Val Cys Ser
            20

<210> SEQ ID NO 286
<211> LENGTH: 16
<212> TYPE: PRT
<213> ORGANISM: Artificial Sequence
<220> FEATURE:
<223> OTHER INFORMATION: Artificial peptide sequenc
<220> FEATURE:
<221> NAME/KEY: MISC_FEATURE
<222> LOCATION: (10)..(10)
<223> OTHER INFORMATION: X in position 10 is an N-epsilon-methylated Lys
      residue

<400> SEQUENCE: 286

Arg Arg Gly Asn Trp Ala Lys Val Leu Xaa Asn Trp Ala Lys Val Ile
1               5                   10                  15

<210> SEQ ID NO 287
<211> LENGTH: 21
<212> TYPE: PRT
<213> ORGANISM: Artificial Sequence
<220> FEATURE:
<223> OTHER INFORMATION: Artificial peptide sequence

<400> SEQUENCE: 287

Arg Arg Gly Leu Leu Ala Asp Ala Arg Val Gly Glu Gly Ser Gly Ala
1               5                   10                  15

Asp Arg Val Cys Ser
            20

<210> SEQ ID NO 288
<211> LENGTH: 21
<212> TYPE: PRT
<213> ORGANISM: Artificial Sequence
<220> FEATURE:
<223> OTHER INFORMATION: Artificial peptide sequence

<400> SEQUENCE: 288

Arg Arg Gly Leu Leu Ala Asp Ala Arg Val Gly Asp Gly Ser Gly Ala
```

```
1               5                   10                  15

Asp Arg Val Cys Ser
            20

<210> SEQ ID NO 289
<211> LENGTH: 16
<212> TYPE: PRT
<213> ORGANISM: Artificial Sequence
<220> FEATURE:
<223> OTHER INFORMATION: Artificial peptide sequence

<400> SEQUENCE: 289

Arg Arg Gly Asn Trp Ala Lys Val Leu Glu Asn Trp Ala Lys Val Ile
1               5                   10                  15

<210> SEQ ID NO 290
<211> LENGTH: 22
<212> TYPE: PRT
<213> ORGANISM: Artificial Sequence
<220> FEATURE:
<223> OTHER INFORMATION: Artificial peptide sequence
<220> FEATURE:
<221> NAME/KEY: MISC_FEATURE
<222> LOCATION: (12)..(12)
<223> OTHER INFORMATION: X in position 12 is N-epsilon-methylated Lys
      residue
<220> FEATURE:
<221> NAME/KEY: misc_feature
<222> LOCATION: (13)..(13)
<223> OTHER INFORMATION: Xaa can be any naturally occurring amino acid

<400> SEQUENCE: 290

Arg Arg Gly Leu Leu Ala Asp Ala Arg Val Gly Lys Xaa Gly Ser Gly
1               5                   10                  15

Ala Asp Arg Val Cys Ser
            20

<210> SEQ ID NO 291
<211> LENGTH: 16
<212> TYPE: PRT
<213> ORGANISM: Artificial Sequence
<220> FEATURE:
<223> OTHER INFORMATION: Artificial peptide sequence

<400> SEQUENCE: 291

Arg Arg Gly Asn Trp Ala Lys Val Leu Asp Asn Trp Ala Lys Val Ile
1               5                   10                  15

<210> SEQ ID NO 292
<211> LENGTH: 26
<212> TYPE: PRT
<213> ORGANISM: Artificial Sequence
<220> FEATURE:
<223> OTHER INFORMATION: Artificial peptide sequence
<220> FEATURE:
<221> NAME/KEY: MISC_FEATURE
<222> LOCATION: (11)..(11)
<223> OTHER INFORMATION: X in position 11 is Dpr

<400> SEQUENCE: 292

Arg Ser Leu Glx Thr Asp Ile Glu Thr Pro Xaa Ile Asp Thr Pro Ile
1               5                   10                  15

Arg Gly Thr Pro Ile Asx Gln Asp Trp Gly
            20                  25

<210> SEQ ID NO 293
<211> LENGTH: 28
```

<212> TYPE: PRT
<213> ORGANISM: Artificial Sequence
<220> FEATURE:
<223> OTHER INFORMATION: Artificial peptide sequence
<220> FEATURE:
<221> NAME/KEY: MISC_FEATURE
<222> LOCATION: (14)..(14)
<223> OTHER INFORMATION: X in position 14 is Har
<220> FEATURE:
<221> NAME/KEY: MISC_FEATURE
<222> LOCATION: (18)..(18)
<223> OTHER INFORMATION: X in position 18 is Dpr(ser)

<400> SEQUENCE: 293

Arg Arg Ile Asp Thr Pro Ile Arg Gly Gly Thr Pro Ile Xaa Gln Glu
1               5                   10                  15

Trp Xaa Ser Leu Glx Thr Asp Ile Glu Thr Pro Gly
            20                  25

<210> SEQ ID NO 294
<211> LENGTH: 19
<212> TYPE: PRT
<213> ORGANISM: Artificial Sequence
<220> FEATURE:
<223> OTHER INFORMATION: Artificial peptide sequence

<400> SEQUENCE: 294

Met Ser Leu Leu Thr Glu Val Glu Thr Pro Ile Arg Asn Glu Trp Gly
1               5                   10                  15

Cys Arg Cys

<210> SEQ ID NO 295
<211> LENGTH: 21
<212> TYPE: PRT
<213> ORGANISM: Artificial Sequence
<220> FEATURE:
<223> OTHER INFORMATION: Artificial peptide sequence

<400> SEQUENCE: 295

Gly Gly Ala Lys Arg Arg Val Val Gln Arg Glu Lys Arg Ala Gly Glu
1               5                   10                  15

Arg Glu Lys Arg Ala
            20

<210> SEQ ID NO 296
<211> LENGTH: 21
<212> TYPE: PRT
<213> ORGANISM: Artificial Sequence
<220> FEATURE:
<223> OTHER INFORMATION: Artificial peptide sequence

<400> SEQUENCE: 296

Gly Gly Ile Glu Glu Gly Gly Arg Asp Arg Asp Arg Gly Gly Glu
1               5                   10                  15

Gln Asp Arg Asp Arg
            20

<210> SEQ ID NO 297
<211> LENGTH: 23
<212> TYPE: PRT
<213> ORGANISM: Artificial Sequence
<220> FEATURE:
<223> OTHER INFORMATION: Artificial peptide sequence

<400> SEQUENCE: 297

Gly Gly Ala Lys Arg Arg Val Val Gln Arg Glu Lys Arg Ala Gly Glu

```
1               5                   10                  15
Arg Glu Lys Arg Ala Gly Gly
            20

<210> SEQ ID NO 298
<211> LENGTH: 23
<212> TYPE: PRT
<213> ORGANISM: Artificial Sequence
<220> FEATURE:
<223> OTHER INFORMATION: Artificial peptide sequence

<400> SEQUENCE: 298

Gly Gly Ile Glu Glu Glu Gly Gly Arg Asp Arg Asp Arg Gly Gly Glu
1               5                   10                  15

Gln Asp Arg Asp Arg Gly Gly
            20

<210> SEQ ID NO 299
<211> LENGTH: 22
<212> TYPE: PRT
<213> ORGANISM: Artificial Sequence
<220> FEATURE:
<223> OTHER INFORMATION: Artificial peptide sequence

<400> SEQUENCE: 299

Gly Lys Gly Gly Ile Glu Glu Glu Gly Gly Arg Asp Arg Asp Arg Gly
1               5                   10                  15

Gly Gln Asp Arg Asp Arg
            20

<210> SEQ ID NO 300
<211> LENGTH: 22
<212> TYPE: PRT
<213> ORGANISM: Artificial Sequence
<220> FEATURE:
<223> OTHER INFORMATION: Artificial peptide sequence

<400> SEQUENCE: 300

Gly Lys Gly Gly Ile Glu Glu Glu Gly Gly Arg Asp Arg Asp Arg Gly
1               5                   10                  15

Gly Gln Asp Arg Asp Arg
            20

<210> SEQ ID NO 301
<211> LENGTH: 31
<212> TYPE: PRT
<213> ORGANISM: Artificial Sequence
<220> FEATURE:
<223> OTHER INFORMATION: Artificial peptide sequence
<220> FEATURE:
<221> NAME/KEY: MISC_FEATURE
<222> LOCATION: (10)..(10)
<223> OTHER INFORMATION: X in position 10 is Dpr(Ser)

<400> SEQUENCE: 301

Gly Ala Lys Arg Arg Val Val Gly Gly Xaa Gly Gly Ala Lys Arg Arg
1               5                   10                  15

Val Val Gln Arg Glu Lys Arg Ala Gly Glu Arg Glu Lys Arg Ala
            20                  25                  30

<210> SEQ ID NO 302
<211> LENGTH: 5
<212> TYPE: PRT
<213> ORGANISM: Artificial Sequence
<220> FEATURE:
```

<223> OTHER INFORMATION: Artificial peptide sequence
<220> FEATURE:
<221> NAME/KEY: MISC_FEATURE
<222> LOCATION: (3)..(3)
<223> OTHER INFORMATION: X in position 3 is Dpr(Ser)

<400> SEQUENCE: 302

Gly Gly Xaa Gly Gly
1               5

<210> SEQ ID NO 303
<211> LENGTH: 7
<212> TYPE: PRT
<213> ORGANISM: Artificial Sequence
<220> FEATURE:
<223> OTHER INFORMATION: Artificial peptide sequence
<220> FEATURE:
<221> NAME/KEY: MISC_FEATURE
<222> LOCATION: (4)..(4)
<223> OTHER INFORMATION: X in position 4 is Har

<400> SEQUENCE: 303

Thr Pro Ile Xaa Gln Glu Trp
1               5

<210> SEQ ID NO 304
<211> LENGTH: 8
<212> TYPE: PRT
<213> ORGANISM: Artificial Sequence
<220> FEATURE:
<223> OTHER INFORMATION: Artificial peptide sequence

<400> SEQUENCE: 304

Glu Gln Asp Arg Asp Arg Gly Gly
1               5

<210> SEQ ID NO 305
<211> LENGTH: 7
<212> TYPE: PRT
<213> ORGANISM: Artificial Sequence
<220> FEATURE:
<223> OTHER INFORMATION: Artificial peptide sequence

<400> SEQUENCE: 305

Gly Asn Trp Ala Lys Val Leu
1               5

<210> SEQ ID NO 306
<211> LENGTH: 7
<212> TYPE: PRT
<213> ORGANISM: Artificial Sequence
<220> FEATURE:
<223> OTHER INFORMATION: Artificial peptide sequence

<400> SEQUENCE: 306

Leu Leu Ala Asp Ala Arg Val
1               5

<210> SEQ ID NO 307
<211> LENGTH: 6
<212> TYPE: PRT
<213> ORGANISM: Artificial Sequence
<220> FEATURE:
<223> OTHER INFORMATION: Artificial peptide sequence

<400> SEQUENCE: 307

Asn Trp Ala Lys Val Ile
1               5

<210> SEQ ID NO 308
<211> LENGTH: 6
<212> TYPE: PRT
<213> ORGANISM: Artificial Sequence
<220> FEATURE:
<223> OTHER INFORMATION: Artificial peptide sequence

<400> SEQUENCE: 308

Ser Gly Ala Asp Arg Val
1               5

<210> SEQ ID NO 309
<211> LENGTH: 1370
<212> TYPE: PRT
<213> ORGANISM: Artificial
<220> FEATURE:
<223> OTHER INFORMATION: Synthetic peptide sequence

<400> SEQUENCE: 309

Met Glu Asn Trp Ser Ala Leu Glu Leu Leu Pro Lys Val Gly Ile Pro
1               5                   10                  15

Thr Asp Phe Leu Thr His Val Lys Thr Ser Ala Gly Glu Glu Met Phe
            20                  25                  30

Glu Ala Leu Arg Ile Tyr Tyr Gly Asp Asp Pro Glu Arg Tyr Asn Ile
        35                  40                  45

His Phe Glu Ala Ile Phe Gly Thr Phe Cys Asn Arg Leu Glu Trp Val
    50                  55                  60

Tyr Phe Leu Thr Ser Gly Leu Ala Ala Ala His Ala Ile Lys Phe
65                  70                  75                  80

His Asp Leu Asn Lys Leu Thr Thr Gly Lys Met Leu Phe His Val Gln
                85                  90                  95

Val Pro Arg Val Ala Ser Gly Ala Gly Leu Pro Thr Ser Arg Gln Thr
            100                 105                 110

Thr Ile Met Val Thr Lys Tyr Ser Glu Lys Ser Pro Ile Thr Ile Pro
            115                 120                 125

Phe Glu Leu Ser Ala Ala Cys Leu Thr Tyr Leu Arg Glu Thr Phe Glu
    130                 135                 140

Gly Thr Ile Leu Asp Lys Ile Leu Asn Val Glu Ala Met His Thr Val
145                 150                 155                 160

Leu Arg Ala Leu Lys Asn Thr Ala Asp Ala Met Glu Arg Gly Leu Ile
                165                 170                 175

His Ser Phe Leu Gln Thr Leu Arg Lys Ala Pro Pro Tyr Phe Val
            180                 185                 190

Val Gln Thr Leu Val Glu Asn Ala Thr Leu Ala Arg Gln Ala Leu Asn
            195                 200                 205

Arg Ile Gln Arg Ser Asn Ile Leu Gln Ser Phe Lys Ala Lys Met Leu
    210                 215                 220

Ala Thr Leu Phe Leu Leu Asn Arg Thr Arg Asp Arg Asp Tyr Val Leu
225                 230                 235                 240

Lys Phe Leu Thr Arg Leu Ala Glu Ala Ala Thr Asp Ser Ile Leu Asp
                245                 250                 255

Asn Pro Thr Thr Tyr Thr Thr Ser Ser Gly Ala Lys Ile Ser Gly Val
            260                 265                 270

Met Val Ser Thr Ala Asn Val Met Gln Ile Ile Met Ser Leu Leu Ser
            275                 280                 285

Ser His Ile Thr Lys Glu Thr Val Ser Ala Pro Ala Thr Tyr Gly Asn

```
            290                 295                 300
    Phe Val Leu Ser Pro Glu Asn Ala Val Thr Ala Ile Ser Tyr His Ser
    305                 310                 315                 320

Ile Leu Ala Asp Phe Asn Ser Tyr Lys Ala His Leu Thr Ser Gly Gln
                    325                 330                 335

Pro His Leu Pro Asn Asp Ser Leu Ser Gln Ala Gly Ala His Ser Leu
                    340                 345                 350

Thr Pro Leu Ser Met Asp Val Ile Arg Leu Gly Glu Lys Thr Val Ile
                    355                 360                 365

Met Glu Asn Leu Arg Arg Val Tyr Lys Asn Thr Asp Thr Lys Asp Pro
                    370                 375                 380

Leu Glu Arg Asn Val Asp Leu Thr Phe Phe Pro Val Gly Leu Tyr
    385                 390                 395                 400

Leu Pro Glu Asp Arg Gly Tyr Thr Thr Val Glu Ser Lys Val Lys Leu
                    405                 410                 415

Asn Asp Thr Val Arg Asn Ala Leu Pro Thr Thr Ala Tyr Leu Leu Asn
                    420                 425                 430

Arg Asp Arg Ala Val Gln Lys Ile Asp Phe Val Asp Ala Leu Lys Thr
                    435                 440                 445

Leu Cys His Pro Val Leu His Glu Pro Ala Pro Cys Leu Gln Thr Phe
                    450                 455                 460

Thr Glu Arg Gly Pro Pro Ser Glu Pro Ala Met Gln Arg Leu Leu Glu
    465                 470                 475                 480

Cys Arg Phe Gln Gln Glu Pro Met Gly Gly Ala Ala Arg Arg Ile Pro
                    485                 490                 495

His Phe Tyr Arg Val Arg Arg Glu Val Pro Arg Thr Val Asn Glu Met
                    500                 505                 510

Lys Gln Asp Phe Val Val Thr Asp Phe Tyr Lys Val Gly Asn Ile Thr
                    515                 520                 525

Leu Tyr Thr Glu Leu His Pro Phe Phe Asp Phe Thr His Cys Gln Glu
                    530                 535                 540

Asn Ser Glu Thr Val Ala Leu Cys Thr Pro Arg Ile Val Ile Gly Asn
    545                 550                 555                 560

Leu Pro Asp Gly Leu Ala Pro Gly Pro Phe His Glu Leu Arg Thr Trp
                    565                 570                 575

Glu Ile Met Glu His Met Arg Leu Arg Pro Pro Asp Tyr Glu Glu
                    580                 585                 590

Thr Leu Arg Leu Phe Lys Thr Thr Val Thr Ser Pro Asn Tyr Pro Glu
                    595                 600                 605

Leu Cys Tyr Leu Val Asp Val Leu Val His Gly Asn Val Asp Ala Phe
                    610                 615                 620

Leu Leu Ile Arg Thr Phe Val Ala Arg Cys Ile Val Asn Met Phe His
    625                 630                 635                 640

Thr Arg Gln Leu Leu Val Phe Ala His Ser Tyr Ala Leu Val Thr Leu
                    645                 650                 655

Ile Ala Glu His Leu Ala Asp Gly Ala Leu Pro Pro Gln Leu Leu Phe
                    660                 665                 670

His Tyr Arg Asn Leu Val Ala Val Leu Arg Leu Val Thr Arg Ile Ser
                    675                 680                 685

Ala Leu Pro Gly Leu Asn Asn Gly Gln Leu Ala Glu Glu Pro Leu Ser
                    690                 695                 700

Ala Tyr Val Asn Ala Leu His Asp His Arg Leu Trp Pro Pro Phe Val
    705                 710                 715                 720
```

-continued

```
Thr His Leu Pro Arg Asn Met Glu Gly Val Gln Val Ala Asp Arg
            725                 730                 735
Gln Pro Leu Asn Pro Ala Asn Ile Glu Ala Arg His His Gly Val Ser
        740                 745                 750
Asp Val Pro Arg Leu Gly Ala Met Asp Ala Asp Glu Pro Leu Phe Val
    755                 760                 765
Asp Asp Tyr Arg Ala Thr Asp Asp Glu Trp Thr Leu Gln Lys Val Phe
770                 775                 780
Tyr Leu Cys Leu Met Pro Ala Met Thr Asn Asn Arg Ala Cys Gly Leu
785                 790                 795                 800
Gly Leu Asn Leu Lys Thr Leu Leu Val Asp Leu Phe Tyr Arg Pro Ala
                805                 810                 815
Phe Leu Leu Met Pro Ala Ala Thr Ala Val Ser Thr Ser Gly Thr Thr
            820                 825                 830
Ser Lys Glu Ser Thr Ser Gly Val Thr Pro Glu Asp Ser Ile Ala Ala
        835                 840                 845
Gln Arg Gln Ala Val Gly Glu Met Leu Thr Glu Leu Val Glu Asp Val
    850                 855                 860
Ala Thr Asp Ala His Thr Pro Leu Leu Gln Ala Cys Arg Glu Leu Phe
865                 870                 875                 880
Leu Ala Val Gln Phe Val Gly Glu His Val Lys Val Leu Glu Val Arg
                885                 890                 895
Ala Pro Leu Asp His Ala Gln Arg Gln Gly Leu Pro Asp Phe Ile Ser
            900                 905                 910
Arg Gln His Val Leu Tyr Asn Gly Cys Cys Val Val Thr Ala Pro Lys
        915                 920                 925
Thr Leu Ile Glu Tyr Ser Leu Pro Val Pro Phe His Arg Phe Tyr Ser
    930                 935                 940
Asn Pro Thr Ile Cys Ala Ala Leu Ser Asp Asp Ile Lys Arg Tyr Val
945                 950                 955                 960
Thr Glu Phe Pro His Tyr His Arg His Asp Gly Gly Phe Pro Leu Pro
                965                 970                 975
Thr Ala Phe Ala His Glu Tyr His Asn Trp Leu Arg Ser Pro Phe Ser
            980                 985                 990
Arg Tyr Ser Ala Thr Cys Pro Asn  Val Leu His Ser Val  Met Thr Leu
        995                 1000                1005
Ala Ala  Met Leu Tyr Lys Ile  Ser Pro Val Ser Leu  Val Leu Gln
        1010                1015                1020
Thr Lys  Ala His Ile His Pro  Gly Phe Ala Leu Thr  Ala Val Arg
        1025                1030                1035
Thr Asp  Thr Phe Glu Val Asp  Met Leu Leu Tyr Ser  Gly Lys Ser
        1040                1045                1050
Cys Thr  Ser Val Ile Ile Asn  Asn Pro Ile Val Thr  Lys Glu Glu
        1055                1060                1065
Arg Asp  Ile Ser Thr Thr Tyr  His Val Thr Gln Asn  Ile Asn Thr
        1070                1075                1080
Val Asp  Met Gly Leu Gly Tyr  Thr Ser Asn Thr Cys  Val Ala Tyr
        1085                1090                1095
Val Asn  Arg Val Arg Thr Asp  Met Gly Val Arg Val  Gln Asp Leu
        1100                1105                1110
Phe Arg  Val Phe Pro Met Asn  Val Tyr Arg His Asp  Glu Val Asp
        1115                1120                1125
```

```
Arg Trp Ile Arg His Ala Ala Gly Val Glu Arg Pro Gln Leu Leu
    1130                1135                1140

Asp Thr Glu Thr Ile Ser Met Leu Thr Phe Gly Ser Met Ser Glu
    1145                1150                1155

Arg Asn Ala Ala Ala Thr Val His Gly Gln Lys Ala Ala Cys Glu
    1160                1165                1170

Leu Ile Leu Thr Pro Val Thr Met Asp Val Asn Tyr Phe Lys Ile
    1175                1180                1185

Pro Asn Asn Pro Arg Gly Arg Ala Ser Cys Met Leu Ala Val Asp
    1190                1195                1200

Pro Tyr Asp Thr Glu Ala Ala Thr Lys Ala Ile Tyr Asp His Arg
    1205                1210                1215

Glu Ala Asp Ala Gln Thr Phe Ala Ala Thr His Asn Pro Trp Ala
    1220                1225                1230

Ser Gln Ala Gly Cys Leu Ser Asp Val Leu Tyr Asn Thr Arg His
    1235                1240                1245

Arg Glu Arg Leu Gly Tyr Asn Ser Lys Phe Tyr Ser Pro Cys Ala
    1250                1255                1260

Gln Tyr Phe Asn Thr Glu Glu Ile Ile Ala Ala Asn Lys Thr Leu
    1265                1270                1275

Phe Lys Thr Ile Asp Glu Tyr Leu Leu Arg Ala Lys Asp Cys Ile
    1280                1285                1290

Arg Gly Asp Thr Asp Thr Gln Tyr Val Cys Val Glu Gly Thr Glu
    1295                1300                1305

Gln Leu Ile Glu Asn Pro Cys Arg Leu Thr Gln Glu Ala Leu Pro
    1310                1315                1320

Ile Leu Ser Thr Thr Thr Leu Ala Leu Met Glu Thr Lys Leu Lys
    1325                1330                1335

Gly Gly Ala Gly Ala Phe Ala Thr Ser Glu Thr His Phe Gly Asn
    1340                1345                1350

Tyr Val Val Gly Glu Ile Ile Pro Leu Gln Gln Ser Met Leu Phe
    1355                1360                1365

Asn Ser
    1370

<210> SEQ ID NO 310
<211> LENGTH: 345
<212> TYPE: PRT
<213> ORGANISM: Artificial
<220> FEATURE:
<223> OTHER INFORMATION: Synthetic peptide sequence

<400> SEQUENCE: 310

Met Ala Trp Arg Ser Gly Leu Cys Glu Thr Asp Ser Arg Thr Leu Lys
1               5                   10                  15

Gln Phe Leu Gln Glu Glu Cys Met Trp Lys Leu Val Gly Lys Ser Arg
                20                  25                  30

Lys His Arg Glu Tyr Arg Ala Val Ala Cys Arg Ser Thr Ile Phe Ser
            35                  40                  45

Pro Glu Asp Asp Gly Ser Cys Ile Leu Cys Gln Leu Leu Leu Phe Tyr
        50                  55                  60

Arg Asp Gly Glu Trp Ile Leu Cys Leu Cys Cys Asn Gly Arg Tyr Gln
65                  70                  75                  80

Gly His Tyr Gly Val Gly His Val His Arg Arg Arg Arg Ile Cys
                85                  90                  95
```

His Leu Pro Thr Leu Tyr Gln Leu Ser Phe Gly Gly Pro Leu Gly Pro
                100                 105                 110

Ala Ser Ile Asp Phe Leu Pro Ser Phe Ser Gln Val Thr Ser Ser Met
        115                 120                 125

Thr Cys Asp Gly Ile Thr Pro Asp Val Ile Tyr Glu Val Cys Met Leu
    130                 135                 140

Val Pro Gln Asp Glu Ala Lys Arg Ile Leu Val Lys Gly His Gly Ala
145                 150                 155                 160

Met Asp Leu Thr Cys Gln Lys Ala Val Thr Leu Gly Gly Ala Gly Ala
                165                 170                 175

Trp Leu Leu Pro Arg Pro Glu Gly Tyr Thr Leu Phe Phe Tyr Ile Leu
        180                 185                 190

Cys Tyr Asp Leu Phe Thr Ser Cys Gly Asn Arg Cys Asp Ile Pro Ser
    195                 200                 205

Met Thr Arg Leu Met Ala Ala Ala Thr Ala Cys Gly Gln Ala Gly Cys
    210                 215                 220

Ser Phe Cys Thr Asp His Glu Gly His Val Asp Pro Thr Gly Asn Tyr
225                 230                 235                 240

Val Gly Cys Thr Pro Asp Met Gly Arg Cys Leu Cys Tyr Val Pro Cys
                245                 250                 255

Gly Pro Met Thr Gln Ser Leu Ile His Asn Glu Glu Pro Ala Thr Phe
        260                 265                 270

Phe Cys Glu Ser Asp Asp Ala Lys Tyr Leu Cys Ala Val Gly Ser Lys
    275                 280                 285

Thr Ala Ala Gln Val Thr Leu Gly Asp Gly Leu Asp Tyr His Ile Gly
    290                 295                 300

Val Lys Asp Ser Glu Gly Arg Trp Leu Pro Val Lys Thr Asp Val Trp
305                 310                 315                 320

Asp Leu Val Lys Val Glu Glu Pro Val Ser Arg Met Ile Val Cys Ser
                325                 330                 335

Cys Pro Val Leu Lys Asn Leu Val His
        340                 345

<210> SEQ ID NO 311
<211> LENGTH: 188
<212> TYPE: PRT
<213> ORGANISM: Artificial
<220> FEATURE:
<223> OTHER INFORMATION: Synthetic peptide sequence

<400> SEQUENCE: 311

Met Thr Ser Arg Arg Ala Pro Asp Gly Gly Leu Asn Leu Asp Asp Phe
1               5                   10                  15

Met Arg Arg Gln Arg Gly Arg His Leu Asp Leu Pro Tyr Pro Arg Gly
                20                  25                  30

Tyr Thr Leu Phe Val Cys Asp Val Glu Glu Thr Ile Leu Thr Pro Arg
            35                  40                  45

Asp Val Glu Tyr Trp Lys Leu Leu Val Thr Gln Gly Gln Leu Arg
        50                  55                  60

Val Ile Gly Thr Ile Gly Leu Ala Asn Leu Phe Ser Trp Asp Arg Ser
65                  70                  75                  80

Val Ala Gly Val Ala Ala Asp Gly Ser Val Leu Cys Tyr Glu Ile Ser
                85                  90                  95

Arg Glu Asn Phe Val Val Arg Ala Ala Asp Ser Leu Pro Gln Leu Leu
            100                 105                 110

Glu Arg Gly Leu Leu His Ser Tyr Phe Glu Asp Val Glu Arg Ala Ala
            115                 120                 125

Gln Gly Arg Leu Arg His Gly Asn Arg Ser Gly Leu Arg Arg Asp Ala
        130                 135                 140

Asp Gly Gln Val Ile Arg Glu Ser Ala Cys Tyr Val Ser Arg Ala Leu
145                 150                 155                 160

Leu Arg His Arg Val Thr Pro Gly Lys Gln Glu Ile Thr Asp Ala Met
            165                 170                 175

Phe Glu Ala Gly Asn Val Pro Ser Ala Leu Leu Pro
        180                 185

<210> SEQ ID NO 312
<211> LENGTH: 742
<212> TYPE: PRT
<213> ORGANISM: Artificial
<220> FEATURE:
<223> OTHER INFORMATION: Synthetic peptide sequence

<400> SEQUENCE: 312

Met Glu Leu His Ser Arg Gly Arg His Asp Ala Pro Ser Leu Ser Ser
1               5                   10                  15

Leu Ser Glu Arg Glu Arg Ala Arg Arg Ala Arg Phe Cys Leu
            20                  25                  30

Asp Tyr Glu Pro Val Pro Arg Lys Phe Arg Arg Glu Arg Ser Pro Thr
            35                  40                  45

Ser Pro Ser Thr Arg Asn Gly Ala Ala Ser Glu Tyr His Leu Ala
        50                  55                  60

Glu Asp Thr Val Gly Ala Ser His His Arg Pro Cys Val Pro
65                  70                  75                  80

Ala Arg Arg Pro Arg Tyr Ser Lys Asp Asp Thr Glu Gly Asp Pro
            85                  90                  95

Asp His Tyr Pro Pro Leu Pro Pro Ser Ser Arg His Ala Leu Gly
        100                 105                 110

Gly Thr Gly Gly His Ile Ile Met Gly Thr Ala Gly Phe Arg Gly Gly
            115                 120                 125

His Arg Ala Ser Ser Phe Lys Arg Arg Val Ala Ala Ser Ala Ser
        130                 135                 140

Val Pro Leu Asn Pro His Tyr Gly Lys Ser Tyr Asp Asn Asp Gly
145                 150                 155                 160

Glu Pro His His His Gly Gly Asp Ser Thr His Leu Arg Arg Val
            165                 170                 175

Pro Ser Cys Pro Thr Thr Phe Gly Ser Ser His Pro Ser Ser Ala Asn
        180                 185                 190

Asn His His Gly Ser Ser Ala Gly Pro Gln Gln Gln Met Leu Ala
            195                 200                 205

Leu Ile Asp Asp Glu Leu Asp Ala Met Asp Glu Asp Glu Leu Gln Gln
        210                 215                 220

Leu Ser Arg Leu Ile Glu Lys Lys Arg Ala Arg Leu Gln Arg Gly
225                 230                 235                 240

Ala Ala Ser Ser Gly Thr Ser Pro Ser Ser Thr Ser Pro Val Tyr Asp
            245                 250                 255

Leu Gln Arg Tyr Thr Ala Glu Ser Leu Arg Leu Ala Pro Tyr Pro Ala
            260                 265                 270

Asp Leu Lys Val Pro Thr Ala Phe Pro Gln Asp His Gln Pro Arg Gly
        275                 280                 285

```
Arg Ile Leu Leu Ser His Asp Glu Leu Met His Thr Asp Tyr Leu Leu
    290                 295                 300

His Ile Arg Gln Gln Phe Asp Trp Leu Glu Glu Pro Leu Leu Arg Lys
305                 310                 315                 320

Leu Val Val Glu Lys Ile Phe Ala Val Tyr Asn Ala Pro Asn Leu His
                325                 330                 335

Thr Leu Leu Ala Ile Ile Asp Glu Thr Leu Ser Tyr Met Lys Tyr His
                340                 345                 350

His Leu His Gly Leu Pro Val Asn Pro His Asp Pro Tyr Leu Glu Thr
                355                 360                 365

Val Gly Gly Met Arg Gln Leu Leu Phe Asn Lys Leu Asn Asn Leu Asp
370                 375                 380

Leu Gly Cys Ile Leu Asp His Gln Asp Gly Trp Gly Asp His Cys Ser
385                 390                 395                 400

Thr Leu Lys Arg Leu Val Lys Pro Gly Gln Met Ser Ala Trp Leu
                405                 410                 415

Arg Asp Asp Val Cys Asp Leu Gln Lys Arg Pro Pro Glu Thr Phe Ser
                420                 425                 430

Gln Pro Met His Arg Ala Met Ala Tyr Val Cys Ser Phe Ser Arg Val
                435                 440                 445

Ala Val Ser Leu Arg Arg Ala Leu Gln Val Thr Gly Thr Pro Gln
450                 455                 460

Phe Phe Asp Gln Phe Asp Thr Asn Asn Ala Met Gly Thr Tyr Arg Cys
465                 470                 475                 480

Gly Ala Val Ser Asp Leu Ile Leu Gly Ala Leu Gln Cys His Glu Cys
                485                 490                 495

Gln Asn Glu Met Cys Glu Leu Arg Ile Gln Arg Ala Leu Ala Pro Tyr
                500                 505                 510

Arg Phe Met Ile Ala Tyr Cys Pro Phe Asp Glu Gln Ser Leu Leu Asp
                515                 520                 525

Leu Thr Val Phe Ala Gly Thr Thr Thr Thr Ala Ser Asn His Ala
    530                 535                 540

Thr Ala Gly Gly Gln Gln Arg Gly Gly Asp Gln Ile His Pro Thr Asp
545                 550                 555                 560

Glu Gln Cys Ala Ser Met Glu Ser Arg Thr Asp Pro Ala Thr Leu Thr
                565                 570                 575

Ala Tyr Asp Lys Lys Asp Arg Glu Gly Ser His Arg His Pro Ser Pro
                580                 585                 590

Met Ile Ala Ala Ala Pro Pro Ala Gln Pro Ser Gln Pro Gln
                595                 600                 605

Gln His Tyr Ser Glu Gly Glu Leu Glu Glu Asp Glu Asp Ser Asp Asp
610                 615                 620

Ala Ser Ser Gln Asp Leu Val Arg Ala Thr Asp Arg His Gly Asp Thr
625                 630                 635                 640

Val Val Tyr Lys Thr Thr Ala Val Pro Pro Ser Pro Ala Pro Leu
                645                 650                 655

Ala Gly Val Arg Ser His Arg Gly Glu Leu Asn Leu Met Thr Pro Ser
                660                 665                 670

Pro Ser His Gly Gly Ser Pro Gln Val Pro His Lys Gln Pro Ile
                675                 680                 685

Ile Pro Val Gln Ser Ala Asn Gly Asn His Ser Thr Thr Ala Thr Gln
690                 695                 700

Gln Gln Gln Pro Pro Pro Pro Pro Val Pro Gln Glu Asp Asp Ser
```

```
                705                 710                 715                 720
Val Val Met Arg Cys Gln Thr Pro Asp Tyr Glu Asp Met Leu Cys Tyr
                    725                 730                 735
Ser Asp Asp Met Asp Asp
            740
```

<210> SEQ ID NO 313
<211> LENGTH: 13
<212> TYPE: PRT
<213> ORGANISM: Artificial
<220> FEATURE:
<223> OTHER INFORMATION: Synthetic peptide sequence

<400> SEQUENCE: 313

```
Gly Gly Gln Leu Ile Gly Gly Ile Tyr Leu Ile Pro Gly
1               5                   10
```

<210> SEQ ID NO 314
<211> LENGTH: 11
<212> TYPE: PRT
<213> ORGANISM: Artificial
<220> FEATURE:
<223> OTHER INFORMATION: Synthetic peptide sequence

<400> SEQUENCE: 314

```
Val Ile Thr Tyr Ser Ile Phe Leu Ile Val Ser
1               5                   10
```

<210> SEQ ID NO 315
<211> LENGTH: 9
<212> TYPE: PRT
<213> ORGANISM: Artificial
<220> FEATURE:
<223> OTHER INFORMATION: Synthetic peptide sequence

<400> SEQUENCE: 315

```
Thr Ala Asn Trp Ala Arg Val Ile Ser
1               5
```

<210> SEQ ID NO 316
<211> LENGTH: 10
<212> TYPE: PRT
<213> ORGANISM: Artificial
<220> FEATURE:
<223> OTHER INFORMATION: Synthetic peptide sequence

<400> SEQUENCE: 316

```
Gly Tyr Leu Pro Ala Val Gly Ala Pro Ile
1               5                   10
```

<210> SEQ ID NO 317
<211> LENGTH: 9
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (5)..(5)
<223> OTHER INFORMATION: Xaa can be any naturally occurring amino acid

<400> SEQUENCE: 317

```
Asn Ile Val Pro Xaa Val Val Thr Ala
1               5
```

<210> SEQ ID NO 318

```
<211> LENGTH: 9
<212> TYPE: PRT
<213> ORGANISM: Artificial
<220> FEATURE:
<223> OTHER INFORMATION: Synthetic peptide sequence

<400> SEQUENCE: 318

Val Thr Pro Ala Asp Leu Ile Gly Ala
1               5

<210> SEQ ID NO 319
<211> LENGTH: 10
<212> TYPE: PRT
<213> ORGANISM: Artificial
<220> FEATURE:
<223> OTHER INFORMATION: Synthetic peptide sequence

<400> SEQUENCE: 319

Pro Arg Pro Glu Gly Tyr Thr Leu Phe Phe
1               5                   10

<210> SEQ ID NO 320
<211> LENGTH: 11
<212> TYPE: PRT
<213> ORGANISM: Artificial
<220> FEATURE:
<223> OTHER INFORMATION: Synthetic peptide sequence

<400> SEQUENCE: 320

Leu Pro Tyr Pro Arg Gly Tyr Thr Leu Phe Val
1               5                   10

<210> SEQ ID NO 321
<211> LENGTH: 9
<212> TYPE: PRT
<213> ORGANISM: Artificial
<220> FEATURE:
<223> OTHER INFORMATION: Synthetic peptide sequence

<400> SEQUENCE: 321

Glu Thr Ile Leu Thr Pro Arg Asp Val
1               5

<210> SEQ ID NO 322
<211> LENGTH: 9
<212> TYPE: PRT
<213> ORGANISM: Artificial
<220> FEATURE:
<223> OTHER INFORMATION: Synthetic peptide sequence

<400> SEQUENCE: 322

Ser Ser Thr Ser Pro Val Tyr Asp Leu
1               5

<210> SEQ ID NO 323
<211> LENGTH: 10
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (6)..(6)
<223> OTHER INFORMATION: Xaa can be any naturally occurring amino acid

<400> SEQUENCE: 323

Thr Ala Tyr Glu Arg Xaa Cys Asn Ile Leu
1               5                   10
```

```
<210> SEQ ID NO 324
<211> LENGTH: 11
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (7)..(7)
<223> OTHER INFORMATION: Xaa can be any naturally occurring amino acid

<400> SEQUENCE: 324

Thr Val Ile Gly Ala Ser Xaa Ile Pro Leu Leu
1               5                   10

<210> SEQ ID NO 325
<211> LENGTH: 10
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (6)..(7)
<223> OTHER INFORMATION: Xaa can be any naturally occurring amino acid

<400> SEQUENCE: 325

Ala Ala Phe Glu Glu Xaa Xaa Ile Thr Ser
1               5                   10

<210> SEQ ID NO 326
<211> LENGTH: 12
<212> TYPE: PRT
<213> ORGANISM: Artificial
<220> FEATURE:
<223> OTHER INFORMATION: Synthetic peptide sequence

<400> SEQUENCE: 326

Gly Leu Glu Pro Leu Val Ile Ala Gly Ile Leu Ala
1               5                   10

<210> SEQ ID NO 327
<211> LENGTH: 9
<212> TYPE: PRT
<213> ORGANISM: Artificial
<220> FEATURE:
<223> OTHER INFORMATION: Synthetic peptide sequence

<400> SEQUENCE: 327

Thr Ala Phe Leu Val Arg Asn Val Ala
1               5

<210> SEQ ID NO 328
<211> LENGTH: 12
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 328

Thr Pro Ile Xaa Gln Asp Trp Gly Asn Arg Ala Asn
1               5                   10
```

-continued

```
<210> SEQ ID NO 329
<211> LENGTH: 12
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 329

Thr Pro Thr Xaa Asn Gly Trp Asp Val Lys Leu Ser
1               5                   10

<210> SEQ ID NO 330
<211> LENGTH: 11
<212> TYPE: PRT
<213> ORGANISM: Artificial
<220> FEATURE:
<223> OTHER INFORMATION: Synthetic peptide sequence

<400> SEQUENCE: 330

Leu Glu Cys Val Tyr Cys Lys Gln Gln Leu Leu
1               5                   10

<210> SEQ ID NO 331
<211> LENGTH: 11
<212> TYPE: PRT
<213> ORGANISM: Artificial
<220> FEATURE:
<223> OTHER INFORMATION: Synthetic peptide sequence

<400> SEQUENCE: 331

Gly Val Tyr Asp Phe Ala Phe Arg Asp Leu Cys
1               5                   10

<210> SEQ ID NO 332
<211> LENGTH: 11
<212> TYPE: PRT
<213> ORGANISM: Artificial
<220> FEATURE:
<223> OTHER INFORMATION: Synthetic peptide sequence

<400> SEQUENCE: 332

Gly Val Phe Asp Tyr Ala Phe Arg Asp Ile Asn
1               5                   10

<210> SEQ ID NO 333
<211> LENGTH: 10
<212> TYPE: PRT
<213> ORGANISM: Artificial
<220> FEATURE:
<223> OTHER INFORMATION: Synthetic peptide sequence

<400> SEQUENCE: 333

Val Asp Ile Arg Thr Leu Glu Asp Leu Leu
1               5                   10

<210> SEQ ID NO 334
<211> LENGTH: 11
<212> TYPE: PRT
<213> ORGANISM: Artificial
<220> FEATURE:
<223> OTHER INFORMATION: Synthetic peptide sequence

<400> SEQUENCE: 334

Glu Val Tyr Asp Phe Ala Phe Arg Asp Leu Cys
```

```
<210> SEQ ID NO 335
<211> LENGTH: 11
<212> TYPE: PRT
<213> ORGANISM: Artificial
<220> FEATURE:
<223> OTHER INFORMATION: Synthetic peptide sequence

<400> SEQUENCE: 335

Gly Phe Ala Phe Arg Asp Leu Cys Ile Val Tyr
1               5                   10

<210> SEQ ID NO 336
<211> LENGTH: 11
<212> TYPE: PRT
<213> ORGANISM: Artificial
<220> FEATURE:
<223> OTHER INFORMATION: Synthetic peptide sequence

<400> SEQUENCE: 336

Gly Phe Ala Tyr Arg Asp Ile Asn Leu Ala Tyr
1               5                   10

<210> SEQ ID NO 337
<211> LENGTH: 10
<212> TYPE: PRT
<213> ORGANISM: Artificial
<220> FEATURE:
<223> OTHER INFORMATION: Synthetic peptide sequence

<400> SEQUENCE: 337

Gly Thr Leu Gly Ile Val Cys Pro Ile Gly
1               5                   10

<210> SEQ ID NO 338
<211> LENGTH: 12
<212> TYPE: PRT
<213> ORGANISM: Artificial
<220> FEATURE:
<223> OTHER INFORMATION: Synthetic peptide sequence

<400> SEQUENCE: 338

Gly Leu Glu Pro Leu Val Ile Ala Gly Ile Leu Ala
1               5                   10

<210> SEQ ID NO 339
<211> LENGTH: 12
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 339

Thr Pro Ile Xaa Gln Asp Trp Glu Asn Arg Ala Asn
1               5                   10

<210> SEQ ID NO 340
<211> LENGTH: 12
<212> TYPE: PRT
<213> ORGANISM: Artificial
<220> FEATURE:
<223> OTHER INFORMATION: Synthetic peptide sequence
<220> FEATURE:
```

```
<221> NAME/KEY: misc_feature
<222> LOCATION: (7)..(9)
<223> OTHER INFORMATION: Xaa can be any naturally occurring amino acid

<400> SEQUENCE: 340

Val Ala Phe Glu Asp Leu Xaa Xaa Xaa Ser Phe Ile
1               5                   10

<210> SEQ ID NO 341
<211> LENGTH: 9
<212> TYPE: PRT
<213> ORGANISM: Artificial
<220> FEATURE:
<223> OTHER INFORMATION: Synthetic peptide sequence

<400> SEQUENCE: 341

Arg Phe Gln Thr Val Val Gln Asx Ala
1               5

<210> SEQ ID NO 342
<211> LENGTH: 11
<212> TYPE: PRT
<213> ORGANISM: Artificial
<220> FEATURE:
<223> OTHER INFORMATION: Synthetic peptide sequence

<400> SEQUENCE: 342

Gly Ser Leu Val Gly Leu Leu His Ile Val Leu
1               5                   10

<210> SEQ ID NO 343
<211> LENGTH: 15
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (9)..(10)
<223> OTHER INFORMATION: Xaa can be any naturally occurring amino acid

<400> SEQUENCE: 343

Ser Ile Ala Arg Ser Val Thr Ile Xaa Xaa Ala Ser Val Val His
1               5                   10                  15

<210> SEQ ID NO 344
<211> LENGTH: 12
<212> TYPE: PRT
<213> ORGANISM: Artificial
<220> FEATURE:
<223> OTHER INFORMATION: Synthetic peptide sequence

<400> SEQUENCE: 344

Thr Pro Thr Arg Gln Glu Trp Asp Cys Arg Ile Ser
1               5                   10

<210> SEQ ID NO 345
<211> LENGTH: 12
<212> TYPE: PRT
<213> ORGANISM: Artificial
<220> FEATURE:
<223> OTHER INFORMATION: Synthetic peptide sequence

<400> SEQUENCE: 345

Thr Pro Thr Arg Gln Glu Trp Asp Ala Arg Ile Ser
1               5                   10
```

```
<210> SEQ ID NO 346
<211> LENGTH: 15
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 346

Thr Pro Ile Xaa Gln Glu Trp Xaa Ser Leu Xaa Asn Gln Glu Trp
1               5                   10                  15

<210> SEQ ID NO 347
<211> LENGTH: 9
<212> TYPE: PRT
<213> ORGANISM: Artificial
<220> FEATURE:
<223> OTHER INFORMATION: Synthetic peptide sequence

<400> SEQUENCE: 347

Ile Gly Asp Leu Ile Val Ala Gln Val
1               5

<210> SEQ ID NO 348
<211> LENGTH: 9
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (8)..(8)
<223> OTHER INFORMATION: Xaa can be any naturally occurring amino acid

<400> SEQUENCE: 348

Gln Tyr Asn Pro Val Ala Val Xaa Phe
1               5

<210> SEQ ID NO 349
<211> LENGTH: 8
<212> TYPE: PRT
<213> ORGANISM: Artificial
<220> FEATURE:
<223> OTHER INFORMATION: Synthetic peptide sequence

<400> SEQUENCE: 349

Gly Tyr Thr Leu Phe Phe Thr Ser
1               5

<210> SEQ ID NO 350
<211> LENGTH: 8
<212> TYPE: PRT
<213> ORGANISM: Artificial
<220> FEATURE:
<223> OTHER INFORMATION: Synthetic peptide sequence

<400> SEQUENCE: 350

Gly Tyr Thr Leu Phe Val Ser Asp
1               5
```

```
<210> SEQ ID NO 351
<211> LENGTH: 9
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 351

Asn Thr Leu Xaa Thr Pro Arg Asp Val
1               5

<210> SEQ ID NO 352
<211> LENGTH: 9
<212> TYPE: PRT
<213> ORGANISM: Artificial
<220> FEATURE:
<223> OTHER INFORMATION: Synthetic peptide sequence

<400> SEQUENCE: 352

Ser Ser Thr Ser Pro Val Tyr Asn Leu
1               5

<210> SEQ ID NO 353
<211> LENGTH: 11
<212> TYPE: PRT
<213> ORGANISM: Artificial
<220> FEATURE:
<223> OTHER INFORMATION: Synthetic peptide sequence

<400> SEQUENCE: 353

Val Ile Thr Phe Ser Ile Tyr Leu Ile Val Ser
1               5                   10

<210> SEQ ID NO 354
<211> LENGTH: 13
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (10)..(10)
<223> OTHER INFORMATION: Xaa can be any naturally occurring amino acid

<400> SEQUENCE: 354

Gly Gly Asn Val Ile Gly Gly Ile Tyr Xaa Ile Pro Arg
1               5                   10

<210> SEQ ID NO 355
<211> LENGTH: 8
<212> TYPE: PRT
<213> ORGANISM: Artificial
<220> FEATURE:
<223> OTHER INFORMATION: Synthetic peptide sequence

<400> SEQUENCE: 355

Ala Asn Trp Ala Lys Val Ile Leu
1               5

<210> SEQ ID NO 356
<211> LENGTH: 11
<212> TYPE: PRT
<213> ORGANISM: Artificial
```

<220> FEATURE:
<223> OTHER INFORMATION: Synthetic peptide sequence

<400> SEQUENCE: 356

Val Ile Arg Val Ile Ala His Gly Leu Arg Leu
1               5                   10

<210> SEQ ID NO 357
<211> LENGTH: 28
<212> TYPE: PRT
<213> ORGANISM: Artificial
<220> FEATURE:
<223> OTHER INFORMATION: Synthetic peptide sequence

<400> SEQUENCE: 357

Arg Arg Gly Gly Gln Leu Ile Gly Gly Ile Tyr Leu Ile Pro Gly Arg
1               5                   10                  15

Arg Val Ile Thr Phe Ser Ile Tyr Leu Ile Val Ser
            20                  25

<210> SEQ ID NO 358
<211> LENGTH: 29
<212> TYPE: PRT
<213> ORGANISM: Artificial
<220> FEATURE:
<223> OTHER INFORMATION: Synthetic peptide sequence

<400> SEQUENCE: 358

Arg Arg Arg Gly Gly Gln Leu Ile Gly Gly Ile Tyr Leu Ile Pro Gly
1               5                   10                  15

Arg Arg Val Ile Thr Phe Ser Ile Tyr Leu Ile Val Ser
            20                  25

<210> SEQ ID NO 359
<211> LENGTH: 29
<212> TYPE: PRT
<213> ORGANISM: Artificial
<220> FEATURE:
<223> OTHER INFORMATION: Synthetic peptide sequence

<400> SEQUENCE: 359

Arg Arg Gly Gly Gln Leu Ile Gly Gly Ile Tyr Leu Ile Pro Gly Arg
1               5                   10                  15

Arg Arg Val Ile Thr Phe Ser Ile Tyr Leu Ile Val Ser
            20                  25

<210> SEQ ID NO 360
<211> LENGTH: 29
<212> TYPE: PRT
<213> ORGANISM: Artificial
<220> FEATURE:
<223> OTHER INFORMATION: Synthetic peptide sequence

<400> SEQUENCE: 360

Arg Arg Gly Gly Gln Leu Ile Gly Gly Ile Tyr Leu Ile Pro Gly Arg
1               5                   10                  15

Arg Val Ile Thr Phe Ser Ile Tyr Leu Ile Val Ser Arg
            20                  25

<210> SEQ ID NO 361
<211> LENGTH: 30
<212> TYPE: PRT
<213> ORGANISM: Artificial
<220> FEATURE:
<223> OTHER INFORMATION: Synthetic peptide sequence

<400> SEQUENCE: 361

Arg Arg Gly Gly Gln Leu Ile Gly Gly Ile Tyr Leu Ile Pro Gly Arg
1               5                   10                  15

Arg Val Ile Thr Phe Ser Ile Tyr Leu Ile Val Ser Arg Arg
            20                  25                  30

<210> SEQ ID NO 362
<211> LENGTH: 28
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (25)..(25)
<223> OTHER INFORMATION: Xaa can be any naturally occurring amino acid

<400> SEQUENCE: 362

Arg Arg Val Ile Thr Tyr Ser Ile Phe Leu Ile Val Ser Arg Arg Gly
1               5                   10                  15

Gly Asn Val Ile Gly Gly Ile Tyr Xaa Ile Pro Arg
            20                  25

<210> SEQ ID NO 363
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (26)..(26)
<223> OTHER INFORMATION: Xaa can be any naturally occurring amino acid

<400> SEQUENCE: 363

Arg Arg Arg Val Ile Thr Tyr Ser Ile Phe Leu Ile Val Ser Arg Arg
1               5                   10                  15

Gly Gly Asn Val Ile Gly Gly Ile Tyr Xaa Ile Pro Arg
            20                  25

<210> SEQ ID NO 364
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (26)..(26)
<223> OTHER INFORMATION: Xaa can be any naturally occurring amino acid

<400> SEQUENCE: 364

Arg Arg Val Ile Thr Tyr Ser Ile Phe Leu Ile Val Ser Arg Arg Arg
1               5                   10                  15

Gly Gly Asn Val Ile Gly Gly Ile Tyr Xaa Ile Pro Arg
            20                  25

<210> SEQ ID NO 365
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (27)..(27)

<223> OTHER INFORMATION: Xaa can be any naturally occurring amino acid

<400> SEQUENCE: 365

Arg Arg Arg Val Ile Thr Tyr Ser Ile Phe Leu Ile Val Ser Arg
1               5                   10                  15
Arg Gly Gly Asn Val Ile Gly Gly Ile Tyr Xaa Ile Pro Arg
            20                  25                  30

<210> SEQ ID NO 366
<211> LENGTH: 28
<212> TYPE: PRT
<213> ORGANISM: Artificial
<220> FEATURE:
<223> OTHER INFORMATION: Synthetic peptide sequence

<400> SEQUENCE: 366

Arg Arg Gly Thr Ala Asn Trp Ala Arg Val Ile Ser Arg Ala Asn Trp
1               5                   10                  15
Ala Lys Val Ile Leu Arg Asn Trp Ala Lys Val Ile
            20                  25

<210> SEQ ID NO 367
<211> LENGTH: 28
<212> TYPE: PRT
<213> ORGANISM: Artificial
<220> FEATURE:
<223> OTHER INFORMATION: Synthetic peptide sequence

<400> SEQUENCE: 367

Arg Gly Thr Ala Asn Trp Ala Arg Val Ile Ser Arg Arg Ala Asn Trp
1               5                   10                  15
Ala Lys Val Ile Leu Arg Asn Trp Ala Lys Val Ile
            20                  25

<210> SEQ ID NO 368
<211> LENGTH: 27
<212> TYPE: PRT
<213> ORGANISM: Artificial
<220> FEATURE:
<223> OTHER INFORMATION: Synthetic peptide sequence

<400> SEQUENCE: 368

Arg Gly Thr Ala Asn Trp Ala Arg Val Ile Ser Arg Ala Asn Trp Ala
1               5                   10                  15
Lys Val Ile Leu Arg Asn Trp Ala Lys Val Ile
            20                  25

<210> SEQ ID NO 369
<211> LENGTH: 28
<212> TYPE: PRT
<213> ORGANISM: Artificial
<220> FEATURE:
<223> OTHER INFORMATION: Synthetic peptide sequence

<400> SEQUENCE: 369

Arg Gly Thr Ala Asn Trp Ala Arg Val Ile Ser Arg Gly Ala Asn Trp
1               5                   10                  15
Ala Lys Val Ile Leu Arg Asn Trp Ala Lys Val Ile
            20                  25

<210> SEQ ID NO 370
<211> LENGTH: 28
<212> TYPE: PRT
<213> ORGANISM: Artificial

```
<220> FEATURE:
<223> OTHER INFORMATION: Synthetic peptide sequence

<400> SEQUENCE: 370

Arg Arg Gly Thr Ala Asn Trp Ala Arg Val Ile Ser Arg Ala Asn Trp
1               5                   10                  15

Ala Arg Val Ile Leu Arg Asn Trp Ala Lys Val Ile
            20                  25

<210> SEQ ID NO 371
<211> LENGTH: 28
<212> TYPE: PRT
<213> ORGANISM: Artificial
<220> FEATURE:
<223> OTHER INFORMATION: Synthetic peptide sequence

<400> SEQUENCE: 371

Arg Gly Thr Ala Asn Trp Ala Arg Val Ile Ser Arg Ala Asn Trp
1               5                   10                  15

Ala Arg Val Ile Leu Arg Asn Trp Ala Lys Val Ile
            20                  25

<210> SEQ ID NO 372
<211> LENGTH: 27
<212> TYPE: PRT
<213> ORGANISM: Artificial
<220> FEATURE:
<223> OTHER INFORMATION: Synthetic peptide sequence

<400> SEQUENCE: 372

Arg Gly Thr Ala Asn Trp Ala Arg Val Ile Ser Arg Ala Asn Trp Ala
1               5                   10                  15

Arg Val Ile Leu Arg Asn Trp Ala Lys Val Ile
            20                  25

<210> SEQ ID NO 373
<211> LENGTH: 28
<212> TYPE: PRT
<213> ORGANISM: Artificial
<220> FEATURE:
<223> OTHER INFORMATION: Synthetic peptide sequence

<400> SEQUENCE: 373

Arg Gly Thr Ala Asn Trp Ala Arg Val Ile Ser Arg Gly Ala Asn Trp
1               5                   10                  15

Ala Arg Val Ile Leu Arg Asn Trp Ala Lys Val Ile
            20                  25

<210> SEQ ID NO 374
<211> LENGTH: 26
<212> TYPE: PRT
<213> ORGANISM: Artificial
<220> FEATURE:
<223> OTHER INFORMATION: Synthetic peptide sequence

<400> SEQUENCE: 374

Arg Gly Tyr Leu Pro Ala Val Gly Ala Pro Ile Arg Arg Val Ile
1               5                   10                  15

Arg Val Ile Ala His Gly Leu Arg Leu Arg
            20                  25

<210> SEQ ID NO 375
<211> LENGTH: 26
<212> TYPE: PRT
```

```
<213> ORGANISM: Artificial
<220> FEATURE:
<223> OTHER INFORMATION: Synthetic peptide sequence

<400> SEQUENCE: 375

Arg Arg Gly Tyr Leu Pro Ala Val Gly Ala Pro Ile Arg Arg Val Ile
1               5                   10                  15

Arg Val Ile Ala His Gly Leu Arg Leu Arg
            20                  25

<210> SEQ ID NO 376
<211> LENGTH: 26
<212> TYPE: PRT
<213> ORGANISM: Artificial
<220> FEATURE:
<223> OTHER INFORMATION: Synthetic peptide sequence

<400> SEQUENCE: 376

Arg Arg Gly Tyr Leu Pro Ala Val Gly Ala Pro Ile Arg Arg Arg Val
1               5                   10                  15

Ile Arg Val Ile Ala His Gly Leu Arg Leu
            20                  25

<210> SEQ ID NO 377
<211> LENGTH: 25
<212> TYPE: PRT
<213> ORGANISM: Artificial
<220> FEATURE:
<223> OTHER INFORMATION: Synthetic peptide sequence

<400> SEQUENCE: 377

Arg Arg Gly Tyr Leu Pro Ala Val Gly Ala Pro Ile Arg Arg Val Ile
1               5                   10                  15

Arg Val Ile Ala His Gly Leu Arg Leu
            20                  25

<210> SEQ ID NO 378
<211> LENGTH: 25
<212> TYPE: PRT
<213> ORGANISM: Artificial
<220> FEATURE:
<223> OTHER INFORMATION: Synthetic peptide sequence

<400> SEQUENCE: 378

Arg Gly Tyr Leu Pro Ala Val Gly Ala Pro Ile Arg Arg Val Ile Arg
1               5                   10                  15

Val Ile Ala His Gly Leu Arg Leu Arg
            20                  25

<210> SEQ ID NO 379
<211> LENGTH: 24
<212> TYPE: PRT
<213> ORGANISM: Artificial
<220> FEATURE:
<223> OTHER INFORMATION: Synthetic peptide sequence

<400> SEQUENCE: 379

Arg Gly Tyr Leu Pro Ala Val Gly Ala Pro Ile Arg Val Ile Arg Val
1               5                   10                  15

Ile Ala His Gly Leu Arg Leu Arg
            20

<210> SEQ ID NO 380
<211> LENGTH: 24
```

```
<212> TYPE: PRT
<213> ORGANISM: Artificial
<220> FEATURE:
<223> OTHER INFORMATION: Synthetic peptide sequence

<400> SEQUENCE: 380

Arg Gly Tyr Leu Pro Ala Val Gly Ala Pro Ile Arg Arg Val Ile Arg
1               5                   10                  15

Val Ile Ala His Gly Leu Arg Leu
            20

<210> SEQ ID NO 381
<211> LENGTH: 22
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (7)..(7)
<223> OTHER INFORMATION: Xaa can be any naturally occurring amino acid

<400> SEQUENCE: 381

Arg Gly Asn Ile Val Pro Xaa Val Val Thr Ala Arg Arg Ile Gly Asp
1               5                   10                  15

Leu Ile Val Ala Gln Val
            20

<210> SEQ ID NO 382
<211> LENGTH: 22
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (7)..(7)
<223> OTHER INFORMATION: Xaa can be any naturally occurring amino acid

<400> SEQUENCE: 382

Arg Arg Asn Ile Val Pro Xaa Val Val Thr Ala Arg Arg Ile Gly Asp
1               5                   10                  15

Leu Ile Val Ala Gln Val
            20

<210> SEQ ID NO 383
<211> LENGTH: 23
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (8)..(8)
<223> OTHER INFORMATION: Xaa can be any naturally occurring amino acid

<400> SEQUENCE: 383

Arg Arg Arg Asn Ile Val Pro Xaa Val Val Thr Ala Arg Arg Ile Gly
1               5                   10                  15

Asp Leu Ile Val Ala Gln Val
            20

<210> SEQ ID NO 384
<211> LENGTH: 23
<212> TYPE: PRT
<213> ORGANISM: Artificial
<220> FEATURE:
```

```
<223> OTHER INFORMATION: Synthetic peptide sequence
<220> FEATURE:
<221> NAME/KEY: misc_feature
<222> LOCATION: (7)..(7)
<223> OTHER INFORMATION: Xaa can be any naturally occurring amino acid

<400> SEQUENCE: 384

Arg Arg Asn Ile Val Pro Xaa Val Val Thr Ala Arg Arg Arg Ile Gly
1               5                   10                  15

Asp Leu Ile Val Ala Gln Val
            20

<210> SEQ ID NO 385
<211> LENGTH: 22
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (21)..(21)
<223> OTHER INFORMATION: Xaa can be any naturally occurring amino acid

<400> SEQUENCE: 385

Arg Gly Val Thr Pro Ala Asp Leu Ile Gly Ala Arg Arg Gln Tyr Asn
1               5                   10                  15

Pro Val Ala Val Xaa Phe
            20

<210> SEQ ID NO 386
<211> LENGTH: 22
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (21)..(21)
<223> OTHER INFORMATION: Xaa can be any naturally occurring amino acid

<400> SEQUENCE: 386

Arg Arg Val Thr Pro Ala Asp Leu Ile Gly Ala Arg Arg Gln Tyr Asn
1               5                   10                  15

Pro Val Ala Val Xaa Phe
            20

<210> SEQ ID NO 387
<211> LENGTH: 23
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (22)..(22)
<223> OTHER INFORMATION: Xaa can be any naturally occurring amino acid

<400> SEQUENCE: 387

Arg Arg Arg Val Thr Pro Ala Asp Leu Ile Gly Ala Arg Arg Gln Tyr
1               5                   10                  15

Asn Pro Val Ala Val Xaa Phe
            20

<210> SEQ ID NO 388
<211> LENGTH: 23
<212> TYPE: PRT
<213> ORGANISM: Artificial
```

```
<220> FEATURE:
<223> OTHER INFORMATION: Synthetic peptide sequence
<220> FEATURE:
<221> NAME/KEY: misc_feature
<222> LOCATION: (22)..(22)
<223> OTHER INFORMATION: Xaa can be any naturally occurring amino acid

<400> SEQUENCE: 388

Arg Arg Val Thr Pro Ala Asp Leu Ile Gly Ala Arg Arg Gln Tyr
1               5                   10                  15

Asn Pro Val Ala Val Xaa Phe
            20

<210> SEQ ID NO 389
<211> LENGTH: 23
<212> TYPE: PRT
<213> ORGANISM: Artificial
<220> FEATURE:
<223> OTHER INFORMATION: Synthetic peptide sequence

<400> SEQUENCE: 389

Arg Arg Gly Pro Arg Pro Glu Gly Tyr Thr Leu Phe Phe Arg Gly Tyr
1               5                   10                  15

Thr Leu Phe Phe Thr Ser Arg
            20

<210> SEQ ID NO 390
<211> LENGTH: 23
<212> TYPE: PRT
<213> ORGANISM: Artificial
<220> FEATURE:
<223> OTHER INFORMATION: Synthetic peptide sequence

<400> SEQUENCE: 390

Arg Gly Pro Arg Pro Glu Gly Tyr Thr Leu Phe Phe Arg Gly Tyr
1               5                   10                  15

Thr Leu Phe Phe Thr Ser Arg
            20

<210> SEQ ID NO 391
<211> LENGTH: 24
<212> TYPE: PRT
<213> ORGANISM: Artificial
<220> FEATURE:
<223> OTHER INFORMATION: Synthetic peptide sequence

<400> SEQUENCE: 391

Arg Arg Gly Pro Arg Pro Glu Gly Tyr Thr Leu Phe Phe Arg Arg Gly
1               5                   10                  15

Tyr Thr Leu Phe Phe Thr Ser Arg
            20

<210> SEQ ID NO 392
<211> LENGTH: 25
<212> TYPE: PRT
<213> ORGANISM: Artificial
<220> FEATURE:
<223> OTHER INFORMATION: Synthetic peptide sequence

<400> SEQUENCE: 392

Arg Arg Gly Pro Arg Pro Glu Gly Tyr Thr Leu Phe Phe Arg Arg
1               5                   10                  15

Gly Tyr Thr Leu Phe Phe Thr Ser Arg
            20                  25
```

<210> SEQ ID NO 393
<211> LENGTH: 25
<212> TYPE: PRT
<213> ORGANISM: Artificial
<220> FEATURE:
<223> OTHER INFORMATION: Synthetic peptide sequence

<400> SEQUENCE: 393

Arg Arg Arg Gly Pro Arg Pro Glu Gly Tyr Thr Leu Phe Phe Arg Arg
1               5                   10                  15

Gly Tyr Thr Leu Phe Phe Thr Ser Arg
            20                  25

<210> SEQ ID NO 394
<211> LENGTH: 24
<212> TYPE: PRT
<213> ORGANISM: Artificial
<220> FEATURE:
<223> OTHER INFORMATION: Synthetic peptide sequence

<400> SEQUENCE: 394

Arg Gly Leu Pro Tyr Pro Arg Gly Tyr Thr Leu Phe Val Arg Gly
1               5                   10                  15

Tyr Thr Leu Phe Val Ser Asp Arg
            20

<210> SEQ ID NO 395
<211> LENGTH: 25
<212> TYPE: PRT
<213> ORGANISM: Artificial
<220> FEATURE:
<223> OTHER INFORMATION: Synthetic peptide sequence

<400> SEQUENCE: 395

Arg Arg Gly Leu Pro Tyr Pro Arg Gly Tyr Thr Leu Phe Val Arg Arg
1               5                   10                  15

Gly Tyr Thr Leu Phe Val Ser Asp Arg
            20                  25

<210> SEQ ID NO 396
<211> LENGTH: 26
<212> TYPE: PRT
<213> ORGANISM: Artificial
<220> FEATURE:
<223> OTHER INFORMATION: Synthetic peptide sequence

<400> SEQUENCE: 396

Arg Arg Gly Leu Pro Tyr Pro Arg Gly Tyr Thr Leu Phe Val Arg Arg
1               5                   10                  15

Arg Gly Tyr Thr Leu Phe Val Ser Asp Arg
            20                  25

<210> SEQ ID NO 397
<211> LENGTH: 26
<212> TYPE: PRT
<213> ORGANISM: Artificial
<220> FEATURE:
<223> OTHER INFORMATION: Synthetic peptide sequence

<400> SEQUENCE: 397

Arg Arg Arg Gly Leu Pro Tyr Pro Arg Gly Tyr Thr Leu Phe Val Arg
1               5                   10                  15

Arg Gly Tyr Thr Leu Phe Val Ser Asp Arg
            20                  25

```
<210> SEQ ID NO 398
<211> LENGTH: 25
<212> TYPE: PRT
<213> ORGANISM: Artificial
<220> FEATURE:
<223> OTHER INFORMATION: Synthetic peptide sequence

<400> SEQUENCE: 398

Arg Arg Gly Leu Pro Tyr Pro Arg Gly Tyr Thr Leu Phe Val Arg Arg
1               5                   10                  15

Gly Tyr Thr Leu Phe Val Ser Asp Arg
            20                  25

<210> SEQ ID NO 399
<211> LENGTH: 23
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (17)..(17)
<223> OTHER INFORMATION: Xaa can be any naturally occurring amino acid

<400> SEQUENCE: 399

Arg Arg Gly Glu Thr Ile Leu Thr Pro Arg Asp Val Arg Asn Thr Leu
1               5                   10                  15

Xaa Thr Pro Arg Asp Val Arg
            20

<210> SEQ ID NO 400
<211> LENGTH: 23
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (17)..(17)
<223> OTHER INFORMATION: Xaa can be any naturally occurring amino acid

<400> SEQUENCE: 400

Arg Gly Glu Thr Ile Leu Thr Pro Arg Asp Val Arg Arg Asn Thr Leu
1               5                   10                  15

Xaa Thr Pro Arg Asp Val Arg
            20

<210> SEQ ID NO 401
<211> LENGTH: 22
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (16)..(16)
<223> OTHER INFORMATION: Xaa can be any naturally occurring amino acid

<400> SEQUENCE: 401

Arg Gly Glu Thr Ile Leu Thr Pro Arg Asp Val Arg Asn Thr Leu Xaa
1               5                   10                  15

Thr Pro Arg Asp Val Arg
            20

<210> SEQ ID NO 402
```

```
<211> LENGTH: 23
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (17)..(17)
<223> OTHER INFORMATION: Xaa can be any naturally occurring amino acid

<400> SEQUENCE: 402

Arg Gly Glu Thr Ile Leu Thr Pro Arg Asp Val Arg Gly Asn Thr Leu
1               5                   10                  15

Xaa Thr Pro Arg Asp Val Arg
            20

<210> SEQ ID NO 403
<211> LENGTH: 23
<212> TYPE: PRT
<213> ORGANISM: Artificial
<220> FEATURE:
<223> OTHER INFORMATION: Synthetic peptide sequence

<400> SEQUENCE: 403

Arg Arg Ser Ser Thr Ser Pro Val Tyr Asp Leu Arg Arg Ser Ser Thr
1               5                   10                  15

Ser Pro Val Tyr Asn Leu Arg
            20

<210> SEQ ID NO 404
<211> LENGTH: 24
<212> TYPE: PRT
<213> ORGANISM: Artificial
<220> FEATURE:
<223> OTHER INFORMATION: Synthetic peptide sequence

<400> SEQUENCE: 404

Arg Arg Ser Ser Thr Ser Pro Val Tyr Asp Leu Arg Arg Arg Ser Ser
1               5                   10                  15

Thr Ser Pro Val Tyr Asn Leu Arg
            20

<210> SEQ ID NO 405
<211> LENGTH: 24
<212> TYPE: PRT
<213> ORGANISM: Artificial
<220> FEATURE:
<223> OTHER INFORMATION: Synthetic peptide sequence

<400> SEQUENCE: 405

Arg Arg Arg Ser Ser Thr Ser Pro Val Tyr Asp Leu Arg Arg Ser Ser
1               5                   10                  15

Thr Ser Pro Val Tyr Asn Leu Arg
            20

<210> SEQ ID NO 406
<211> LENGTH: 25
<212> TYPE: PRT
<213> ORGANISM: Artificial
<220> FEATURE:
<223> OTHER INFORMATION: Synthetic peptide sequence

<400> SEQUENCE: 406

Arg Arg Arg Ser Ser Thr Ser Pro Val Tyr Asp Leu Arg Arg Arg Ser
1               5                   10                  15
```

Ser Thr Ser Pro Val Tyr Asn Leu Arg
            20                  25

<210> SEQ ID NO 407
<211> LENGTH: 26
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (8)..(8)
<223> OTHER INFORMATION: Xaa can be any naturally occurring amino acid

<400> SEQUENCE: 407

Arg Arg Thr Ala Tyr Glu Arg Xaa Cys Asn Ile Leu Arg Arg Gly Leu
1               5                   10                  15

Glu Pro Leu Val Ile Ala Gly Ile Leu Ala
            20                  25

<210> SEQ ID NO 408
<211> LENGTH: 27
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (9)..(9)
<223> OTHER INFORMATION: Xaa can be any naturally occurring amino acid

<400> SEQUENCE: 408

Arg Arg Arg Thr Ala Tyr Glu Arg Xaa Cys Asn Ile Leu Arg Arg Gly
1               5                   10                  15

Leu Glu Pro Leu Val Ile Ala Gly Ile Leu Ala
            20                  25

<210> SEQ ID NO 409
<211> LENGTH: 27
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (8)..(8)
<223> OTHER INFORMATION: Xaa can be any naturally occurring amino acid

<400> SEQUENCE: 409

Arg Arg Thr Ala Tyr Glu Arg Xaa Cys Asn Ile Leu Arg Arg Arg Gly
1               5                   10                  15

Leu Glu Pro Leu Val Ile Ala Gly Ile Leu Ala
            20                  25

<210> SEQ ID NO 410
<211> LENGTH: 27
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (8)..(8)
<223> OTHER INFORMATION: Xaa can be any naturally occurring amino acid

<400> SEQUENCE: 410

Arg Arg Thr Ala Tyr Glu Arg Xaa Cys Asn Ile Leu Arg Arg Gly Leu
1               5                   10                  15

Glu Pro Leu Val Ile Ala Gly Ile Leu Ala Arg
            20                  25

<210> SEQ ID NO 411
<211> LENGTH: 28
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (8)..(8)
<223> OTHER INFORMATION: Xaa can be any naturally occurring amino acid

<400> SEQUENCE: 411

Arg Arg Thr Ala Tyr Glu Arg Xaa Cys Asn Ile Leu Arg Arg Gly Leu
1               5                   10                  15

Glu Pro Leu Val Ile Ala Gly Ile Leu Ala Arg Arg
            20                  25

<210> SEQ ID NO 412
<211> LENGTH: 27
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 412

Arg Arg Thr Val Ile Gly Ala Ser Xaa Ile Pro Leu Leu Arg Gly Thr
1               5                   10                  15

Pro Ile Xaa Gln Asp Trp Glu Asn Arg Ala Asn
            20                  25

<210> SEQ ID NO 413
<211> LENGTH: 28
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 413

Arg Arg Arg Thr Val Ile Gly Ala Ser Xaa Ile Pro Leu Leu Arg Gly
1               5                   10                  15

Thr Pro Ile Xaa Gln Asp Trp Glu Asn Arg Ala Asn
            20                  25

<210> SEQ ID NO 414
<211> LENGTH: 28
<212> TYPE: PRT
<213> ORGANISM: Artificial
<220> FEATURE:
<223> OTHER INFORMATION: Synthetic peptide sequence

```
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 414

Arg Arg Thr Val Ile Gly Ala Ser Xaa Ile Pro Leu Leu Arg Arg Gly
1               5                   10                  15

Thr Pro Ile Xaa Gln Asp Trp Glu Asn Arg Ala Asn
            20                  25

<210> SEQ ID NO 415
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid

<400> SEQUENCE: 415

Arg Arg Arg Thr Val Ile Gly Ala Ser Xaa Ile Pro Leu Leu Arg Arg
1               5                   10                  15

Gly Thr Pro Ile Xaa Gln Asp Trp Glu Asn Arg Ala Asn
            20                  25

<210> SEQ ID NO 416
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid

<400> SEQUENCE: 416

Arg Arg Arg Thr Val Ile Gly Ala Ser Xaa Ile Pro Leu Leu Arg Arg
1               5                   10                  15

Gly Thr Pro Ile Xaa Gln Asp Trp Glu Asn Arg Ala Asn Arg
            20                  25                  30

<210> SEQ ID NO 417
<211> LENGTH: 26
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (21)..(23)
```

```
<223> OTHER INFORMATION: Xaa can be any naturally occurring amino acid

<400> SEQUENCE: 417

Arg Arg Ala Ala Phe Glu Glu Xaa Xaa Ile Thr Ser Arg Arg Val Ala
1               5                   10                  15

Phe Glu Asp Leu Xaa Xaa Xaa Ser Phe Ile
            20                  25

<210> SEQ ID NO 418
<211> LENGTH: 27
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (22)..(24)
<223> OTHER INFORMATION: Xaa can be any naturally occurring amino acid

<400> SEQUENCE: 418

Arg Arg Arg Ala Ala Phe Glu Glu Xaa Xaa Ile Thr Ser Arg Arg Val
1               5                   10                  15

Ala Phe Glu Asp Leu Xaa Xaa Xaa Ser Phe Ile
            20                  25

<210> SEQ ID NO 419
<211> LENGTH: 28
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (23)..(25)
<223> OTHER INFORMATION: Xaa can be any naturally occurring amino acid

<400> SEQUENCE: 419

Arg Arg Arg Ala Ala Phe Glu Glu Xaa Xaa Ile Thr Ser Arg Arg Gly
1               5                   10                  15

Val Ala Phe Glu Asp Leu Xaa Xaa Xaa Ser Phe Ile
            20                  25

<210> SEQ ID NO 420
<211> LENGTH: 28
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (23)..(25)
<223> OTHER INFORMATION: Xaa can be any naturally occurring amino acid

<400> SEQUENCE: 420

Arg Arg Arg Ala Ala Phe Glu Glu Xaa Xaa Ile Thr Ser Arg Arg Arg
1               5                   10                  15
```

Val Ala Phe Glu Asp Leu Xaa Xaa Xaa Ser Phe Ile
            20                  25

<210> SEQ ID NO 421
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (23)..(25)
<223> OTHER INFORMATION: Xaa can be any naturally occurring amino acid

<400> SEQUENCE: 421

Arg Arg Arg Ala Ala Phe Glu Glu Xaa Xaa Ile Thr Ser Arg Arg Arg
1               5                   10                  15

Val Ala Phe Glu Asp Leu Xaa Xaa Xaa Ser Phe Ile Gly Arg
            20                  25                  30

<210> SEQ ID NO 422
<211> LENGTH: 24
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (8)..(8)
<223> OTHER INFORMATION: Xaa can be any naturally occurring amino acid

<400> SEQUENCE: 422

Arg Arg Thr Ala Tyr Glu Arg Xaa Cys Asn Ile Leu Arg Arg Gly Arg
1               5                   10                  15

Phe Gln Thr Val Val Gln Asx Ala
            20

<210> SEQ ID NO 423
<211> LENGTH: 25
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (8)..(8)
<223> OTHER INFORMATION: Xaa can be any naturally occurring amino acid

<400> SEQUENCE: 423

Arg Arg Thr Ala Tyr Glu Arg Xaa Cys Asn Ile Leu Arg Arg Gly Arg
1               5                   10                  15

Phe Gln Thr Val Val Gln Asx Ala Arg
            20                  25

<210> SEQ ID NO 424
<211> LENGTH: 23
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (7)..(7)
<223> OTHER INFORMATION: Xaa can be any naturally occurring amino acid

```
<400> SEQUENCE: 424

Arg Thr Ala Tyr Glu Arg Xaa Cys Asn Ile Leu Arg Gly Arg Phe Gln
1               5                   10                  15

Thr Val Val Gln Asx Ala Arg
            20

<210> SEQ ID NO 425
<211> LENGTH: 23
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (8)..(8)
<223> OTHER INFORMATION: Xaa can be any naturally occurring amino acid

<400> SEQUENCE: 425

Arg Arg Thr Ala Tyr Glu Arg Xaa Cys Asn Ile Leu Arg Gly Arg Phe
1               5                   10                  15

Gln Thr Val Val Gln Asx Ala
            20

<210> SEQ ID NO 426
<211> LENGTH: 27
<212> TYPE: PRT
<213> ORGANISM: Artificial
<220> FEATURE:
<223> OTHER INFORMATION: Synthetic peptide sequence

<400> SEQUENCE: 426

Asx Arg Gly Leu Glu Pro Leu Val Ile Ala Gly Ile Leu Ala Arg Arg
1               5                   10                  15

Gly Ser Leu Val Gly Leu Leu His Ile Val Leu
            20                  25

<210> SEQ ID NO 427
<211> LENGTH: 27
<212> TYPE: PRT
<213> ORGANISM: Artificial
<220> FEATURE:
<223> OTHER INFORMATION: Synthetic peptide sequence

<400> SEQUENCE: 427

Arg Arg Gly Leu Glu Pro Leu Val Ile Ala Gly Ile Leu Ala Arg Arg
1               5                   10                  15

Gly Ser Leu Val Gly Leu Leu His Ile Val Leu
            20                  25

<210> SEQ ID NO 428
<211> LENGTH: 28
<212> TYPE: PRT
<213> ORGANISM: Artificial
<220> FEATURE:
<223> OTHER INFORMATION: Synthetic peptide sequence

<400> SEQUENCE: 428

Arg Arg Gly Leu Glu Pro Leu Val Ile Ala Gly Ile Leu Ala Arg Arg
1               5                   10                  15

Gly Ser Leu Val Gly Leu Leu His Ile Val Leu Arg
            20                  25

<210> SEQ ID NO 429
<211> LENGTH: 28
```

```
<212> TYPE: PRT
<213> ORGANISM: Artificial
<220> FEATURE:
<223> OTHER INFORMATION: Synthetic peptide sequence

<400> SEQUENCE: 429

Arg Arg Gly Leu Glu Pro Leu Val Ile Ala Gly Ile Leu Ala Arg Arg
1               5                   10                  15

Arg Gly Ser Leu Val Gly Leu Leu His Ile Val Leu
            20                  25

<210> SEQ ID NO 430
<211> LENGTH: 29
<212> TYPE: PRT
<213> ORGANISM: Artificial
<220> FEATURE:
<223> OTHER INFORMATION: Synthetic peptide sequence

<400> SEQUENCE: 430

Arg Arg Gly Leu Glu Pro Leu Val Ile Ala Gly Ile Leu Ala Arg Arg
1               5                   10                  15

Arg Gly Ser Leu Val Gly Leu Leu His Ile Val Leu Arg
            20                  25

<210> SEQ ID NO 431
<211> LENGTH: 26
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (20)..(21)
<223> OTHER INFORMATION: Xaa can be any naturally occurring amino acid

<400> SEQUENCE: 431

Arg Thr Ala Phe Leu Val Arg Asn Val Ala Arg Ser Ile Ala Arg Ser
1               5                   10                  15

Val Thr Ile Xaa Xaa Ala Ser Val Val His
            20                  25

<210> SEQ ID NO 432
<211> LENGTH: 27
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (21)..(22)
<223> OTHER INFORMATION: Xaa can be any naturally occurring amino acid

<400> SEQUENCE: 432

Arg Thr Ala Phe Leu Val Arg Asn Val Ala Arg Arg Ser Ile Ala Arg
1               5                   10                  15

Ser Val Thr Ile Xaa Xaa Ala Ser Val Val His
            20                  25

<210> SEQ ID NO 433
<211> LENGTH: 27
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (21)..(22)
```

<223> OTHER INFORMATION: Xaa can be any naturally occurring amino acid

<400> SEQUENCE: 433

Arg Arg Thr Ala Phe Leu Val Arg Asn Val Ala Arg Ser Ile Ala Arg
1               5                   10                  15

Ser Val Thr Ile Xaa Xaa Ala Ser Val Val His
            20                  25

<210> SEQ ID NO 434
<211> LENGTH: 28
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (22)..(23)
<223> OTHER INFORMATION: Xaa can be any naturally occurring amino acid

<400> SEQUENCE: 434

Arg Arg Thr Ala Phe Leu Val Arg Asn Val Ala Arg Arg Ser Ile Ala
1               5                   10                  15

Arg Ser Val Thr Ile Xaa Xaa Ala Ser Val Val His
            20                  25

<210> SEQ ID NO 435
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (22)..(23)
<223> OTHER INFORMATION: Xaa can be any naturally occurring amino acid

<400> SEQUENCE: 435

Arg Arg Thr Ala Phe Leu Val Arg Asn Val Ala Arg Arg Ser Ile Ala
1               5                   10                  15

Arg Ser Val Thr Ile Xaa Xaa Ala Ser Val Val His Arg
            20                  25

<210> SEQ ID NO 436
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (22)..(23)
<223> OTHER INFORMATION: Xaa can be any naturally occurring amino acid

<400> SEQUENCE: 436

Arg Arg Thr Ala Phe Leu Val Arg Asn Val Ala Arg Arg Ser Ile Ala
1               5                   10                  15

Arg Ser Val Thr Ile Xaa Xaa Ala Ser Val Val His Arg Arg
            20                  25                  30

<210> SEQ ID NO 437
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature

```
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 437

Arg Gly Xaa Thr Pro Ile Xaa Gln Asp Trp Gly Asn Arg Ala Asn Arg
1               5                   10                  15

Gly Thr Pro Thr Arg Gln Glu Trp Asp Cys Arg Ile Ser
            20                  25

<210> SEQ ID NO 438
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 438

Arg Gly Xaa Thr Pro Ile Xaa Gln Asp Trp Gly Asn Arg Ala Asn Arg
1               5                   10                  15

Gly Thr Pro Thr Arg Gln Glu Trp Asp Ala Arg Ile Ser
            20                  25

<210> SEQ ID NO 439
<211> LENGTH: 28
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (6)..(6)
<223> OTHER INFORMATION: Xaa can be any naturally occurring amino acid

<400> SEQUENCE: 439

Arg Gly Thr Pro Ile Xaa Gln Asp Trp Gly Asn Arg Ala Asn Arg Gly
1               5                   10                  15

Thr Pro Thr Arg Gln Glu Trp Asp Cys Arg Ile Ser
            20                  25

<210> SEQ ID NO 440
<211> LENGTH: 28
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (6)..(6)
<223> OTHER INFORMATION: Xaa can be any naturally occurring amino acid

<400> SEQUENCE: 440

Arg Gly Thr Pro Ile Xaa Gln Asp Trp Gly Asn Arg Ala Asn Arg Gly
1               5                   10                  15

Thr Pro Thr Arg Gln Glu Trp Asp Ala Arg Ile Ser
            20                  25
```

<210> SEQ ID NO 441
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (7)..(7)
<223> OTHER INFORMATION: Xaa can be any naturally occurring amino acid

<400> SEQUENCE: 441

Arg Gly Cys Thr Pro Ile Xaa Gln Asp Trp Gly Asn Arg Ala Asn Arg
1               5                   10                  15

Gly Thr Pro Thr Arg Gln Glu Trp Asp Cys Arg Ile Ser
            20                  25

<210> SEQ ID NO 442
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (7)..(7)
<223> OTHER INFORMATION: Xaa can be any naturally occurring amino acid

<400> SEQUENCE: 442

Arg Gly Cys Thr Pro Ile Xaa Gln Asp Trp Gly Asn Arg Ala Asn Arg
1               5                   10                  15

Gly Thr Pro Thr Arg Gln Glu Trp Asp Ala Arg Ile Ser
            20                  25

<210> SEQ ID NO 443
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (7)..(7)
<223> OTHER INFORMATION: Xaa can be any naturally occurring amino acid

<400> SEQUENCE: 443

Arg Gly Lys Thr Pro Ile Xaa Gln Asp Trp Gly Asn Arg Ala Asn Arg
1               5                   10                  15

Gly Thr Pro Thr Arg Gln Glu Trp Asp Cys Arg Ile Ser
            20                  25

<210> SEQ ID NO 444
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (7)..(7)
<223> OTHER INFORMATION: Xaa can be any naturally occurring amino acid

<400> SEQUENCE: 444

Arg Gly Lys Thr Pro Ile Xaa Gln Asp Trp Gly Asn Arg Ala Asn Arg
1               5                   10                  15

Gly Thr Pro Thr Arg Gln Glu Trp Asp Ala Arg Ile Ser
            20                  25

<210> SEQ ID NO 445
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 445

Arg Gly Xaa Thr Pro Ile Xaa Gln Asp Trp Gly Asn Arg Ala Asn Arg
1               5                   10                  15

Gly Thr Pro Thr Arg Gln Glu Trp Asp Cys Arg Ile Ser
            20                  25

<210> SEQ ID NO 446
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 446

Arg Gly Xaa Thr Pro Ile Xaa Gln Asp Trp Gly Asn Arg Ala Asn Arg
1               5                   10                  15

Gly Thr Pro Thr Arg Gln Glu Trp Asp Ala Arg Ile Ser
            20                  25

<210> SEQ ID NO 447
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (7)..(7)
<223> OTHER INFORMATION: Xaa can be any naturally occurring amino acid

<400> SEQUENCE: 447

Arg Gly Asp Thr Pro Ile Xaa Gln Asp Trp Gly Asn Arg Ala Asn Arg
1               5                   10                  15

Gly Thr Pro Thr Arg Gln Glu Trp Asp Cys Arg Ile Ser
            20                  25

<210> SEQ ID NO 448
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (7)..(7)

<223> OTHER INFORMATION: Xaa can be any naturally occurring amino acid

<400> SEQUENCE: 448

Arg Gly Asp Thr Pro Ile Xaa Gln Asp Trp Gly Asn Arg Ala Asn Arg
1               5                   10                  15

Gly Thr Pro Thr Arg Gln Glu Trp Asp Ala Arg Ile Ser
            20                  25

<210> SEQ ID NO 449
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (7)..(7)
<223> OTHER INFORMATION: Xaa can be any naturally occurring amino acid

<400> SEQUENCE: 449

Arg Gly Glu Thr Pro Ile Xaa Gln Asp Trp Gly Asn Arg Ala Asn Arg
1               5                   10                  15

Gly Thr Pro Thr Arg Gln Glu Trp Asp Cys Arg Ile Ser
            20                  25

<210> SEQ ID NO 450
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (7)..(7)
<223> OTHER INFORMATION: Xaa can be any naturally occurring amino acid

<400> SEQUENCE: 450

Arg Gly Glu Thr Pro Ile Xaa Gln Asp Trp Gly Asn Arg Ala Asn Arg
1               5                   10                  15

Gly Thr Pro Thr Arg Gln Glu Trp Asp Ala Arg Ile Ser
            20                  25

<210> SEQ ID NO 451
<211> LENGTH: 32
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid

<400> SEQUENCE: 451

-continued

```
Arg Gly Xaa Thr Pro Thr Xaa Asn Gly Trp Asp Val Lys Leu Ser Arg
1               5                   10                  15

Gly Thr Pro Ile Xaa Gln Glu Trp Xaa Ser Leu Xaa Asn Gln Glu Trp
                20                  25                  30
```

<210> SEQ ID NO 452
<211> LENGTH: 31
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 452

```
Arg Gly Thr Pro Thr Xaa Asn Gly Trp Asp Val Lys Leu Ser Arg Gly
1               5                   10                  15

Thr Pro Ile Xaa Gln Glu Trp Xaa Ser Leu Xaa Asn Gln Glu Trp
            20                  25                  30
```

<210> SEQ ID NO 453
<211> LENGTH: 32
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid

<400> SEQUENCE: 453

```
Arg Gly Lys Thr Pro Thr Xaa Asn Gly Trp Asp Val Lys Leu Ser Arg
1               5                   10                  15

Gly Thr Pro Ile Xaa Gln Glu Trp Xaa Ser Leu Xaa Asn Gln Glu Trp
                20                  25                  30
```

<210> SEQ ID NO 454
<211> LENGTH: 32
<212> TYPE: PRT
<213> ORGANISM: Artificial
<220> FEATURE:
<223> OTHER INFORMATION: Synthetic peptide sequence
<220> FEATURE:

```
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid

<400> SEQUENCE: 454

Arg Gly Cys Thr Pro Thr Xaa Asn Gly Trp Asp Val Lys Leu Ser Arg
1               5                   10                  15

Gly Thr Pro Ile Xaa Gln Glu Trp Xaa Ser Leu Xaa Asn Gln Glu Trp
            20                  25                  30

<210> SEQ ID NO 455
<211> LENGTH: 32
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid

<400> SEQUENCE: 455

Arg Gly Xaa Thr Pro Thr Xaa Asn Gly Trp Asp Val Lys Leu Ser Arg
1               5                   10                  15

Gly Thr Pro Ile Xaa Gln Glu Trp Xaa Ser Leu Xaa Asn Gln Glu Trp
            20                  25                  30

<210> SEQ ID NO 456
<211> LENGTH: 32
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
```

<220> FEATURE:
<221> NAME/KEY: misc_feature
<222> LOCATION: (28)..(28)
<223> OTHER INFORMATION: Xaa can be any naturally occurring amino acid

<400> SEQUENCE: 456

Arg Gly Asp Thr Pro Thr Xaa Asn Gly Trp Asp Val Lys Leu Ser Arg
1               5                   10                  15

Gly Thr Pro Ile Xaa Gln Glu Trp Xaa Ser Leu Xaa Asn Gln Glu Trp
            20                  25                  30

<210> SEQ ID NO 457
<211> LENGTH: 32
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid

<400> SEQUENCE: 457

Arg Gly Glu Thr Pro Thr Xaa Asn Gly Trp Asp Val Lys Leu Ser Arg
1               5                   10                  15

Gly Thr Pro Ile Xaa Gln Glu Trp Xaa Ser Leu Xaa Asn Gln Glu Trp
            20                  25                  30

<210> SEQ ID NO 458
<211> LENGTH: 26
<212> TYPE: PRT
<213> ORGANISM: Artificial
<220> FEATURE:
<223> OTHER INFORMATION: Synthetic peptide sequence

<400> SEQUENCE: 458

Arg Arg Leu Glu Cys Val Tyr Cys Lys Gln Gln Leu Leu Arg Arg Glu
1               5                   10                  15

Val Tyr Asp Phe Ala Phe Arg Asp Leu Cys
            20                  25

<210> SEQ ID NO 459
<211> LENGTH: 28
<212> TYPE: PRT
<213> ORGANISM: Artificial
<220> FEATURE:
<223> OTHER INFORMATION: Synthetic peptide sequence

<400> SEQUENCE: 459

Arg Arg Leu Glu Cys Val Tyr Cys Lys Gln Gln Leu Leu Arg Arg Arg
1               5                   10                  15

Gly Glu Val Tyr Asp Phe Ala Phe Arg Asp Leu Cys
            20                  25

<210> SEQ ID NO 460

<211> LENGTH: 28
<212> TYPE: PRT
<213> ORGANISM: Artificial
<220> FEATURE:
<223> OTHER INFORMATION: Synthetic peptide sequence

<400> SEQUENCE: 460

Arg Arg Arg Leu Glu Cys Val Tyr Cys Lys Gln Gln Leu Leu Arg Arg
1               5                   10                  15
Gly Glu Val Tyr Asp Phe Ala Phe Arg Asp Leu Cys
            20                  25

<210> SEQ ID NO 461
<211> LENGTH: 29
<212> TYPE: PRT
<213> ORGANISM: Artificial
<220> FEATURE:
<223> OTHER INFORMATION: Synthetic peptide sequence

<400> SEQUENCE: 461

Arg Arg Arg Leu Glu Cys Val Tyr Cys Lys Gln Gln Leu Leu Arg Arg
1               5                   10                  15
Arg Gly Glu Val Tyr Asp Phe Ala Phe Arg Asp Leu Cys
            20                  25

<210> SEQ ID NO 462
<211> LENGTH: 30
<212> TYPE: PRT
<213> ORGANISM: Artificial
<220> FEATURE:
<223> OTHER INFORMATION: Synthetic peptide sequence

<400> SEQUENCE: 462

Arg Arg Arg Gly Leu Glu Cys Val Tyr Cys Lys Gln Gln Leu Leu Arg
1               5                   10                  15
Arg Arg Gly Glu Val Tyr Asp Phe Ala Phe Arg Asp Leu Cys
            20                  25                  30

<210> SEQ ID NO 463
<211> LENGTH: 27
<212> TYPE: PRT
<213> ORGANISM: Artificial
<220> FEATURE:
<223> OTHER INFORMATION: Synthetic peptide sequence

<400> SEQUENCE: 463

Arg Arg Gly Val Tyr Asp Phe Ala Phe Arg Asp Leu Cys Arg Gly
1               5                   10                  15
Phe Ala Phe Arg Asp Leu Cys Ile Val Tyr Arg
            20                  25

<210> SEQ ID NO 464
<211> LENGTH: 28
<212> TYPE: PRT
<213> ORGANISM: Artificial
<220> FEATURE:
<223> OTHER INFORMATION: Synthetic peptide sequence

<400> SEQUENCE: 464

Arg Arg Gly Val Tyr Asp Phe Ala Phe Arg Asp Leu Cys Arg Arg Arg
1               5                   10                  15
Gly Gly Phe Ala Phe Arg Asp Leu Cys Ile Val Tyr
            20                  25

```
<210> SEQ ID NO 465
<211> LENGTH: 29
<212> TYPE: PRT
<213> ORGANISM: Artificial
<220> FEATURE:
<223> OTHER INFORMATION: Synthetic peptide sequence

<400> SEQUENCE: 465

Arg Arg Arg Gly Val Tyr Asp Phe Ala Phe Arg Asp Leu Cys Arg Arg
1               5                   10                  15

Gly Gly Phe Ala Phe Arg Asp Leu Cys Ile Val Tyr Arg
            20                  25

<210> SEQ ID NO 466
<211> LENGTH: 29
<212> TYPE: PRT
<213> ORGANISM: Artificial
<220> FEATURE:
<223> OTHER INFORMATION: Synthetic peptide sequence

<400> SEQUENCE: 466

Arg Arg Arg Gly Val Tyr Asp Phe Ala Phe Arg Asp Leu Cys Arg Arg
1               5                   10                  15

Arg Gly Gly Phe Ala Phe Arg Asp Leu Cys Ile Val Tyr
            20                  25

<210> SEQ ID NO 467
<211> LENGTH: 31
<212> TYPE: PRT
<213> ORGANISM: Artificial
<220> FEATURE:
<223> OTHER INFORMATION: Synthetic peptide sequence

<400> SEQUENCE: 467

Arg Arg Arg Gly Gly Val Tyr Asp Phe Ala Phe Arg Asp Leu Cys Arg
1               5                   10                  15

Arg Arg Gly Gly Phe Ala Phe Arg Asp Leu Cys Ile Val Tyr Arg
            20                  25                  30

<210> SEQ ID NO 468
<211> LENGTH: 27
<212> TYPE: PRT
<213> ORGANISM: Artificial
<220> FEATURE:
<223> OTHER INFORMATION: Synthetic peptide sequence

<400> SEQUENCE: 468

Arg Arg Gly Val Phe Asp Tyr Ala Phe Arg Asp Ile Asn Arg Arg Gly
1               5                   10                  15

Phe Ala Tyr Arg Asp Ile Asn Leu Ala Tyr Arg
            20                  25

<210> SEQ ID NO 469
<211> LENGTH: 28
<212> TYPE: PRT
<213> ORGANISM: Artificial
<220> FEATURE:
<223> OTHER INFORMATION: Synthetic peptide sequence

<400> SEQUENCE: 469

Arg Arg Gly Val Tyr Asp Phe Ala Phe Arg Asp Leu Cys Arg Arg
1               5                   10                  15

Gly Gly Phe Ala Phe Arg Asp Leu Cys Ile Val Tyr
            20                  25
```

-continued

<210> SEQ ID NO 470
<211> LENGTH: 29
<212> TYPE: PRT
<213> ORGANISM: Artificial
<220> FEATURE:
<223> OTHER INFORMATION: Synthetic peptide sequence

<400> SEQUENCE: 470

Arg Arg Arg Gly Val Tyr Asp Phe Ala Phe Arg Asp Leu Cys Arg Arg
1               5                   10                  15

Gly Gly Phe Ala Phe Arg Asp Leu Cys Ile Val Tyr Arg
            20                  25

<210> SEQ ID NO 471
<211> LENGTH: 29
<212> TYPE: PRT
<213> ORGANISM: Artificial
<220> FEATURE:
<223> OTHER INFORMATION: Synthetic peptide sequence

<400> SEQUENCE: 471

Arg Arg Arg Gly Val Tyr Asp Phe Ala Phe Arg Asp Leu Cys Arg Arg
1               5                   10                  15

Arg Gly Gly Phe Ala Phe Arg Asp Leu Cys Ile Val Tyr
            20                  25

<210> SEQ ID NO 472
<211> LENGTH: 31
<212> TYPE: PRT
<213> ORGANISM: Artificial
<220> FEATURE:
<223> OTHER INFORMATION: Synthetic peptide sequence

<400> SEQUENCE: 472

Arg Arg Arg Gly Gly Val Tyr Asp Phe Ala Phe Arg Asp Leu Cys Arg
1               5                   10                  15

Arg Arg Gly Gly Phe Ala Phe Arg Asp Leu Cys Ile Val Tyr Arg
            20                  25                  30

<210> SEQ ID NO 473
<211> LENGTH: 25
<212> TYPE: PRT
<213> ORGANISM: Artificial
<220> FEATURE:
<223> OTHER INFORMATION: Synthetic peptide sequence

<400> SEQUENCE: 473

Arg Arg Val Asp Ile Arg Thr Leu Glu Asp Leu Leu Arg Arg Gly Thr
1               5                   10                  15

Leu Gly Ile Val Cys Pro Ile Gly Arg
            20                  25

<210> SEQ ID NO 474
<211> LENGTH: 26
<212> TYPE: PRT
<213> ORGANISM: Artificial
<220> FEATURE:
<223> OTHER INFORMATION: Synthetic peptide sequence

<400> SEQUENCE: 474

Arg Arg Val Asp Ile Arg Thr Leu Glu Asp Leu Leu Arg Arg Arg Gly
1               5                   10                  15

Gly Thr Leu Gly Ile Val Cys Pro Ile Gly
            20                  25

<210> SEQ ID NO 475
<211> LENGTH: 27
<212> TYPE: PRT
<213> ORGANISM: Artificial
<220> FEATURE:
<223> OTHER INFORMATION: Synthetic peptide sequence

<400> SEQUENCE: 475

Arg Arg Arg Val Asp Ile Arg Thr Leu Glu Asp Leu Leu Arg Arg Gly
1               5                   10                  15

Gly Thr Leu Gly Ile Val Cys Pro Ile Gly Arg
            20                  25

<210> SEQ ID NO 476
<211> LENGTH: 27
<212> TYPE: PRT
<213> ORGANISM: Artificial
<220> FEATURE:
<223> OTHER INFORMATION: Synthetic peptide sequence

<400> SEQUENCE: 476

Arg Arg Arg Val Asp Ile Arg Thr Leu Glu Asp Leu Leu Arg Arg Arg
1               5                   10                  15

Gly Gly Thr Leu Gly Ile Val Cys Pro Ile Gly
            20                  25

<210> SEQ ID NO 477
<211> LENGTH: 29
<212> TYPE: PRT
<213> ORGANISM: Artificial
<220> FEATURE:
<223> OTHER INFORMATION: Synthetic peptide sequence

<400> SEQUENCE: 477

Arg Arg Arg Gly Val Asp Ile Arg Thr Leu Glu Asp Leu Leu Arg Arg
1               5                   10                  15

Arg Gly Gly Thr Leu Gly Ile Val Cys Pro Ile Gly Arg
            20                  25

<210> SEQ ID NO 478
<211> LENGTH: 9
<212> TYPE: PRT
<213> ORGANISM: Artificial Sequence
<220> FEATURE:
<223> OTHER INFORMATION: Synthetic peptide

<400> SEQUENCE: 478

Ile Gly Asp Leu Ile Val Gln Ala Val
1               5

<210> SEQ ID NO 479
<211> LENGTH: 22
<212> TYPE: PRT
<213> ORGANISM: Artificial Sequence
<220> FEATURE:
<223> OTHER INFORMATION: Synthetic peptide

<400> SEQUENCE: 479

Arg Gly Asn Ile Val Pro Glx Val Val Thr Ala Arg Arg Ile Gly Asp
1               5                   10                  15

Leu Ile Val Gln Ala Val
            20

-continued

```
<210> SEQ ID NO 480
<211> LENGTH: 22
<212> TYPE: PRT
<213> ORGANISM: Artificial Sequence
<220> FEATURE:
<223> OTHER INFORMATION: Synthetic peptide

<400> SEQUENCE: 480

Arg Arg Asn Ile Val Pro Glx Val Val Thr Ala Arg Arg Ile Gly Asp
1               5                   10                  15

Leu Ile Val Gln Ala Val
            20

<210> SEQ ID NO 481
<211> LENGTH: 23
<212> TYPE: PRT
<213> ORGANISM: Artificial Sequence
<220> FEATURE:
<223> OTHER INFORMATION: Synthetic peptide

<400> SEQUENCE: 481

Arg Arg Arg Asn Ile Val Pro Glx Val Val Thr Ala Arg Arg Ile Gly
1               5                   10                  15

Asp Leu Ile Val Gln Ala Val
            20

<210> SEQ ID NO 482
<211> LENGTH: 23
<212> TYPE: PRT
<213> ORGANISM: Artificial Sequence
<220> FEATURE:
<223> OTHER INFORMATION: Synthetic peptide

<400> SEQUENCE: 482

Arg Arg Asn Ile Val Pro Glx Val Val Thr Ala Arg Arg Arg Ile Gly
1               5                   10                  15

Asp Leu Ile Val Gln Ala Val
            20

<210> SEQ ID NO 483
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: QIKIWFQN
<222> LOCATION: (1)..(8)

<400> SEQUENCE: 483

Gln Ile Lys Ile Trp Phe Gln Asn
1               5

<210> SEQ ID NO 484
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MKWKK
<222> LOCATION: (1)..(5)

<400> SEQUENCE: 484

Met Lys Trp Lys Lys
1               5
```

```
<210> SEQ ID NO 485
<211> LENGTH: 7
<212> TYPE: PRT
<213> ORGANISM: Artificial
<220> FEATURE:
<223> OTHER INFORMATION: Synthetic

<400> SEQUENCE: 485

Pro Val Val His Leu Thr Leu
1               5

<210> SEQ ID NO 486
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: QAGDDFSR
<222> LOCATION: (1)..(8)

<400> SEQUENCE: 486

Gln Ala Gly Asp Asp Phe Ser Arg
1               5
```